(12) United States Patent
Brode, III et al.

(10) Patent No.: US 6,475,765 B1
(45) Date of Patent: Nov. 5, 2002

(54) SUBTILISIN DY VARIANTS HAVING DECREASED ADSORPTION AND INCREASED HYDROLYSIS

(75) Inventors: Philip Frederick Brode, III, Cincinnati, OH (US); Bobby Lee Barnett, Cincinnati, OH (US); Donn Nelton Rubingh, Cincinnati, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/401,575

(22) Filed: Mar. 9, 1995

(51) Int. Cl.[7] .......................... C12N 9/56; C12N 15/57; C12N 15/74; C11D 3/386

(52) U.S. Cl. ................... 435/221; 435/69.1; 435/252.3; 435/320.1; 435/471; 510/392; 536/23.2

(58) Field of Search .................... 252/174.12, DIG. 12; 435/219–225, 69.1, 471, 220, 221; 536/23.2; 510/392

(56) References Cited

U.S. PATENT DOCUMENTS

| | | | |
|---|---|---|---|
| 4,760,025 A | | 7/1988 | Estell et al. ................. 435/222 |
| 4,908,773 A | | 3/1990 | Pantoliano et al. .......... 364/496 |
| 4,914,031 A | * | 4/1990 | Zukowski et al. ........... 435/222 |
| 4,980,288 A | | 12/1990 | Bryan et al. ................ 435/222 |
| 4,990,452 A | | 2/1991 | Bryan et al. ................ 435/222 |
| 5,013,657 A | | 5/1991 | Bryan et al. ............. 435/172.3 |
| 5,116,741 A | | 5/1992 | Bryan et al. .................. 435/87 |
| 5,118,623 A | * | 6/1992 | Boguslawski et al. ....... 435/221 |
| 5,155,033 A | * | 10/1992 | Estell et al. ................. 435/221 |
| 5,182,204 A | * | 1/1993 | Estell et al. ................. 435/222 |
| 5,185,258 A | * | 2/1993 | Caldwell et al. ............ 435/220 |
| 5,208,158 A | * | 5/1993 | Bech et al. .................. 435/219 |
| 5,217,878 A | * | 6/1993 | van Eekelen et al. ....... 435/69.1 |
| 5,244,791 A | * | 9/1993 | Estell ......................... 435/68.1 |
| 5,246,849 A | | 9/1993 | Bryan et al. ................ 435/220 |
| 5,260,207 A | * | 11/1993 | Pantoliano et al. .......... 435/220 |
| 5,275,945 A | * | 1/1994 | Hsiao et al. ................. 435/221 |
| 5,310,675 A | * | 5/1994 | Estell et al. ............. 435/320.1 |
| 5,316,941 A | * | 5/1994 | Estell et al. ............. 435/252.3 |
| 5,324,653 A | * | 6/1994 | van Eekelen et al. ....... 435/221 |
| 5,336,611 A | * | 8/1994 | van Eekelen et al. ....... 435/221 |
| 5,340,735 A | * | 8/1994 | Christianson et al. ....... 435/221 |
| 5,346,823 A | * | 9/1994 | Estell et al. ................. 435/221 |
| 5,352,603 A | * | 10/1994 | Vetter et al. ................ 435/221 |
| 5,371,008 A | * | 12/1994 | Carter et al. ................ 435/220 |
| 5,371,190 A | * | 12/1994 | Carter et al. ................ 530/350 |
| 5,389,307 A | * | 2/1995 | Lindegaard et al. ........ 510/320 |
| 5,403,737 A | * | 4/1995 | Abrahmsen et al. ..... 435/252.3 |
| 5,441,882 A | * | 8/1995 | Estell et al. ................. 435/222 |
| 5,453,372 A | * | 9/1995 | Vetter et al. ................ 435/222 |
| 5,470,733 A | * | 11/1995 | Bryan et al. ................ 435/222 |
| 5,472,855 A | * | 12/1995 | Carter et al. .............. 435/68.1 |
| 5,482,849 A | * | 1/1996 | Branner et al. ............. 435/222 |
| 5,500,364 A | * | 3/1996 | Christianson et al. ....... 435/221 |
| 5,567,601 A | * | 10/1996 | Bryan et al. ................ 435/222 |
| 5,629,173 A | * | 5/1997 | Abrahmsen et al. ....... 435/69.1 |
| 5,631,217 A | * | 5/1997 | Branner et al. ............. 510/320 |
| 5,652,136 A | * | 7/1997 | Carter et al. ............. 435/252.3 |
| 5,677,272 A | * | 10/1997 | Ghosh et al. ............... 510/306 |
| 5,679,630 A | * | 10/1997 | Baeck et al. ................ 510/305 |
| 5,700,676 A | * | 12/1997 | Bott et al. ................... 435/221 |
| 5,707,848 A | * | 1/1998 | Bryan et al. .................... 435/8 |
| 5,736,512 A | * | 4/1998 | Abrahmsen et al. .......... 514/12 |
| 5,741,664 A | * | 4/1998 | Ballinger et al. .......... 435/68.1 |
| 5,741,694 A | * | 4/1998 | Hastrup et al. ............. 435/222 |
| 5,763,257 A | * | 6/1998 | Bott et al. ................... 435/221 |
| 5,801,038 A | * | 9/1998 | Bott et al. ................... 435/221 |
| 5,801,039 A | * | 9/1998 | Maurer et al. .............. 435/221 |
| 5,955,340 A | * | 9/1999 | Bott et al. ................... 435/221 |
| 5,972,682 A | * | 10/1999 | Bott et al. ................... 435/221 |
| 5,985,639 A | * | 11/1999 | Christianson et al. ....... 435/221 |
| 6,197,567 B1 | * | 3/2001 | Aaslyng et al. ............. 435/221 |
| 6,197,589 B1 | * | 3/2001 | Maurer et al. .............. 435/221 |
| 6,271,012 B1 | * | 8/2001 | van Eekelen et al. ....... 435/221 |
| 6,287,841 B1 | * | 9/2001 | Mulleners et al. .......... 435/221 |

FOREIGN PATENT DOCUMENTS

| | | |
|---|---|---|
| AU | 8772281 | 11/1987 |
| EP | 0 251 446 A3 | 4/1987 |
| EP | 0 251 446 A2 | 4/1987 |
| EP | 0 251 446 A2 * | 4/1987 |
| EP | 0 260 105 | 3/1988 |
| EP | 0328229 * | 8/1989 |
| EP | 0 328 229 | 8/1989 |
| EP | 0 357 157 A1 * | 3/1990 |
| EP | 0 380 362 | 8/1990 |

(List continued on next page.)

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*

(List continued on next page.)

*Primary Examiner*—Charles L. Patterson, Jr.
*Assistant Examiner*—William W. Moore
(74) *Attorney, Agent, or Firm*—Frank Taffy; C. Brant Cook; Kim W. Zerby

(57) ABSTRACT

The present invention relates to Subtilisin DY variants having a modified amino acid sequence of wild-type Subtilisin DY amino acid sequence, the wild-type amino acid sequence comprising a first loop region, a second loop region, a third loop region, a fourth loop region, a fifth loop region and a sixth loop region; wherein the modified amino acid sequence comprises different amino acids than that occurring in wild-type Subtilisin DY (i.e., substitution) at specifically identified positions in one or more of the loop regions whereby the Subtilisin DY variant has decreased adsorption to, and increased hydrolysis of, an insoluble substrate as compared to the wild-type Subtilisin DY. The present invention also relates to DNA sequences encoding such Subtilisin DY variants. The present invention also relates to compositions comprising such Subtilisin DY variants for cleaning a variety of surfaces.

65 Claims, No Drawings

FOREIGN PATENT DOCUMENTS

| EP | 0 398 539 | | 11/1990 |
|---|---|---|---|
| EP | 0 405 901 | A1 | 1/1991 |
| EP | 0 405 902 | A1 | 1/1991 |
| WO | 87/04461 | | 7/1987 |
| WO | 87/05050 | | 8/1987 |
| WO | WO 88/08033 | A1 * | 10/1988 |
| WO | 89/06279 | | 1/1989 |
| WO | WO 89/07462 | A1 * | 8/1989 |
| WO | 89/09830 | | 10/1989 |
| WO | 91/00345 | | 1/1991 |
| WO | WO 91/14420 | A1 * | 11/1991 |
| WO | WO 92/02615 | A1 * | 2/1992 |
| WO | WO 92/08778 | A1 * | 5/1992 |
| WO | 92/11357 | | 7/1992 |
| WO | 94/02618 | | 2/1994 |
| WO | 95/07991 | | 3/1995 |
| WO | 95/30010 | | 3/1995 |
| WO | WO 95/30010 | A1 * | 4/1995 |
| WO | WO 95/30011 | A1 * | 4/1995 |
| WO | 95/30011 | | 4/1995 |
| WO | WO 88/08028 | A1 * | 10/1998 |

OTHER PUBLICATIONS

Russell, A. J. & Fersht, A. R., 1987, "Rational modification of enzyme catalysis by engineering surface charge", Nature, vol. 328, pp. 496–500.*

*Structural and Molecular Biology of Protease Function and Inhibition* "Surface Active Variants of Subtilisin BPN': Interfacial Hydrolysis", Philip F. Brode, Christopher R. Erwin, Deborah S. Rauch, Ellen S. Wang, James M. Armpriester, Bobby L. Barnett, Mark D. Bauer, Philip R. Green, Deborah A. Thaman, and Donn N. Rubingh, Journal of Cell. Biology, Supplement 18D, p. 151, 1994.

Abrahmsén, L., J. Tom, J. Burnier, K. A. Butcher, A. Kossiakoff and J. A. Wells, "Engineering Subtilisin and Its Substrates for Efficient Ligation of Peptide Bonds in Aqueous Solution", Biochemistry, vol. 30, No. 17, pp. 4151–4159 (no month identified 1991).

Arnold, F.H., "Engineering Enzymes for Non–aqueous Solvents", TibTech, vol. 8, pp. 244–249 (Sep. 1990).

Braxton, S. and J. A. Wells, "The Importance of a Distal Hydrogen Bonding Group in Stabilizing the Transition State in Subtilisin BPN'", The Journal of Biological Chemistry, vol. 266, No. 18, pp. 11797–11800 (Jun. 1991).

Brode, P. F., III and D. S. Rauch, "Subtilisin BPN': Activity on an Immobilized Substrate", Langmuir, vol. 8, No. 5, pp. 1325–1329 (no month identified 1992).

Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).

Carter, P., L. Abrahmsen and J. A. Wells, "Probing the Mechansim and Improving the Rate of Substrate–Assisted Catalysis in Subtilisin BPN'", Biochemistry, vol. 30, No. 25, pp. 6142–6148 (no month identified 1991).

Carter, P. and J. A. Wells, "Functional Interaction Among Catalytic Residues in Subtilisin BPN'", Proteins: Structure, Function, and Genetics, vol. 7, pp. 335–342, (no month identified 1990).

Cunningham, B. C. and J. A. Wells, "Improvement in the Alkaline Stability of Subtilisin Using An Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vlieg, "Engineering Surface Charges In a Subtilisin", First International Symposium on Subtilsin Enzymes, Hamburg, Germany, (Sep. 1992).

Estell, D. A., "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN'", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis ater Mutating Threonine 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen, R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunningham, T.P. Graycar and D.A. Estell, "Recruitment of Substrate–specificity Properties from One Enzyme into a Related One by Protein Engineering", Proc. Natl. Acad. Sci., USA, vol. 84, pp. 5167–5171 (Aug. 1987).

Wells, J.A. and D.A. Estell, "Subtilisin–An Enzyme Designed to be Engineered", TIBS 13, pp. 291–297 (Aug. 1988).

Wong, C.–H., S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

* cited by examiner

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 274 amino acids
      (B) TYPE: amino acid
      (C) STRANDEDNESS: single
      (D) TOPOLOGY: linear (xi) SEQUENCE DESCRIPTION: SEQ ID NO:1:

```
Ala Gln Thr Val Pro Tyr Gly Ile Pro Leu Ile Lys Ala Asp Lys Val
1               5                   10                  15

Gln Ala Gln Gly Tyr Lys Gly Ala Asn Val Lys Val Gly Ile Ile Asp
                20                  25                  30

Thr Gly Ile Ala Ala Ser His Thr Asp Leu Lys Val Val Gly Gly Ala
            35                  40                  45

Ser Phe Val Ser Gly Glu Ser Tyr Asn Thr Asp Gly Asn Gly His Gly
        50                  55                  60

Thr His Val Ala Gly Thr Val Ala Ala Leu Asp Asn Thr Thr Gly Val
65                  70                  75                  80

Leu Gly Val Ala Pro Asn Val Ser Leu Tyr Ala Ile Lys Val Leu Asn
                85                  90                  95

Ser Ser Gly Ser Gly Thr Tyr Ser Ala Ile Val Ser Gly Ile Glu Trp
            100                 105                 110

Ala Thr Gln Asn Gly Leu Asp Val Ile Asn Met Ser Leu Gly Gly Pro
            115                 120                 125

Ser Gly Ser Thr Ala Leu Lys Gln Ala Val Asp Lys Ala Tyr Ala Ser
    130                 135                 140

Gly Ile Val Val Val Ala Ala Gly Asn Ser Gly Ser Ser Gly Ser Ser
145                 150                 155                 160

Gln Asn Thr Ile Gly Tyr Pro Ala Lys Tyr Asp Ser Val Ile Ala Val
                165                 170                 175

Gly Ala Val Asp Ser Asn Lys Asn Arg Ala Ser Phe Ser Ser Val Gly
            180                 185                 190

Ala Glu Leu Glu Val Met Ala Pro Gly Val Ser Val Tyr Ser Thr Tyr
    195                 200                 205

Pro Ser Asn Thr Tyr Thr Ser Leu Asn Gly Thr Ser Met Ala Ser Pro
    210                 215                 220

His Val Ala Gly Ala Ala Ala Leu Ile Leu Ser Lys Tyr Pro Thr Leu
225                 230                 235                 240

Ser Ala Ser Gln Val Arg Asn Arg Leu Ser Ser Thr Ala Thr Asn Leu
                245                 250                 255

Gly Asp Ser Phe Tyr Tyr Gly Lys Gly Leu Ile Asn Val Glu Ala Ala
            260                 265                 270

Ala Gln
```

US 6,475,765 B1

SUBTILISIN DY VARIANTS HAVING DECREASED ADSORPTION AND INCREASED HYDROLYSIS

TECHNICAL FIELD

The present invention relates to novel enzyme variants useful in a variety of cleaning compositions, and DNA sequences encoding such enzyme variants.

BACKGROUND

Enzymes make up the largest class of naturally occurring proteins. Each class of enzyme generally catalyzes (accelerates a reaction without being consumed) a different kind of chemical reaction. One class of enzymes known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and wide-specificity proteases can substantially improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide Subtilisin DY enzyme variants having improved hydrolysis versus the wild-type of the enzyme.

It is also an object of the present invention to provide cleaning compositions comprising these subtilisin enzyme variants.

SUMMARY

The present invention relates to Subtilisin DY variants having a modified amino acid sequence of wild-type Subtilisin DY amino acid sequence, the wild-type amino acid sequence comprising a first loop region, a second loop region, a third loop region, a fourth loop region and a fifth loop region; wherein the modified amino acid sequence comprises different amino acids than that occurring in wild-type Subtilisin DY (i.e., substitution) at specifically identified positions in one or more of the loop regions whereby the Subtilisin DY variant has decreased adsorption to, and increased hydrolysis of, an insoluble substrate as compared to the wild-type Subtilisin DY. The present invention also relates to DNA sequences encoding such Subtilisin DY variants. The present invention also relates to compositions comprising such Subtilisin DY variants for cleaning a variety of surfaces.

DESCRIPTION

I. Subtilisin DY Variants

This invention pertains to subtilisin enzymes, in particular Subtilisin DY, that have been modified by mutating the various nucleotide sequences that code for the enzyme, thereby modifying the amino acid sequence of the enzyme. The modified subtilisin enzymes (hereinafter, "Subtilisin DY variants") of the present invention have decreased adsorption to and increased hydrolysis of an insoluble substrate as compared to the wild-type subtilisin. The present invention also pertains to DNA sequences encoding for such Subtilisin DY variants.

The subtilisin enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would increase with increasing surface concentration. This has been shown to be the case. (Brode, P. F. III and D. S. Rauch, *Langmuir*, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in *Polymer Solutions, Blends And Interfaces*, Ed. by I. Noda and D. N. Rubingh, Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In Subtilisin DY, certain amino acids form exterior loops on the enzyme molecule. For purposes of discussion, these loops shall be referred to as first, second, third, fourth and fifth loop regions. Specifically, positions 58–65 form the first loop region; positions 94–106 form the second loop region; positions 125–132 form the third loop region; positions 153–166 form the fourth loop region; positions 186–190 form the fifth loop region; and positions 199–219 form the sixth loop region (position numbering analagous to positions in the amino acid sequence for wild-type subtilisin Subtilisin DY (SEQ ID NO:1)).

It is believed that these loop regions play a significant role in the adsorption of the enzyme molecule to a surface-bound peptide, and specific mutations in one or more of these loop regions will have a significant effect on this adsorption. While not wishing to be bound by theory, it is believed that the loop regions are important to the adsorption of the Subtilisin DY molecule for at least two reasons. First, the amino acids which comprise the loop regions can make close contacts with any surfaces to which the molecule is exposed. Second, the proximity of the loop regions to the active-site and binding pocket of the Subtilisin DY molecule gives them a role in the catalytically productive adsorption of the enzyme to surface-bound substrates (peptides/protein soils).

As used herein, "variant" means an enzyme having an amino acid sequence which differs from that of wild-type.

As used herein, "mutant Subtilisin DY DNA" means a DNA sequence coding for a Subtilisin DY variant.

As used herein, "wild-type Subtilisin DY" refers to an enzyme represented by SEQ ID NO:1. The amino acid sequence for Subtilisin DY is further described by Nedkov, P., Oberthur, W. and Braunitzer, G., *Biol. Chem.*, Vol. 366, pp. 421430 (1985), incorporated herein by reference.

As used herein, the term "Subtilisin DY wild-type amino acid sequence" encompasses SEQ ID NO:1 as well as SEQ ID NO:1 having modifications to the amino acid sequence other than at any of positions 58, 59, 60, 61, 62, 64, 65, 94, 95, 96, 97, 98, 99, 100, 101, 102, 103, 104, 105, 106, 125, 126, 127, 128, 129, 130, 131, 132, 153, 154, 155, 156, 157, 158, 159, 160, 161, 162, 163, 164, 165, 166, 186, 187, 188, 189, 190, 199, 200, 201, 202, 203, 204, 205, 206, 207, 208, 209, 210, 211, 212, 213, 214, 215, 216, 217, 218 or 219.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", *Proceedings of the National Academy of Science USA*, Vol. 78, pp. 3824–3828, 1981, incorporated herein by reference).

TABLE 1

| Amino Acid | Hydrophilicity Value |
| --- | --- |
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |
| Ser | 0.3 |
| Arg$^+$, Lys$^+$, Glu$^-$, Asp$^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

In one embodiment of the present invention, the Subtilisin DY variant has a modified amino acid sequence of Subtilisin DY wild-type amino acid sequence, wherein the wild-type amino acid sequence comprises a substitution at one or more positions in one or more of the first loop region, the second loop region, the third loop region, the fourth loop region, the fifth loop region or the sixth loop region; whereby the Subtilisin DY variant has decreased adsorption to, and increased hydrolysis of, an insoluble substrate as compared to the wild-type Subtilisin DY.

In a preferred embodiment of the present invention, the substituting amino acid for one or more of the positions in one or more of the loop regions is, with reference to Table 1, neutral or negatively charged and equally or more hydrophylic, preferably more hydrophylic, than the amino acid at the subject position in the wild-type amino acid sequence.

A. Substitutions in the First Loop Region

When a substitution occurs in the first loop region, the substitution occurs at one or more of positions 58, 59, 60, 61, 62, 64 or 65.

When a substitution occurs at position 58, the substituting amino acid is Asn, Asp, Gln, Glu, Gly, Pro or Ser.

When a substitution occurs at position 59, the substituting amino acid is Glu.

When a substitution occurs at position 60, the substituting amino acid is Asn, Asp, Gln, Glu, Pro or Ser.

When a substitution occurs at position 61, the substituting amino acid is Asp, Gln, Glu or Ser.

When a substitution occurs at position 62, the substituting amino acid is Asn, Asp, Gln, Glu, Pro or Ser.

When a substitution occurs at position 64, the substituting amino acid is Asn, Asp, Gln, Glu, Pro or Ser.

When a substitution occurs at position 65, the substituting amino acid is Asn, Asp, Gln, Glu, Gly, Pro or Ser.

B. Substitutions in the Second Loop Region

When a substitution occurs in the second loop region, the substitution occurs at one or more of positions 94, 95, 96, 97, 98, 99, 100, 101, 102, 103, 104, 105 or 106.

When a substitution occurs at position 94, the substituting amino acid is Ala, Asn, Asp, Cys, Gln, Glu, Gly, His, Met, Pro, Ser or Thr.

When a substitution occurs at position 95, the substituting amino acid is Ala, Asn, Asp, Cys, Gln, Glu, Gly, His, Ile, Met, Pro, Ser, Thr or Val.

When a substitution occurs at position 96, the substituting amino acid is Asp, Gln, Glu or Ser.

When a substitution occurs at position 97, the substituting amino acid is Asp or Glu.

When a substitution occurs at position 98, the substituting amino acid is Asp or Glu.

When a substitution occurs at position 99, the substituting amino acid is Asn, Asp, Gln, Glu, Pro or Ser.

When a substitution occurs at position 100, the substituting amino acid is Asp or Glu.

When a substitution occurs at position 101, the substituting amino acid is Asn, Asp, Gln, Glu, Pro or Ser.

When a substitution occurs at position 102, the substituting amino acid is Asn, Asp, Gln, Glu, Gly, Pro or Ser.

When a substitution occurs at position 103, the substituting amino acid is Ala, Asn, Asp, Cys, Gln, Glu, Gly, His, Ile, Leu, Met, Pro, Ser, Thr or Val.

When a substitution occurs at position 104, the substituting amino acid is Asp or Glu.

When a substitution occurs at position 105, the substituting amino acid is Asn, Asp, Gln, Glu, Gly, His, Pro, Ser or Thr.

When a substitution occurs at position 106, the substituting amino acid is Ala, Asn, Asp, Cys, Gln, Glu, Gly, His, Leu, Met, Pro, Ser, Thr or Val.

C. Substitutions in the Third Loop Region

When a substitution occurs in the third loop region, the substitution occurs at one or more of positions 125, 126, 127, 128, 129, 130, 131 or 132.

When a substitution occurs at position 125, the substituting amino acid is Ala, Asn, Asp, Cys, Gln, Glu, Gly, His, Ile, Met, Pro, Ser, Thr or Val.

When a substitution occurs at position 126, the substituting amino acid is Asn, Asp, Gln, Glu, Pro or Ser.

When a substitution occurs at position 127, the substituting amino acid is Asn, Asp, Gln, Glu, Pro or Ser.

When a substitution occurs at position 128, the substituting amino acid is Asn, Asp, Gln, Glu, Gly, or Ser.

When a substitution occurs at position 129, the substituting amino acid is Asp or Glu.

When a substitution occurs at position 130, the substituting amino acid is Asn, Asp, Gln, Glu, Pro or Ser.

When a substitution occurs at position 131, the substituting amino acid is Asp or Glu.

When a substitution occurs at position 132, the substituting amino acid is Asn, Asp, Gln, Glu, Gly, Pro or Ser.

D. Substitutions in the Fourth Loop Region When a substitution occurs in the fourth loop region, the substitution occurs at one or more of positions 153, 154, 155, 156, 157, 158, 159, 160, 161, 162, 163, 164, 165 or 166.

When a substitution occurs at position 153, the substituting amino acid is Asn, Asp, Gln, Glu, Pro or Ser.

When a substitution occurs at position 154, the substituting amino acid is Asp, Gln, Glu or Ser.

When a substitution occurs at position 155, the substituting amino acid is Asp or Glu.

When a substitution occurs at position 156, the substituting amino acid is Asn, Asp, Gln, Glu, Pro or Ser.

When a substitution occurs at position 157, the substituting amino acid is Asp or Glu.

When a substitution occurs at position 158, the substituting amino acid is Asp or Glu.

When a substitution occurs at position 159, the substituting amino acid is Asn, Asp, Gln, Glu, Pro or Ser.

When a substitution occurs at position 160, the substituting amino acid is Asp or Glu.

When a substitution occurs at position 161, the substituting amino acid is Asn, Asp, Glu or Ser.

When a substitution occurs at position 162, the substituting amino acid is Asp, Gln, Glu or Ser.

When a substitution occurs at position 163, the substituting amino acid is Asn, Asp, Gln, Glu, Gly, Pro or Ser.

When a substitution occurs at position 164, the substituting amino acid is Ala, Asn, Asp, Cys, Gln, Glu, Gly, His, Leu, Met, Pro, Ser, Thr or Val.

When a substitution occurs at position 165, the substituting amino acid is Asn, Asp, Gln, Glu, Pro or Ser.

When a substitution occurs at position 166, the substituting amino acid is Ala, Asn, Asp, Cys, Gln, Glu, Gly, His, Ile, Leu, Met, Pro, Ser, Thr or Val.

E. Substitutions in the Fifth Loop Region

When a substitution occurs in the fifth loop region, the substitution occurs at one or more of positions 186, 187, 188, 189 or 190.

When a substitution occurs at position 186, the substituting amino acid is Asn, Asp, Gln, Glu, Gly, His, Pro, Ser or Thr.

When a substitution occurs at position 187, the substituting amino acid is Asp or Glu.

When a substitution occurs at position 188, the substituting amino acid is Ala, Asn, Asp, Cys, Gln, Glu, Gly, His, Ile, Leu, Met, Pro, Ser, Thr, Tyr or Val.

When a substitution occurs at position 189, the substituting amino acid is Asp or Glu.

When a substitution occurs at position 190, the substituting amino acid is Asp or Glu.

F. Substitutions in the Sixth Loop Region

When a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219.

When a substitution occurs at position 199, the substituting amino acid is Asn, Asp, Gln, Glu, Gly, His, Pro, Ser or Thr.

When a substitution occurs at position 200, the substituting amino acid is Asn, Asp, Gln, Glu, Gly, or Ser.

When a substitution occurs at position 201, the substituting amino acid is Asn, Asp, Gln, Glu, Pro or Ser.

When a substitution occurs at position 202, the substituting amino acid is Ala, Asn, Asp, Cys, gin, Glu, Gly, His, Met, Pro, Ser or Thr.

When a substitution occurs at position 203, the substituting amino acid is Asp or Glu.

When a substitution occurs at position 204, the substituting amino acid is Ala, Asn, Asp, Cys, Gln, Glu, Gly, His, Met, Pro, Ser, or Thr.

When a substitution occurs at position 205, the substituting amino acid is Ala, Asn, Asp, Cys, Gln, Glu, Gly, His, Ile, Leu, Met, Pro, Ser, Thr or Val.

When a substitution occurs at position 206, the substituting amino acid is Asp or Glu.

When a substitution occurs at position 207, the substituting amino acid is Asn, Asp, Gln, Glu, Gly, Pro or Ser.

When a substitution occurs at position 208, the substituting amino acid is Ala, Asn, Asp, Cys, Gln, Glu, Gly, His, Ile, Leu, Met, Phe, Pro, Ser, Thr or Val.

When a substitution occurs at position 209, the substituting amino acid is Asn, Asp, gin, Glu, Gly, or Ser.

When a substitution occurs at position 210, the substituting amino acid is Asp or Glu.

When a substitution occurs at position 21 1, the substituting amino acid is Asp, Gln, Glu or Ser.

When a substitution occurs at position 212, the substituting amino acid is Asn, Asp, gin, Glu, Gly, Pro or Ser.

When a substitution occurs at position 213, the substituting amino acid is Ala, Asn, Asp, Cys, Gln, Glu, Gly, His, Ile, Leu, Met, Pro, Ser, Thr or Val.

When a substitution occurs at position 214, the substituting amino acid is Asn, Asp, Gln, Glu, Gly, Pro or Ser.

When a substitution occurs at position 215, the substituting amino acid is Asp or Glu.

When a substitution occurs at position 216, the substituting amino acid is Ala, Asn, Asp, Cys, Gln, Glu, Gly, His, Ile, Met, Pro, Ser, Thr or Val.

When a substitution occurs at position 217, the substituting amino acid is Asp, gin, Glu or Ser.

When a substitution occurs at position 218, the substituting amino acid is Asn, Asp, Gln, Glu, Pro or Ser.

When a substitution occurs at position 219, the substituting amino acid is Asn, Asp, Gln, Glu, Gly, Pro or Ser.

G. Preparation of Enzyme Variants

EXAMPLE 1

Mutant Subtilisin DY DNA

A phagemid ("DYP") containing the wild type Subtilisin DY gene is constructed. The 2.8 Kbp Pvu II restriction enzyme fragment of plasmid pUC119, (Vieira, J. and Messing, J., "Production of Single-Stranded Plasmid DNA", 153 *Methods in Enzymology* 3–11 (1989)) is cloned into the Pvu II site of plasmid pUB110 (Bacillus Genetic Stock Center, Columbus, Ohio 1E9). The pUC119-pUB110 hybrid plasmid is named pJMA601. Into the BamHI restriction site of pJMA601 is cloned the polymerase chain reaction— amplified subtilisin DY gene from chromosomal DNA giving phagemid DYP. Phagemid DYP is transformed into *Escherichia coli* Ung⁻ strain CJ236 and a single stranded uracil-containing DNA template is produced using the VCSM13 helper phage (Kunkel, T. A., J. D. Roberts and R. A. Zakour, "Rapid and efficient site-specific mutagenesis without phenotypic selection", *Methods in Enzymology*, VOl. 154, pp. 367–382, (1987); as modified by Yuckenberg, P. D., F. Witney, J. Geisselsoder and J. McClary, "Site-directed in vitro mutagenesis using uracil-containing DNA and phagemid vectors", *Directed Mutagenesis-A Pratical Approach*, ed. M. J. McPherson, pp. 2748, (1991); both of which are incorporated herein by reference). A single primer site-directed mutagenesis modification of the method of Zoller and Smith (Zoller, M. J., and M. Smith, "Oligonucleotide-directed mutagenesis using M13-derived vectors: an efficient and general procedure for the production of point mutations in any fragment of DNA", *Nucleic Acids Research*, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into *Escherichia coli* strain MM294 (American Type Culture Collection *E. coli*. 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of *Bacillus subtilis* and the Use of the Cloned Gene to Create an In Vitro-derived Deletion Mutation", *Journal of Bacterilogy*, Vol. 160, pp. 15–21). For some of the loop mutants a modified DYP with a frameshift-stop codon mutation in the corresponding loop is used to produce the uracil template. Oligonucleotides are designed to restore the proper reading frame and to encode for random substitutions at positions 58, 59, 60, 61, 62, 64, 65, 94, 95, 96, 97, 98, 99, 100, 101, 102, 103, 104, 105, 106, 125, 126, 127, 128, 129, 130, 131, 132, 153, 154, 155, 156, 157, 158, 159, 160, 161, 162, 163, 164, 165, 166, 186, 187, 188, 189, 190, 199, 200, 201, 202, 203, 204, 205, 206, 207, 208, 209, 210, 211, 212, 213, 214, 215, 216, 217, 218 or 219 (equimolar and/or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BG2036) containing a subtilisin mutant of interest are grown to mid-log phase in a one liter culture of LB-glucose broth and inoculated into a Biostat ED fermenter (B. Braun Biotech, Inc., Allentown, Pa.) in a total volume of 10 liters. The fermentation media contains Yeast Extract, starch, antifoam, buffers and trace minerals (see *Fermentation: a Practical Approach*, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2-(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K., *Protein Purification Principles and Practice*, Springer-Verlag, New York (1984), incorporated herein by reference).

The pNA assay (DelMar, E. G., C. Largman, J. W. Brodrick and M. C. Geokas, *Anal. Biochem.*, Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sMPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SDS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Mo.). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M Tris buffer (Tris (hydroxymethyl-aminomethane) containing 0.01M $CaCl_2$ and pH adjusted to 8.6 with HCl. All experiments are carried out at pH 8.6 in Tris buffer thermostated at 25° C.

H. Characterization of Enzyme Variants

EXAMPLE 4

Model Surface Preparation

Aminopropyl controlled pore glass (CPG) purchased from CPG Inc. (Fairfield, N.J.) is used as a support for covalently attaching the sAAPF-pNA substrate purchased from Bachem, Inc. (Torrence, Calif.). The reaction is carried out in dimethyl sulfoxide and (1-ethyl-3-[3-(dimethylamino) propyl] carbodiimide hydrochloride) (EDC) is used as a coupling agent. Upon completion (monitored by pNA assay), the excess solvent is removed, and the CPG:sMPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P. F. III, and D. S. Rauch, "Subtilisin BPN': Activity on an Immobilized Substrate," *Langmuir*, Vol. 8, p. 1325–1329, (1992), incorporated herein by reference.

The CPG surface will have 62,000±7,000 pNA molecules/ $\mu m^2$. The surface area will remain unchanged from the value of 50.0 $m^2/g$ reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sAAPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes—and every 10 minutes towards the end of the experiment). The CPG:sAAPF-pNA is allowed to settle and the solution is sampled. Both the experimental procedure and the calculation of the adsorption and hydrolysis are conducted as described by Brode et al., 1992, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 $\mu M$ sAAPF-pNA for each kinetic determination. An adsorbance data point is taken each second over a period of 900 seconds and the data are transferred to a Lotus™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_O$. The $v_O$ and $s_O$ data are plotted in the standard inverse fashion to give $K_M$ and $k_{cat}$.

I. Example Subtilisin DY Variants

Subtilisin DY variants of the present invention which have decreased adsorption to and increased hydrolysis of surface bound substrates are exemplified in Tables 2–36, below. In describing the specific mutations, the original amino acid occurring in wild-type is given first, the position number second, and the substituted amino acid third.

TABLE 2

Loop 1 - Single Mutation Variants

| |
|---|
| Thr58Asn |
| Thr58Asp |
| Thr58Gln |
| Thr58Glu |
| Thr58Gly |
| Thr58Pro |
| Thr58Ser |
| Asp59Glu |
| Gly60Asn |
| Gly60Asp |
| Gly60Gln |
| Gly60Glu |
| Gly60Pro |
| Gly60Ser |
| Asn61Asp |
| Asn61Gln |
| Asn61Glu |
| Asn61Ser |
| Gly62Asn |
| Gly62Asp |
| Gly62Gln |
| Gly62Glu |
| Gly62Pro |
| Gly62Ser |
| Gly64Asn |
| Gly64Asp |
| Gly64Gln |
| Gly64Glu |
| Gly64Pro |
| Gly64Ser |
| Thr65Asn |
| Thr65Asp |
| Thr65Gln |
| Thr65Glu |
| Thr65Gly |
| Thr65Pro |
| Thr65Ser |

TABLE 3

Loop 1 - Double Mutation Variants

| | | |
|---|---|---|
| Thr58Gln | + | Asn61Glu |
| Thr58Asn | + | Asn61Asp |
| Asp59Glu | + | Gly64Pro |
| Thr58Glu | + | Gly62Pro |
| Asp59Glu | + | Gly60Ser |
| Gly60Asn | + | Gly64Asn |
| Asn61Asp | + | Thr65Gln |
| Thr58Asp | + | Asn61Ser |
| Thr58Asp | + | Thr65Pro |
| Gly64Glu | + | Thr65Gly |
| Gly64Asp | + | Thr65Asn |
| Thr58Glu | + | Gly62Gln |
| Gly60Asn | + | Asn61Glu |
| Thr58Asn | + | Gly64Ser |
| Thr58Pro | + | Asp59Glu |
| Gly64Glu | + | Thr65Gln |
| Thr58Pro | + | Gly62Ser |

TABLE 3-continued

Loop 1 - Double Mutation Variants

| | | |
|---|---|---|
| Thr58Gly | + | Gly64Asn |
| Asn61Gln | + | Gly64Gln |
| Thr58Gly | + | Asn61Asp |
| Gly60Pro | + | Asn61Asp |
| Gly62Asn | + | Gly64Pro |
| Gly62Asp | + | Thr65Asn |
| Thr58Asn | + | Gly62Asn |
| Thr58Pro | + | Gly62Asn |
| Gly64Glu | + | Thr65Ser |
| Gly60Pro | + | Gly62Glu |
| Gly60Glu | + | Thr65Gln |
| Gly60Pro | + | Gly62Ser |
| Thr58Asp | + | Asn61Gln |
| Gly60Asn | + | Asn61Asp |
| Thr58Ser | + | Gly62Glu |
| Gly60Glu | + | Gly64Ser |
| Gly60Pro | + | Asn61Glu |
| Thr58Gln | + | Asn61Ser |
| Gly60Asp | + | Thr65Pro |
| Asn61Asp | + | Thr65Ser |
| Asn61Ser | + | Gly64Asp |

TABLE 4

Loop 1 - Triple Mutation Variants

| | | | | | |
|---|---|---|---|---|---|
| Thr58Asn | + | Gly60Gln | + | Gly64Pro |
| Thr58Gly | + | Asn61Ser | + | Thr65Ser |
| Asp59Glu | + | Gly60Pro | + | Thr65Ser |
| Asn61Glu | + | Gly62Pro | + | Gly64Asn |
| Thr58Asp | + | Gly60Asn | + | Thr65Gln |
| Thr58Ser | + | Gly62Ser | + | Thr65Gly |
| Thr58Pro | + | Asp59Glu | + | Gly62Pro |
| Gly60Glu | + | Asn61Gln | + | Thr65Gln |
| Gly60Glu | + | Gly64Asn | + | Thr65Pro |
| Gly60Asn | + | Gly62Asp | + | Thr65Ser |
| Thr58Asn | + | Asn61Glu | + | Thr65Gln |
| Thr58Asn | + | Asp59Glu | + | Gly62Pro |
| Gly60Gln | + | Gly62Gln | + | Gly64Glu |
| Asn61Gln | + | Gly62Pro | + | Thr65Ser |
| Asn61Gln | + | Gly62Asn | + | Thr65Gln |
| Asn61Ser | + | Gly62Gln | + | Thr65Gly |
| Gly60Ser | + | Gly64Gln | + | Thr65Gly |
| Thr58Pro | + | Gly60Pro | + | Gly64Gln |
| Thr58Asn | + | Gly60Asn | + | Thr65Pro |
| Asp59Glu | + | Gly62Gln | + | Thr65Asn |
| Thr58Ser | + | Gly60Gln | + | Gly62Asp |
| Thr58Asn | + | Gly64Ser | + | Thr65Asn |
| Gly60Pro | + | Gly62Asp | + | Thr65Gln |
| Asn61Glu | + | Gly64Ser | + | Thr65Gly |
| Thr58Pro | + | Asn61Asp | + | Gly64Gln |
| Asp59Glu | + | Asn61Ser | + | Gly62Ser |
| Thr58Asn | + | Gly60Asp | + | Thr65Asn |
| Asp59Glu | + | Asn61Gln | + | Gly62Asn |
| Thr58Asn | + | Gly60Asp | + | Asn61Asp |
| Thr58Asn | + | Gly60Glu | + | Asn61Glu |

TABLE 5

Loop 1 - Quadruple Mutation Variants

| | | | | | | | |
|---|---|---|---|---|---|---|---|
| Thr58Asn | + | Gly60Glu | + | Gly64Pro | + | Thr65Gln |
| Asp59Glu | + | Gly60Ser | + | Gly64Pro | + | Thr65Pro |
| Thr58Ser | + | Gly60Asn | + | Asn61Gln | + | Thr65Pro |
| Asp59Glu | + | Gly60Ser | + | Gly64Ser | + | Thr65Gly |
| Asp59Glu | + | Gly60Asn | + | Asn61Ser | + | Gly62Ser |
| Asp59Glu | + | Gly60Asn | + | Asn61Ser | + | Gly64Asn |
| Thr58Gln | + | Asn61Gln | + | Gly62Glu | + | Gly64Asn |
| Thr58Asn | + | Asp59Glu | + | Gly60Gln | + | Thr65Pro |
| Thr58Gly | + | Gly60Gln | + | Gly62Pro | + | Gly64Glu |
| Gly60Asp | + | Asn61Asp | + | Gly62Pro | + | Gly64Gln |
| Thr58Pro | + | Gly60Glu | + | Asn61Asp | + | Gly64Asn |
| Thr58Asp | + | Asp59Glu | + | Gly62Asn | + | Thr65Gln |
| Thr58Asp | + | Asp59Glu | + | Gly60Ser | + | Gly64Asn |
| Thr58Glu | + | Asp59Glu | + | Gly62Asn | + | Thr65Ser |
| Thr58Asp | + | Asp59Glu | + | Gly60Pro | + | Asn61Ser |
| Thr58Asn | + | Gly60Gln | + | Asn61Glu | + | Gly62Asp |
| Asp59Glu | + | Gly60Glu | + | Asn61Glu | + | Gly62Ser |
| Thr58Gln | + | Asp59Glu | + | Gly60Glu | + | Asn61Glu |
| Thr58Pro | + | Asp59Glu | + | Gly60Glu | + | Asn61Glu |
| Thr58Gln | + | Asp59Glu | + | Gly60Asp | + | Asn61Asp |
| Thr58Pro | + | Gly60Glu | + | Asn61Asp | + | Gly62Glu |
| Gly60Glu | + | Asn61Glu | + | Gly62Glu | + | Thr65Gly |
| Gly60Asp | + | Asn61Asp | + | Gly62Asp | + | Thr65Gln |
| Thr58Asp | + | Asp59Glu | + | Gly60Glu | + | Thr65Ser |
| Asp59Glu | + | Asn61Asp | + | Gly62Asp | + | Thr65Gln |
| Asp59Glu | + | Asn61Asp | + | Gly62Glu | + | Thr65Gly |
| Asp59Glu | + | Gly60Asp | + | Gly62Asp | + | Thr65Gln |
| Thr58Ser | + | Asp59Glu | + | Gly60Asp | + | Gly62Asp |

TABLE 6

Loop 2 - Single Mutation Variants

Val 94Ala
Val94Asn
Val94Asp
Val94Cys
Val94Gln
Val94Glu
Val94Gly
Val94His
Val94Met
Val94Pro
Val94Ser
Val94Thr
Leu95Ala
Leu95Asn
Leu95Asp
Leu95Cys
Leu95Gln
Leu95Glu
Leu95Gly
Leu95His
Leu95Ile
Leu95Met
Leu95Pro
Leu95Ser
Leu95Thr
Leu95Val
Asn96Asp
Asn96Gln
Asn96Glu
Asn96Ser
Ser97Asp
Ser97Glu
Ser98Asp
Ser98Glu
Gly99Asn
Gly99Asp
Gly99Gln
Gly99Glu
Gly99Pro
Gly99Ser
Ser100Asp
Ser100Glu
Gly101Asn
Gly101Asp
Gly101Gln
Gly101Glu
Gly101Pro
Gly101Ser
Thr102Asn
Thr102Asp
Thr102Gln
Thr102Glu

TABLE 6-continued

Loop 2 - Single Mutation Variants

Thr102Gly
Thr102Pro
Thr102Ser
Tyr103Ala
Tyr103Asn
Tyr103Asp
Tyr103Cys
Tyr103Gln
Tyr103Glu
Tyr103Gly
Tyr103His
Tyr103Ile
Tyr103Leu
Tyr103Met
Tyr103Pro
Tyr103Ser
Tyr103Thr
Tyr103Val
Ser104Asp
Ser104Glu
Ala105Asn
Ala105Asp
Ala105Gln
Ala105Glu
Ala105Gly
Ala105His
Ala105Pro
Ala105Ser
Ala105Thr
Ile106Ala
Ile106Asn
Ile106Asp
Ile106Cys
Ile106Gln
Ile106Glu
Ile106Gly
Ile106His
Ile106Leu
Ile106Met
Ile106Pro
Ile106Ser
Ile106Thr
Ile106Val

TABLE 7

Loop 2 - Double Mutation Variants

| | | |
|---|---|---|
| Val94Gln | + | Ser100Glu |
| Asn96Ser | + | Gly99Gln |
| Val94Asp | + | Thr102Gln |
| Val94His | + | Ala105Pro |
| Val94Pro | + | Ser97Glu |
| Asn96Ser | + | Ile106Asp |
| Ser97Glu | + | Gly101Ser |
| Leu95Gly | + | Thr102Glu |
| Ser100Glu | + | Ile106Thr |
| Asn96Ser | + | Gly99Ser |
| Ala105Ser | + | Ile106Pro |
| Asn96Ser | + | Gly101Ser |
| Thr102Asn | + | Ile106Gln |
| Val94His | + | Asn96Gln |
| Leu95Cys | + | Ala105Asp |
| Leu95Gly | + | Asn96Asp |
| Leu95Cys | + | Asn96Asp |
| Thr102Ser | + | Ile106Cys |
| Asn96Gln | + | Thr102Gln |
| Gly101Ser | + | Tyr103Gly |
| Asn96Ser | + | Ile106Thr |
| Ser98Asp | + | Gly99Gln |
| Leu95Ser | + | Ser100Glu |
| Leu95Met | + | Thr102Gly |
| Leu95His | + | Thr102Glu |
| Asn96Asp | + | Tyr103His |

TABLE 7-continued

Loop 2 - Double Mutation Variants

| | | |
|---|---|---|
| Tyr103Gln | + | Ile106Asp |
| Ser104Asp | + | Ile106Gln |
| Thr102Asn | + | Tyr103Asp |
| Val94Asn | + | Ser97Glu |
| Val94Gly | + | Gly101Ser |
| Leu95Gln | + | Ile106Asp |
| Asn96Ser | + | Ser104Asp |
| Tyr103Glu | + | Ile106His |
| Thr102Ser | + | Tyr103Glu |
| Val94Cys | + | Ser104Asp |
| Leu95Gln | + | Thr102Asp |
| Asn96Glu | + | Gly101Ser |
| Leu95Glu | + | Ala105Ser |
| Val94Met | + | Leu95Pro |
| Val94Thr | + | Gly101Gln |
| Tyr103Gly | + | Ile106His |
| Thr102Asn | + | Ile106Gly |
| Ser104Asp | + | Ile106Thr |
| Gly99Ser | + | Ser100Asp |
| Val94Glu | + | Gly99Asn |
| Gly99Gln | + | Gly101Ser |
| Val94Thr | + | Asn96Asp |
| Ser97Glu | + | Ile106Leu |
| Thr102Asp | + | Tyr103Met |
| Ser97Asp | + | Ala105His |
| Asn96Gln | + | Ser100Asp |
| Gly101Asn | + | Ile106Gln |
| Asn96Glu | + | Tyr103Ser |
| Tyr103Thr | + | Ile106Pro |
| Ser100Asp | + | Tyr103Ile |
| Gly101Glu | + | Tyr103Leu |
| Ser100Asp | + | Thr102Asn |
| Val94His | + | Leu95Thr |
| Ser104Asp | + | Ala105Asn |

TABLE 8

Loop 2 - Triple Mutation Variants

| | | | | | |
|---|---|---|---|---|---|
| Val94Gln | + | Leu95Thr | + | Ser100Glu |
| Ser98Asp | + | Ala105Ser | + | Ile106Asn |
| Val94Gly | + | Gly99Pro | + | Ile106Val |
| Val94Ser | + | Leu95Gln | + | Ser104Glu |
| Val94His | + | Tyr103Glu | + | Ile106Gly |
| Val94Pro | + | Asn96Gln | + | Ile106Cys |
| Val94Thr | + | Ser98Asp | + | Ile106Cys |
| Val94Met | + | Ser100Asp | + | Gly101Ser |
| Val94Ala | + | Ser97Asp | + | Gly99Gln |
| Leu95Gly | + | Gly99Pro | + | Ala105Gly |
| Val94Cys | + | Ser100Asp | + | Tyr103Ala |
| Gly101Asn | + | Thr102Asp | + | Ile106Ala |
| Gly99Ser | + | Ser104Glu | + | Ile106Val |
| Asn96Gln | + | Ser100Glu | + | Tyr103Thr |
| Leu95Met | + | Thr102Pro | + | Ile106Leu |
| Asn96Glu | + | Thr102Ser | + | Ala105His |
| Ser100Glu | + | Thr102Asn | + | Tyr103Val |
| Ser98Glu | + | Gly99Gln | + | Ile106Met |
| Asn96Asp | + | Gly99Ser | + | Ala105Thr |
| Gly101Asp | + | Thr102Asn | + | Tyr103Thr |
| Val94Ala | + | Gly99Gln | + | Tyr103His |
| Thr102Gly | + | Tyr103Glu | + | Ala105Gly |
| Ser97Glu | + | Gly101Ser | + | Thr102Gln |
| Val94Pro | + | Gly99Ser | + | Gly101Asp |
| Ser97Asp | + | Gly99Ser | + | Ile106Gly |
| Val94Cys | + | Leu95Val | + | Gly101Gln |
| Ser100Asp | + | Gly101Asn | + | Tyr103Gln |
| Thr102Asp | + | Tyr103Leu | + | Ile106Val |
| Val94Cys | + | Ser104Glu | + | Ala105Asn |
| Val94Ser | + | Thr102Asn | + | Ala105Thr |
| Ser98Glu | + | Gly99Asn | + | Tyr103Val |
| Leu95Val | + | Gly101Gln | + | Ala105Asp |
| Ser97Glu | + | Gly99Pro | + | Thr102Ser |
| Val94Ser | + | Gly101Glu | + | Ile106Ala |
| Gly99Asn | + | Gly101Asp | + | Thr102Glu |

TABLE 8-continued

Loop 2 - Triple Mutation Variants

| | | | | | |
|---|---|---|---|---|---|
| Gly99Asp | + | Ser100Glu | + | Thr102Asn |
| Val94Thr | + | Gly99Glu | + | Ser100Asp |
| Gly99Asp | + | Ser100Asp | + | Tyr103Pro |
| Gly99Glu | + | Ser100Glu | + | Gly101Gln |
| Asn96Glu | + | Ser97Glu | + | Ala105Asn |
| Asn96Glu | + | Ser97Asp | + | Gly101Pro |
| Leu95Met | + | Asn96Asp | + | Ser97Glu |
| Gly99Ser | + | Ser104Asp | + | Ala105Glu |
| Ser97Asp | + | Ser98Glu | + | Gly101Ser |
| Asn96Asp | + | Ser98Asp | + | Gly99Glu |
| Asn96Glu | + | Ser97Glu | + | Gly99Glu |
| Leu95Asp | + | Ser100Glu | + | Ile106Leu |
| Asn96Asp | + | Ser100Glu | + | Gly101Glu |
| Ser104Asp | + | Ala105Thr | + | Ile106Glu |
| Asn96Glu | + | Ser98Asp | + | Tyr103Ala |
| Leu95Asn | + | Ser98Asp | + | Ser100Glu |
| Leu95Gly | + | Ser98Glu | + | Ser100Glu |
| Ser98Asp | + | Ser100Glu | + | Ala105Ser |
| Ser98Glu | + | Ser100Asp | + | Thr102Asn |
| Val94Asn | + | Ser97Glu | + | Gly99Glu |
| Asn96Glu | + | Ser100Glu | + | Thr102Pro |
| Val94Asp | + | Gly101Asp | + | Thr102Pro |
| Gly101Glu | + | Thr102Asp | + | Ser104Asp |
| Ser98Glu | + | Ser100Asp | + | Gly101Asp |
| Leu95Glu | + | Gly101Asp | + | Ile106Glu |

TABLE 9

Loop 2 - Quadruple Mutation Variants

| | | | | | | | |
|---|---|---|---|---|---|---|---|
| Gly99Asn | + | Gly101Gln | + | Thr102Glu | + | Tyr103Val |
| Val94Asn | + | Gly101Asp | + | Tyr103Ile | + | Ala105Thr |
| Val94Asn | + | Gly99Ser | + | Ser100Glu | + | Thr102Ser |
| Leu95Cys | + | Ser98Asp | + | Gly101Pro | + | Ile106Ala |
| Leu95His | + | Gly101Ser | + | Tyr103Ile | + | Ala105Ser |
| Val94Ser | + | Leu95Val | + | Gly99Pro | + | Ser100Glu |
| Gly99Ser | + | Ser100Glu | + | Tyr103Ile | + | Ala105Ser |
| Val94Ala | + | Ser97Glu | + | Thr102Ser | + | Ala105Pro |
| Val94Thr | + | Tyr103Gly | + | Ser104Asp | + | Ala105Gln |
| Val94Ala | + | Leu95Pro | + | Ser100Glu | + | Ile106Ser |
| Leu95Asn | + | Ser98Asp | + | Tyr103Gly | + | Ala105Pro |
| Asn96Ser | + | Gly101Glu | + | Tyr103Leu | + | Ala105Pro |
| Leu95Met | + | Ser98Glu | + | Gly99Asn | + | Tyr103Thr |
| Val94Ala | + | Leu95Ala | + | Ser97Asp | + | Thr102Asn |
| Gly99Gln | + | Ser100Glu | + | Thr102Ser | + | Ile106Leu |
| Asn96Glu | + | Gly99Gln | + | Ala105Pro | + | Ile106Thr |
| Val94Gly | + | Gly101Glu | + | Tyr103Gln | + | Ile106His |
| Val94Thr | + | Ser97Asp | + | Gly101Gln | + | Ala105Thr |
| Val94Gly | + | Leu95Val | + | Asn96Gln | + | Ser104Glu |
| Leu95Gln | + | Gly99Glu | + | Ser100Glu | + | Thr102Pro |
| Leu95Met | + | Ser100Asp | + | Gly101Asp | + | Tyr103Ser |
| Leu95Ile | + | Thr102Pro | + | Ser104Asp | + | Ala105Asp |
| Ser97Asp | + | Ser98Asp | + | Tyr103Met | + | Ala105Pro |
| Leu95Ser | + | Ser97Asp | + | Ser98Asp | + | Thr102Ser |
| Ser97Glu | + | Ser98Glu | + | Ala105Pro | + | Ile106Asn |
| Ser97Glu | + | Ser98Glu | + | Gly101Ser | + | Ile106Cys |
| Ser97Asp | + | Ser98Asp | + | Gly101Pro | + | Thr102Pro |
| Leu95Glu | + | Ser100Glu | + | Gly101Asp | + | Thr102Ser |
| Val94Met | + | Leu95Glu | + | Asn96Glu | + | Gly101Asp |
| Leu95His | + | Gly99Glu | + | Ser100Glu | + | Gly101Glu |
| Asn96Glu | + | Gly99Glu | + | Gly101Ser | + | Ile106Asn |
| Leu95Val | + | Asn96Asp | + | Ser98Glu | + | Tyr103Gln |
| Asn96Asp | + | Ser98Glu | + | Gly99Ser | + | Thr102Asn |
| Asn96Glu | + | Ser98Glu | + | Gly101Ser | + | Thr102Pro |
| Leu95Val | + | Asn96Glu | + | Ser98Asp | + | Ile106Ala |
| Val94Gly | + | Asn96Glu | + | Ser98Asp | + | Tyr103Thr |
| Ser98Glu | + | Gly99Gln | + | Ser100Asp | + | Gly101Pro |
| Ser98Glu | + | Gly99Gln | + | Ser100Asp | + | Thr102Gln |
| Asn96Glu | + | Ser100Glu | + | Tyr103Gln | + | Ile106Pro |
| Asn96Asp | + | Gly99Asn | + | Ser100Glu | + | Tyr103Ile |
| Leu95Glu | + | Asn96Gln | + | Ser98Glu | + | Gly99Glu |
| Ser97Asp | + | Ser98Glu | + | Ser100Asp | + | Ile106Val |
| Ser97Asp | + | Ser98Asp | + | Ser100Glu | + | Thr102Ser |
| Ser97Asp | + | Ser98Asp | + | Ser100Glu | + | Gly101Gln |

TABLE 9-continued

Loop 2 - Quadruple Mutation Variants

| | | | | | | | |
|---|---|---|---|---|---|---|---|
| Leu95Thr | + | Ser97Asp | + | Ser98Glu | + | Ser100Asp |
| Val94Met | + | Asn96Glu | + | Gly99Asp | + | Gly101Asp |
| Ser98Asp | + | Ser100Glu | + | Gly101Glu | + | Ala105Ser |
| Val94Cys | + | Ser98Asp | + | Ser100Asp | + | Gly101Asp |
| Val94Glu | + | Ser100Glu | + | Gly101Glu | + | Tyr103Ile |
| Leu95Glu | + | Ser97Asp | + | Ser98Asp | + | Ala105Ser |
| Leu95Ala | + | Asn96Asp | + | Gly101Asp | + | Thr102Asp |
| Val94Cys | + | Gly99Asp | + | Gly101Asp | + | Ile106Pro |
| Leu95Ser | + | Ser100Glu | + | Gly101Gln | + | Thr102Glu |
| Leu95Met | + | Ser100Asp | + | Thr102Glu | + | Ile106Gln |
| Asn96Ser | + | Gly101Asp | + | Tyr103Asn | + | Ile106Asp |
| Leu95Cys | + | Gly101Glu | + | Ala105Pro | + | Ile106Asp |
| Val94Asp | + | Gly99Glu | + | Ser100Asp | + | Ala105Ser |
| Ser97Glu | + | Ser98Glu | + | Gly101Asp | + | Tyr103Ser |
| Ser97Asp | + | Ser100Glu | + | Thr102Gln | + | Tyr103Thr |
| Ser97Glu | + | Ser100Asp | + | Tyr103Ser | + | Ala105Gly |

TABLE 10

Loop 3 - Single Mutation Variants

Leu125Ala
Leu125Asn
Leu125Asp
Leu125Cys
Leu125Gln
Leu125Glu
Leu125Gly
Leu125His
Leu125Ile
Leu125Met
Leu125Pro
Leu125Ser
Leu125Thr
Leu125Val
Gly126Asn
Gly126Asp
Gly126Gln
Gly126Glu
Gly126Pro
Gly126Ser
Gly127Asn
Gly127Asp
Gly127Gln
Gly127Glu
Gly127Pro
Gly127Ser
Pro128Asn
Pro128Asp
Pro128Gln
Pro128Glu
Pro128Gly
Pro128Ser
Ser129Asp
Ser129Glu
Gly130Asn
Gly130Asp
Gly130Gln
Gly130Glu
Gly130Pro
Gly130Ser
Ser131Asp
Ser131Glu
Thr132Asn
Thr132Asp
Thr132Gln
Thr132Glu
Thr132Gly
Thr132Pro
Thr132Ser

TABLE 11

| Loop 3 - Double Mutation Variants | | |
|---|---|---|
| Leu125Gln | + | Ser129Glu |
| Leu125Pro | + | Gly126Ser |
| Gly127Gln | + | Ser131Asp |
| Gly130Ser | + | Thr132Gly |
| Leu125Met | + | Gly130Asp |
| Leu125Pro | + | Pro128Asp |
| Ser129Asp | + | Gly130Asn |
| Leu125Asp | + | Pro128Asn |
| Gly127Ser | + | Ser131Glu |
| Leu125Ile | + | Gly130Ser |
| Leu125Thr | + | Thr132Asp |
| Leu125Thr | + | Thr132Asn |
| Leu125Pro | + | Gly127Glu |
| Leu125Glu | + | Thr132Asn |
| Pro128Asn | + | Thr132Pro |
| Leu125Thr | + | Gly130Asp |
| Gly127Pro | + | Thr132Ser |
| Gly127Asn | + | Thr132Asn |
| Gly126Gln | + | Ser131Asp |
| Leu125Val | + | Thr132Gly |
| Gly126Gln | + | Gly130Ser |
| Ser129Asp | + | Thr132Gly |
| Gly126Asp | + | Gly130Pro |
| Leu125Cys | + | Pro128Gln |
| Gly127Gln | + | Thr132Gly |
| Leu125His | + | Gly126Asp |
| Leu125Val | + | Ser129Glu |
| Gly126Ser | + | Pro128Asp |
| Leu125Val | + | Gly126Glu |
| Gly127Glu | + | Pro128Ser |
| Leu125Asn | + | Thr132Pro |
| Leu125Met | + | Gly126Asp |
| Leu125Ser | + | Ser129Glu |
| Leu1253er | + | Gly126Asn |
| Leu125Val | + | Thr132Gln |
| Leu125Val | + | Gly130Asp |
| Ser129Glu | + | Thr132Ser |
| Pro128Gly | + | Ser129Asp |
| Gly126Pro | + | Thr132Asp |
| Gly126Asp | + | Thr132Ser |
| Pro128Asp | + | Thr132Gln |
| Gly126Pro | + | Ser129Asp |
| Gly130Ser | + | Thr132Glu |
| Gly127Glu | + | Pro128Gln |
| Gly126Asn | + | Gly130Pro |
| Pro128Asn | + | Ser129Glu |
| Gly130Asp | + | Thr132Gly |
| Gly126Gln | + | Ser131Glu |
| Gly127Glu | + | Gly130Ser |
| Gly126Asn | + | Ser129Glu |
| Pro128Asp | + | Gly130Asn |
| Pro128Asp | + | Thr132Gly |
| Gly126Gln | + | Pro128Asp |
| Ser131Glu | + | Thr132Gly |
| Gly130Glu | + | Thr132Asn |
| Leu125Val | + | Pro128Gly |
| Leu125Ile | + | Gly130Pro |
| Pro128Asn | + | 3er131Asp |
| Gly130Asn | + | Thr132Asp |
| Gly127Ser | + | Pro128Glu |

TABLE 12

| Loop 3 - Triple Mutation Variants | | | | |
|---|---|---|---|---|
| Gly127Asp | + | Gly130Gln | + | Thr132Ser |
| Pro128Asp | + | Gly130Prb | + | Thr132Ser |
| Gly127Asn | + | Ser131Asp | + | Thr132Pro |
| Leu125Ser | + | Ser131Asp | + | Thr132Pro |
| Leu125Met | + | Pro128Glu | + | Thr132Pro |
| Leu125Asp | + | Gly126Ser | + | Thr132Gln |
| Gly127Asn | + | Pro128Glu | + | Gly130Asn |
| Gly127Ser | + | Pro128Gln | + | Ser129Glu |
| Gly126Pro | + | Gly127Pro | + | Ser131Glu |

TABLE 12-continued

| Loop 3 - Triple Mutation Variants | | | | |
|---|---|---|---|---|
| Leu125Ile | + | Gly127Asp | + | Thr132Gln |
| Gly126Asn | + | Gly130Ser | + | Thr132Pro |
| Gly126Pro | + | Gly127Gln | + | Thr132Asp |
| Gly126Asp | + | Gly130Asn | + | Thr132Gln |
| Leu125Ser | + | Pro128Gln | + | Thr132Asn |
| Gly126Pro | + | Gly127Pro | + | Pro128Glu |
| Leu125Met | + | Gly126Glu | + | Gly130Gln |
| Leu125Met | + | Ser129Asp | + | Thr132Gln |
| Leu125His | + | Ser129Asp | + | Gly130Ser |
| Gly127Pro | + | Ser129Glu | + | Gly130Ser |
| Pro128Gln | + | Gly130Asn | + | Thr132Gln |
| Gly126Asn | + | Gly127Pro | + | Gly130Gln |
| Leu125Pro | + | Gly126Ser | + | Gly127Gln |
| Leu125His | + | Gly127Ser | + | Ser131Glu |
| Leu125His | + | Gly127Asn | + | Thr132Glu |
| Gly126Glu | + | Gly130Pro | + | Thr132Gln |
| Leu125His | + | Gly127Gln | + | Gly130Glu |
| Gly127Pro | + | Pro128Gly | + | Thr132Asn |
| Leu125Gly | + | Pro128Gly | + | Gly130Asp |
| Gly126Asn | + | Pro128Asn | + | Ser129Glu |
| Gly126Pro | + | Gly130Ser | + | Thr132Gly |
| Leu125Ser | + | Gly126Pro | + | Ser131Glu |
| Leu125Val | + | Gly126Glu | + | Thr132Gly |
| Pro128Asn | + | Ser131Asp | + | Thr132Pro |
| Leu125Gly | + | Pro128Asn | + | Thr132Pro |
| Gly127Glu | + | Pro128Ser | + | Thr132Pro |
| Gly127Gln | + | Ser129Glu | + | Thr132Gln |
| Leu125Ile | + | Gly127Pro | + | Gly130Asp |
| Gly126Ser | + | Gly127Asp | + | Gly130Asn |
| Pro128Glu | + | Gly130Pro | + | Thr132Gln |
| Leu125Val | + | Gly126Asp | + | Gly127Asp |
| Pro128Asn | + | Gly130Asp | + | Ser131Asp |
| Gly130Glu | + | Ser131Asp | + | Thr132Gln |
| Gly126Pro | + | Gly130Glu | + | Ser131Asp |
| Gly127Glu | + | Pro128Glu | + | Thr132Ser |
| Gly130Gln | + | Ser131Glu | + | Thr132Asp |
| Leu125Gln | + | Ser131Asp | + | Thr132Asp |
| Gly130Ser | + | Ser131Glu | + | Thr132Glu |
| Gly130Pro | + | Ser131Asp | + | Thr132Asp |
| Gly127Pro | + | Ser131Glu | + | Thr132Asp |
| Leu125Asn | + | Ser131Asp | + | Thr132Asp |
| Pro128Gln | + | Ser131Asp | + | Thr132Glu |
| Pro128Gly | + | Ser131Asp | + | Thr132Asp |
| Gly126Gln | + | Ser129Asp | + | Gly130Asp |
| Leu125Ile | + | Ser129Asp | + | Gly130Glu |
| Gly127Glu | + | Pro128Asp | + | Ser129Glu |
| Ser129Asp | + | Gly130Asp | + | Ser131Asp |
| Ser129Glu | + | Gly130Asp | + | Ser131Glu |
| Ser129Glu | + | Gly130Glu | + | Ser131Asp |
| Gly126Glu | + | Gly127Glu | + | Pro128Glu |
| Gly130Glu | + | Ser131Asp | + | Thr132Asp |

TABLE 13

| Loop 3 - Quadruple Mutation Variants | | | | | | |
|---|---|---|---|---|---|---|
| Gly126Ser | + | Pro128Glu | + | Gly130Ser | + | Thr132Ser |
| Leu125Cys | + | Gly127Gln | + | Ser129Glu | + | Thr132Pro |
| Leu125Gln | + | Gly126Pro | + | Pro128Ser | + | Ser129Glu |
| Leu125Thr | + | Ser129Glu | + | Gly130Ser | + | Thr132Pro |
| Gly127Gln | + | Pro128Gln | + | Ser129Glu | + | Gly130Pro |
| Gly127Asn | + | Pro128Asn | + | Ser131Glu | + | Thr132Gly |
| Leu125Met | + | Gly127Glu | + | Gly130Asn | + | Thr132Gly |
| Leu125Met | + | Gly127Asn | + | Pro128Asn | + | Ser129Glu |
| Leu125Met | + | Gly126Ser | + | Gly127Gln | + | Ser131Asp |
| Leu125Asn | + | Gly126Asp | + | Gly127Gln | + | Thr132Ser |
| Leu125Gln | + | Gly127Gln | + | Gly130Glu | + | Thr132Pro |
| Leu125Ala | + | Gly130Asn | + | Ser131Asp | + | Thr132Pro |
| Leu125Met | + | Gly126Pro | + | Gly127Ser | + | Ser131Asp |
| Leu125Cys | + | Gly126Pro | + | Ser129Glu | + | Thr132Asn |
| Leu125Gly | + | Pro128Gly | + | Ser131Asp | + | Thr132Gln |
| Leu125Met | + | Gly130Asn | + | Ser131Asp | + | Thr132Gln |
| Leu125Val | + | Gly126Pro | + | Gly130Gln | + | Thr132Asp |
| Gly126Asn | + | Gly127Pro | + | Pro128Gln | + | Ser129Glu |

TABLE 13-continued

Loop 3 - Quadruple Mutation Variants

| | | | |
|---|---|---|---|
| Leu125Gln + | Gly126Glu + | Gly127Glu + | Gly130Asn |
| Leu125Val + | Gly126Asp + | Gly127Glu + | Gly130Pro |
| Leu125Asp + | Gly126Glu + | Gly127Pro + | Thr132Pro |
| Leu125Glu + | Gly126Glu + | Gly127Asn + | Thr132Ser |
| Leu125Glu + | Gly127Pro + | Gly130Glu + | Ser131Asp |
| Leu125Cys + | Gly130Glu + | Ser131Asp + | Thr132Gln |
| Gly126Gln + | Gly127Glu + | Pro128Glu + | Gly130Asn |
| Gly126Ser + | Gly127Asp + | Pro128Asp + | Gly130Ser |
| Leu125Thr + | Gly127Ser + | Ser131Glu + | Thr132Asp |
| Pro128Asn + | Gly130Asn + | Ser131Asp + | Thr132Glu |
| Leu125Met + | Gly126Ser + | Ser129Asp + | Gly130Asp |
| Gly126Gln + | Pro128Gln + | Ser129Glu + | Gly130Glu |
| Gly127Asn + | Pro128Asn + | Ser129Glu + | Gly130Glu |
| Gly127Ser + | Ser129Glu + | Gly130Asp + | Thr132Gln |
| Gly127Asp + | Pro128Glu + | Ser129Asp + | Gly130Asn |
| Gly127Asp + | Pro128Glu + | Ser129Asp + | Thr132Ser |
| Leu125Gln + | Ser129Glu + | Gly130Asp + | Ser131Asp |
| Leu125Cys + | Ser129Glu + | Gly130Asp + | Ser131Glu |
| Gly127Gln + | Pro128Glu + | Ser129Glu + | Gly130Asp |
| Leu125Met + | Gly126Asp + | Gly127Glu + | Pro128Glu |
| Gly127Glu + | Pro128Glu + | Ser129Glu + | Thr132Ser |
| Leu125Pro + | Gly127Asp + | Pro128Ser + | Ser129Asp |
| Gly126Pro + | Gly127Glu + | Pro128Gly + | Ser129Asp |
| Leu125Pro + | Gly127Asp + | Ser129Glu + | Gly130Glu |
| Gly127Asp + | Pro128Ser + | Ser129Glu + | Gly130Asp |
| Gly127Glu + | Ser129Glu + | Gly130Glu + | Thr132Pro |
| Leu125Ile + | Gly127Glu + | Ser129Asp + | Gly130Asp |
| Gly126Glu + | Gly127Glu + | Ser129Glu + | Gly130Pro |
| Gly126Asp + | Gly127Glu + | Ser129Asp + | Thr132Pro |
| Leu125Met + | Gly126Asp + | Gly127Asp + | Ser129Asp |
| Gly126Ser + | Ser129Asp + | Ser131Glu + | Thr132Gln |
| Gly127Gln + | Pro128Asn + | Ser129Asp + | Ser131Asp |
| Pro128Gln + | Ser129Glu + | Ser131Asp + | Thr132Ser |
| Gly126Pro + | Ser129Asp + | Ser131Glu + | Thr132Ser |
| Leu125Ala + | Ser129Glu + | Gly130Pro + | Ser131Asp |
| Gly127Gln + | Ser129Glu + | Gly130Ser + | Ser131Asp |
| Gly127Ser + | Ser129Glu + | Ser131Glu + | Thr132Gln |
| Gly127Gln + | Pro128Gln + | Ser129Glu + | Ser131Asp |
| Leu125Ala + | Gly126Ser + | Ser129Asp + | Ser131Glu |
| Gly126Pro + | Pro128Gln + | Ser129Asp + | Ser131Asp |
| Gly126Ser + | Pro128Ser + | Ser129Asp + | Ser131Glu |
| Gly126Glu + | Pro128Asp + | Ser129Asp + | Thr132Asn |

TABLE 14

Loop 4 - Single Mutation Variants

Gly153Asn
Gly153Asp
Gly153Gln
Gly153Glu
Gly153Pro
Gly153Ser
Asn154Asp
Asn154Gln
Asn154Glu
Asn154Ser
Ser155Asp
Ser155Glu
Gly156Asn
Gly156Asp
Gly156Gln
Gly156Glu
Gly156Pro
Gly156Ser
Ser157Asp
Ser157Glu
Ser158Asp
Ser158Glu
Gly159Asn
Gly159Asp
Gly159Gln
Gly159Glu
Gly159Pro

TABLE 14-continued

Loop 4 - Single Mutation Variants

Gly159Ser
Ser160Asp
Ser160Glu
Gln161Asn
Gln161Asp
Gln161Glu
Gln161Ser
Asn162Asp
Asn162Gln
Asn162Glu
Asn162Ser
Thr163Asn
Thr163Asp
Thr163Gln
Thr163Glu
Thr163Gly
Thr163Pro
Thr163Ser
Ile164Ala
Ile164Asn
Ile164Asp
Ile164Cys
Ile164Gln
Ile164Glu
Ile164Gly
Ile164His
Ile164Leu
Ile164Met
Ile164Pro
Ile164Ser
Ile164Thr
Ile164Val
Gly165Asn
Gly165Asp
Gly165Gln
Gly165Glu
Gly165Pro
Gly165Ser
Tyr166Ala
Tyr166Asn
Tyr166Asp
Tyr166Cys
Tyr166Gln
Tyr166Glu
Tyr166Gly
Tyr166His
Tyr166Ile
Tyr166Leu
Tyr166Met
Tyr166Pro
Tyr166Ser
Tyr166Thr
Tyr166Val

TABLE 15

Loop 4 - Double Mutation Variants

Asn154Ser + Ser155Glu
Gly165Glu + Tyr166Cys
Ser158Asp + Gly165Pro
Ser157Asp + Thr163Asn
Gly156Pro + Thr163Ser
Asn154Glu + Ile164Cys
Gly153Asn + Thr163Asn
Thr163Glu + Ile164Gly
Gly156Gln + Ile164Thr
Ser157Asp + Ile164His
Ser158Glu + Tyr166His
Gly153Pro + Tyr166Asp
Gly153Pro + Gly165Gln
Ser157Glu + Gly159Asn
Asn154Ser + Gly159Pro
Gly156Glu + Asn162Gln
Gln161Asp + Ile164Met
Ser157Asp + Thr163Ser

TABLE 15-continued

Loop 4 - Double Mutation Variants

Ser157Glu + Tyr166Ile
Gln161Glu + Ile164His
Ser157Glu + Asn162Gln
Gly159Pro + Tyr166Asp
Asn162Asp + Ile164Cys
Gln161Ser + Asn162Asp
Asn154Asp + Asn162Gln
Ser158Glu + Gly165Asn
Ile164Met + Tyr166Val
Gln161Asn + Gly165Pro
Ser155Asp + Gly159Pro
Ser160Asp + Asn162Ser
Gly156Glu + Ile164Cys
Thr163Asp + Gly165Pro
Gly153Asn + Ser155Glu
Ser158Asp + Thr163Gly
Ser160Asp + Ile164Met
Gly159Asp + Thr163Gln
Ser155Glu + Tyr166Cys
Gln161Ser + Tyr166Gly
Ser160Asp + Ile164Ala
Ser157Asp + Gln161Ser
Ser160Glu + Asn162Gln
Gly153Asn + Gly156Gln
Ser157Asp + Ile164Val
Asn162Gln + Thr163Glu
Ser155Asp + Gln161Ser
Gly159Glu + Gly165Gln
Ser160Glu + Ile164His
Gly153Ser + Ser160Asp
Gly159Gln + Gly165Glu
Gly153Glu + Gly159Gln
Gly156Glu + Thr163Gly
Gly156Ser + Tyr166Asn
Gly153Asp + Thr163Asn
Asn154Ser + Ser157Glu
Thr163Ser + Ile164Pro
Ser155Glu + Asn162Ser
Gly156Pro + Ile164Gly
Thr163Glu + Gly165Asn
Gly153Gln + Ser155Glu
Ile164Ser + Tyr166Cys

TABLE 16

Loop 4 - Triple Mutation Variants

Gly153Gln + Asn154Ser + Ser155Glu
Ser155Asp + Thr163Pro + Tyr166Gln
Gly156Gln + Thr163Glu + Ile164Gly
Gly159Gln + Gln161Ser + Gly165Ser
Asn154Gln + Thr163Asp + Tyr166Gln
Asn154Gln + Gly159Pro + Ile164Thr
Asn162Gln + Ile164Gln + Gly165Glu
Gly153Asp + Gln161Ser + Thr163Pro
Gly153Gln + Asn154Gln + Tyr166Ile
Asn154Gln + Gln161Asn + Tyr166Pro
Gly153Gln + Ser158Glu + Tyr166Ser
Ser157Asp + Ile164Val + Tyr166Ala
Thr163Gly + Gly165Asp + Tyr166Pro
Gln161Glu + Asn162Gln + Tyr166Thr
Gly156Pro + Gln161Glu + Thr163Ser
Ser158Glu + Gly159Pro + Gln161Asn
Ser158Glu + Gln161Asn + Asn162Ser
Asn154Glu + Gln161Ser + Gly165Asn
Gly153Asn + Asn154Gln + Ser158Asp
Ser157Glu + Ile164Val + Tyr166Val
Ser155Asp + Gln161Asn + Tyr166Ile
Gly153Glu + Gln161Asn + Gly165Ser
Gly156Pro + Asn162Asp + Gly165Pro
Gly156Asn + Asn162Asp + Ile164Leu
Asn154Gln + Thr163Asn + Gly165Ser
Ser158Asp + Gly159Asn + Gln161Asn
Ser155Glu + Gln161Asn + Tyr166Leu

TABLE 16-continued

Loop 4 - Triple Mutation Variants

Ser158Glu + Asn162Ser + Tyr166His
Asn154Asp + Thr163Gln + Ile164Met
Gly156Asp + Ser157Asp + Gly159Ser
Gly159Asp + Ser160Glu + Thr163Gln
Ser158Asp + Gly159Asp + Tyr166Cys
Asn154Glu + Ser155Glu + Gly156Ser
Ser155Asp + Gly156Asp + Asn162Ser
Ser157Asp + Ser158Glu + Gly159Pro
Ser160Asp + Gln161Asp + Ile164Ala
Gly159Gln + Ser160Asp + Gln161Asp
Gly156Asp + Ser157Asp + Ser158Asp
Gly159Asp + Gln161Glu + Gly165Gln
Gly153Pro + Gly159Glu + Gly165Glu
Ser157Glu + Ser158Asp + Gln161Glu
Ser157Glu + Gly159Glu + Gly165Ser
Ser157Glu + Gly159Glu + Ser160Glu
Ser158Asp + Ser160Asp + Ile164Thr
Ser158Asp + Ser160Glu + Tyr166Val
Asn154Gln + Ser158Asp + Ser160Asp
Ser158Glu + Ser160Asp + Tyr166His
Gly153Asp + Asn154Glu + Gly165Glu
Ser155Asp + Ser157Asp + Tyr166Ile
Ser155Glu + Ser157Asp + Gly159Pro
Gly153Asn + Ser157Glu + Thr163Glu
Ser155Asp + Ser157Asp + Ser158Glu
Ser157Asp + Gly159Asp + Gln161Glu
Ser155Asp + Gly156Glu + Ser158Asp
Asn154Gln + Ser160Glu + Asn162Asp
Ser158Glu + Ser160Glu + Asn162Glu
Ser157Glu + Gln161Asp + Thr163Asp
Asn154Glu + Ser155Glu + Ser157Glu
Ser157Asp + Ser160Glu + Tyr166Gly
Gly153Asn + Ser157Glu + Ser160Asp

TABLE 17

Loop 4 - Quadruple Mutation Variants

Asn154Ser + Gly159Asp + Ile164Met + Gly165Pro
Ser155Glu + Gly156Ser + Asn162Gln + Thr163Asn
Gly156Gln + Ser157Asp + Gly159Ser + Asn162Ser
Ser155Asp + Gly159Pro + Gln161Ser + Ile164Cys
Asn154Gln + Gly156Asp + Thr163Gly + Tyr166Met
Asn154Gln + Ser155Asp + Thr163Asn + Gly165Ser
Gln161Ser + Asn162Gln + Thr163Gly + Tyr166Gly
Ser155Asp + Gly159Pro + Gly165Pro + Tyr166Gln
Asn154Ser + Ser155Asp + Thr163Gly + Ile164Val
Gly159Asp + Gln161Ser + Thr163Gln + Ile164Thr
Gly153Pro + Ser158Asp + Asn162Gln + Ile164Cys
Gly153Pro + Gly156Asp + Ile164Ser + Tyr166Leu
Gly153Glu + Gly156Pro + Gln161Ser + Tyr166Met
Ser155Glu + Thr163Asp + Gly165Pro + Tyr166Leu
Ser157Asp + Thr163Gly + Ile164Gln + Tyr166Gly
Gly153Ser + Ser155Asp + Thr163Pro + Ile164Pro
Asn154Ser + Gly159Gln + Gln161Glu + Tyr166Met
Asn154Ser + Ser160Asp + Ile164Gln + Gly165Ser
Gly159Asn + Asn162Glu + Gly165Gln + Tyr166Cys
Gly156Pro + Gly159Pro + Ile164Gln + Gly165Gln
Gly153Ser + Gly156Asn + Asn162Gln + Gly165Asp
Ser158Asp + Gly159Glu + Gln161Ser + Ile164Thr
Gly153Gln + Asn154Glu + Ser155Glu + Tyr166Gly
Gly153Ser + Ser155Asp + Gly156Asp + Ile164Gln
Asn154Ser + Ser155Glu + Gly156Asp + Tyr166Val
Ser155Glu + Gly156Glu + Thr163Asn + Ile164Leu
Ser157Glu + Ser158Asp + Gln161Asn + Ile164Cys
Ser160Glu + Gln161Asp + Thr163Gln + Gly165Pro
Ser157Asp + Ser158Glu + Gly159Asp + Ile164Cys
Asn154Gln + Ser160Glu + Gln161Glu + Asn162Asp
Gly153Glu + Gly159Gln + Gln161Asn + Gly165Glu
Asn154Ser + Ser158Asp + Gly159Asn + Gln161Glu
Asn154Glu + Gly156Asp + Thr163Ser + Tyr166Asn
Ser158Glu + Ser160Asp + Gln161Asn + Thr163Pro
Asn154Glu + Ser155Asp + Gly156Gln + Thr163Asp
Ser158Glu + Gln161Glu + Thr163Asp + Ile164His

TABLE 17-continued

| Loop 4 - Quadruple Mutation Variants |
|---|
| Ser155Glu + Ser157Asp + Asn162Ser + Gly165Pro |
| Ser155Asp + Ser157Asp + Gly159Pro + Ile164Cys |
| Gly159Glu + Ser160Asp + Asn162Glu + Ile164Asn |
| Ser157Glu + Gln161Asp + Thr163Asp + Gly165Gln |
| Asn154Glu + Ser155Glu + Ser157Asp + Gly159Pro |
| Asn154Gln + Ser160Asp + Gln161Asp + Thr163Asp |
| Ser160Asp + Gln161Asp + Asn162Gln + Thr163Asp |
| Ser155Asp + Thr163Asp + Ile164Gly + Gly165Asp |
| Gly156Ser + Ser158Asp + Thr163Asp + Ile164Leu |
| Ser155Glu + Ser158Glu + Thr163Glu + Ile164Met |
| Gly153Glu + Gly156Pro + Thr163Asp + Tyr166His |
| Gly156Ser + Ser157Asp + Ser160Glu + Asn162Asp |
| Gly153Asn + Ser157Glu + Asn162Asp + Ile164Leu |
| Gly153Glu + Ser155Glu + Ser157Asp + Ile164Met |
| Gly156Pro + Ser157Asp + Gly159Gln + Ser160Glu |
| Gly153Pro + Ser155Glu + Gly156Glu + Gly165Asp |
| Ser155Asp + Ser158Glu + Gln161Asn + Gly165Pro |
| Ser155Asp + Ser158Glu + Gly159Gln + Ile164Gly |
| Gly153Asp + Ser157Glu + Gly159Pro + Thr163Glu |
| Ser155Asp + Gly156Pro + Gln161Ser + Gly165Asp |
| Gly156Glu + Ser157Glu + Ser160Asp + Ile164Ser |
| Asn154Ser + Gly156Asp + Ser158Asp + Ser160Asp |
| Gly153Gln + Ser155Asp + Ser158Asp + Gly159Glu |
| Asn154Asp + Gly156Glu + Ser158Glu + Ile164Ala |

TABLE 18

| Loop 5 - Single Mutation Variants |
|---|
| Ala186Asn |
| Ala186Asp |
| Ala186Gly |
| Ala186Gln |
| Ala186Pro |
| Ala186Ser |
| Ala186Thr |
| Ser187Asp |
| Ser187Glu |
| Phe188Ala |
| Phe188Asn |
| Phe188Asp |
| Phe188Cys |
| Phe188Gln |
| Phe188Glu |
| Phe188Gly |
| Phe188His |
| Phe188Ile |
| Phe188Leu |
| Phe188Met |
| Phe188Pro |
| Phe188Ser |
| Phe188Thr |
| Phe188Tyr |
| Phe188Val |
| Ser189Asp |
| Ser189Glu |
| Ser190Asp |
| Ser190Glu |

TABLE 19

| Loop 5 - Double Mutation Variants |
|---|
| Phe188Met + Ser190Glu |
| Ala186Ser + Ser187Glu |
| Phe188Ser + Ser190Asp |
| Ala186His + Ser187Glu |
| Ser187Asp + Phe188Cys |
| Ala186Ser + Ser190Glu |
| Ala186Pro + Ser190Asp |
| Phe188Ser + Ser190Glu |
| Ala186Gln + Ser187Glu |

TABLE 19-continued

| Loop 5 - Double Mutation Variants |
|---|
| Phe188Asn + Ser190Asp |
| Ala186Glu + Phe188Met |
| Ala186Ser + Phe188Ala |
| Ser187Glu + Phe188Thr |
| Ala186Thr + Phe188Asp |
| Ser187Asp + Phe188Leu |
| Ala186Gly + Phe188Cys |
| Phe188Val + Ser190Glu |
| Ala186Asp + Phe188Pro |
| Ala186Asn + Ser187Asp |
| Phe188Leu + Ser190Glu |
| Ser187Asp + Phe188Asn |
| Ala186Ser + Ser187Asp |
| Phe188Ala + Ser190Glu |
| Ala186Gly + Ser187Glu |
| Ala186Glu + Phe188His |
| Ala186Gly + Phe188Glu |
| Ser187Glu + Phe188Gly |
| Ala186Glu + Phe188Asn |
| Ser187Glu + Phe188His |
| Ala186Ser + Phe188Asp |
| Ala186Gly + Ser187Asp |
| Phe188Ile + Ser190Glu |
| Ala186Thr + Ser190Glu |
| Ala186Gly + Ser190Glu |
| Phe188His + Ser190Asp |
| Phe188Leu + Ser190Asp |
| Ala186Ser + Ser190Asp |
| Ser187Glu + Phe188Ile |
| Ala186Thr + Phe188His |
| Phe188Gln + Ser190Glu |
| Ala186His + Ser187Asp |
| Phe188Tyr + Ser190Glu |
| Ala186Pro + Phe188Thr |
| Ala186Gln + Ser187Asp |
| Ser187Glu + Phe188Ala |
| Ala186Asp + Phe188Ile |
| Ala186Ser + Phe188Pro |
| Ala186Asn + Ser187Glu |
| Phe188His + Ser190Glu |
| Ala186Glu + Phe188Ser |
| Ala186Ser + Phe188Leu |
| Phe188Pro + Ser190Glu |
| Ser187Asp + Phe188Thr |
| Ala186His + Phe188Ala |
| Ala186Asn + Phe188Asp |
| Phe188Ile + Ser190Asp |
| Ala186Thr + Phe188Met |
| Ala186Asp + Phe188His |
| Ser187Asp + Phe188Ala |
| Ala186Pro + Ser190Glu |

TABLE 20

| Loop 5 - Triple Mutation Variants |
|---|
| Ala186His + Phe188Ala + Ser190Asp |
| Ala186Asn + Ser187Asp + Phe188Ala |
| Ala186Gly + Phe188Asn + Ser190Asp |
| Ala186Pro + Phe188Met + Ser190Asp |
| Ala186Gly + Phe188Leu + Ser190Glu |
| Ala186Gln + Ser187Asp + Phe188Ile |
| Ala186Thr + Ser187Glu + Phe188Cys |
| Ala186Ser + Phe188Ala + Ser190Glu |
| Ala186Gln + Ser187Asp + Phe188Ser |
| Ala186Gln + Ser187Glu + Phe188Ile |
| Ala186Ser + Phe188Gly + Ser190Asp |
| Ala186Ser + Ser187Asp + Phe188Met |
| Ala186Gly + Ser187Glu + Phe188Gly |
| Ala186Gln + Phe188Pro + Ser190Asp |
| Ala186Asn + Phe188Ala + Ser190Glu |
| Ala186Ser + Phe188Pro + Ser190Glu |
| Ala186Asn + Ser187Glu + Phe188Pro |
| Ala186Gln + Phe188Gly + Ser190Glu |

TABLE 20-continued

Loop 5 - Triple Mutation Variants

Ala186Asn + Ser187Glu + Phe188Ile
Ala186His + Ser187Glu + Phe188Gly
Ala186His + Phe188Cys + Ser190Asp
Ala186Thr + Ser187Glu + Phe188Val
Ala186Gln + Ser187Glu + Phe188Met
Ala186His + Phe188Ala + Ser190Glu
Ala186Gly + Phe188Met + Ser190Glu
Ala186Ser + Ser187Glu + Phe188His
Ala186Asn + Phe188Gly + Ser190Glu
Ala186Asn + Phe188Pro + Ser190Asp
Ala186Asn + Phe188Tyr + Ser190Asp
Ala186Gly + Phe188Thr + Ser190Glu
Ala186His + Ser187Asp + Phe188Leu
Ala186Ser + Phe188Pro + Ser190Asp
Ala186Thr + Ser167Glu + Phe188Pro
Ala186Pro + Phe188Pro + Ser190Glu
Ala186Thr + Phe188Asn + Ser190Asp
Ala186Pro + Ser187Glu + Phe188His
Ala186Asp + Ser187Glu + Phe188Met
Ala186Asp + Ser187Glu + Phe188Gln
Ala186Asp + Ser187Glu + Phe188Cys
Ala186Glu + Ser187Asp + Phe188Pro
Ala186Asp + Ser187Glu + Phe188Tyr
Ala186Glu + Ser187Asp + Phe188Thr
Ala186Asp + Ser187Asp + Phe188Val
Ala186Glu + Ser187Glu + Phe188Asn
Ala186Asp + Ser187Asp + Phe188His
Ala186Asp + Ser187Glu + Phe188Ala
Ala186His + Ser187Asp + Phe188Asp
Ala186Gly + Ser187Asp + Phe188Asp
Ala186Gln + Ser187Glu + Phe188Glu
Ala186Asn + Ser187Asp + Phe188Glu
Ala186Pro + Ser187Glu + Phe188Asp
Ala186Asp + Ser187Glu + Phe188Asp
Ala186Glu + Ser187Glu + Phe188Glu
Ala186Asp + Ser187Asp + Phe188Glu
Ala186Thr + Phe188Asp + Ser190Glu
Ala186Ser + Phe188Glu + Ser190Glu
Ala186Thr + Phe188Glu + Ser190Asp
Ala186Pro + Phe188Glu + Ser190Glu
Ser187Glu + Phe188Glu + Ser190Glu
Ser187Asp+ Phe188Asp + Ser190Glu

TABLE 21

Loop 5 - Quadruple Mutation Variants

Ala186Gly + Ser187Glu + Phe188Asp + Ser190Glu
Ala186Gly + Ser187Asp + Phe188Asp + Ser190Asp
Ala186Gln + Ser187Asp + Phe188Asp.+ Ser190Asp
Ala186Gln + Ser187Glu + Phe188Asp + Ser190Glu
Ala186Ser + Ser187Asp + Phe188Glu + Ser190Glu
Ala186Pro + Ser187Glu + Phe188Asp + Ser190Asp
Ala186Thr + Ser187Glu + Phe188Asp + Ser190Asp
Ala186Thr + Ser187Glu + Phe188Asp + Ser190Glu
Ala186His + Ser187Asp + Phe188Glu + Ser190Asp
Ala186Asn + Ser187Glu + Phe188Asp + Ser190Asp
Ala186Gly + Ser187Glu + Phe188Glu + Ser190Asp
Ala186Gln + Ser187Asp + Phe188Glu + Ser190Glu
Ala186Gln + Ser187Asp + Phe188Glu + Ser190Asp
Ala186Gly + Ser187Glu + Phe188Asp + Ser190Asp
Ala186Gln + Ser187Glu + Phe188Gly + Ser190Asp
Ala186Asp + Ser187Asp + Phe188Gln + Ser190Asp
Ala186Glu + Ser187Glu + Phe188Val + Ser190Asp
Ala186Asp + Ser187Glu + Phe188Pro + Ser190Glu
Ala186Glu + Ser187Asp + Phe188Met + Ser190Glu
Ala186Glu + Ser187Asp + Phe188Ala + Ser190Glu
Ala186Asp + Ser187Asp + Phe188His + Ser190Asp
Ala186Glu + Ser187Glu + Phe188Met + Ser190Glu
Ala186Asp + Ser187Asp + Phe188Ala + Ser190Glu
Ala186Glu + Ser187Glu + Phe188Cys + Ser190Asp
Ala186Glu + Ser187Glu + Phe188Thr + Ser190Glu
Ala186Asp + Ser187Asp + Phe188His + Ser190Asp
Ala186Asp + Ser187Asp + Phe188Gln + Ser190Glu

TABLE 21-continued

Loop 5 - Quadruple Mutation Variants

Ala186Asp + Ser187Asp + Phe188Tyr + Ser190Asp
Ala186Glu + Ser187Asp + Phe188Ser + Ser190Asp
Ala186Glu + Ser187Asp + Phe188Gly + Ser190Asp
Ala186Asp + Ser187Asp + Phe188Asn + Ser190Asp
Ala186Glu + Ser187Glu + Phe188Cys + Ser190Glu
Ala186Glu + Ser187Asp + Phe188Ile + Ser190Glu
Ala186Glu + Ser187Glu + Phe188Val + Ser190Glu
Ala186Asp + Ser187Asp + Phe188Cys + Ser190Asp
Ala186Asp + Ser187Glu + Phe188Val + Ser190Glu
Ala186Asp + Ser187Glu + Phe188Ser + Ser190Asp
Ala186Asp + Ser187Asp + Phe188Ala + Ser190Asp
Ala186Asp + Ser187Asp + Phe188Gly + Ser190Glu
Ala186Asp + Ser187Asp + Phe188Thr + Ser190Glu
Ala186Glu + Ser187Glu + Phe188His + Ser190Glu
Ala186Glu + Ser187Asp + Phe188Pro + Ser190Glu
Ala186Glu + Ser187Glu + Phe188Ile + Ser190Glu
Ala186Glu + Ser187Glu + Phe188Pro + Ser190Glu
Ala186Glu + Ser187Glu + Phe188Gly + Ser190Asp
Ala186Glu + Ser187Glu + Phe188Pro + Ser190Asp
Ala186Glu + Ser187Asp + Phe188Ser + Ser190Glu
Ala186Asp + Ser187Asp + Phe188Tyr + Ser190Glu
Ala186Asp + Ser187Glu + Phe188His + Ser190Glu
Ala186Ser + Ser187Glu + Phe188Ser + Ser190Glu
Ala186His + Ser187Glu + Phe188Ser + Ser190Glu
Ala186Ser + Ser187Asp + Phe188Cys + Ser190Glu
Ala186Ser + Ser187Glu + Phe188Asn + Ser190Glu
Ala186Gln + Ser187Glu + Phe188Ala + Ser190Asp
Ala186Gln + Ser187Asp + Phe188Met + Ser190Glu
Ala186Asn + Ser187Glu + Phe188His + Ser199Asp
Ala186Thr + Ser187Glu + Phe188Ala + Ser190Glu
Ala186Pro + Ser187Asp + Phe188Cys + Ser190Glu
Ala186Pro + Ser187Asp + Phe188Leu + Ser190Asp
Ala186Asn + Ser187Asp + Phe188Gln + Ser190Glu

TABLE 22

Loop 6 - Single Mutation Variants

Ala199Asn
Ala199Asp
Ala199Gln
Ala199Glu
Ala199Gly
Ala199His
Ala199Pro
Ala199Ser
Ala199Thr
Pro200Asn
Pro200Asp
Pro200Gln
Pro200Glu
Pro200Gly
Pro200Ser
Gly201Asn
Gly201Asp
Gly201Gln
Gly201Glu
Gly201Pro
Gly201Ser
Val202Ala
Val202Asn
Val202Asp
Val202Cys
Val202Gln
Val202Glu
Val202Gly
Val202His
Val202Met
Val202Pro
Val202Ser
Val202Thr
Ser203Asp
Ser203Glu
Val204Ala

TABLE 22-continued

Loop 6 - Single Mutation Variants

Val204Asn
Val204Asp
Val204Cys
Val204Gln
Val204Glu
Val204Gly
Val204His
Val204Met
Val204Pro
Val204Ser
Val204Thr
Tyr205Ala
Tyr205Asn
Tyr205Asp
Tyr205Cys
Tyr205Gln
Tyr205Glu
Tyr205Gly
Tyr205His
Tyr205Ile
Tyr205Leu
Tyr205Met
Tyr205Pro
Tyr205Ser
Tyr205Thr
Tyr205Val
Ser206Asp
Ser206Glu
Thr207Asn
Thr207Asp
Thr207Gln
Thr207Glu
Thr207Gly
Thr207Pro
Thr207Ser
Tyr208Ala
Tyr208Asn
Tyr208Asp
Tyr208Cys
Tyr208Gln
Tyr208Glu
Tyr208Gly
Tyr208His
Tyr208Ile
Tyr208Leu
Tyr208Met
Tyr208Pro
Tyr208Ser
Tyr208Thr
Tyr208Val
Pro209Asn
Pro209Asp
Pro209Gln
Pro209Glu
Pro209Gly
Pro209Ser
Ser210Asp
Ser210Glu
Asn211Asp
Asn211Gln
Asn211Glu
Asn211Ser
Thr212Asn
Thr212Asp
Thr212Gln
Thr212Glu
Thr212Gly
Thr212Pro
Thr212Ser
Tyr213Ala
Tyr213Asn
Tyr213Asp
Tyr213Cys
Tyr213Gln
Tyr213Glu
Tyr213Gly
Tyr213His

TABLE 22-continued

Loop 6 - Single Mutation Variants

Tyr213Ile
Tyr213Leu
Tyr213Met
Tyr213Pro
Tyr213Ser
Tyr213Thr
Tyr213Val
Thr214Asn
Thr214Asp
Thr214Gln
Thr214Glu
Thr214Gly
Thr214Pro
Thr214Ser
Ser215Asp
Ser215Glu
Leu216Ala
Leu216Asn
Leu216Asp
Leu216Cys
Leu216Gln
Leu216Glu
Leu216Gly
Leu216His
Leu216Ile
Leu216Met
Leu216Pro
Leu216Ser
Leu216Thr
Leu216Val
Asn217Asp
Asn217Gln
Asn217Glu
Asn217Ser
Gly218Asn
Gly218Asp
Gly218Gln
Gly218Glu
Gly218Pro
Gly218Ser
Thr219Asn
Thr219Asp
Thr219Gln
Thr219Glu
Thr219Gly
Thr219Pro
Thr219Ser

TABLE 23

Loop 6 - Double Mutation Variants

Val204Ser + Ser210Glu
Pro200Gly + Thr214Gly
Thr212Asn + Thr219Gly
Thr207Ser + Asn211Glu
Val204Asn + Tyr208Thr
Ser215Asp + Asn217Gln
Pro200Gly + Ser215Glu
Tyr208Gln + Tyr213Glu
Pro200Gln + Leu216Glu
Thr207Gln + Ser215Asp
Tyr205Gly + Thr219Gly
Tyr208Gly + Asn211Glu
Val202Cys + Gly218Asn
Tyr205Ser + Tyr213Leu
Ala199Asn + Gly218Pro
Thr207Gln + Thr214Glu
Asn211Gln + Ser215Asp
Ala199Gly + Gly218Glu
Pro200Asn + Thr214Glu
Val204Thr + Pro209Asp
Pro209Gly + Tyr213Cys
Thr214Gln + Asn217Glu

TABLE 23-continued

Loop 6 - Double Mutation Variants

Pro200Gln + Pro209Glu
Asn211Asp + Thr219Gly
Ser203Asp + Val204Gln
Tyr205Val + Gly218Glu
Tyr205Gln + Thr219Glu
Ser203Asp + Leu216Ala
Ser210Asp + Gly218Pro
Val202Ala + Val204Ser
Ala199Pro + Val204Ala
Tyr205Gln + Tyr213Gln
Tyr205Leu + Pro209Asp
Val204Ser + Tyr208Met
Thr212Asp + Tyr213Met
Val202Ser + Asn211Asp
Val202Asp + Tyr213Ser
Ser203Asp + Tyr205Ser
Tyr213His + Thr219Glu
Val202Pro + Asn217Glu
Val202Ser + Ser210Asp
Val202Thr + Ser215Asp
Tyr205Ser + Tyr208Pro
Val204Gly + Ser210Glu
Thr212Glu + Thr219Gln
Tyr208Ala + Gly218Glu
Pro200Gly + Tyr213Asp
Thr207Pro + Asn211Asp
Pro209Gly + Tyr213Ala
Val204Met + Ser210Asp
Thr214Pro + Asn217Ser
Val204Gln + Gly218Pro
Tyr205Pro + Thr214Glu
Ala199Gln + Ser215Asp
Ala199Pro + Ser203Asp
Gly201Pro + Thr212Ser
Tyr205Pro + Tyr213His
Val204Gln + Thr207Ser
Thr207Gly + Thr219Asn
Pro200Gln + Thr214Pro
Val202Cys + Ser215Asp
Gly201Pro + Thr214Ser
Val204Ser + Pro209Glu
Ser203Asp + Asn211Gln
Val202Met + Thr212Pro
Tyr205Gln + Thr207Asn
Ala199Gln + Tyr213Met
Gly201Ser + Ser210Asp
Gly201Ser + Thr212Asn
Tyr208His + Pro209Gly
Pro209Gln + Ser215Glu
Tyr208Pro + Leu216Thr
Tyr213Asp + Thr219Gln
Pro209Gln + Thr212Gly
Tyr208Met + Pro209Gly
Pro209Gly + Asn211Asp
Asn211Asp + Tyr213Ser
Val202Gln + Ser210Glu
Ser203Glu + Thr207Gln
Pro200Gln + Val204Thr
Asn211Asp + Thr214Ser
Ser210Asp + Thr212Gln
Val204Gln + Thr219Glu
Val202Gln + Tyr205His
Thr214Glu + Gly218Pro
Pro209Asn + Asn211Ser
Ala199Gln + Asn217Glu
Pro200Gly + Asn211Ser
Gly201Pro + Tyr208Val
Val202Asn + Tyr208Cys
Val202Gln + Ser215Asp
Ala199Pro + Thr219Ser
Gly218Pro + Thr219Glu
Ala199Gln + Pro200Ser
Thr207Pro + Asn217Asp
Val204Ser + Asn217Gln
Ser203Asp + Val204Met
Ser203Asp + Thr219Pro
Thr212Pro + Thr219Pro

TABLE 23-continued

Loop 6 - Double Mutation Variants

Tyr205Ser + Ser210Glu
Ala199His + Gly201Gln
Pro209Gly + Ser210Glu
Tyr208Gln + Leu216Asn
Gly201Ser + Tyr205Leu
Val202Met + Thr214Glu
Tyr205Ser + Pro209Asp
Pro209Ser + Thr212Glu
Tyr205Gly + Asn217Asp
Pro200Ser + Leu216Ser
Ala199His + Tyr208His
Asn211Glu + Thr219Asn
Ala199Asn + Ser210Glu
Tyr205Val + Tyr208His
Thr207Ser + Asn211Asp
Gly201Ser + Thr207Ser
Thr207Asn + Tyr208Val
Tyr205Glu + Asn217Gln
Tyr208Pro + Thr212Glu
Val204Thr + Asn211Glu
Tyr205Cys + Asn217Asp
Leu216Glu + Thr219Ser
Tyr208Ala + Thr212Pro
Ala199Ser + Ser203Glu
Val204His + Thr212Ser
Val204Gln + Gly218Ser
Ala199Asn + Ser203Glu
Pro200Gln + Val202Met
Ala199Asn + Ser203Asp
Tyr205Pro + Leu216Asp
Tyr205Gln + Ser210Asp
Ser210Asp + Asn211Gln
Ala199Pro + Asn217Asp
Ala199Gly + Asn211Asp
Tyr205Ile + Leu216Met
Tyr205Gly + Thr214Asn
Pro209Glu + Thr219Ser
Pro200Gln + Ser210Glu
Ala199Gly + Pro200Asn
Tyr205Asp + Tyr213Val
Ser203Asp + Asn217Gln
Val204Met + Thr219Ser
Val202Thr + Gly218Ser
Pro200Gly + Tyr205Cys
Thr207Gly + Thr219Asp
Ser215Glu + Gly218Pro
Gly201Pro + Tyr205Met
Tyr205Ser + Asn217Asp
Val202Ser + Pro209Gln
Pro200Gly + Gly218Asn
Tyr208Ser + Pro209Asp
Pro209Gln + Ser215Asp
Ala199Thr + Asn217Glu
Thr214Asn + Leu216Asp
Ser210Asp + Tyr213Val
Thr207Asn + Gly218Asp
Thr212Pro + Thr219Glu
Tyr213Asn + Leu216Glu
Gly201Pro + Thr212Asp
Gly201Gln + Asn211Ser
Val202Met + Leu216Ala
Ser215Asp + Leu216Gly
Gly201Gln + Leu216Cys
Leu216Gly + Thr219Ser
Val204Gln + Thr214Gln
Thr207Ser + Ser215Glu
Thr207Gly + Asn217Glu
Pro200Asn + Tyr213Ala
Thr212Asp + Thr219Pro
Tyr205Glu + Leu216Ile
Val202Asp + Tyr208Gly
Tyr208Cys + Pro209Asp
Thr207Asn + Tyr208Ile
Pro200Gly + Ser210Asp
Asn211Glu + Thr212Pro
Ala199His + Leu216Ser
Val204Thr + Asn211Asp

TABLE 23-continued

Loop 6 - Double Mutation Variants

Gly218Ser + Thr219Gly
Ser203Glu + Val204Ala
Val202Thr + Thr219Gly
Thr212Asp + Asn217Gln

TABLE 24

Loop 6 - Triple Mutation Variants

Thr207Ser + Thr212Asn + Thr219Gly
Ala199Asn + Thr207Ser + Asn211Glu
Pro200Gln + Leu216Glu + Gly218Asn
Tyr205Gly + Thr207Gln + Ser215Asp
Tyr208Gly + Asn211Glu + Thr219Gly
Val204Thr + Pro209Asp + Tyr213Cys
Val204Asn + Thr212Gly + Asn217Glu
Pro200Ser + Tyr208Ser + Thr214Gly
Ala199Ser + Gly201Ser + Thr214Ser
Ala199Gly + Val202Met + Ser210Glu
Gly201Asn + Tyr205His + Thr214Gln
Ala199Thr + Asn211Asp + Gly218Ser
Thr207Gln + Tyr213Gln + Leu216Met
Ala199Gly + Val202Cys + Ser210Asp
Val204Gln + Tyr213Ala + Thr214Pro
Tyr213Leu + Asn217Ser + Thr219Glu
Pro200Gly + Thr214Pro + Asn217Asp
Pro200Gly + Leu216Val + Thr219Gln
Pro200Gly + Gly201Ser + Ser210Asp
Gly201Gln + Val202His + Thr212Glu
Tyr208His + Asn211Ser + Asn217Asp
Thr207Ser + Ser210Asp + Gly218Ser
Thr212Asn + Leu216Asn + Thr219Glu
Val202Pro + Val204Met + Pro209Asp
Val202Asn + Thr212Pro + Thr214Glu
Tyr208Ile + Thr212Asp + Tyr213His
Ser210Asp + Thr212Ser + Leu216Ala
Pro200Gln + Thr214Pro + Leu216His
Tyr208Met + Pro209Asp + Leu216Ile
Val202Met + Leu216Gly + Thr219Gly
Pro200Ser + Tyr205Val + Leu216Cys
Val204Thr + Tyr205Glu + Asn217Gln
Thr212Glu + Leu216Ile + Asn217Ser
Val204Thr + Tyr208Pro + Asn211Glu
Thr207Gly + Leu216Glu + Thr219Ser
Ser203Glu + Tyr208Ala + Thr212Pro
Ala199Ser + Val204His + Thr212Ser
Ala199Asn + Val204Gln + Gly218Ser
Pro200Gln + Thr214Pro + Gly218Asp
Ala199Asn + Val202Met + Ser203Asp
Pro200Gln + Ser210Asp + Asn211Gln
Tyr205Ile + Thr214Asn + Leu216Met
Pro200Gln + Pro209Glu + Thr219Ser
Ala199Gly + Pro200Asn + Ser210Glu
Val204Met + Asn217Gln + Thr219Ser
Val202Thr + Thr214Asp + Gly218Ser
Gly201Pro + Tyr205Met + Gly218Pro
Val202Ser + Tyr205Ser + Asn217Asp
Pro200Gly + Pro209Gln + Gly218Asn
Ala199Thr + Thr214Asn + Asn217Glu
Thr207Asn + Thr212Pro + Gly218Asp
Gly201Pro + Asn211Ser + Thr212Asp
Gly201Gln + Ser215Asp + Leu216Gly
Val204Gln + Leu216Cys + Thr219Ser
Thr207Ser + Thr214Gln + Ser215Glu
Pro200Asn + Thr207Gly + Asn217Glu
Thr212Asp + Tyr213Ala + Thr219Pro
Thr207Asn + Tyr208Ile + Pro209Glu
Ala199His + Asn211Glu + Thr212Pro
Val204Thr + Asn211Asp + Leu216Ser
Ser203Glu + Val204Ala + Thr219Gly
Thr207Gly + Thr212Gly + Leu216His
Gly201Asn + Thr207Gly + Tyr208Gly
Gly201Asn + Val202Glu + Thr207Ser
Thr207Gln + Leu216Glu + Gly218Ser

TABLE 24-continued

Loop 6 - Triple Mutation Variants

Tyr205His + Ser210Asp + Thr219Pro
Pro200Gly + Tyr208Val + Ser210Asp
Ala199Ser + Ser203Asp + Tyr208Gln
Gly201Ser + Asn211Glu + Tyr213Pro
Ala199Gln + Tyr205His + Thr219Glu
Pro200Ser + Thr207Pro + Thr214Ser
Pro200Gln + Tyr205Met + Thr212Pro
Ala199Gly + Va 204His + Asn211Glu
Thr207Asn + Thr212Ser + Thr219Asn
Tyr205Pro + Thr207Gln + Ser215Glu
Val204His + Gly218Glu + Thr219Gly
Tyr205Pro + Tyr208Ile + Ser215Glu
Ala199Asn + Pro200Ser + Ser203Glu
Tyr208Gln + Tyr213Met + Thr219Glu
Val202Glu + Val204Thr + Asn217Ser
Val204Gln + Pro209Gln + Thr214Gly
Thr214Gln + Ser215Asp + Leu216Gly
Val204Thr + Tyr213Ile + Ser215Glu
Val204Gly + Asn211Gln + Ser215Glu
Pro200Ser + Val204Gly + Tyr213Ile
Pro200Gly + Thr212Asp + Leu216His
Asn211Glu + Tyr213Thr + Leu216Pro
Leu216Asn + Asn217Asp + Gly218Ser
Gly201Gln + Pro209Asn + Ser215Glu
Gly201Asn + Ser203Glu + Pro209Asn
Gly201Asn + Val202Ser + Leu216Gly
Asn211Asp + Tyr213His + Thr219Gln
Thr207Gln + Asn217Asp + Gly218Ser
Tyr208Gly + Ser210Glu + Thr214Gly
Thr207Gln + Tyr208Gln + Tyr213Asp
Ala199Asn + Tyr205Ile + Gly218Pro
Pro200Asn + Val202Gln + Val204Ser
Val204Asn + Ser215Glu + Leu216Pro
Pro200Ser + Gly201Ser + Tyr208Ala
Tyr208Thr + Tyr213Val + Leu216Asp
Thr207Gly + Thr212Ser + Tyr213Ala
Gly201Asn + Gly218Asp + Thr219Asn
Ala199Gly + Tyr205Cys + Tyr208Thr
Gly201Gln + Tyr213Cys + Thr214Gly
Ala199Gln + Pro200Ser + Thr214Asp
Ala199Ser + Gly201Asn + Thr219Pro
Val204Gly + Leu216Val + Thr219Gln
Gly201Asn + Ser203Glu + Thr212Gly
Gly201Ser + Ser203Glu + Asn217Gln
Pro200Gly + Thr207Gln + Asn217Asp
Ala199Thr + Tyr208Gln + Thr219Pro
Thr207Ser + Thr212Ser + Gly218Asp
Pro200Ser + Tyr208Ile + Asn217Ser
Val204Pro + Tyr205Asp + Thr214Pro
Gly201Ser + Tyr205Glu + Thr207Asn
Pro200Ser + Thr207Gln + Asn217Gln
Gly201Asn + Val202Glu + Leu216Cys
Ala199Ser + Pro209Ser + Gly218Asp
Gly201Pro + Tyr205Met + Asn211Asp
Gly201Ser + Thr214Pro + Ser215Asp
Val204Pro + Thr212Gly + Tyr213Val
Gly201Pro + Tyr208Ser + Thr212Glu
Ala199Gln + Ser203Asp + Leu216Ser
Val202Gly + Asn211Glu + Tyr213Leu
Ser203Asp + Thr212Gly + Thr214Gln
Gly201Pro + Tyr205Gln + Thr207Gly
Gly201Asn + Tyr208Asn + Tyr213Pro
Pro200Ser + Tyr213Asp + Gly218Pro
Ala199Asn + Pro200Gly + Thr214Ser
Ser210Glu + Tyr213Gln + Gly218Asn
Ala199Pro + Tyr213Thr + Ser215Asp
Val202Pro + Tyr208Cys + Asn211Gln
Ala199Gln + Ser203Glu + Asn211Ser
Thr207Gln + Pro209Ser + Ser210Glu
Pro200Ser + Val202Asn + Gly218Ser
Tyr205Val + Tyr213Asn + Gly218Glu
Val202Glu + Val204His + Tyr205Gln
Ala199Gly + Thr207Pro + Asn211Glu
Val202Glu + Tyr208Met + Pro209Gly
Val204Ser + Tyr208Ile + Leu216Met
Tyr205Thr + Tyr208Ser + Asn217Ser
Thr207Ser + Pro209Ser + Leu216Asn

TABLE 24-continued

Loop 6 - Triple Mutation Variants

Gly201Asn + Pro209Asp + Tyr213Met
Gly201Asn + Pro209Gln + Thr214Asn
Pro200Asn + Val202Gln + Thr207Gln
Ala199Asn + Ser203Glu + Val204Gln
Ser203Asp + Pro209Gly + Leu216Ala
Ala199Thr + Pro200Asn + Ser210Glu
Ala199Thr + Tyr205Leu + Asn217Glu
Gly201Asn + Val202Met + Thr214Asp
Thr212Gln + Thr214Glu + Thr219Ser
Tyr205Glu + Tyr208Gly + Tyr213Leu
Pro200Ser + Asn217Glu + Gly218Gln
Ser210Glu + Thr214Pro + Leu216Asn
Tyr208Asn + Pro209Asn + Tyr213Ser
Ala199Pro + Gly201Pro + Ser210Asp
Gly201Gln + Thr207Gly + Gly218Glu
Pro200Gln + Tyr208Gly + Ser215Asp
Pro200Ser + Thr214Pro + Leu216Gly
Ala199Gln + Asn217Asp + Gly218Pro
Pro200Asn + Val202Asp + Pro209Ser
Thr212Gly + Tyr213Asn + Ser215Asp
Gly201Gln + Tyr205Met + Thr219Glu
Pro200Gly + Tyr213Gly + Thr219Glu
Pro200Gly + Ser203Glu + Thr214Gln
Tyr208Thr + Ser215Glu + Gly218Ser
Ser210Asp + Asn211Ser + Leu216Asn
Asn211Gln + Thr214Glu + Ser215Asp
Pro209Glu + Ser210Asp + Leu216Cys
Tyr208Pro + Asn217Asp + Gly218Asp
Tyr213Cys + Ser215Asp + Leu216Asp
Thr212Asp + Tyr213Asp + Gly218Ser
Ser210Asp + Asn211Glu + Tyr213Gln
Val204Cys + Ser210Glu + Asn211Glu
Tyr205Glu + Tyr208Ala + Ser215Glu
Val202Glu + Ser203Glu + Asn217Asp
Pro200Gln + Ser203Glu + Ser215Asp
Ala199Asn + Ser203Glu + Asn217Glu
Ser203Asp + Tyr208Cys + Asn217Glu
Tyr205Asp + Asn211Gln + Thr214Glu

TABLE 25

Loop 6 - Quadruple Mutation Variants

| | | | | | | | |
|---|---|---|---|---|---|---|---|
| Gly201Asn | + | Tyr205Gly | + | Thr207Gln | + | Tyr213Ile |
| Val202Cys | + | Tyr205Ser | + | Thr212Pro | + | Gly218Asn |
| Ala199Ser | + | Tyr213His | + | Thr214Gln | + | Leu216Asn |
| Ala199Ser | + | Pro200Ser | + | Tyr208Ser | + | Thr214Ser |
| Ala199Gly | + | Gly201Ser | + | Val202Met | + | Ser210Glu |
| Gly201Asn | + | Tyr205His | + | Thr207Gln | + | Thr214Gln |
| Val202Cys | + | Thr207Gln | + | Tyr213Gln | + | Leu216Met |
| Val204Gln | + | Tyr205Asp | + | Tyr213Ala | + | Thr214Pro |
| Pro200Gly | + | Tyr213Leu | + | Thr214Pro | + | Asn217Ser |
| Pro200Gly | + | Leu216Val | + | Asn217Asp | + | Thr219Gln |
| Ala199Thr | + | Val204Ala | + | Asn217Gln | + | Gly218Gln |
| Gly201Gln | + | Val204Gln | + | Thr207Gln | + | Leu216His |
| Pro200Asn | + | Val202Pro | + | Thr207Gly | + | Ser215Asp |
| Ala199Ser | + | Gly201Pro | + | Ser215Asp | + | Leu216Ser |
| Ala199Thr | + | Tyr205Gly | + | Ser215Gln | + | Asn217Ser |
| Ala199Gly | + | Thr207Gln | + | Tyr208Thr | + | Pro209Gln |
| Ala199His | + | Pro200Gly | + | Gly218Gln | + | Thr219Gln |
| Ala199Gly | + | Thr207Asn | + | Asn211Ser | + | Thr212Ser |
| Pro200Ser | + | Val202Gln | + | Tyr208Ile | + | Thr219Pro |
| Pro200Gln | + | Tyr208Met | + | Pro209Asp | + | Leu216His |
| Ser203Asp | + | Asn211Gln | + | Leu216Thr | + | Gly218Gln |
| Ala199Gly | + | Gly201Ser | + | Tyr205Asp | + | Leu216Gly |
| Ala199Gln | + | Gly201Asn | + | Tyr205Gln | + | Thr214Asp |
| Pro200Ser | + | Gly201Pro | + | Val204Asn | + | Tyr208Pro |
| Gly201Pro | + | Val202Gly | + | Ser210Asp | + | Leu216Met |
| Pro200Gly | + | Val202Cys | + | Ser203Asp | + | Leu216Pro |
| Tyr205Gly | + | Thr207Pro | + | Asn211Gln | + | Asn217Ser |
| Gly201Pro | + | Thr207Gln | + | Thr212Ser | + | Asn217Asp |
| Pro200Gln | + | Tyr208Leu | + | Tyr213Met | + | Leu216Gln |
| Tyr205Met | + | Asn211Gln | + | Tyr213Met | + | Thr219Asp |
| Val202Met | + | Tyr205Leu | + | Tyr208Thr | + | Tyr213Gly |
| Ser203Asp | + | Val204Ser | + | Tyr213Gly | + | Gly218Pro |
| Gly201Gln | + | Val202Met | + | Ser215Asp | + | Leu216Ala |
| Val204Gln | + | Thr214Gln | + | Leu216Cys | + | Thr219Ser |
| Pro200Asn | + | Thr212Asp | + | Tyr213Ala | + | Thr219Pro |
| Ala199His | + | Val204Thr | + | Asn211Asp | + | Leu216Ser |
| Val202Thr | + | Ser203Glu | + | Val204Ala | + | Thr219Asn |
| Thr207Gly | + | Tyr208Gly | + | Thr212Gly | + | Leu216His |
| Gly201Asn | + | Ser203Glu | + | Thr207Gly | + | Asn211Gln |
| Tyr205His | + | Thr207Gln | + | Leu216Gly | + | Gly218Ser |
| Ala199Gln | + | Tyr205His | + | Tyr213Pro | + | Thr219Glu |
| Ala199Gly | + | Tyr205Met | + | Asn211Glu | + | Thr212Pro |
| Gly201Pro | + | Thr207Asn | + | Thr212Gln | + | Thr219Asn |
| Pro200Gln | + | Leu216Thr | + | Asn217Glu | + | Thr219Pro |
| Gly201Ser | + | Tyr205Cys | + | Thr214Asn | + | Leu216Thr |
| Gly201Gln | + | Val204Pro | + | Asn211Asp | + | Gly218Pro |
| Ser203Asp | + | Tyr205Val | + | Thr207Ser | + | Leu216Cys |
| Val202His | + | Pro209Gln | + | Ser215Asp | + | Leu216Gly |
| Pro200Asn | + | Gly201Gln | + | Val202Pro | + | Ser203Glu |
| Pro200Ser | + | Gly201Gln | + | Val202His | + | Leu216Thr |
| Pro200Asn | + | Gly201Asn | + | Leu216Ala | + | Gly218Pro |
| Ala199Pro | + | Val202Ser | + | Val204His | + | Thr214Glu |
| Gly201Gln | + | Ser203Glu | + | Tyr213Ile | + | Gly218Asn |
| Ala199His | + | Ser203Asp | + | Val204Gly | + | Asn211Gln |
| Pro200Gln | + | Val202Ala | + | Val204Pro | + | Thr207Pro |
| Gly201Asn | + | Thr212Ser | + | Tyr213Ala | + | Gly218Asp |
| Gly201Gln | + | Tyr213Cys | + | Thr214Gly | + | Gly218Glu |
| Ala199Gln | + | Pro200Ser | + | Gly201Asn | + | Thr214Asp |
| Ala199Ser | + | Val204Gly | + | Leu216Val | + | Thr219Pro |
| Pro200Gly | + | Val202His | + | Thr207Gln | + | Asn217Asp |
| Ala199Thr | + | Tyr208Gln | + | Thr212Ser | + | Thr219Pro |
| Pro200Ser | + | Thr207Ser | + | Tyr208Ile | + | Gly218Asp |
| Val204Pro | + | Tyr205Asp | + | Thr214Pro | + | Asn217Ser |
| Gly201Pro | + | Tyr205Met | + | Asn211Asp | + | Thr214Pro |
| Gly201Ser | + | Tyr213Val | + | Thr214Pro | + | Ser215Asp |
| Gly201Pro | + | Tyr208Ser | + | Thr212Gly | + | Tyr213Ala |
| Val202Asn | + | Asn211Glu | + | Tyr213Leu | + | Thr219Pro |
| Gly201Pro | + | Tyr205Gln | + | Thr207Gly | + | Thr212Gly |
| Pro200Gln | + | Tyr208Cys | + | Ser215Glu | + | Thr219Gly |
| Gly201Asn | + | Tyr208Asn | + | Tyr213Pro | + | Ser215Glu |
| Pro200Ser | + | Gly201Pro | + | Tyr213Asp | + | Gly218Pro |
| Ala199Pro | + | Pro200Ser | + | Thr212Asp | + | Thr219Ser |
| Pro200Asn | + | Ser203Asp | + | Thr207Gln | + | Thr212Gly |
| Val204Cys | + | Pro209Ser | + | Ser215Asp | + | Gly218Gln |
| Val202Gln | + | Val204Ser | + | Thr212Asp | + | Asn217Gln |
| Ala199Asn | + | Pro209Gly | + | Asn211Glu | + | Thr214Pro |
| Ala199Asn | + | Val204Thr | + | Ser210Asp | + | Tyr213Leu |
| Pro200Asn | + | Val204Met | + | Thr207Gln | + | Tyr213Asp |
| Val204Gln | + | Pro209Gly | + | Thr212Gly | + | Tyr213Cys |
| Pro209Asn | + | Tyr213Ile | + | Thr214Gly | + | Leu216Met |
| Pro200Gly | + | Ser203Asp | + | Leu216Cys | + | Asn217Ser |
| Val204Ser | + | Tyr208Ile | + | Asn211Asp | + | Leu216Met |
| Gly201Asn | + | Tyr205Ile | + | Pro209Gln | + | Leu216Val |
| Ser203Glu | + | Val204Gln | + | Tyr213Leu | + | Gly218Asn |
| Pro200Gln | + | Ser210Asp | + | Thr214Ser | + | Leu216Cys |
| Ala199Thr | + | Pro200Asn | + | Ser210Glu | + | Leu216Cys |
| Ala199Thr | + | Val202Met | + | Tyr205Leu | + | Thr214Asp |
| Gly201Asn | + | Thr212Gln | + | Thr214Glu | + | Thr219Ser |
| Gly201Pro | + | Tyr208Asn | + | Pro209Asn | + | Tyr213Ser |
| Ala199Pro | + | Gly201Gln | + | Thr207Gly | + | Ser210Asp |
| Ala199Gly | + | Pro200Gln | + | Tyr208Asn | + | Leu216Thr |
| Pro200Asn | + | Val202Asp | + | Pro209Ser | + | Gly218Pro |
| Pro200Gly | + | Thr207Asn | + | Leu216Asn | + | Thr219Asp |
| Ala199Ser | + | Pro200Gly | + | Val202Asp | + | Thr207Ser |
| Val204Ala | + | Thr207Ser | + | Ser210Glu | + | Tyr213Met |
| Pro200Gln | + | Gly201Ser | + | Tyr205Thr | + | Ser215Glu |
| Ala199His | + | Gly201Asn | + | Tyr208Ala | + | Ser210Asp |
| Pro200Gln | + | Val204Met | + | Tyr205Ala | + | Pro209Glu |
| Val202Ala | + | Tyr205Leu | + | Thr214Glu | + | Thr219Gln |
| Thr207Gln | + | Pro209Asn | + | Ser210Glu | + | Thr214Pro |
| Gly201Asn | + | Ser203Asp | + | Tyr208Val | + | Asn211Gln |
| Ala199Ser | + | Pro200Gly | + | Leu216Val | + | Gly218Pro |
| Gly201Gln | + | Asn211Gln | + | Thr212Glu | + | Leu216Ala |
| Val202Cys | + | Thr207Asn | + | Tyr213Pro | + | Leu216Asp |
| Ala199Gly | + | Val202His | + | Val204Ala | + | Ser215Glu |
| Ala199Gln | + | Thr212Pro | + | Tyr213Glu | + | Leu216Ala |
| Pro200Gln | + | Val202Gln | + | Thr214Gln | + | Gly218Glu |
| Gly201Gln | + | Thr207Pro | + | Tyr208Met | + | Thr219Pro |

TABLE 25-continued

| Loop 6 - Quadruple Mutation Variants | | | | | | |
|---|---|---|---|---|---|---|
| Ser203Asp | + | Val204Gln | + | Tyr208Ser | + | Leu216Pro |
| Ala199Asn | + | Ser203Glu | + | Val204Asn | + | Tyr208Pro |
| Pro200Gly | + | Tyr213Met | + | Leu216Val | + | Gly218Asn |
| Tyr205Ile | + | Tyr213Ile | + | Thr214Asn | + | Thr219Pro |
| Pro200Gln | + | Thr207Gly | + | Ser215Glu | + | Leu216Met |
| Ala199Ser | + | Tyr208Ala | + | Asn211Gln | + | Thr219Asp |
| Gly201Pro | + | Val204Ser | + | Tyr205His | + | Thr219Asp |
| Val202Met | + | Thr207Pro | + | Thr212Gly | + | Asn217Glu |
| Pro200Gln | + | Gly201Pro | + | Tyr208Thr | + | Ser215Giu |
| Val204Thr | + | Thr212Gly | + | Thr214Glu | + | Gly218Ser |
| Pro200Gln | + | Tyr208Ala | + | Tyr213Glu | + | Asn217Ser |
| Tyr213Met | + | Thr214Ser | + | Ser215Asp | + | Leu216Pro |
| Thr207Ser | + | Pro209Asp | + | Thr212Gly | + | Thr219Gln |
| Thr207Gln | + | Asn211Gln | + | Thr214Glu | + | Ser215Asp |
| Tyr205Ala | + | Tyr213Met | + | Thr214Glu | + | Ser215Asp |
| Tyr205Met | + | Thr214Asp | + | Ser215Glu | + | Asn217Gln |
| Thr207Asn | + | Thr214Gly | + | Leu216Glu | + | Asn217Asp |
| Val202Thr | + | Val204His | + | Asn211Glu | + | Thr212Asp |
| Pro200Gln | + | Asn211Asp | + | Thr212Glu | + | Thr214Ser |
| Asn211Glu | + | Thr212Glu | + | Tyr213Ile | + | Thr214Asn |
| Gly201Asn | + | Val202Glu | + | Ser203Glu | + | Thr212Gly |
| Thr212Asp | + | Tyr213Asp | + | Gly218Ser | + | Thr219Gly |
| Val204Ala | + | Thr212Glu | + | Tyr213Glu | + | Thr214Asn |
| Pro200Gly | + | Ser210Asp | + | Asn211Glu | + | Thr212Pro |
| Pro209Gln | + | Ser210Asp | + | Asn211Glu | + | Thr219Pro |
| Pro200Ser | + | Val204Met | + | Ser210Asp | + | Asn211Glu |
| Ala199Pro | + | Val202Ala | + | Ser210Glu | + | Asn211Glu |
| Pro209Asp | + | Ser210Asp | + | Asn211Glu | + | Thr212Pro |
| Val202Asp | + | Ser203Asp | + | Tyr213Gin | + | Asn217Glu |
| Ser203Asp | + | Ser215Asp | + | Leu216Glu | + | Thr219Asn |
| Pro200Ser | + | Ser203Glu | + | Leu216Glu | + | Asn217Glu |
| Ser203Asp | + | Pro209Gly | + | Ser215Glu | + | Leu216Ala |
| Ser203Glu | + | Thr214Gln | + | Ser215Glu | + | Gly218Ser |
| Gly201Asn | + | Ser203Asp | + | Tyr213Ala | + | Ser215Glu |
| Ser203Glu | + | Thr207Ser | + | Tyr213Gly | + | Ser215Asp |
| Ala199Gln | + | Ser203Glu | + | Thr214Pro | + | Asn217Asp |
| Ser203Glu | + | Val204Asn | + | Thr212Gly | + | Asn217Glu |
| Ser203Asp | + | Thr207Gln | + | Tyr208Cys | + | Asn217Glu |
| Gly201Ser | + | Ser203Glu | + | Thr214Pro | + | Asn217Asp |

TABLE 25-continued

| Loop 6 - Quadruple Mutation Variants | | | | | | |
|---|---|---|---|---|---|---|
| Asn211Glu | + | Thr212Asp | + | Tyr213Glu | + | Thr219Gly |
| Ala199Pro | + | Ser203Asp | + | Val204Pro | + | Leu216Glu |
| Ala199Asn | + | Pro209Asp | + | Asn211Glu | + | Tyr213Ile |
| Pro200Gln | + | Tyr205Leu | + | Pro209Glu | + | Thr212Asp |
| Ser203Asp | + | Tyr205Glu | + | Tyr208Gly | + | Tyr213Leu |
| Ala199Ser | + | Val202Glu | + | Leu216Cys | + | Gly218Asp |
| Pro200Ser | + | Thr212Pro | + | Thr214Glu | + | Leu216Glu |
| Ala199Asn | + | Val202Pro | + | Ser215Glu | + | Asn217Asp |
| Pro200Gly | + | Thr207Ser | + | Ser215Glu | + | Asn217Glu |
| Gly201Asn | + | Val202Glu | + | Thr207Ser | + | Leu216Glu |
| Ala199Asn | + | Ser203Glu | + | Tyr205Glu | + | Asn217Glu |
| Tyr205Glu | + | Thr214Pro | + | Ser215Asp | + | Asn217Glu |
| Gly201Gln | + | Thr212Ser | + | Tyr213Glu | + | Ser215Glu |
| Ala199Ser | + | Tyr213Asp | + | Thr214Pro | + | Ser215Glu |
| Asn211Ser | + | Ser215Asp | + | Asn217Glu | + | Gly218Asp |
| Ser203Asp | + | Thr212Gln | + | Ser215Asp | + | Gly218Asp |
| Val202Glu | + | Thr212Gly | + | Ser215Asp | + | Leu216Gln |
| Val202Asp | + | Val204Cys | + | Tyr208Pro | + | Thr219Glu |
| Ser203Asp | + | Pro209Gln | + | Tyr213Thr | + | Thr214Asp |
| Val202Asp | + | Tyr205Glu | + | Tyr208Gly | + | Leu216Ile |
| Tyr208Gly | + | Thr214Asp | + | Asn217Glu | + | Gly218Asp |
| Pro200Gln | + | Tyr208Gln | + | Tyr213Glu | + | Leu216Glu |
| Gly201Gln | + | Tyr205Leu | + | Thr214Glu | + | Asn217Asp |
| Ser203Asp | + | Val204Gly | + | Thr212Glu | + | Ser215Asp |
| Gly201Gln | + | Val202Pro | + | Asn211Glu | + | Thr214Glu |
| Thr207Gln | + | Pro209Ser | + | Asn211Asp | + | Thr214Glu |
| Tyr205Ala | + | Ser210Glu | + | Thr212Asp | + | Ser215Asp |
| Ala199Gln | + | Thr214Glu | + | Leu216Glu | + | Thr219Glu |
| Thr212Asp | + | Thr214Glu | + | Leu216Asn | + | Asn217Glu |
| Gly201Asn | + | Asn211Glu | + | Thr214Asp | + | Leu216Glu |
| Pro209Asp | + | Ser215Asp | + | Leu216Asp | + | Gly218Gln |
| Gly201Pro | + | Val202Cys | + | Ser203Asp | + | Thr219Asp |
| Ser203Glu | + | Thr212Gln | + | Gly218Gln | + | Thr219Glu |

TABLE 26

| Loop 6 - Quintuple Substitution Variants | | | | | | | | |
|---|---|---|---|---|---|---|---|---|
| Gly201Asn | + | Thr207Gln | + | Ser210Glu | + | Tyr213Ile | + | Leu216Ile |
| Val202Cys | + | Tyr205Ser | + | Thr212Pro | + | Tyr213Leu | + | Gly218Asn |
| Ala199Ser | + | Pro200Ser | + | Tyr213His | + | Thr214Gln | + | Leu216Asn |
| Ala199Ser | + | Gly201Ser | + | Tyr208Ser | + | Ser210Glu | + | Thr214Ser |
| Ala199G1y | + | Gly201Asn | + | Val202Met | + | Tyr205His | + | Thr214Gln |
| Pro200Gly | + | Tyr213Leu | + | Thr214Pro | + | Asn217Ser | + | Thr219Glu |
| Ala199Thr | + | Tyr205Gln | + | Thr207Gln | + | Thr212Asp | + | Gly218Gln |
| Val204Gly | + | Tyr205Ala | + | Tyr208Gly | + | Asn211Gln | + | Gly218Asp |
| Ala199Ser | + | Gly201Pro | + | Tyr205Gly | + | Ser215Glu | + | Leu216Ser |
| Ala199His | + | Thr207Gln | + | Tyr208Thr | + | Gly218Gln | + | Thr219Gln |
| Ala199Gly | + | Pro209Gly | + | Asn211Ser | + | Thr212Ser | + | Tyr213Ser |
| Pro200Ser | + | Val202Gln | + | Thr207Asn | + | Tyr208Ile | + | Thr219Pro |
| Pro200Ser | + | Gly201Ser | + | Tyr208Gln | + | Ser210Glu | + | Asn217Gln |
| Ala199Gly | + | Gly201Ser | + | Val202Gly | + | Tyr205Asp | + | Leu216Gly |
| Ala199Gln | + | Pro200Ser | + | Gly201Ser | + | Tyr205Gln | + | Thr214Asp |
| Ala199Pro | + | Gly201Pro | + | Val204Asn | + | Tyr208Pro | + | Thr214Gly |
| Pro200Gly | + | Val202Gly | + | Ser203Asp | + | Asn211Ser | + | Leu216Pr9 |
| Tyr205Gly | + | Thr207Pro | + | Pro209Asp | + | Asn211Gln | + | Asn217Ser |
| Pro200Gln | + | Val204Ala | + | Tyr208Leu | + | Thr212Glu | + | Tyr213Met |
| Tyr205Met | + | Asn211Gln | + | Tyr213Met | + | Thr214Asn | + | Thr219Asp |
| Ser203Asp | + | Val204Ser | + | Tyr213Gly | + | Thr214Asn | + | Gly218Pro |
| Gly201Gln | + | Val204Gln | + | Ser215Asp | + | Leu216Ala | + | Thr219Ser |
| Gly201Asn | + | Thr207Gly | + | Tyr208Gly | + | Thr212Gly | + | Leu216His |
| Gly201Asn | + | Tyr205His | + | Thr207Ser | + | Leu216Glu | + | Gly218Ser |
| Ala199Gln | + | Pro200Ser | + | Tyr205His | + | Thr214Ser | + | Thr219Glu |
| Pro200Gln | + | Gly201Gln | + | Leu216His | + | Asn217Asp | + | Gly218Gln |
| Ala199Gly | + | Val204His | + | Tyr205Met | + | Asn211Glu | + | Thr212Pro |
| Val204His | + | Tyr205Pro | + | Tyr208Ile | + | Gly218Glu | + | Thr219Gly |
| Pro206Ser | + | Val202Gln | + | Val204Gly | + | Tyr213Ile | + | Ser215Glu |
| Ala199Ser | + | Pro200Asn | + | Asn211Glu | + | Tyr213Thr | + | Leu216Pro |

TABLE 26-continued

| Loop 6 - Quintuple Substitution Variants | | | | | | | | |
|---|---|---|---|---|---|---|---|---|
| Ser203Asp | + | Val204Gly | + | Asn211Gln | + | Tyr213Ile | + | Gly218Asn |
| Ala199Asn | + | Pro200Gln | + | Val202Ala | + | Val204Pro | + | Thr207Pro |
| Ala199Thr | + | Gly201Gln | + | Val202Gly | + | Ser215Asp | + | Leu216Ala |
| Thr212Gln | + | Tyr213Val | + | Leu216His | + | Gly218Gln | + | Thr219Glu |
| Ala199Gln | + | Pro200Ser | + | Gly201Asn | + | Tyr205Ala | + | Thr214Gly |
| Gly201Asn | + | Val204Gly | + | Thr212Gly | + | Leu216Val | + | Thr219Pro |
| Pro200Gly | + | Val202His | + | Thr207Gln | + | Tyr208Gln | + | Asn217Asp |
| Ala199Thr | + | Thr207Ser | + | Thr212Ser | + | Gly218Asp | + | Thr219Pro |
| Pro200Ser | + | Val204Pro | + | Tyr208Ile | + | Thr214Pro | + | Asn217Ser |
| Pro200Gln | + | Val202Ser | + | Tyr205Ser | + | Asn211Ser | + | Ser215Asp |
| Val202Thr | + | Thr212Gln | + | Ser215Asp | + | Asn217Ser | + | Thr219Asn |
| Val204Pro | + | Thr212Gly | + | Tyr213Val | + | Thr214Pro | + | Ser215Asp |
| Gly201Ser | + | Val204His | + | Tyr208Leu | + | Thr212Ser | + | Gly218Glu |
| Ser203Asp | + | Tyr205Gln | + | Thr207Gly | + | Thr212Gly | + | Thr214Gln |
| Pro200Gln | + | Tyr208Cys | + | Thr212Gly | + | Ser215Glu | + | Thr219Gly |
| Pro200Ser | + | Gly201Pro | + | Val202Ala | + | Tyr213Asp | + | Gly218Pro |
| Val204Gly | + | Ser210Asp | + | Thr212Asn | + | Thr214Pro | + | Thr219Ser |
| Pro200Gly | + | Ser203Asp | + | Pro209Asn | + | Leu216Cys | + | Asn217Ser |
| Tyr205Thr | + | Thr207Ser | + | Tyr208Ser | + | Pro209Ser | + | Asn217Ser |
| Gly201Asn | + | Tyr205Ile | + | Pro209Gln | + | Thr214Asn | + | Leu216Val |
| Ala199Asn | + | Ser203Glu | + | Val204Gln | + | Tyr213Leu | + | Gly218Asn |
| Ala199Thr | + | Val202Met | + | Tyr205Leu | + | Asn211Ser | + | Asn217Glu |
| Ala199Pro | + | Gly201Pro | + | Pro209Asn | + | Ser210Asp | + | Tyr213ser |
| Ala199Ser | + | Gly201Pro | + | Pro209Gly | + | Tyr213Pro | + | Gly218Pro |
| Pro200Ser | + | Pro209Gly | + | Thr212Pro | + | Thr214Pro | + | Leu216Glu |
| Gly201Ser | + | Thr207Gly | + | Ser210Asp | + | Asn211Ser | + | Leu216Ile |
| Ala199Ser | + | Gly201Gln | + | Val204Asn | + | Tyr205Leu | + | Thr219Asp |
| Thr207Pro | + | Tyr208Thr | + | Ser210Glu | + | Thr212Gly | + | Asn217Ser |
| Gly201Gln | + | Tyr205Asn | + | Thr207Asn | + | Pro209Asp | + | Thr212Gly |
| Pro200Asn | + | Tyr205Glu | + | Tyr208Met | + | Tyr213Val | + | Leu216Ile |
| Tyr205Ala | + | Tyr213His | + | Thr214Ser | + | Asn217Gln | + | Thr219Gln |
| Ala199Gln | + | Pro200Gly | + | Val202Met | + | Leu216Met | + | Gly218Pro |
| Pro200Ser | + | Val204Ala | + | Ser210Glu | + | Asn211Gln | + | Gly218Ser |
| Ala199Ser | + | Pro200Ser | + | Val202Asn | + | Leu216Val | + | Gly218Pro |
| Pro200Gln | + | Val202Gln | + | Tyr213Leu | + | Thr214Pro | + | Gly218Glu |
| Pro200Ser | + | Gly201Gln | + | Thr207Pro | + | Gly218Pro | + | Thr219Pro |
| Ala199Asn | + | Ser203Asp | + | Val204Asn | + | Tyr208Pro | + | Leu216Pro |
| Tyr205Ile | + | Tyr213Ile | + | Thr214Asn | + | Ser215Glu | + | Thr219Pro |
| Gly201Ser | + | Val204His | + | Asn211Gln | + | Thr212Gln | + | Leu216Met |
| Ala199Ser | + | Gly201Pro | + | Asn211Glu | + | Gly218Gln | + | Thr219Ser |
| Ala199Ser | + | Thr207Ser | + | Thr214Gln | + | Ser215Glu | + | Leu216Asn |
| Ala199His | + | Val204Cys | + | Asn211Ser | + | Thr214Gly | + | Thr219Glu |
| Ala199Asn | + | Val202His | + | Tyr208Asn | + | Leu216Thr | + | Thr219Gly |
| Ser203Glu | + | Thr207Pro | + | Tyr208Leu | + | Thr212Ser | + | Asn217Gln |
| Pro200Ser | + | Val202Asp | + | Val204Asn | + | Tyr208Met | + | Thr212Gln |
| Gly201Ser | + | Thr207Asn | + | Tyr208Leu | + | Ser210Asp | + | Asn217Ser |
| Val202Asp | + | Val204Gln | + | Tyr208Cys | + | Pro209Gln | + | Tyr213Val |
| Ala199Gly | + | Val202Thr | + | Thr207Gln | + | Thr212Glu | + | Thr214Gln |
| Gly201Pro | + | Val202Cys | + | Ser210Asp | + | Thr212Pro | + | Tyr213Cys |
| Ala199Asn | + | Gly201Ser | + | Val204Met | + | Pro209Asn | + | Thr214Pro |
| Gly201Asn | + | Ser203Asp | + | Val204Thr | + | Thr207Ser | + | Leu216Ala |
| Val202Thr | + | Tyr205Gly | + | Thr207Gln | + | Asn211Asp | + | Leu216Ala |
| Ala199Gln | + | Val204Gly | + | Thr207Pro | + | Asn211Asp | + | Thr214Gly |
| Gly201Pro | + | Val202Asn | + | Tyr205Ser | + | Asn211Glu | + | Gly218Asn |
| Val204Gly | + | Pro209Asn | + | Asn211Asp | + | Asn217Gln | + | Thr219Gly |
| Val202Gly | + | Val204Gly | + | Ser210Glu | + | Gly218Ser | + | Thr219Ser |
| Ala199Ser | + | Asn211Ser | + | Tyr213Met | + | Thr214Asp | + | Thr219Pro |
| Ala199Asn | + | Gly201Asn | + | Ser203Glu | + | Tyr213His | + | Leu216Ile |
| Ala199Gln | + | Pro200Asn | + | Thr207Ser | + | Pro209Ser | + | Asn217Ser |
| Tyr205Met | + | Thr214Asp | + | Ser215Glu | + | Leu216cys | + | Asn217Gln |
| Ala199Pro | + | Val202His | + | Tyr208Met | + | Thr214Glu | + | Ser215Asp |
| Pro200Asn | + | Pro209Glu | + | Ser210Asp | + | Thr214Ser | + | Leu216cys |
| Val204Ser | + | Tyr208Pro | + | Leu216Met | + | Asn217Asp | + | Gly218Asp |
| Tyr205Pro | + | Thr207Pro | + | Leu216Asn | + | Asn217Asp | + | Gly218Asp |
| Pro200Gly | + | Tyr205Asn | + | Tyr208Gly | + | Asn217Glu | + | Gly218Glu |
| Val202Thr | + | Val204His | + | Pro209Gly | + | Asn211Glu | + | Thr212Asp |
| Gly201Gln | + | Val202Asn | + | Thr207Asn | + | Ser215Glu | + | Leu216Asp |
| Ala199His | + | Pro200Gly | + | Ser210Asp | + | Asn211Glu | + | Thr212Pro |
| Pro209Gln | + | Ser210Asp | + | Asn211Glu | + | Asn217Gln | + | Thr219Pro |
| Ala199Pro | + | Val202Ala | + | Ser210Glu | + | Asn211Asp | + | Gly218Asn |
| Ala199Asn | + | Thr207Asn | + | Ser210Asp | + | Asn211Asp | + | Thr212Gly |
| Val204Ala | + | Tyr205Glu | + | Thr212Ser | + | Ser215Glu | + | Asn217Gln |
| Gly201Pro | + | Val202Asp | + | Thr207Gln | + | Thr212Ser | + | Asn217Asp |
| Thr207Ser | + | Pro209Asp | + | Ser210Glu | + | Asn211Asp | + | Tyr213Asn |
| Gly201Ser | + | Val202Glu | + | Ser203Glu | + | Thr214Pro | + | Asn217Asp |
| Ser203Glu | + | Thr207Asn | + | Thr214Gly | + | Leu216Glu | + | Asn217Asp |
| Gly201Ser | + | Ser203Asp | + | Tyr208Ile | + | Leu216Asp | + | Asn217Asp |

TABLE 26-continued

| Loop 6 - Quintuple Substitution Variants | | | | | | | | |
|---|---|---|---|---|---|---|---|---|
| Gly201Pro | + | Tyr208Gly | + | Leu216Asp | + | Asn217Glu | + | Gly218Asp |
| Ser203Glu | + | Val204Pro | + | Thr207Gly | + | Tyr213Leu | + | Ser215Asp |
| Gly201Asn | + | Ser203Asp | + | Tyr208Val | + | Asn211Gln | + | Ser215Asp |
| Ala199Asn | + | Pro200Ser | + | Ser203Glu | + | Tyr213Met | + | Ser215Glu |
| Ala199Ser | + | Ser203Glu | + | Asn211Gln | + | Ser215Glu | + | Leu216cys |
| Ser203Glu | + | Val204Gln | + | Thr214Gln | + | Ser215Asp | + | Leu216Gly |
| Ala199Pro | + | Gly201Pro | + | Ser203Asp | + | Tyr205Val | + | Ser215Glu |
| Ala199Thr | + | Ser203Asp | + | Val204Gln | + | Tyr213Gly | + | Ser215Asp |
| Val202Cys | + | Ser203Asp | + | Tyr205Met | + | Tyr213Gln | + | Asn217Glu |
| Ser203Glu | + | Val204Asn | + | Thr212Gly | + | Asn217Glu | + | Thr219Gln |
| Gly201Asn | + | Ser203Asp | + | Tyr208Val | + | Pro209Ser | + | Asn217Glu |
| Ser203Asp | + | Thr212Pro | + | Tyr213Gly | + | Asn217Glu | + | Gly218Ser |
| Val204Thr | + | Asn211Asp | + | Thr212Asp | + | Tyr213Asp | + | Leu216Ser |
| Val202Ala | + | Ser203Asp | + | Val204Gln | + | Tyr205Met | + | Leu216Glu |
| Ser203Glu | + | Val204Ser | + | Thr207Gly | + | Tyr208Val | + | Leu216Asp |
| Pro200Gln | + | Pro209Gln | + | Ser210Glu | + | Thr212Glu | + | Thr214Gly |
| Pro209Glu | + | Asn211Asp | + | Asn217Gln | + | Gly218Gln | + | Thr219Pro |
| Pro200Ser | + | Tyr205Pro | + | Pro209Asp | + | Asn211Glu | + | Tyr213Ile |
| Ala199Asn | + | Ser203Asp | + | Tyr205Glu | + | Thr207Asn | + | Leu216Glu |
| Ser203Glu | + | Tyr205Glu | + | Tyr213Met | + | Leu216Ile | + | Asn217Gln |
| Val202Glu | + | Ser203Glu | + | Asn211Gln | + | Leu216Met | + | Gly218Glu |
| Ala199Ser | + | Val2025er | + | Tyr205Asp | + | Tyr208Gly | + | Tyr213Asp |
| Pro200Ser | + | Thr207Pro | + | Thr212Asp | + | Thr214Asp | + | Thr219Ser |
| Pro200Gly | + | Thr207Ser | + | Thr214Gln | + | Ser215Glu | + | Asn217Glu |
| Pro200Gln | + | Thr207Gly | + | Ser215Asp | + | Leu216Gln | + | Asn217Asp |
| Ala199Asn | + | Tyr205Glu | + | Tyr208Ala | + | Ser215Glu | + | Asn217Glu |
| Gly201Pro | + | Val204Ser | + | Tyr205His | + | Asn217Glu | + | Thr219Asp |
| Ala199Ser | + | Tyr208Gln | + | Tyr213Asp | + | Thr214Pro | + | Ser215Glu |
| Thr207Asn | + | Tyr208Gln | + | Thr212Ser | + | Tyr213Glu | + | Ser215Glu |
| Gly201Gln | + | Tyr205Gly | + | Pro209Glu | + | Thr212Pro | + | Tyr213Glu |
| Ser203Asp | + | Pro209Ser | + | Thr212Gln | + | Ser215Asp | + | Gly218Asp |
| Ser203Asp | + | Pro209Gly | + | Ser215Glu | + | Leu216Ala | + | Gly218Asp |
| Pro200Ser | + | Ser203Asp | + | Thr207Gln | + | Leu216Gln | + | Gly218Glu |
| Pro200Asn | + | Gly201Pro | + | Ser203Glu | + | Thr207Gly | + | Gly218Glu |
| Val202Asp | + | Val204Cys | + | Tyr208Ala | + | Gly218Gln | + | Thr219Glu |
| Val202Glu | + | Val204Thr | + | Tyr208Gln | + | Asn217Ser | + | Thr219Glu |
| Pro200Ser | + | Gly201Pro | + | Val202Asp | + | Asn211Gln | + | Thr219Glu |
| Gly201Asn | + | Ser203Glu | + | Thr212Gln | + | Thr214Asp | + | Thr219Ser |
| Gly201Asn | + | Ser203Asp | + | Thr214Glu | + | Leu216Cys | + | Thr219Gly |
| Gly201Asn | + | Val202Cys | + | Ser203Asp | + | Thr214Asp | + | Thr219Pro |
| Val202Cys | + | Ser203Asp | + | Tyr208Thr | + | Thr214Asp | + | Thr219Pro |
| Val204Ser | + | Tyr208Leu | + | Ser210Asp | + | Tyr213Asp | + | Thr214Asp |
| Ala199His | + | Ser203Asp | + | Tyr208Ser | + | Tyr213Glu | + | Thr214Asp |
| Val204Cys | + | Ser210Asp | + | Asn211Ser | + | Tyr213Asp | + | Thr219Gln |
| Ala199Asn | + | Ser210Glu | + | Thr212Asn | + | Tyr213Glu | + | Thr214Gln |
| Ser203Asp | + | Tyr205Glu | + | Tyr208Gly | + | Tyr213Leu | + | Gly218Asp |
| Val202Glu | + | Tyr205Glu | + | Pro209Asn | + | Leu216Thr | + | Gly218Glu |
| Tyr208Val | + | Ser215Asp | + | Asn217Ser | + | Gly218Asp | + | Thr219Glu |
| Tyr205Leu | + | Thr214Asp | + | Ser215Glu | + | Gly218Glu | + | Thr219Asn |
| Ala199Pro | + | Pro209Asp | + | Thr212Asp | + | Ser215Asp | + | Gly218Ser |
| Ser203Glu | + | Thr212Glu | + | Tyr213Ser | + | Thr214Glu | + | Leu216Cys |
| Ser203Asp | + | Tyr208Cys | + | Thr212Asp | + | Tyr213Ile | + | Thr214Asp |
| Val202Met | + | Val204Thr | + | Asn211Asp | + | Thr214Asp | + | Ser215Asp |
| Pro209Asn | + | Asn211Asp | + | Thr214Glu | + | Ser215Glu | + | Leu216Gly |
| Pro200Asn | + | Tyr205Glu | + | Thr212Asp | + | Tyr213Ala | + | Thr219Pro |
| Pro200Asn | + | Ser203Asp | + | Tyr205His | + | Thr212Asp | + | Ser215Asp |
| Ser203Asp | + | Val204Thr | + | Thr212Glu | + | Tyr213Ile | + | Ser215Glu |
| Tyr205Gly | + | Thr207Gln | + | Tyr208Ile | + | Thr212Glu | + | Ser215Glu |
| Ala199Asn | + | Tyr205Asp | + | Ser210Glu | + | Thr212Glu | + | Thr214Gly |
| Val202Met | + | Tyr205Ala | + | Ser210Glu | + | Thr212Asp | + | Ser215Asp |
| Thr207Gln | + | Tyr208Leu | + | Asn211Glu | + | Tyr213Glu | + | Leu216Glu |
| Val204Met | + | Pro209Ser | + | Asn211Asp | + | Thr214Glu | + | Leu216Asp |
| Pro200Ser | + | Ser203Glu | + | Tyr213Glu | + | Leu216Gly | + | Asn217Glu |
| Ala199Gly | + | Tyr213Pro | + | Thr214Asp | + | Asn217Asp | + | Thr219Asp |
| Ala199Gln | + | Tyr208Ala | + | Thr214Glu | + | Asn217Glu | + | Thr219Asp |
| Ala199His | + | Val202His | + | Ser203Glu | + | Thr207Gly | + | Thr219Asp |
| Gly201Ser | + | Val202Gly | + | Ser203Glu | + | Tyr205Thr | + | Thr219Asp |
| Gly201Pro | + | Pro209Glu | + | Ser210Asp | + | Ser215Glu | + | Leu216Met |
| Tyr205Glu | + | Ser215Glu | + | Leu216Cys | + | Gly218Gln | + | Thr219Glu |
| Ser203Asp | + | Pro209Ser | + | Asn211Glu | + | Thr214Asp | + | Leu216Asn |
| Ala199Thr | + | Ser203Glu | + | Thr207Gln | + | Asn211Asp | + | Thr214Glu |
| Gly201Ser | + | Ser203Asp | + | Tyr205Gly | + | Pro209Asp | + | Ser215Asp |
| Pro209Glu | + | Thr214Asn | + | Leu216Glu | + | Asn217Asp | + | Thr219Asn |

TABLE 27

Loop 6 - Sextuple Substitution Variants

| | | | | | | | | | | |
|---|---|---|---|---|---|---|---|---|---|---|
| Gly201Asn | + | Tyr205Gly | + | Thr207Gln | + | Ser210Glu | + | Tyr213Ile | + | Thr219Gly |
| Pro200Asn | + | Gly201Ser | + | Tyr208Gly | + | Asn211Asp | + | Thr212Ser | + | Thr219Asn |
| Gly201Pro | + | Ser203Asp | + | Val204Gln | + | Tyr205Pro | + | Thr212Ser | + | Tyr213His |
| Pro200Gln | + | Val204His | + | Thr207Ser | + | Thr214Pro | + | Ser215Asp | + | Thr219Asn |
| Ala199Pro | + | Pro200Ser | + | Gly201Pro | + | Val204Asn | + | Tyr208Pro | + | Thr214Gly |
| Pro200Gln | + | Val204Ala | + | Tyr208Leu | + | Thr212Glu | + | Tyr213Met | + | Leu216Gln |
| Ala199Pro | + | Val202Met | + | Ser203Glu | + | Tyr205Leu | + | Asn211Gln | + | Tyr213Gly |
| Gly201Gln | + | Val204Gln | + | Thr214Gln | + | Ser215Asp | + | Leu216Gly | + | Thr219Ser |
| Val204Thr | + | Tyr208Met | + | Pro209Glu | + | Tyr213Gly | + | Thr214Pro | + | Gly218Ser |
| Ser203Asp | + | Val204Met | + | Thr207Gln | + | Pro209Gln | + | Asn217Ser | + | Thr219Asn |
| Pro200Ser | + | Val202Met | + | Val204Gly | + | Pro209Gln | + | Tyr213Ile | + | Ser215Glu |
| Ala199His | + | Ser203Asp | + | Val204Gly | + | Thr207Gly | + | Asn211Gln | + | Thr214Ser |
| Ala199Gln | + | Pro200Gln | + | Gly201Gln | + | Pro209Glu | + | Leu216Ile | + | Asn217Ser |
| Pro200Gln | + | Tyr20811e | + | Pro209Gln | + | Thr212Gly | + | Ser215Glu | + | Thr219Gly |
| Pro200Asn | + | Ser203Asp | + | Val204Cys | + | Thr207Gln | + | Pro209Ser | + | Thr214Asn |
| Ala199Asn | + | Val202Gln | + | Val204Ser | + | Pro209Gly | + | Thr212Asp | + | Asn217Gln |
| Pro200Asn | + | Val204Met | + | Thr207Gln | + | Pro209Gly | + | Thr212Gly | + | Tyr213Asp |
| Pro200Gly | + | Val204Gln | + | Pro209Asn | + | Tyr213Ile | + | Thr214Gly | + | Leu216Met |
| Ala199Asn | + | Tyr205Thr | + | Tyr208Ser | + | Pro209Ser | + | Thr214Asp | + | Asn217Ser |
| Tyr205Ser | + | Thr207Gln | + | Tyr208Cys | + | Pro209Asn | + | Thr212Asn | + | Leu216Glu |
| Ala199Asn | + | Pro200Ser | + | Ser203Asp | + | Tyr205Cys | + | Tyr208Asn | + | Thr214Gln |
| Thr207Pro | + | Tyr213Ser | + | Thr214Asn | + | Asn217Ser | + | Gly218Ser | + | Thr219Glu |
| Ala199Pro | + | Gly201Pro | + | Thr207Gly | + | Pro209Asn | + | Ser210Asp | + | Tyr213Ser |
| Ala199Gln | + | Pro200Gly | + | Val202Met | + | Thr212Asp | + | Leu216Met | + | Gly218Pro |
| Ala199Ser | + | Pro200Gly | + | Val202Asn | + | Asn211Gln | + | Leu216Val | + | Gly218Pro |
| Ala199His | + | Pro200Gln | + | Val202Gln | + | Thr214Gln | + | Leu216Thr | + | Gly218Glu |
| Pro200Ser | + | Gly201Gln | + | Thr207Pro | + | Tyr208Thr | + | Gly218Pro | + | Thr219Pro |
| Pro200Gln | + | Val204Met | + | Thr207Gly | + | Ser215Glu | + | Leu216Met | + | Thr219Pro |
| Thr207Ser | + | Pro209Asp | + | Thr212G1y | + | Thr214Ser | + | Leu216Pro | + | Thr219Gln |
| Pro200Asn | + | Gly201Ser | + | Thr207Asn | + | Tyr208Leu | + | Ser210Asp | + | Asn217Ser |
| Ala199Asn | + | Val202Ser | + | Tyr205Cys | + | Thr207Gln | + | Tyr213Leu | + | Asn217Ser |
| Val202Ser | + | Pro209Gln | + | Tyr213Asp | + | Leu216Met | + | Asn217Ser | + | Thr219Gly |
| Gly201Gln | + | Val204Gly | + | Pro209Asn | + | Asn211Asp | + | Asn217Gln | + | Thr219Gly |
| Val202Gly | + | Ser203Glu | + | Val204Gly | + | Tyr213Met | + | Gly218Ser | + | Thr219Ser |
| Ala199Gln | + | Pro200Asn | + | Tyr205Thr | + | Thr207Ser | + | Thr214Gln | + | Asn217Ser |
| Ala199Ser | + | Gly201Asn | + | Val202Met | + | Val204Asn | + | Asn211Gln | + | Gly218Glu |
| Pro200Asn | + | Val2d2Pro | + | Val204Gln | + | Tyr208Pro | + | Gly218Gln | + | Thr219Glu |
| Thr207Gly | + | Tyr208Ile | + | Pro209Gly | + | Tyr213Gly | + | Thr214Pro | + | Leu216Asn |
| Val202Met | + | Ser203Asp | + | Val204Met | + | Thr212Asn | + | Thr214Asn | + | Leu216Gly |
| Ala199Ser | + | Val202Met | + | Val204Ala | + | Thr212Gly | + | Tyr213Thr | + | Thr214Pro |
| Tyr208Val | + | Pro209Gln | + | Thr214Ser | + | Leu216Cys | + | Asn217Glu | + | Thr219Asn |
| Pro200Gln | + | Gly201Gln | + | Tyr205Ala | + | Pro209Gln | + | Leu216Pro | + | Thr219Glu |
| Ala199Gly | + | Pro200Gln | + | Gly201Ser | + | Tyr208Gln | + | Ser215Asp | + | Gly218Asn |
| Ala199Asn | + | Pro200Asn | + | Val202Asn | + | Val204Gln | + | Thr214Gly | + | Asn217Glu |
| Pro200Gly | + | Gly201Gln | + | Tyr213Gly | + | Thr214Asn | + | Leu216Gln | + | Thr219Ser |
| Gly201Gln | + | Val202Gly | + | Thr207Gly | + | Asn211Gln | + | Thr214Gly | + | Ser215Asp |
| Ala199Thr | + | Pro200Ser | + | Tyr208Ala | + | Thr212Ser | + | Ser215Asp | + | Asn217Ser |
| Ala199His | + | Val202Asn | + | Ser203Glu | + | Val204His | + | Tyr213Ile | + | Asn217Gln |
| Gly201Asn | + | Val202Cys | + | Tyr205Cys | + | Tyr213Ile | + | Leu216Pro | + | Asn217Asp |
| Ala199Thr | + | Gly201Ser | + | Val202Gly | + | Tyr205Pro | + | Leu216Thr | + | Gly218Glu |
| Ala199Ser | + | Val204Cys | + | Tyr208Cys | + | Pro209Gly | + | Tyr213Ala | + | Leu216Asp |
| Ala199Gly | + | Gly201Asn | + | Val204Met | + | Thr207Pro | + | Thr214Glu | + | Leu216Met |
| Pro200Gly | + | Tyr205Met | + | Tyr208Val | + | Thr212Gly | + | Tyr213Ser | + | Leu216Val |
| Gly201Pro | + | Tyr208Val | + | Pro209Glu | + | Asn211Gln | + | Tyr213Ala | + | Thr219Gly |
| Ala199Ser | + | Pro200Ser | + | Val202Thr | + | Tyr205Gln | + | Gly218Asp | + | Thr219Pro |
| Ala199Gln | + | Ser203Glu | + | Val204Pro | + | Thr214Ser | + | Gly218G1n | + | Thr219Pro |
| Ala199Thr | + | Pro200Gly | + | Gly201Gln | + | Thr212Ser | + | Leu216Val | + | Gly218Ser |
| Pro200Ser | + | Val204Gln | + | Thr207Pro | + | Thr214Gly | + | Ser215Glu | + | Gly218Gln |
| Ala199Gly | + | Gly201Gln | + | Val204His | + | Tyr205Asp | + | Pro209Gln | + | Thr212Ser |
| Pro200Gln | + | Tyr208Asn | + | Asn211Ser | + | Thr212Ser | + | Tyr213Thr | + | Leu216Asp |
| Ala199His | + | Tyr208Leu | + | Thr212Pro | + | Ser215Glu | + | Leu216Ser | + | Gly218Gln |
| Gly201Pro | + | Val204Cys | + | Pro209Gln | + | Thr212Ser | + | Tyr213Cys | + | Thr214Gln |
| Val204Ser | + | Tyr20SSer | + | Thr207Asn | + | Tyr208Cys | + | Ser215Asp | + | Asn217Ser |
| Pro200Asn | + | Tyr208Ala | + | Tyr213Pro | + | Thr214Glu | + | Ser215Asp | + | Thr219Gly |
| Val202His | + | Tyr208Met | + | Pro209Asn | + | Thr212Asn | + | Thr214Glu | + | Ser215Asp |
| Pro200Gln | + | Gly201Ser | + | Val202Pro | + | Val204Ser | + | Thr214Asp | + | Ser215Glu |
| Ala199Gln | + | Gly201Ser | + | Val204Gly | + | Thr207Ser | + | Thr214Asp | + | Ser215Glu |
| Val202Asn | + | Tyr205Gly | + | Pro209Gln | + | Thr212Ser | + | Thr214Glu | + | Ser215Glu |
| Pro200Asn | + | Pro209Glu | + | Ser210Asp | + | Asn211Ser | + | Thr214Ser | + | Leu216Cys |
| Pro200Ser | + | Val204Pro | + | Tyr208Ile | + | Thr214Pro | + | Asn217Asp | + | Gly218Asp |
| Gly201Gln | + | Tyr205Asn | + | Tyr208Gly | + | Thr212Gly | + | Asn217Glu | + | Gly218Glu |
| Val202His | + | Thr207Asn | + | Tyr208Gln | + | Tyr213Pro | + | Ser215Glu | + | Leu216Asp |
| Ala199Asn | + | Gly201Ser | + | Val202Pro | + | Tyr205Thr | + | Ser215Asp | + | Leu216Asp |
| Pro200Gly | + | Val202Ala | + | Val204Ala | + | Ser210Glu | + | Asn211Glu | + | Gly218Ser |
| Val204Asn | + | Pro209Ser | + | Ser210Asp | + | Asn211Asp | + | Tyr213Asn | + | Leu216Met |
| Ala199Asn | + | Val204Thr | + | Ser210Asp | + | Asn211Glu | + | Tyr213Leu | + | Thr214Pro |
| Val202Cys | + | Val204Ala | + | Tyr205Glu | + | Thr212Ser | + | Ser215Glu | + | Asn217Gln |

TABLE 27-continued

Loop 6 - Sextuple Substitution Variants

| | | | | | | | | | | |
|---|---|---|---|---|---|---|---|---|---|---|
| Thr207Pro | + | Ser210Asp | + | Asn211Glu | + | Thr212Glu | + | Asn217Ser | + | Thr219Ser |
| Pro200Asn | + | Val202Asp | + | Tyr205Ala | + | Pro209Ser | + | Asn217Asp | + | Gly218Pro |
| Val202Gln | + | Pro209Glu | + | Ser210Glu | + | Asn211Glu | + | Thr212Gln | + | Asn217Gln |
| Val202Asp | + | Ser203Asp | + | Thr207Gln | + | Thr212Ser | + | Tyr213Gln | + | Asn217Glu |
| Ala199Asn | + | Ser203Glu | + | Val204Asn | + | Tyr208Pro | + | Leu216Glu | + | Asn217Asp |
| Val204Thr | + | Thr212Gly | + | Thr214Glu | + | Ser215Asp | + | Leu216Glu | + | Gly218Ser |
| Ala199Gln | + | Ser203Asp | + | Val204Cys | + | Thr207Gly | + | Ser215Glu | + | Leu216Gln |
| Ala199Pro | + | Pro200Gln | + | Ser203Asp | + | Asn211Ser | + | Ser215Asp | + | Leu216Asn |
| Ser203Glu | + | Tyr208Thr | + | Tyr213Cys | + | Thr214Gln | + | Ser215Glu | + | Gly218Ser |
| Ala199Thr | + | Pro200Gln | + | Gly201Gln | + | Ser203Asp | + | Ser215Asp | + | Gly218Ser |
| Pro200Gly | + | Val202Cys | + | Ser203Asp | + | Asn211Ser | + | Ser215Glu | + | Leu216Pro |
| Ala199Gln | + | Ser203Glu | + | Tyr205Gly | + | Tyr213Met | + | Ser215Glu | + | Asn217Ser |
| Pro200Ser | + | Gly201Asn | + | Ser203Asp | + | Tyr208Val | + | Pro209Ser | + | Asn217Glu |
| Pro200Ser | + | Gly201Ser | + | Val202His | + | Ser203Asp | + | Asn217Glu | + | Gly218Pro |
| Val202Asn | + | Tyr205Glu | + | Thr207Gln | + | Tyr208Leu | + | Thr214Asp | + | Gly218Pro |
| Ser203Asp | + | Val204Thr | + | Tyr205Glu | + | Thr212Ser | + | Tyr213Ile | + | Ser215Glu |
| Ala199Asn | + | Pro200Ser | + | Tyr205Pro | + | Pro209Asp | + | Asn211Glu | + | Tyr213Ile |
| Gly201Pro | + | Val202Cys | + | Val204Ser | + | Pro209Glu | + | Thr212Glu | + | Thr214Ser |
| Ala199Asn | + | Val202Asp | + | Ser203Asp | + | Tyr208Cys | + | Ser215Asp | + | Leu216Asn |
| Ala199Asn | + | Ser203Glu | + | Tyr205Cys | + | Thr212Gly | + | Thr214Glu | + | Ser215Asp |
| Ala199Thr | + | Pro200Ser | + | Tyr208Met | + | Thr214Ser | + | Ser215Glu | + | Asn217Asp |
| Ala199Pro | + | Tyr208Gly | + | Ser215Asp | + | Leu216Val | + | Asn217Asp | + | Thr219Ser |
| Pro200Asn | + | Pro209Gly | + | Tyr213Pro | + | Ser215Asp | + | Leu216Gly | + | Asn217Asp |
| Pro200Ser | + | Gly201Pro | + | Val202Ala | + | Asn211Glu | + | Tyr213Asp | + | Gly218Pro |
| Val202Met | + | Val204Ser | + | Tyr205His | + | Thr212Gly | + | Asn217Glu | + | Thr219Asp |
| Tyr205Val | + | Tyr208Pro | + | Ser215Glu | + | Leu216Met | + | Asn217Asp | + | Gly218Asp |
| Val202Ser | + | Tyr208Ala | + | Asn211Ser | + | Thr214Glu | + | Leu216Asp | + | Asn217Asp |
| Gly201Pro | + | Tyr208Gln | + | Thr212Asp | + | Tyr213Asp | + | Ser215Asp | + | Asn217Ser |
| Ala199Gln | + | Gly201Gln | + | Tyr205Gly | + | Pro209Glu | + | Thr212Pro | + | Tyr213Glu |
| Ser203Asp | + | Pro209Ser | + | Asn211Gln | + | Thr212Gln | + | Ser215Asp | + | Gly218Asp |
| Ser203Asp | + | Pro209Gly | + | Tyr213Leu | + | Ser215Glu | + | Leu216Ala | + | Gly218Asp |
| Val202Glu | + | Val204Cys | + | Thr212Gly | + | Ser215Asp | + | Leu216Gln | + | Gly218Gln |
| Pro200Gly | + | Gly201Gln | + | Val202Glu | + | Val204Ala | + | Thr207Pro | + | Ser215Asp |
| Ala199Gln | + | Pro200Ser | + | Gly201Ser | + | Ser203Asp | + | Gly218Glu | + | Thr219Asp |
| Ala199Gln | + | Gly201Ser | + | Tyr205Gln | + | Ser210Asp | + | Thr212Glu | + | Thr214Asp |
| Gly201Asn | + | Val202Pro | + | Ser210Glu | + | Thr212Glu | + | Tyr213Thr | + | Thr214Glu |
| Pro200Gln | + | Val202Met | + | Ser203Asp | + | Val204Gly | + | Tyr208Ile | + | Gly218Asp |
| Pro200Ser | + | Gly201Pro | + | Val202Asp | + | Tyr208Cys | + | Asn211Gln | + | Thr219Glu |
| Ser203Asp | + | Tyr208Pro | + | Pro209Ser | + | Asn211Ser | + | Thr214Asp | + | Thr219Pro |
| Ala199His | + | Gly201Asn | + | Ser203Glu | + | Tyr213His | + | Thr214Glu | + | Leu216Ile |
| Ser203Glu | + | Tyr208Pro | + | Tyr213His | + | Thr214Asp | + | Leu216Cys | + | Asn217Ser |
| Val202Asp | + | Tyr205Met | + | Thr214Asp | + | Ser215Glu | + | Leu216Cys | + | Asn217Gln |
| Val202Cys | + | Val204Ser | + | Tyr208Leu | + | Ser210Asp | + | Tyr213Asp | + | Thr214Asp |
| Gly201Asn | + | Tyr205Gln | + | Pro209Asn | + | Ser210Glu | + | Tyr213Glu | + | Leu216Ala |
| Val202Cys | + | Pro209Asp | + | Tyr213Asp | + | Thr214Asn | + | Ser215Glu | + | Asn217Gln |
| Ala199Gly | + | Gly201Gln | + | Ser215Asp | + | Leu216Asp | + | Gly218Asn | + | Thr219Glu |
| Ala199His | + | Thr207Asn | + | Asn211Ser | + | Leu216Glu | + | Asn217Gln | + | Thr219Asp |
| Val202Met | + | Thr207Gln | + | Pro209Gly | + | Thr214Glu | + | Ser215Asp | + | Gly218Asp |
| Pro200Gln | + | Val202Ala | + | Val204Pro | + | Thr207Gln | + | Pro209Glu | + | Thr214Glu |
| Gly201Pro | + | Tyr208Gly | + | Thr214Asp | + | Leu216Cys | + | Asn217Glu | + | Gly218Asp |
| Ala199Gln | + | Thr207Pro | + | Tyr208Cys | + | Pro209Gln | + | Tyr213Asp | + | Leu216Asp |
| Ser203Asp | + | Thr214Gly | + | Ser215Glu | + | Leu216Ala | + | Asn217Ser | + | Thr219Glu |
| Pro200Gln | + | Ser203Glu | + | Val204His | + | Thr212Asp | + | Thr214Asp | + | Gly218Gln |
| Ala199His | + | Gly201Ser | + | Ser203Glu | + | Tyr205Ser | + | Thr214Glu | + | Gly218Glu |
| Gly201Pro | + | Ser203Glu | + | Thr207Gly | + | Tyr208Cys | + | Thr214Asp | + | Gly21eGlu |
| Ser203Glu | + | Tyr205Leu | + | Thr207Asn | + | Thr212Asp | + | Tyr213Met | + | Ser215Glu |
| Ala199Pro | + | Ser203Asp | + | Pro209Ser | + | Thr212Glu | + | Ser215Asp | + | Gly218Gln |
| Ser203Glu | + | Tyr205His | + | Thr212Asp | + | Tyr213Met | + | Ser215Asp | + | Thr219Ser |
| Ser203Asp | + | Val204Gly | + | Thr212Glu | + | Thr214Pro | + | Ser215Asp | + | Asn217Ser |
| Gly201Pro | + | Tyr205Gln | + | Thr207Gly | + | Asn211Glu | + | Thr212Gly | + | Thr214Glu |
| Pro200Asn | + | Val202Gln | + | Thr207Gln | + | Pro209Ser | + | Asn211Asp | + | Thr214Glu |
| Gly201Gln | + | Thr207Gly | + | Pro209Gln | + | Thr212Glu | + | Ser215Glu | + | Gly218Gln |
| Val202Met | + | Tyr205Ala | + | Ser210Glu | + | Thr212Asp | + | Ser215Asp | + | Leu216Ala |
| Gly201Gln | + | Pro209Gly | + | Asn211Asp | + | Tyr213Asp | + | Thr214Gly | + | Leu216Asp |
| Ala199Gly | + | Val202Glu | + | Ser203Glu | + | Tyr213Glu | + | Thr214Pro | + | Thr219Ser |
| Gly201Ser | + | Val202Cys | + | Ser203Asp | + | Tyr205Asp | + | Leu216Gly | + | Thr219Asp |
| Pro200Ser | + | Ser203Glu | + | Tyr213Glu | + | Leu216Gly | + | Asn217Glu | + | Thr219Gly |
| Tyr205Asn | + | Pro209Asn | + | Thr212Glu | + | Tyr213Met | + | Ser215Glu | + | Asn217Asp |
| Ala199Gln | + | Tyr208Ala | + | Asn211Gln | + | Thr214Glu | + | Asn217Glu | + | Thr219Asp |
| Gly201Pro | + | Val202Gly | + | Ser203Glu | + | Tyr205Thr | + | Tyr208Ala | + | Thr219Asp |
| Pro200Asn | + | Gly201Pro | + | Ser203Asp | + | Thr207Gln | + | Gly218Ser | + | Thr219Glu |
| Gly201Asn | + | Ser203Asp | + | Val204Gly | + | Tyr208Val | + | Asn211Gln | + | Thr219Asp |
| Ala199His | + | Pro200Asn | + | Ser203Asp | + | Tyr205Thr | + | Pro209Asp | + | Thr214Glu |
| Gly201Pro | + | Val202Gly | + | Pro209Glu | + | Ser210Asp | + | Ser215Glu | + | Leu216Met |
| Ala199Gly | + | Val202His | + | Val204Ala | + | Pro209Asp | + | Ser210Glu | + | Ser215Glu |
| Gly201Asn | + | Val204Gln | + | Tyr208Leu | + | Thr214Glu | + | Ser215Glu | + | Thr219Glu |
| Ser203Glu | + | Tyr205Gln | + | Tyr208Gly | + | Asn211Glu | + | Thr214Glu | + | Thr219Ser |

TABLE 27-continued

| Loop 6 - Sextuple Substitution Variants | | | | | | | | | | |
|---|---|---|---|---|---|---|---|---|---|---|
| Gly201Ser | + | Ser203Asp | + | Tyr205Ala | + | Pro209Asp | + | Tyr213Met | + | Ser215Asp |
| Val202Asn | + | Pro209Asp | + | Asn211Glu | + | Thr212Ser | + | Tyr213Leu | + | Ser215Glu |
| Ala199Pro | + | Val204Thr | + | Tyr205Glu | + | Ser210Glu | + | Asn211Asp | + | Tyr213Leu |
| Val202Ala | + | Ser203Asp | + | Val204Gln | + | Tyr205Met | + | Thr212Glu | + | Leu216Glu |
| Gly201Pro | + | Ser203Asp | + | Tyr208Thr | + | Thr214Asp | + | Asn217Gln | + | Thr219Asp |
| Pro200Gln | + | Gly201Asn | + | Thr207Gln | + | Tyr213Glu | + | Asn217Asp | + | Gly218Asp |
| Pro200Gln | + | Thr207Gly | + | Tyr208Ala | + | Thr212Glu | + | Tyr213Glu | + | Asn217Glu |
| Thr207Ser | + | Tyr208Ser | + | Pro209Glu | + | Thr214Glu | + | Asn217Glu | + | Thr219Asn |
| Ala199Gly | + | Tyr205Pro | + | Pro209Glu | + | Thr214Glu | + | Leu216Asn | + | Asn217Asp |
| Ala199His | + | Gly201Asn | + | Tyr205Pro | + | Pro209Glu | + | Ser215Glu | + | Asn217Glu |
| Pro200Gly | + | Pro209Asp | + | Tyr213Gln | + | Ser215Glu | + | Leu216Ile | + | Asn217Asp |
| Ala199His | + | Val204Ser | + | Thr207Gln | + | Pro209Asp | + | Ser210Asp | + | Thr219Asp |
| Ala199Thr | + | Thr207Pro | + | Tyr208Val | + | Pro209Glu | + | Ser210Asp | + | Thr219Asp |
| Tyr208His | + | Pro209Glu | + | Ser210Glu | + | Tyr213Val | + | Leu216Cys | + | Thr219Asp |
| Tyr205Met | + | Thr207Gly | + | Ser210Asp | + | Thr212Ser | + | Asn217Glu | + | Gly218Asp |
| Ser210Glu | + | Thr212Pro | + | Thr214Gln | + | Asn217Asp | + | Gly218Glu | + | Thr219Ser |
| Pro200Gln | + | Val204Thr | + | Tyr208Asn | + | Asn211Asp | + | Ser215Glu | + | Leu216Glu |
| Gly201Pro | + | Tyr208Gln | + | Asn211Glu | + | Thr212Asp | + | Asn217Glu | + | Thr219Ser |
| Val202Asp | + | Ser203Asp | + | Asn211Glu | + | Thr212Pro | + | Tyr213Leu | + | Thr214Asn |
| Val202Glu | + | Ser203Asp | + | Tyr205Leu | + | Pro209Gly | + | Thr212Asp | + | Thr219Ser |
| Ala199Gly | + | Pro200Asn | + | Tyr208Leu | + | Ser210Asp | + | Asn211Asp | + | Asn217Asp |
| Pro200Ser | + | Gly201Ser | + | Val202Asp | + | Tyr208Gln | + | Ser210Glu | + | Asn211Asp |
| Val202Asp | + | Thr207Gln | + | Tyr208Thr | + | Ser210Glu | + | Thr214Gln | + | Asn217Glu |
| Thr207Gln | + | Asn211Asp | + | Thr214Glu | + | Leu216His | + | Asn217Asp | + | Gly218Gln |
| Ser203Glu | + | Thr207Ser | + | Pro209Gly | + | Asn211Asp | + | Tyr213Gly | + | Ser215Asp |
| Ser203Glu | + | Tyr205Val | + | Pro209Gly | + | Asn211Asp | + | Ser215Asp | + | Thr219Gly |

TABLE 28

| Loop 6 - Heptuple Substitution Mutation Variants |
|---|
| Ala199Ser + Pro200Ser + Val204Met + Tyr208Ser + Tyr213His + Thr214Gln + Leu216Ala |
| Ala199Ser + Gly201Ser + Val202Met + Thr207Gln + Ser210Glu + Thr214Ser + Asn217Gln |
| Gly201Gln + Val204Gly + Tyr205Ala + Thr207Gln + Tyr208Gly + Asn211Gln + Gly218Asp |
| Ala199Gly + Pro200Gly + Thr207Gln + Tyr208Thr + Pro209Gln + Gly218Gln + Thr219Gln |
| Ala199Gly + Pro200Ser + Val202Gln + Thr207Asn + Asn211Ser + Thr212Ser + Thr219Pro |
| Pro200Gln + Val204Ala + Tyr208Leu + Thr212Glu + Tyr213Met + Thr214Asn + Leu216Gln |
| Ser203Asp + Val204Met + Thr207Gln + Tyr208Met + Pro209Gln + Asn217Ser + Thr219Asn |
| Ala199Gln + Pro200Ser + Gly201Gln + Tyr205Ala + Tyr213Cys + Thr214Gly + Gly218Glu |
| Ala199Thr + Pro200Ser + Thr207Gln + Tyr208Gln + Thr212Ser + Gly218Asp + Thr219Pro |
| Gly201Ser + Val204Pro + Tyr208Ser + Thr212Gly + Tyr213Val + Thr214Pro + Ser215Asp |
| Pro200Gln + Tyr208Cys + Pro209Gln + Thr212Gly + Tyr213Pro + Ser215Glu + Thr219Gly |
| Val204Met + Thr207Gln + Pro209Gly + Thr212Gly + Tyr213Cys + Thr214Gly + Leu216Met |
| Pro200Gly + Ser203Asp + Thr207Asn + Pro209Asn + Tyr213Ile + Leu216Cys + Asn217Ser |
| Pro200Asn + Gly201Asn + Tyr205Ile + Pro209Asp + Tyr213Met + Thr214Asn + Leu216Val |
| Ala199Asn + Ser203Glu + Val204Met + Pro209Gly + Tyr213Leu + Leu216Ala + Gly218Asn |
| Ala199His + Thr207Pro + Tyr213Ser + Thr214Asn + Asn217Ser + Gly218Ser + Thr219Glu |
| Ala199Ser + Gly201Pro + Val204Gln + Thr207Ser + Thr212Asn + Tyr213Pro + Gly218Glu |
| Ala199Ser + Pro200Asn + Tyr205Met + Tyr208Met + Thr212Asn + Thr214Gly + Leu216Met |
| Gly201Gln + Tyr205Asn + Thr207Asn + Pro209Asp + Thr212Gly + Tyr213Val + Leu216Ile |
| Pro200Asn + Tyr205Glu + Tyr208Met + Tyr213His + Thr214Ser + Asn217Gln + Thr219Gln |
| Ala199Gln + Pro200Gly + Val202Met + Tyr208Ile + Thr212Asp + Leu216Met + Gly218Pro |

TABLE 28-continued

| Loop 6 - Heptuple Substitution Mutation Variants |
|---|
| Ala199Ser + Pro200Gly + Gly201Gln + Val202Asn + Asn211Gln + Leu216Val + Gly218Pro |
| Ala199Asn + Val202Ser + Tyr205Cys + Thr207Gly + Tyr213Leu + Thr214Asp + Asn217Ser |
| Gly201Pro + Val202Asn + Val204Asn + Tyr205Ser + Asn211Glu + Thr212Ser + Gly218Asn |
| Ala199Ser + Val204Cys + Thr207Ser + Asn211Ser + Thr214Gln + Ser215Glu + Asn217Gln |
| Pro200Ser + Val202Met + Tyr205Gly + Tyr208Pro + Ser210Glu + Thr212Ser + Tyr213Gly |
| Pro200Ser + Val202Gln + Ser203Glu + Tyr205Cys + Thr207Gln + Tyr208Ile + Asn211Ser |
| Ala199Pro + Gly201Ser + Val204Ala + Thr207Ser + Pro209Gln + Tyr213Asp + Leu216His |
| Gly201Ser + Ser203Asp + Val204Gln + Tyr208Thr + Asn211Gln + Leu216Ser + Thr219Ser |
| Ala199Thr + Gly201Ser + Tyr205Pro + Tyr213Pro + Thr214Gly + Leu216Thr + Gly218Glu |
| Pro200Asn + Gly201Gln + Tyr208Val + Thr214Gln + Ser215Asp + Gly218Ser + Thr219Asn |
| Pro200Gln + Val202Met + Val204Gly + Tyr208Gly + Asn211Ser + Tyr213Pro + Gly218Asp |
| Ala199Asn + Pro200Gly + Tyr205Thr + Tyr208Val + Thr212Gly + Tyr213Ser + Leu216Val |
| Ala199Ser + Gly201Ser + Val202Gly + Tyr205Leu + Thr214Asn + Leu216Ala + Gly218Glu |
| Ala199Ser + Gly201Gln + Val204Ser + Tyr208Asn + Pro209Ser + Thr214Asn + Ser215Glu |
| Ala199Pro + Gly201Asn + Tyr208Cys + Tyr213Gly + Thr214Glu + Asn217Ser + Gly218Gln |
| Ala199Pro + Val202His + Tyr208Met + Pro209Asn + Thr212Asn + Thr214Glu + Ser215Asp |
| Ala199His + Val202Gly + Val204Ser + Thr207Gln + Pro209Asp + Ser210Asp + Asn211Ser |
| Ala199Gly + Pro209Glu + Ser210Glu + Thr212Gln + Tyr213Ala + Leu216Pro + Thr219Asn |
| Ala199His + Gly201Gln + Val202Met + Val204His + Thr207Gly + Pro209Glu + Ser210Asp |
| Ala199His + Val202Gln + Thr207Gly + Thr214Gln + Leu216Thr + Asn217Asp + Gly218Glu |
| Gly201Gln + Val204Thr + Tyr205Pro + Thr207Gly + Leu216Asn + Asn217Asp + Gly218Asp |

TABLE 28-continued

| Loop 6 - Heptuple Substitution Mutation Variants |
|---|
| Gly201Ser + Tyr208Thr + Pro209Gln + Tyr213Ser + Asn217Asp + Gly218Glu + Thr219Gly |
| Gly201Ser + Val202Cys + Tyr205Val + Thr207Gln + Tyr213Ile + Leu216Asp + Asn217Asp |
| Gly201Asn + Val202Glu + Ser203Glu + Val204Gly + Thr212Gly + Leu216Val + Thr219Pro |
| Val202Asp + Ser203Glu + Val204Asn + Thr207Pro + Tyr208Leu + Thr212Ser + Asn217Gln |
| Gly201Gln + Tyr208Ser + Pro209Asn + Asn211Gln + Tyr213Asp + Thr214Asp + Asn217Gln |
| Ala199Asn + Pro200Asn + Val204Thr + Ser210Asp + Asn211Glu + Tyr213Leu + Thr214Pro |
| Gly201Ser + Val202Ala + Tyr208Met + Ser210Asp + Asn211Asp + Thr212Asp + Asn217Ser |
| Ala199Ser + Pro200Gly + Gly201Asn + Val202Glu + Leu216Cys + Asn217Asp + Gly218Asn |
| Ala199Asn + Pro200Ser + Ser203Asp + Tyr205Cys + Tyr208Asn + Thr214Gln + Ser215Glu |
| Ala199Gln + Val202Gly + Ser203Glu + Tyr205Gly + Tyr213Met + Ser215Glu + Asn217Ser |
| Gly201Asn + Val202Gly + Ser203Asp + Tyr208Ile + Tyr213Pro + Ser215Glu + Asn217Ser |
| Val202Met + Ser203Glu + Thr207Asn + Thr214Gly + Ser215Asp + Leu216Glu + Asn217Asp |
| Ala199Gln + Ser203Glu + Val204Cys + Asn211Ser + Thr214Gly + Asn217Glu + Thr219Pro |
| Ala199Gln + Ser203Asp + Tyr205Thr + Thr207Ser + Thr212Asn + Asn217Asp + Gly218Asn |
| Pro200Ser + Val202Ser + Ser203Asp + Val204Gly + Thr212Asn + Tyr213Met + Asn217Glu |
| Ser203Glu + Tyr205Met + Tyr208Thr + Pro209Gly + Asn217Glu + Gly218Asn + Thr219Ser |
| Ala199Gln + Tyr205Leu + Tyr208Pro + Asn211Glu + Thr212Asp + Tyr213Asp + Thr214Gly |
| Gly201Pro + Val202Thr + Val204His + Tyr205Met + Asn211Glu + Thr212Asp + Tyr213Asp |
| Gly201Pro + Ser203Glu + Tyr205Asp + Thr207Ser + Ser215Asp + Leu216His + Thr219Ser |
| Ala199Asn + Val202Gln + Val204Ser + Pro209Gly + Ser210Glu + Thr212Asp + Asn217Gln |
| Pro200Gly + Gly201Pro + Tyr208Val + Pro209Glu + Asn211Asp + Thr212Gln + Thr219Ser |
| Ala199Asn + Pro200Gln + Val202Ala + Val204Pro + Thr207Asn + Pro209Glu + Asn211Glu |
| Ala199Asn + Ser203Asp + Thr207Gly + Asn211Ser + Ser215Glu + Asn217Asp + Gly218Gln |
| Pro200Gln + Ser203Glu + Val204Gly + Tyr213Pro + Ser215Glu + Asn217Glu + Thr219Gln |
| Pro200Gly + Val202Asp + Ser203Asp + Thr207Ser + Thr212Gly + Ser215Glu + Gly218Ser |
| Val202Glu + Ser203Asp + Tyr208Ser + Asn211Gln + Tyr213Ala + Ser215Asp + Thr219Ser |
| Ala199Gln + Ser203Asp + Tyr205Met + Thr214Asp + Ser215Glu + Leu216Cys + Asn217Gln |
| Gly201Gln + Ser203Glu + Tyr205Glu + Pro209Gln + Asn211Ser + Thr214Glu + Leu216Glu |
| Gly201Asn + Val202Cys + Ser203Asp + Tyr205Asp + Thr214Asp + Leu216Gly + Thr219Pro |
| Ala199Gly + Val202Met + Ser203Glu + Val204Pro + Tyr205Glu + Thr207Ser + Thr214Asp |
| Gly201Ser + Val204Met + Pro209Gly + Asn211Ser + Tyr213Cys + Thr214Glu + Leu216Asp |
| Gly201Pro + Val202Asp + Thr207Gln + Thr212Ser + Asn217Asp + Gly218Asn + Thr219Asp |
| Pro200Ser + Val204Gly + Tyr205Gly + Tyr208Cys + Thr214Ser + Ser215Glu + Asn217Glu |
| Gly201Asn + Tyr205Ile + Tyr213Ile + Thr214Asn + Ser215Glu + Asn217Asp + Thr219Pro |
| Pro200Ser + Val202Gln + Tyr208His + Thr212Pro + Thr214Ser + Ser215Glu + Asn217Glu |
| Pro200Gly + Val204Gln + Thr207Ser + Tyr213Leu + Thr214Gln + Ser215Glu + Asn217Glu |
| Thr207Gly + Ser210Asp + Asn211Asp + Thr212Gly + Tyr213Asp + Asn217Gln + Thr219Gln |
| Ser203Glu + Thr207Asn + Tyr208His + Asn211Gln + Thr214Asp + Leu216Glu + Asn217Glu |
| Gly201Pro + Val202Met + Val204Ser + Tyr205His + Thr212Gly + Asn217Glu + Thr219Asp |
| Ala199Asn + Val204Cys + Tyr208Cys + Tyr213Ala + Thr214Glu + Leu216Asp + Asn217Glu |
| Pro200Gln + Thr207Gly + Tyr208Cys + Thr214Asp + Ser215Asp + Leu216Gln + Asn217Asp |
| Ala199Gln + Val204His + Asn211Ser + Thr212Ser + Thr214Glu + Ser215Glu + Asn217Glu |
| Val202Asp + Ser203Asp + Tyr205Ala + Thr207Gln + Tyr213Met + Thr214Glu + Ser215Asp |
| Ala199Gly + Pro200Gln + Val204Cys + Thr212Glu + Thr214Glu + Ser215Glu + Leu216Gln |
| Val204Ala + Thr207Gly + Ser210Asp + Asn211Asp + Thr212Glu + Thr214Glu + Asn217Ser |
| Gly201Pro + Pro209Ser + Ser215Glu + Leu216Glu + Asn217Asp + Gly218Ser + Thr219Asp |
| Pro200Asn + Gly201Pro + Ser203Asp + Thr207Gln + Asn217Asp + Gly218Ser + Thr219Glu |
| Ala199Pro + Val202Gly + Ser203Asp + Pro209Gln + Thr212Asn + Ser215Glu + Gly218Asp |
| Ala199Gln + Pro200Ser + Gly201Ser + Tyr205Gln + Ser210Asp + Thr212Glu + Thr214Asp |
| Ala199Pro + Pro200Ser + Thr207Gln + Ser210Glu + Thr212Asp + Thr214Asp + Thr219Ser |
| Ala199His + Ser203Asp + Val204Gly + Thr207Gly + Asn211Gln + Thr214Ser + Gly218Glu |
| Gly201Asn + Val202Asp + Val204Gly + Tyr208Val + Asn211Gln + Asn217Ser + Thr219Asp |
| Val202Asn + Tyr205Glu + Thr207Gln + Tyr208Leu + Thr214Asp + Asn217Asp + Gly218Pro |
| Ala199Asn + Gly201Asn + Ser203Asp + Tyr208Asn + Thr214Glu + Leu216Cys + Thr219Gly |
| Val202Cys + Ser203Asp + Val204Ser + Tyr208Thr + Thr214Asp + Asn217Gln + Thr219Pro |
| Ser203Asp + Tyr208Pro + Pro209Ser + Asn211Ser + Tyr213Met + Thr214Asp + Thr219Pro |
| Ala199Asn + Pro200Gln + Ser203Asp + Thr212Glu + Thr214Asp + Ser215Glu + Asn217Ser |
| Pro200Asn + Gly201Asn + Val202Glu + Ser203Asp + Thr212Gly + Ser215Glu + Thr219Asp |
| Ala199Gln + Gly201Gln + Pro209Gly + Ser210Glu + Thr212Pro + Tyr213Glu + Leu216Ala |
| Pro200Ser + Val204Ser + Thr207Asn + Tyr208Leu + Ser210Asp + Asn211Ser + Tyr213Asp |
| Ala199His + Ser203Asp + Tyr205Asp + Thr207Asn + Tyr208Ile + Leu216Ser + Gly218Asp |
| Ala199Gln + Gly201Pro + Val202Glu + Tyr205Glu + Pro209Gly + Thr214Asp + Leu216Gln |
| Gly201Asn + Val204Pro + Tyr208Cys + Ser210Glu + Asn211Glu + Thr212Pro + Thr214Asp |
| Ala199His + Pro200Asn + Tyr208Val + Thr214Glu + Ser215Glu + Leu216Glu + Thr219Asp |
| Pro200Gly + Val202Glu + Tyr205Pro + Tyr208Ala + Thr214Glu + Asn217Asp + Gly218Asn |
| Val202Glu + Tyr205His + Pro209Gln + Thr214Glu + Ser215Asp + Asn217Ser + Gly218Asp |
| Pro200Ser + Tyr205Leu + Thr212Gln + Thr214Asp + Ser215Glu + Gly218Glu + Thr219Asn |
| Ser203Asp + Val204Gly + Tyr205Ser + Thr212Glu + Thr214Pro + Ser215Asp + Asn217Glu |
| Pro200Asn + Val204Gln + Pro209Glu + Ser210Glu + Asn211Glu + Thr212Asn + Ser215Asp |
| Ala199Gln + Thr207Pro + Tyr208Cys + Pro209Gln + Tyr213Asp + Thr214Asn + Leu216Asp |
| Ala199Gly + Pro209Glu + Ser210Asp + Thr214Glu + Ser215Glu + Gly218Pro + Thr219Gly |
| Ala199His + Thr207Ser + Tyr208Thr + Pro209Gly + Ser215Asp + Asn217Gln + Gly218Glu |
| Ala199Ser + Ser203Glu + Tyr208Ala + Asn211Gln + Ser215Glu + Leu216Cys + Thr219Asp |
| Gly201Pro + Val202Gly + Ser203Glu + Tyr205Thr + Tyr208Ala + Ser215Asp + Thr219Asp |
| Pro200Gln + Val202His + Ser203Glu + Asn211Gln + Thr212Asp + Thr214Asp + Thr219Gly |
| Gly201Pro + Ser203Asp + Thr207Gln + Ser210Glu + Thr214Glu + Ser215Asp + Thr219Ser |
| Ala199Ser + Tyr205Gly + Thr207Ser + Ser210Asp + Tyr213Glu + Ser215Glu + Leu216Glu |

TABLE 28-continued

| Loop 6 - Heptuple Substitution Mutation Variants |
| --- |
| Val204Thr + Thr207Pro + Ser210Glu + Asn211Glu + Thr212Glu + Gly218Asp + Thr219Ser |
| Val202Asp + Ser203Asp + Thr207Gly + Pro209Asn + Asn211Glu + Asn217Asp + Gly218Ser |
| Pro200Ser + Ser203Asp + Val204Pro + Tyr208Ile + Thr214Asp + Asn217Ser + Gly218Asp |
| Pro200Ser + Gly201Pro + Val202Gly + Ser203Glu + Tyr205Glu + Pro209Asp + Tyr213Glu |
| Ala199Gly + Gly201Gln + Val202Ser + Asn211Asp + Ser215Glu + Leu216Asp + Asn217Glu |
| Ala199Thr + Tyr205Gln + Thr207Gln + Pro209Gln + Thr212Asp + Ser215Glu + Gly218Gln |
| Ala199Gln + Val204Ser + Tyr205Glu + Thr207Asn + Ser210Glu + Thr212Glu + Asn217Gln |
| Tyr205Val + Tyr208Pro + Pro209Gln + Ser210Asp + Thr212Glu + Ser215Glu + Leu216Gly |
| Ala199Pro + Gly201Ser + Thr214Glu + Ser215Glu + Asn217Gln + Gly218Glu + Thr219Asp |
| Ser203Glu + Ser210Asp + Asn211Gln + Thr212Glu + Tyr213Ser + Thr214Glu + Leu216Cys |
| Ala199His + Pro200Gln + Pro209Asn + Tyr213Gln + Thr214Asp + Leu216Glu + Thr219Asp |
| Ala199Asn + Ser203Asp + Tyr205Glu + Thr207Asn + Pro209Asn + Asn211Glu + Leu216Glu |
| Ala199Thr + Gly201Pro + Ser210Glu + Thr214Asp + Ser215Asp + Asn217Ser + Thr219Ser |
| Ser203Glu + Thr207Pro + Tyr208Ala + Ser210Asp + Ser215Glu + Asn217Asp + Thr219Pro |
| Val202Asp + Val204Cys + Tyr205Asp + Tyr208Ala + Pro209Gly + Gly218Gln + Thr219Glu |
| Val202Ala + Val204Thr + Tyr208Leu + Asn211Glu + Thr212Glu + Ser215Asp + Leu216Glu |
| Pro200Asn + Val202Gln + Thr207Gln + Pro209Ser + Asn211Asp + Thr214Glu + Leu216Asp |
| Ala199Asn + Val202Met + Thr207Asn + Pro209Glu + Tyr213Glu + Ser215Glu + Asn217Asp |
| Ala199Gly + Val202Cys + Val204Gln + Tyr205Asp + Ser210Asp + Asn211Gln + Thr214Glu |
| Ala199His + Tyr208Thr + Pro209Asp + Ser215Asp + Leu216Met + Asn217Asp + Gly218Asp |
| Ala199Asn + Pro200Asn + Gly201Gln + Pro209Asp + Thr214Ser + Ser215Asp + Leu216Asp |
| Ala199Asn + Pro200Gln + Gly201Ser + Val202Asp + Asn211Asp + Ser215Glu + Leu216Asp |
| Ala199Thr + Val202Asp + Val204Cys + Ser210Asp + Tyr213Ile + Ser215Asp + Leu216Asp |
| Gly201Ser + Val202Glu + Tyr205Gly + Tyr208Leu + Ser210Asp + Ser215Glu + Asn217Asp |
| Gly201Gln + Thr207Ser + Tyr208His + Pro209Glu + Asn211Glu + Tyr213Asp + Asn217Glu |
| Pro200Gly + Gly201Asn + Ser203Glu + Tyr208Cys + Thr212Asn + Asn217Gln + Thr219Glu |
| Ala199Gly + Gly201Asn + Val202His + Val204Ala + Pro209Asp + Ser210Glu + Ser215Glu |
| Gly201Asn + Val202Glu + Pro209Gly + Ser210Glu + Thr212Glu + Tyr213Thr + Thr214Glu |
| Val202Cys + Val204Ala + Tyr205Glu + Thr212Ser+ Ser215Glu + Asn217Gln + Thr219Asp |
| Gly201Ser + Ser203Glu + Ser210Glu + Asn211Ser + Thr212Glu + Ser215Glu + Leu216Pro |
| Ala199His + Ser203Glu + Thr207Gln + Ser210Asp + Thr212Asp + Ser215Asp + Gly218Gln |
| Ala199Gln + Pro200Asn + Gly201Gln + Val204Asn + Thr214Asp + Ser215Glu + Thr219Glu |
| Ala199Pro + Gly201Pro + Ser203Asp + Tyr205Val + Pro209Glu + Ser215Glu + Thr219Pro |
| Pro200Gly + Ser203Asp + Thr207Gln + Asn211Glu + Tyr213Glu + Leu216Thr + Asn217Gln |
| Val202Asp + Tyr205Glu + Tyr208Gly + Thr212Asp + Tyr213Ala + Leu216Ile + Thr219Pro |
| Pro200Ser + Val202Glu + Tyr205Asp + Asn211Glu + Thr212Asp + Tyr213Cys + Thr219Gly |
| Val204Pro + Tyr205Asp + Asn211Asp + Thr214Pro + Ser215Asp + Asn217Ser + Thr219Pro |
| Gly201Asn + Ser203Asp + Pro209Gln + Tyr213Thr + Thr214Asp + Gly218Asn + Thr219Glu |
| Pro200Gln + Val204Thr + Thr212Asn + Tyr213Glu + Thr214Pro + Asn217Asp + Gly218Asp |
| Ala199Gln + Gly201Gln + Val204Asn + Tyr208Met + Ser210Glu + Thr214Glu + Asn217Ser |
| Gly201Pro + Val204Thr + Tyr208Gly + Asn211Asp + Thr214Asp + Asn217Glu + Gly218Asp |
| Pro200Asn + Pro209Glu + Ser210Asp + Asn211Ser + Thr214Ser + Leu216Cys + Thr219Asp |
| Ser203Asp + Thr207Ser + Tyr208Asn + Pro209Asp + Ser210Asp + Thr214Gln + Asn217Gln |
| Val204Ser + Tyr208Pro + Pro209Ser + Asn211Asp + Leu216Met + Asn217Asp + Gly218Asp |
| Tyr205Ser + Tyr208Cys + Pro209Asn + Asn211Asp + Thr212Asn + Leu216Glu + Asn217Asp |
| Pro200Gly + Ser210Asp + Thr212Pro + Tyr213Val + Asn217Ser + Gly218Asp + Thr219Asp |
| Val202Cys + Tyr205Ala + Thr207Asn + Asn211Asp + Tyr213Val + Ser215Asp + Leu216Asp |
| Ala199Gln + Val202Glu + Ser203Asp + Val204Thr + Pro209Gln + Asn211Asp + Tyr213Pro |
| Gly201Pro + Val202Glu + Ser203Glu + Val204Gly + Pro209Gln + Thr212Glu + Leu216Ala |
| Pro200Gln + Val202Asp + Ser203Asp + Tyr208Ala + Thr212Glu + Leu216Val + Gly218Gln |
| Ala199Thr + Gly201Gln + Val202Gly + Ser210Glu + Asn211Asp + Ser215Asp + Leu216Ala |
| Ala199Gly + Gly201Gln + Val204Asn + Ser210Asp + Asn211Asp + Ser215Glu + Thr219Asn |
| Ala199Asn + Val202Ala + Ser203Asp + Val204Gln + Ser210Glu + Thr212Glu + Leu216Glu |
| Val202Asp + Val204Asn + Pro209Ser + Ser210Asp + Asn211Asp + Tyr213Asn + Leu216Met |
| Val202Pro + Ser203Asp + Val204Ser + Thr212Glu + Tyr213Asp + Thr214Asn + Gly218Asp |
| Ser203Glu + Val204Pro + Tyr205Asp + Pro209Glu + Thr212Gln + Tyr213Asn + Gly218Asp |
| Pro200Ser + Thr207Gly + Ser210Glu + Thr212Gly + Thr214Glu + Ser215Asp + Gly218Glu |
| Val202Met + Val204His + Ser210Glu + Thr212Asp + Tyr213Ile + Leu216Asp + Gly218Glu |
| Ser203Glu + Tyr208Ser + Asn211Asp + Thr212Pro + Thr214Asn + Ser215Glu + Gly218Pro |
| Ala199Thr + Gly201Pro + Ser203Asp + Tyr205Gly + Asn211Asp + Ser215Glu + Asn217Ser |
| Pro200Gln + Gly201Asn + Ser203Glu + Pro209Asn + Asn211Asp + Thr212Gly + Ser215Glu |

TABLE 29

| Multi-loop Double Mutation Variants |
| --- |
| Leu 95Gly + Ser203Glu |
| Thr 58Gln + Asp 59Glu |
| Tyr103Cys + Leu216Gln |
| Val202Gln + Thr212Gly |
| Gly126Gln + Gly156Glu |
| Thr214Gly + Ser215Glu |
| Asn 96Gln + Ile106Ala |
| Gly101Asp + Tyr205Pro |
| Asn 61Ser + Gly165Gln |
| Gly 64Gln + Thr132Gly |
| Asp 59Glu + Tyr205Asn |
| Ser100Glu + Tyr205His |
| Gln161Glu + Tyr205Pro |
| Thr 58Asp + Tyr205Ile |
| Asn 61Asp + Asn162Ser |
| Gln161Glu + Pro209Gln |
| Gly 62Asp + Pro209Asn |
| Ile106Leu + Asn211Asp |
| Tyr166Pro + Ser215Glu |
| Ile106Leu + Pro209Glu |
| Thr163Pro + Val202Cys |
| Thr 65Pro + Leu216Ser |
| Thr132Gly + Phe188Val |
| Gly156Glu + Ala186Thr |

TABLE 29-continued

Multi-loop Double Mutation Variants

Pro128Ser + Ser160Asp
Gly 62Gln + Gly165Asp
Leu 95Gln + Pro128Glu
Ser 97Glu + Asn211Ser
Leu 95Asn + Phe188Leu
Leu125Gln + Gly159Glu
Ser187Glu + Tyr213Ala
Tyr205Cys + Asn211Asp
Asn162Gln + Tyr213Pro
Ser158Asp + Leu216Gln
Gly156Asp + Val202Ala
Ser100Asp + Tyr205Ile
Gly 99Asn + Thr214Glu
Thr 58Asp + Gly130Gln
Gly156Glu + Tyr208Pro
Ala105Pro + Leu216Ile
Ser187Asp + Tyr205Gln
Leu125Asn + Ser187Glu
Thr 65Gln + Thr102Glu
Tyr103Ile + Tyr205Glu
Thr132Asp + Gly218Gln
Asn211Ser + Thr212Asp
Thr212Gln + Ser215Glu
Thr132Pro + Tyr205Gly
Tyr103Glu + Thr132Ser
Gly165Gln + Ser203Glu
Gly 60Pro + Thr 65Pro
Gly 99Asn + Gly153Asn
Pro128Asn + Val202His
Ala105Glu + Gly130Ser
Thr212Gly + Gly218Glu
Phe188Val + Tyr205Ser
Asn217Glu + Thr219Gly
Leu 95Gln + Ser215Asp
Val 94Gln + Thr212Glu
Asn 61Ser + Ser203Asp
Ser129Glu + Asn154Gln
Gly 62Glu + Thr219Asn
Ser 97Glu + Tyr213His
Gly 99Asp + Ile164Thr
Gly101Pro + Ser215Asp
Thr 58Pro + Tyr205Gln
Gly101Gln + Tyr208Gln
Asn 61Gln + Thr212Asp
Thr212Asp + Leu216Ile
Asn211Glu + Leu216His
Gly153Glu + Thr163Gln
Thr132Asn + Tyr205Asp
Asn 61Ser + Ser203Glu
Ser215Asp + Leu216Ser
Gly 60Asp + Met198Gln
Ser158Glu + Tyr205Met
Phe188Leu + Thr212Glu
Gly130Pro + Ser190Glu
Gly101Asp + Gly126Ser
Ala105Gly + Ser157Asp
Asn 61Ser + Ser131Asp
Asn 61Ser + Phe188Ser
Ser100Glu + Asn162Gln
Thr 58Gly + Pro128Asp
Ser100Glu + Tyr205Ala
Gly127Glu + Tyr213Thr
Asn154Glu + Leu216Gln
Ser 97Asp + Ala199Pro
Ser203Glu + Leu216Ser
Gly126Gln + Ser215Glu
Gly 60Ser + Asn154Glu
Thr 65Ser + Gly156Asp
Pro128Ser + Thr163Gln
Ser215Asp + Leu216Val
Ser129Glu + Leu216Ala
Asn211Asp + Tyr213Leu
Val 94Ser + Phe188Val
Ser158Glu + Thr212Gln
Gly 99Pro + Asn154Gln
Val202Ser + Tyr205Glu
Tyr205Val + Asn217Glu
Val 94Gly + Ser215Asp
Tyr205Glu + Tyr213Pro
Asn 96Ser + Gly127Glu
Tyr205Thr + Thr214Gly
Gly 62Ser + Thr 65Ser
Thr 65Glu + Pro128Asn
Ser215Asp + Leu216Gln
Asp 59Glu + Gly 60Pro
Val 94Thr + Leu216Met
Ser 97Glu + Thr212Gln
Gly101Asp + Val202Asn
Ser129Asp + Val202Gly
Tyr103Ala + Thr132Ser
Leu 95Met + Leu216Asp
Ser100Asp + Gly101Pro
Ser100Asp + Thr219Pro
Val 94Asn + Ser215Asp
Gly153Asn + Tyr205Asp
Thr 58Glu + Ile106Cys
Thr 65Glu + Tyr103Pro
Val 94Met + Ser 98Glu
Ser210Glu + Gly218Ser
Leu125Pro + Ala199His
Ile106Gly + Thr212Glu
Tyr205Ile + Thr214Pro
Gly130Glu + Tyr208His
Ser187Asp + Leu216Val
Thr102Glu + Thr219Gln
Leu125Ser + Gly153Glu
Gly153Asn + Val202Asp
Thr163Glu + Tyr205Gly
Ser129Glu + Tyr166Pro
Gly153Gln + Pro209Gln
Thr212Ser + Ser215Glu
Thr163Asp + Tyr205His
Asn154Glu + Tyr166Thr
Asn 96Ser + Ala105Gly
Gly101Ser + Phe188Gly
Gly153Glu + Gly218Asn
Ser100Asp + Thr212Pro
Gly126Pro + Gly156Asp
Leu125Ser + Ser215Glu
Asp 59Glu + Thr 65Gly
Gly156Pro + Gly159Asp
Val202Cys + Tyr213Ser
Leu 95Met + Ser131Glu
Ser 97Asp + Gly 99Ser
Asn 61Gln + Leu 95Asp
Gly126Asn + Tyr205Glu
Gly159Pro + Gly218Asn
Leu 95Thr + Leu216Ala
Ala105Glu + Leu216Thr
Thr102Glu + Gly130Pro
Gly 64Gln + Ser215Glu
Tyr103Asp + Gly126Asn
Gly101Glu + Gly127Gln
Thr132Asn + Ser160Asp
Thr 58Pro + Gly153Asn
Ser203Glu + Thr214Ser
Tyr103His + Ser129Asp
Ser 98Asp + Pro209Ser
Asp 59Glu + Tyr205Ser
Gly 60Gln + Ser215Asp
Thr132Asp + Val202Asn
Gly218Ser + Thr219Gly
Ser190Asp + Val202Thr
Asp 59Glu + Gln161Asn
Leu216Asn + Asn217Asp
Val 94Asp + Tyr205Asn
Tyr103Ser + Ser203Asp
Gly 99Pro + Phe188Gln
Ser 97Asp + Leu216His
Thr163Asp + Leu216Asn
Asn 61Asp + Thr132Ser
Leu 95Asn + Ser215Asp
Ser100Asp + Thr132Gly
Tyr166Thr + Asn211Gln

TABLE 29-continued

Multi-loop Double Mutation Variants

Thr207Pro + Leu216Thr
Ile106Ala + Gly165Asp
Tyr205Asn + Ser215Glu
Leu 95Asn + Val202Gln
Ser160Asp + Phe188Gly
Gly 64Ser + Asn 96Gln
Gly101Asp + Asn154Gln
Gly 64Asn + Ser157Glu
Phe 88Asp + Tyr213Asn
Ser215Glu + Leu216Ile
Tyr103His + Ser187Glu
Asn 96Ser + Thr214Asn
Gly 62Asn + Ser 98Asp
Ile106Ser + Ser157Glu
Thr 65Glu + Thr212Gly
Gly127Ser + Ser215Asp
Gly156Ser + Asn217Glu
Ser 98Asp + Tyr103Thr
Gly127Asn + Gly165Pro
Gly153Glu + Leu216Met
Ser129Asp + Gly165Pro
Asn 61Asp + Thr163Gln
Gly126Asn + Tyr205Met
Gly165Gln + Ser215Glu
Thr 65Glu + Gly101Pro
Val 94Gln + Gly165Glu
Tyr103Ile + Ser190Glu
Asn217Gln + Gly218Ser
Ser 98Glu + Gly 99Asn
Thr102Asp + Thr212Ser
Thr212Ser + Ser215Asp
Gly130Glu + Pro209Asn
Pro128Glu + Gly165Pro
Thr 58Asn + Leu125Glu
Leu125His + Thr163Ser
Thr212Asp + Tyr213Ala
Thr 65Pro + Ser210Glu
Val 94Thr + Thr132Gly
Tyr205cys + Thr214Gln
Gly127Gln + Ala186Gln
Gly127Glu + Tyr205cys
Ser 98Glu + Gly130Ser
Gly127Glu + Phe188Tyr
Phe188Asp + Asn211Ser
Gly 64Asn + Leu216Asp
Ser203Glu + Thr212Ser
Tyr166Val + Ser210Asp
Gly165Glu + Tyr205Met
Asn 96Gln + Thr132Glu
Ser 98Glu + Gly101Pro
Leu125Cys + Ser215Asp
Leu125Cys + Gly126Ser
Gly 99Gln + Ser210Asp
Ser160Asp + Phe188Leu
Val204Gln + Ser215Glu
Asn 61Gln + Leu216Asp
Leu125Gly + Ser155Asp
Ala186Pro + Val204Gln
Ile106Met + Ser160Asp
Leu125Ile + Leu216Ser
Gly 60Ser + Ser 97Glu
Gly165Asp + Tyr213Gln
Pro128Glu + Asn154Gln
Gly 60Asp + Gly126Pro
Ser203Glu + Leu216Ala
Gly126Glu + Val202Gly
Thr132Asp + Tyr213Ser
Ser157Asp + Thr212Ser
Gly130Ser + Ser203Glu
Gly 99Asn + Gly130Ser
Asp 59Glu + Gly159Asn
Gly153Asn + Thr212Asp
Glyl53Asp + Tyr205Ser
Ser100Glu + Tyr205Thr
Gly126Asn + Asn154Glu
Ser190Asp + Tyr205Val
Thr102Glu + Tyr166Thr Ser157Glu + Pro209Gly
Ser100Asp + Tyr205Leu
Ser131Glu + Thr132Asn
Gly127Asp + Leu216Thr
Ser210Glu + Asn217Gln
Asn 61Asp + Ile106Gln
Ala105Pro + Tyr205Pro
Ser190Asp + Leu216Cys
Ser203Glu + Tyr205Thr
Leu 95Asp + Asn 96Ser
Tyr205Ala + Thr212Glu
Thr163Gln + Phe188Glu
Tyr103Ala + Thr212Asp
Ser155Glu + Gly218Asn
Val 94Thr + Thr163Ser
Thr102Glu + Asn217Gln
Gly159Ser + Val202Glu
Asn154Ser + Tyr166Ala
Asp 59Glu + Phe188Gly
Thr163Gln + Gly218Ser
Gly153Asn + Tyr205Val
Ser129Glu + Leu216Pro
Gly126Ser + Thr212Glu
Ser203Asp + Leu216Asn
Gly126Glu + Thr212Pro
Val 94Pro + Ala186Glu
Ser129Asp + Gly153Asn
Gly165Ser + Ser215Asp
Gly 60Gln + Ser187Glu
Ser203Asp + Leu216His
Gly101Glu + Ile106Met
Val 94Glu + Gly127Gln
Val202Gly + Leu216His
Asp 59Glu + Thr132Asn
Val202Asn + Tyr205Pro
Leu 95Ile + Ser215Glu
Pro128Glu + Leu216Pro
Ser 97Asp + Tyr213Met
Ser187Glu + Leu216cys
Asn154Ser + Gly156Gln
Leu125Gly + Gly126Ser
Asn154Ser + Leu216Asn
Gly126Asn + Val202Asn
Asn 96Gln + Gly127Ser
Gly 64Ser + Thr212Gly
Ser160Asp + Asn211Ser
Ser210Glu + Gly218Gln
Tyr205Ala + Thr212Asp
Ser158Asp + Leu216Ser
Thr212Gly + Ser215Glu
Ala199Ser + Val202Ala
Ser129Glu + Tyr205Asn
Asn154Gln + Gly201Gln
Ser190Glu + Thr212Ser
Thr 58Pro + Ser160Asp
Gly127Glu + Gly130Ser
Asn154Glu + Thr212Gly
Gly153Ser + Gln161Asn
Tyr205Thr + Ser210Glu
Leu125Gly + Pro200Gln
Tyr103Val + Thr132Gly
Gly126Asp + Leu216Ala
Ser100Glu + Gly127Asn
Ser129Asp + Ala186Ser
Ser160Glu + Tyr205Ser
Thr163Glu + Ile164His
Gly159Ser + Gln161Glu
Asp 59Glu + Gly159Pro
Gly101Asp + Tyr166Cys
Thr 58Asn + Ser129Glu
Asn 61Glu + Thr214Ser
Gly127Ser + Ser203Glu
Gly127Pro + Gly130Asp
Gly127Glu + Val202Gly
Phe188Met + Ser203Glu
Ser 97Glu + Tyr166Asn
Gly 60Glu + Gly 99Asn

TABLE 29-continued

Multi-loop Double Mutation Variants

Asn162Glu + Asn217Ser
Thr102Asp + Leu216Gly
Gly 99Gln + Ala105Thr
Gly153Ser + Ser203Glu
Tyr103Pro + Ser158Glu
Ser187Glu + Tyr205Pro
Ser160Asp + Val204Thr
Ser100Asp + Leu216His
Gly101Asn + Ser203Asp
Asn 96Ser + Tyr205Pro
Thr132Gly + Thr212Pro
Ile106Pro + Val202Cys
Gly 62Ser + Pro209Glu
Phe188Cys + Leu216Asp
Leu 95Cys + Ser104Glu
Ser104Asp + Tyr205Met
Tyr205Glu + Thr214Gly
Gly153Glu + Leu216Asn
Val 94Thr + Ser100Glu
Thr 65Asp + Val202His
Val202Gln + Ser215Asp
Val 94Ser + Ala105Glu
Thr 58Pro + Gly153Asp
Ala105Asn + Ser203Glu
Ser104Asp + Ala105Gly
Gly126Gln + Ile164Val
Gly153Ser + Ser215Glu
Pro200Gly + Ser215Glu

TABLE 33

Multi-loop Triple Mutation Variants

| | | |
|---|---|---|
| Thr58Gln | + Leu95Gly | + Ser203Glu |
| Asp59Glu | + Tyr103Cys | + Leu216Gln |
| Gly156Glu | + Val202Gln | + Thr212Gly |
| Gly126Gln | + Thr214Gly | + Ser215Glu |
| Asn96Gln | + Ile106Ala | + Gly156Glu |
| Asn61Ser | + Gly101Asp | + Tyr205Pro |
| Gly64Gln | + Thr132Gly | + Gly165Gln |
| Thr65Pro | + Thr163Pro | + Val202Cys |
| Thr132Gly | + Phe188Val | + Leu216Ser |
| Leu95Asn | + Ser97Glu | + Asn211Ser |
| Asn162Gln | + Ser187Asp | + Tyr213Pro |
| Ser100Asp | + Val202Ala | + Tyr205Ile |
| Thr58Asp | + Gly99Asn | + Gly130Gln |
| Gly156Glu | + Tyr208Pro | + Leu216Ile |
| Thr65Gln | + Leu125Asn | + Ser187Glu |
| Asn211Ser | + Thr212Asp | + Gly218Gln |
| Tyr205Gly | + Thr212Gln | + Ser215Glu |
| Thr58Glu | + Gly60Pro | + Thr65Pro |
| Asn96Gln | + Gly153Pro | + Leu216Val |
| Gly99Asn | + Gly153Asn | + Pro209Glu |
| Ala105Glu | + Pro128Asn | + Val202His |
| Tyr205Ser | + Thr212Gly | + Gly218Glu |
| Gly99Gln | + Asn217Glu | + Thr219Gly |
| Leu95Gln | + Val202Thr | + Ser215Asp |
| Gly101Pro | + Ile164Thr | + Ser215Asp |
| Thr58Pro | + Gly130Asp | + Tyr205Gln |
| Gly101Gln | + Ser190Glu | + Tyr208Gln |
| Asn61Ser | + Thr212Asp | + Leu216Ile |
| Asn61Ser | + Thr132Asn | + Tyr205Asp |
| Gly130Pro | + Phe188Leu | + Thr212Glu |
| Asn61Ser | + Ala105Gly | + Ser131Asp |
| Asn61Ser | + Asn162Gln | + Phe188Ser |
| Gly126Gln | + Ser203Glu | + Leu216Ser |
| Thr65Ser | + Gly156Asp | + Thr163Gln |
| Pro128Ser | + Ser215Glu | + Leu216Val |
| Val94Ser | + Ser100Asp | + Phe188Val |
| Gly99Pro | + Asn154Gln | + Ser203Glu |
| Tyr166Asp | + Tyr205Thr | + Thr214Gly |
| Gly62Ser | + Thr65Ser | + Asn211Glu |
| Thr65Glu | + Pro128Asn | + Leu216Gln |
| Val94Thr | + Thr212Gln | + Leu216Met |

TABLE 33-continued

Multi-loop Triple Mutation Variants

| | | |
|---|---|---|
| Ser129Asp | + Thr132Ser | + Val202Gly |
| Leu95Met | + Tyr103Ala | + Leu216Asp |
| Val94Met | + Ser98Glu | + Tyr103Pro |
| Leu125Pro | + Ala199His | + Ser203Glu |
| Ile106Gly | + Tyr205Ile | + Thr214Pro |
| Ser129Glu | + Tyr166Pro | + Tyr205Gly |
| Pro209Gln | + Thr212Ser | + Ser215Glu |
| Asn154Glu | + Tyr166Thr | + Tyr205His |
| Asn96Ser | + Gly101Ser | + Ala105Gly |
| Gly153Glu | + Phe188Gly | + Gly218Asn |
| Gly126Pro | + Gly156Asp | + Thr212Pro |
| Gly156Pro | + Gly159Asp | + Val202Cys |
| Leu95Met | + Ser97Asp | + Gly99Ser |
| Gly126Asn | + Gly159Pro | + Gly218Asn |
| Thr65Gln | + Leu95Thr | + Leu216Ala |
| Tyr103Asp | + Gly126Asn | + Gly127Gln |
| Thr58Pro | + Ala105Glu | + Gly153Asn |
| Gly60Gln | + Tyr205Ser | + Ser215Asp |
| Thr132Asp | + Gly218Ser | + Thr219Gly |
| Tyr103Ser | + Phe188Gln | + Ser203Asp |
| Ser97Asp | + Gly99Pro | + Leu216His |
| Asn61Asp | + Thr132Ser | + Leu216Asn |
| Leu95Asn | + Thr132Gly | + Ser215Asp |
| Tyr166Thr | + Asn211Gln | + Leu216Thr |
| Ile106Ala | + Gly165Asp | + Thr207Pro |
| Leu95Asn | + Val202Gln | + Ser215Glu |
| Gly64Ser | + Gly101Asp | + Asn154Gln |
| Thr58Asn | + Gly64Asn | + Ser157Glu |
| Gly62Asn | + Asn96Ser | + Thr214Asn |
| Gly130Asp | + Phe188Asn | + Gly218Pro |
| Gly99Ser | + Pro128Glu | + Leu216Gly |
| Val94Ala | + Pro209Ser | + Ser215Asp |
| Leu95Thr | + Gly126Gln | + Leu216Gly |
| Asp59Glu | + Gly159Ser | + Tyr205Pro |
| Val202Gln | + Ser203Glu | + Tyr205Asn |
| Thr58Ser | + Ser190Glu | + Tyr205Pro |
| Leu95Asn | + Tyr205Ala | + Pro209Glu |
| Thr58Asn | + Gly153Pro | + Ser210Glu |
| Ser131Glu | + Thr132Asn | + Gly165Asn |
| Gly127Ser | + Thr212Asn | + Ser215Asp |
| Thr65Gly | + Thr102Asp | + Gly127Asn |
| Gly60Asn | + Tyr205Thr | + Asn217Asp |
| Ala199Ser | + Val202Ala | + Thr212Gly |
| Thr58Pro | + Gly130Ser | + Ser160Asp |
| Gly153Ser | + Asn154Glu | + Thr212Gly |
| Leu125Gly | + Tyr205Thr | + Ser210Glu |
| Tyr103Val | + Thr132Gly | + Pro200Gln |
| Ser100Glu | + Gly127Asn | + Leu216Ala |
| Ser160Glu | + Ala186Ser | + Tyr205Ser |
| Gly159Ser | + Thr163Glu | + Ile164His |
| Phe188Met | + Val202Gly | + Ser203Glu |
| Thr102Asp | + Ala105Thr | + Leu216Gly |
| Thr58Asp | + Asn96Ser | + Tyr205Pro |
| Ser97Asp | + Thr132Gly | + Thr212Pro |
| Ile106Pro | + Val202Cys | + Ser215Asp |
| Leu95Cys | + Phe188Cys | + Leu216Asp |
| Thr65Asp | + Val94Thr | + Val202His |
| Thr58Pro | + Ala105Asn | + Gly153Asp |
| Ser104Asp | + Ala105Gly | + Ile164Val |
| Gly126Gln | + Ser203Asp | + Leu216His |
| Ser160Asp | + Gly218Gln | + Thr219Asn |
| Gly62Ser | + Ala105Glu | + Pro128Ser |
| Thr58Gly | + Ile106Gly | + Leu216Asp |
| Ser97Asp | + Thr163Gln | + Ala186Ser |
| Thr65Glu | + Gly126Gln | + Leu216His |
| Phe188Ile | + Ser203Glu | + Leu216Thr |
| Thr132Gln | + Gly165Asp | + Thr212Ser |
| Ser129Asp | + Asn211Ser | + Leu216Thr |
| Leu125Ile | + Asn154Ser | + Leu216Met |
| Thr65Pro | + Gly101Pro | + Thr212Asp |
| Thr102Asn | + Thr212Gly | + Leu216Asp |
| Thr65Gln | + Tyr205Gln | + Leu216Met |
| Leu125Asn | + Pro209Gly | + Thr214Glu |
| Leu125Pro | + Val202His | + Ser215Asp |
| Ser160Glu | + Gln161Asn | + Tyr205Val |
| Gly126Ser | + Thr212Glu | + Gly218Asn |
| Val94Thr | + Ser155Asp | + Thr207Gly |

TABLE 33-continued

Multi-loop Triple Mutation Variants

| | | | | | |
|---|---|---|---|---|---|
| Ser157Glu | + | Tyr208Gln | + | Thr212Gln | |
| Tyr205Met | + | Thr212Gln | + | Ser215Glu | |
| Pro128Gln | + | Thr132Pro | + | Tyr213Asn | |
| Gly60Ser | + | Gly156Asp | + | Pro209Asn | |
| Asn162Asp | + | Thr163Asn | + | Ala199Gly | |
| Gly165Ser | + | Tyr205Thr | + | Ser215Glu | |
| Ser100Asp | + | Gly156Pro | + | Tyr205Gln | |
| Ala105His | + | Ser157Glu | + | Ala186Asn | |
| Asn162Gln | + | Ser190Glu | + | Val202Ser | |
| Gly99Gln | + | Gly126Gln | + | Gln161Asp | |
| Gly126Asp | + | Gly159Ser | + | Thr212Gly | |
| Gly62Glu | + | Asn154Gln | + | Leu216Gln | |
| Asn154Asp | + | Tyr205Ser | + | Tyr213Met | |
| Asn61Asp | + | Leu95Ser | + | Val204Gln | |
| Thr102Gln | + | Gly159Gln | + | Ser190Glu | |
| Pro128Asn | + | Gly159Asn | + | Asn211Ser | |
| Gly159Ser | + | Thr163Gly | + | Ala199Thr | |
| Asn211Gln | + | Tyr213Gln | + | Ser215Glu | |
| Gly99Ser | + | Leu125Gly | + | Ser215Glu | |
| Thr65Gly | + | Ser190Glu | + | Thr219Ser | |
| Val94Met | + | Asn162Ser | + | Leu216Met | |
| Leu95Ser | + | Tyr103His | + | Gly156Glu | |
| Thr58Gly | + | Asn211Glu | + | Leu216Ala | |
| Ala105Gly | + | Thr212Pro | + | Gly218Glu | |
| Ser158Asp | + | Gly159Ser | + | Tyr205Pro | |
| Thr58Gln | + | Ser158Glu | + | Thr163Gly | |
| Thr65Pro | + | Leu125Met | + | Thr163Gly | |
| Gly62Asn | + | Gly126Pro | + | Ser210Glu | |
| Leu95Met | + | Thr132Asp | + | Asn211Ser | |
| Tyr103Ile | + | Gly159Asp | + | Val202Gly | |
| Gly101Gln | + | Tyr166Pro | + | Asn211Gln | |
| Pro128Gly | + | Tyr132Pro | + | Thr214Gln | |
| Pro200Ser | + | Thr212Asp | + | Leu216Gly | |
| Thr212Asp | + | Leu216Met | + | Gly218Gln | |
| Thr163Gln | + | Tyr205Cys | + | Thr212Pro | |
| Thr58Gln | + | Ser98Glu | + | Thr212Pro | |
| Thr102Pro | + | Ser155Asp | + | Tyr205Asn | |
| Gly62Ser | + | Gly99Glu | + | Val202Ser | |
| Leu95Asp | + | Ile106Gln | + | Gly126Asn | |
| Ser100Glu | + | Gly101Gln | + | Val202Ala | |
| Thr58Ser | + | Ser100Glu | + | Ile164Leu | |
| Gly101Ser | + | Phe188Asp | + | Tyr213Gly | |
| Ser104Glu | + | Gly156Gln | + | Thr212Gly | |
| Thr65Asp | + | Val94Gly | + | Tyr205Met | |
| Ser203Glu | + | Thr212Ser | + | Tyr213Val | |
| Thr65Ser | + | Leu125Glu | + | Gln161Ser | |
| Thr65Gly | + | Tyr205Asp | + | Tyr213Thr | |
| Gly101Pro | + | Ser104Asp | + | Thr163Gln | |
| Ala105Gly | + | Asn154Asp | + | Pro209Gly | |
| Gly126Gln | + | Gln161Ser | + | Leu216Ala | |
| Gly153Asp | + | Tyr166Cys | + | Gly218Asp | |
| Gly99Gln | + | Val204Pro | + | Thr219Glu | |
| Thr58Ser | + | Ser97Asp | + | Thr212Pro | |
| Asn162Ser | + | Met198Gly | + | Val202Thr | |
| Val94Ser | + | Leu125Asp | + | Tyr205Thr | |
| Ser157Asp | + | Tyr205Ser | + | Leu216Thr | |
| Gly165Asn | + | Ser215Glu | + | Leu216Pro | |
| Gly156Asn | + | Thr163Glu | + | Ala199Ser | |
| Pro128Ser | + | Gly156Glu | + | Thr219Gly | |
| Asn96Gln | + | Gly126Gln | + | Ser203Glu | |
| Gly159Asp | + | Gly165Pro | + | Tyr213Ile | |
| Thr58Gln | + | Gly153Ser | + | Asn217Gln | |
| Pro128Ser | + | Thr132Glu | + | Thr212Gly | |
| Gly156Gln | + | Tyr205Pro | + | Ser215Glu | |
| Gly62Ser | + | Tyr205Ile | + | Leu216Asp | |
| Leu125Pro | + | Gly159Glu | + | Gly165Pro | |
| Thr58Gln | + | Ser203Asp | + | Thr212Ser | |
| Thr102Gln | + | Val202His | + | Thr214Ser | |
| Gly99Glu | + | Ile106Gly | + | Gly218Asn | |
| Ser97Asp | + | Leu125Val | + | Tyr213Ile | |
| Ile106Leu | + | Phe188Glu | + | Thr212Asn | |
| Thr58Pro | + | Gly153Pro | + | Asn162Gln | |
| Gly127Ser | + | Pro128Gln | + | Thr212Pro | |
| Tyr103Pro | + | Ser203Asp | + | Tyr205Ile | |
| Thr58Gln | + | Thr163Ser | + | Tyr205Ser | |
| Val94Cys | + | Ser215Glu | + | Gly218Pro | |
| Thr102Pro | + | Gly165Pro | + | Val202Thr | |
| Thr58Glu | + | Tyr103Asn | + | Pro200Gln | |
| Phe188Thr | + | Val202Asn | + | Asn217Ser | |
| Gly99Asn | + | Tyr205Ser | + | Ser215Glu | |
| Thr102Gly | + | Gly165Asp | + | Gly218Gln | |
| Gly60Asp | + | Ala186Pro | + | Tyr205Asn | |
| Thr102Asn | + | Ile106Asn | + | Ser158Glu | |
| Gly62Ser | + | Ser97Glu | + | Gly218Asn | |
| Ile106His | + | Ser129Glu | + | Thr212Asn | |
| Gly126Glu | + | Prt128Asn | + | Val202Asn | |
| Asp59Glu | + | Gly64Asn | + | Tyr213Ser | |
| Thr163Pro | + | Val204Thr | + | Tyr205Cys | |
| Ser129Glu | + | Asn162Ser | + | Leu216Cys | |
| Gly156Asn | + | Phe188Ala | + | Tyr205His | |
| Val94Ser | + | Gly101Ser | + | Leu125Asp | |
| Asn96Glu | + | Tyr166Ala | + | Leu216Cys | |
| Tyr103Gln | + | Phe188Met | + | Ser210Glu | |
| Gly101Ser | + | Thr212Pro | + | Thr219Pro | |
| Ser104Glu | + | Gly159Gln | + | Thr212Pro | |
| Gly62Asp | + | Gly126Ser | + | Leu216Pro | |
| Gly101Asp | + | Gly218Pro | + | Thr219Asn | |
| Ser157Glu | + | Tyr205Pro | + | Thr212Ser | |
| Pro209Glu | + | Ser210Glu | + | Gly218Ser | |
| Asn154Glu | + | Ser155Glu | + | Gly218Pro | |
| Asn211Glu | + | Thr212Asp | + | Leu216His | |
| Tyr205Gly | + | Ser215Glu | + | Leu216Asp | |
| Val202Ser | + | Ser215Asp | + | Leu216Asp | |
| Thr58Asp | + | Asp59Glu | + | Thr212Ser | |
| Tyr205Glu | + | Tyr213Pro | + | Ser215Asp | |
| Gly156Ser | + | Tyr205Asp | + | Ser215Glu | |
| Gly60Glu | + | Ser97Glu | + | Gly99Asn | |
| Ser155Glu | + | Asn162Ser | + | Ser190Glu | |
| Leu95Asn | + | Ser203Asp | + | Ser215Asp | |
| Ser203Asp | + | Ser215Asp | + | Thr219Gln | |
| Gly62Asn | + | Ser203Asp | + | Ser215Glu | |
| Ser203Glu | + | Tyr205Pro | + | Ser215Asp | |
| Phe188Asn | + | Ser203Asp | + | Ser215Asp | |
| Gly62Asn | + | Ser203Glu | + | Ser215Asp | |
| Ser203Glu | + | Ser215Asp | + | Leu216Ser | |
| Gly156Gln | + | Ser203Glu | + | Ser215Asp | |
| Ser203Asp | + | Tyr205Ala | + | Asn217Glu | |
| Tyr205Ala | + | Ser210Glu | + | Thr212Asp | |
| Ile164Cys | + | Ser210Glu | + | Thr212Asp | |
| Ser158Asp | + | Gln161Glu | + | Tyr205Pro | |
| Asp59Glu | + | Asn61Glu | + | Gly130Ser | |
| Gly64Gln | + | Ser98Glu | + | Ser100Asp | |
| Ser97Glu | + | Gly99Asp | + | Tyr213His | |
| Asn154Gln | + | Ser157Glu | + | Ser190Asp | |
| Ser158Asp | + | Ser160Glu | + | Tyr205Cys | |
| Gly201Pro | + | Ser203Glu | + | Tyr205Asp | |
| Gly99Gln | + | Ser129Asp | + | Tyr166Glu | |
| Ser160Asp | + | Asn162Glu | + | Phe188Gly | |
| Ser129Asp | + | Ser131Asp | + | Gly218Asn | |
| Asp59Glu | + | Gly165Asn | + | Pro209Glu | |
| Val94Gly | + | Ser215Asp | + | Asn217Glu | |
| Val202Glu | + | Tyr205Gln | + | Leu216Glu | |
| Gly156Glu | + | Ser158Glu | + | Tyr205Met | |
| Asn61Asp | + | Asn96Glu | + | Gly127Ser | |
| Gly159Asn | + | Phe188Asp | + | Gly218Asp | |
| Tyr103His | + | Asn162Glu | + | Ser190Asp | |
| Ser97Asp | + | Ser100Glu | + | Gly201Asn | |
| Ser157Glu | + | Ser160Glu | + | Tyr205Pro | |
| Gly153Asp | + | Val202Ser | + | Gly218Asp | |
| Ser157Glu | + | Gly159Glu | + | Ser190Asp | |
| Asp59Glu | + | Asn96Glu | + | Tyr205Ser | |
| Gly153Ser | + | Asn154Asp | + | Gly165Asp | |
| Asn154Glu | + | Gly165Asp | + | Asn211Ser | |
| Ser155Asp | + | Gly156Asp | + | Thr219Asp | |
| Ser210Asp | + | Tyr213Asp | + | Thr214Glu | |
| Asn61Glu | + | Ala186Gly | + | Pro209Asp | |
| Asn154Asp | + | Ser157Glu | + | Thr214Ser | |
| Ser100Glu | + | Leu125Glu | + | Tyr213His | |
| Gly60Glu | + | Leu95Glu | + | Ile106Leu | |
| Gly99Glu | + | Gly101Glu | + | Tyr103Glu | |
| Thr58Glu | + | Thr65Glu | + | Ile106Cys | |
| Ser97Glu | + | Gly101Asp | + | Val202Asn | |
| Gly62Asp | + | Ser210Asp | + | Leu216Ala | |
| Asn61Asp | + | Ser100Glu | + | Asn162Ser | |

TABLE 33-continued

Multi-loop Triple Mutation Variants

| | | | | | |
|---|---|---|---|---|---|
| Gly127Glu | + | Asn162Glu | + | Gly165Glu |
| Ile106Asn | + | Gly156Glu | + | Gly159Glu |
| Ser100Glu | + | Gly126Glu | + | Ala186Gln |
| Gly62Asp | + | Phe188Leu | + | Thr212Glu |
| Ile106Gln | + | Ser215Glu | + | Gly218Glu |
| Tyr103His | + | Ser155Glu | + | Gly218Glu |
| Ala186Glu | + | Val202Glu | + | Ser215Asp |
| Gly127Glu | + | Asn154Glu | + | Tyr213Thr |
| Ser157Glu | + | Ser160Asp | + | Ser187Asp |
| Gly62Asp | + | Leu216Glu | + | Thr219Gln |
| Thr58Asp | + | Ser210Asp | + | Thr212Glu |
| Ser155Glu | + | Ser157Asp | + | Gly218Asp |
| Pro128Asp | + | Asn162Glu | + | Asn217Ser |
| Gly156Asp | + | Gly165Glu | + | Tyr205Asn |
| Ser158Glu | + | Phe188Asp | + | Val202Met |
| Thr102Glu | + | Ser104Asp | + | Leu125Glu |
| Ser98Asp | + | Ser100Asp | + | Ser104Glu |
| Gly62Asp | + | Pro209Asn | + | Asn211Asp |
| Ser160Glu | + | Ser187Asp | + | Ser190Asp |
| Gly159Asp | + | Val202Asp | + | Ser203Asp |
| Pro128Glu | + | Thr212Asp | + | Tyr213Asp |
| Leu95Glu | + | Tyr205Glu | + | Ser215Asp |
| Asp59Glu | + | Tyr205Glu | + | Ser215Glu |
| Gly60Ser | + | Thr65Glu | + | Leu216Asp |
| Gly101Ser | + | Asn154Glu | + | Ser158Glu |
| Pro128Asp | + | Ser203Asp | + | Ser215Asp |
| Ser203Asp | + | Ser210Glu | + | Ser215Glu |
| Ser104Glu | + | Ser203Asp | + | Asn217Glu |
| Ser160Asp | + | Ser203Asp | + | Leu216Asp |
| Ser203Glu | + | Ser210Asp | + | Leu216Asp |
| Gly127Glu | + | Ser129Glu | + | Ser215Glu |
| Pro128Glu | + | Ala186Glu | + | Phe188Asp |
| Asp59Glu | + | Asn61Glu | + | Ser203Asp |
| Ser97Asp | + | Gly99Asp | + | Ser210Asp |
| Asn96Glu | + | Ser100Asp | + | Thr212Glu |
| Thr65Asp | + | Thr163Gln | + | Ser215Asp |
| Ser98Asp | + | Thr102Glu | + | Leu216Gln |
| Thr132Glu | + | Ser157Asp | + | Ser190Glu |
| Ser129Glu | + | Ser157Asp | + | Ser190Glu |
| Ser190Glu | + | Ser203Glu | + | Tyr205Glu |
| Asn61Asp | + | Ser98Asp | + | Tyr205Asp |
| Ser129Asp | + | Phe188Glu | + | Ser190Asp |
| Ser100Glu | + | Ser104Glu | + | Tyr205Met |
| Gly127Glu | + | Ser190Asp | + | Tyr205Leu |
| Asp59Glu | + | Ser203Glu | + | Pro209Asp |
| Gln161Glu | + | Ser215Glu | + | Asn217Asp |
| Asp59Glu | + | Ser97Glu | + | Ser157Asp |
| Leu125Glu | + | Gly153Glu | + | Ser203Glu |
| Ser104Glu | + | Ser157Asp | + | Ser160Asp |
| Asp59Glu | + | Asn96Glu | + | Ser187Glu |
| Ser129Asp | + | Thr132Asp | + | Asn162Glu |
| Ser131Asp | + | Ser203Glu | + | Gly218Glu |
| Gly156Asp | + | Ser203Asp | + | Thr214Asp |
| Ser160Glu | + | Thr163Asp | + | Ser215Asp |
| Thr58Asn | + | Gly99Glu | + | Ala105Glu |
| Asp59Glu | + | Phe188Leu | + | Thr212Asp |
| Ser104Asp | + | Ser131Glu | + | Tyr205Glu |
| Gly62Asp | + | Ser104Asp | + | Ser131Asp |
| Ser104Glu | + | Ser131Asp | + | Gly156Glu |
| Gly60Asp | + | Gly101Asp | + | Met198Gln |
| Ser98Glu | + | Ser215Glu | + | Gly218Asp |
| Tyr103Asp | + | Ser129Asp | + | Tyr205Glu |
| Ser100Asp | + | Ile106Glu | + | Ser215Asp |
| Thr65Asp | + | Ser100Glu | + | Ala105Glu |
| Asp59Glu | + | Ser100Asp | + | Tyr205Ile |
| Gly153Glu | + | Asn162Asp | + | Ser203Glu |
| Ser98Asp | + | Thr212Glu | + | Ser215Glu |
| Ser131Asp | + | Thr212Glu | + | Ser215Asp |
| Ala105Asp | + | Thr212Glu | + | Ser215Asp |
| Ser158Glu | + | Thr212Asp | + | Ser215Asp |
| Ser157Asp | + | Ser203Glu | + | Thr219Asp |
| Gly62Gln | + | Thr212Glu | + | Leu216Asp |
| Ser97Glu | + | Ser187Glu | + | Asn217Asp |
| Ser155Glu | + | Asn217Asp | + | Gly218Asn |
| Gly159Glu | + | Ser190Glu | + | Asn211Glu |
| Pro128Asp | + | Ser190Glu | + | Ser215Asp |
| Asp59Glu | + | Gly156Asp | + | Ser160Glu |
| Gly60Asp | + | Ser100Glu | + | Ser215Glu |
| Gly130Glu | + | Gly153Glu | + | Tyr205Asn |
| Thr102Glu | + | Gly153Glu | + | Asn217Asp |
| Ser129Glu | + | Ser155Glu | + | Gln161Asn |
| Tyr205Glu | + | Asn211Glu | + | Leu216Cys |
| Gly153Glu | + | Gln161Asp | + | Ala199Asn |
| Gly62Asn | + | Gly153Glu | + | Val202Asp |
| Ser129Asp | + | Asn162Glu | + | Asn211Glu |
| Gly153Glu | + | Ser158Asp | + | Leu216Asp |
| Ser157Glu | + | Leu216Ile | + | Thr219Asp |
| Ser158Glu | + | Ser215Asp | + | Thr219Asp |

TABLE 34

Multi-loop Quadruple Mutation Variants

| | | | | | | | |
|---|---|---|---|---|---|---|---|
| Tyr103Cys | + | Val202Gln | + | Thr212Gly | + | Leu216Gln |
| Asn61Gln | + | Gly101Asp | + | Ile106Ala | + | Tyr205Pro |
| Asn61Ser | + | Gly64Gln | + | Thr132Gly | + | Gly165Gln |
| Leu95Ile | + | Tyr205Glu | + | Tyr213Ala | + | Thr219Asn |
| Gly126Ser | + | Val202Ser | + | Tyr205Cys | + | Asn217Glu |
| Asn96Ser | + | Asn154Glu | + | Tyr166Thr | + | Tyr205His |
| Gly101Asn | + | Ala105Gly | + | Phe188Gly | + | Gly218Asn |
| Gly165Ser | + | Val202Gln | + | Tyr205Thr | + | Thr212Ser |
| Gly126Asn | + | Ser190Glu | + | Pro209Asn | + | Leu216Val |
| Ile106Glu | + | Gly127Ser | + | Asn154Ser | + | Tyr205Leu |
| Thr58Pro | + | Ser203Asp | + | Tyr213Met | + | Leu216Val |
| Gly62Gln | + | Asn96Glu | + | Ile164Asn | + | Leu216Ile |
| Ser98Glu | + | Tyr166Gln | + | Thr212Asn | + | Leu216Val |
| Gly156Asp | + | Tyr166Ala | + | Tyr208Pro | + | Leu216Ile |
| Thr58Pro | + | Ser98Asp | + | Gly130Pro | + | Tyr205Val |
| Gly130Asp | + | Phe188Asn | + | Leu216Gly | + | Gly218Pro |
| Leu95Thr | + | Gly126Gln | + | Pro209Ser | + | Leu216Gly |
| Val202Gln | + | Ser203Glu | + | Tyr205Asn | + | Gly218Asn |
| Thr58Asn | + | Leu95Asn | + | Gly153Pro | + | Ser210Glu |
| Gly127Ser | + | Ser131Asp | + | Thr132Asn | + | Gly165Asn |
| Thr65Gly | + | Gly127Asn | + | Thr212Gln | + | Thr214Glu |
| Asn96Gln | + | Gly126Asn | + | Gly127Ser | + | Val202Asn |
| Gly64Ser | + | Ser160Asp | + | Asn211Ser | + | Thr212Gly |
| Asp59Glu | + | Ala199Ser | + | Val202Ala | + | Tyr205Ser |
| Leu125Gly | + | Thr132Gly | + | Pro200Gln | + | Tyr205Thr |
| Gly159Ser | + | Thr163Glu | + | Ile164His | + | Tyr205Ser |
| Gly127Pro | + | Phe188Met | + | Val202Gly | + | Ser215Glu |
| Gly101Gln | + | Asn211Gln | + | Thr212Pro | + | Ser215Asp |
| Pro128Gly | + | Pro200Ser | + | Thr214Gln | + | Leu216Gly |
| Tyr205Cys | + | Thr212Pro | + | Leu216Met | + | Gly218Gln |
| Thr102Pro | + | Val202Ser | + | Tyr205Asn | + | Gly218Asp |
| Leu95Asp | + | Ile106Gln | + | Gly126Asn | + | Val202Ala |
| Tyr103Gln | + | Ser203Asp | + | Thr212Asn | + | Leu216Asn |
| Phe188Met | + | Ser210Glu | + | Thr212Pro | + | Thr219Pro |
| Ser104Glu | + | Gly159Gln | + | Thr212Pro | + | Leu216Pro |
| Gly60Gln | + | Ala186Gly | + | Thr212Gly | + | Ser215Asp |
| Thr102Glu | + | Thr132Pro | + | Leu216Pro | + | Asn217Gln |
| Leu95Ala | + | Phe188Thr | + | Tyr205Gln | + | Ser215Asp |
| Thr58Gly | + | Gly60Asp | + | Val202Cys | + | Thr212Pro |
| Gly156Asn | + | Val202Asp | + | Thr212Ser | + | Thr214Gly |
| Thr58Pro | + | Gly165Glu | + | Tyr205Ser | + | Tyr213His |
| Gly99Asn | + | Tyr166Asn | + | Ser203Asp | + | Leu216His |
| Gly62Glu | + | Leu95Met | + | Ala105Ser | + | Gly126Ser |
| Ile106Gln | + | Ser187Glu | + | Tyr205Gly | + | Thr219Pro |
| Ser160Glu | + | Tyr205Ser | + | Thr212Pro | + | Leu216Thr |
| Gly130Gln | + | Ser131Glu | + | Asn162Gln | + | Leu216Asn |
| Gly156Glu | + | Thr163Ser | + | Asn211Ser | + | Thr212Asn |
| Gly165Glu | + | Phe188Leu | + | Val202His | + | Thr212Glu |
| Val94Cys | + | Pro128Asp | + | Val202Thr | + | Tyr205Ala |
| Leu95Thr | + | Gly156Ser | + | Thr214Glu | + | Leu216Ala |
| Gly99Pro | + | Tyr103Glu | + | Gly165Pro | + | Leu216Cys |
| Gly64Asn | + | Thr65Glu | + | Tyr166Ala | + | Phe188Tyr |
| Tyr103Gln | + | Gly156Pro | + | Tyr166Asn | + | Ser215Glu |
| Gly126Gln | + | Pro128Gln | + | Val202Thr | + | Thr212Glu |
| Gly64Ser | + | Val94Met | + | Gly130Asp | + | Tyr213Gly |
| Gly99Asn | + | Val202Pro | + | Thr212Asn | + | Ser215Glu |
| Gly101Pro | + | Asn154Ser | + | Leu216His | + | Asn217Glu |
| Tyr103Asp | + | Gly153Pro | + | Ala186Asn | + | Val202Ser |

TABLE 34-continued

Multi-loop Quadruple Mutation Variants

| | | | | | | | |
|---|---|---|---|---|---|---|---|
| Leu125Thr | + | Gln161Asn | + | Thr212Gly | + | Leu216Asn | |
| Gly64Pro | + | Val94His | + | Ser210Asp | + | Thr212Gly | |
| Asn61Ser | + | Thr65Gln | + | Ser190Asp | + | Val202Gly | |
| Ala105Thr | + | Gly153Gln | + | Gly156Gln | + | Asn211Gln | |
| Asn61Gln | + | Tyr166Ile | + | Ala186Asn | + | Ser215Asp | |
| Gly60Gln | + | Tyr103Gly | + | Gly130Asn | + | Asn217Asp | |
| Leu95Pro | + | Tyr205Leu | + | Asn211Gln | + | Ser215Glu | |
| Thr102Asp | + | Gly126Gln | + | Val202Asn | + | Thr212Gly | |
| Val94Thr | + | Gly153Pro | + | Ala186Pro | + | Tyr205Glu | |
| Ser104Asp | + | Ala105Asn | + | Thr163Ser | + | Tyr205Ala | |
| Gly64Ser | + | Val94Asn | + | Gly130Asp | + | Leu216Cys | |
| Gly101Asn | + | Leu125Asn | + | Gly201Pro | + | Leu216Ser | |
| Gly159Pro | + | Gly165Pro | + | Ala186Thr | + | Thr212Pro | |
| Pro128Gln | + | Ser129Asp | + | Ala186Ser | + | Asn217Ser | |
| Gly60Asn | + | Gly159Ser | + | Phe188Val | + | Ser203Glu | |
| Ser98Glu | + | Gly99Asn | + | Thr102Asn | + | Ala186Pro | |
| Thr65Asn | + | Gly99Gln | + | Thr212Ser | + | Leu216Asp | |
| Val202Gln | + | Tyr205Thr | + | Tyr213Val | + | Ser215Glu | |
| Thr132Ser | + | Gly156Ser | + | Phe188Thr | + | Asn211Glu | |
| Leu125His | + | Gly156Ser | + | Thr212Glu | + | Leu216Asn | |
| Gly126Ser | + | Tyr205Asp | + | Thr214Pro | + | Leu216Asn | |
| Ala186Gly | + | Ser215Glu | + | Gly218Pro | + | Thr219Gln | |
| Thr58Gly | + | Gly60Asn | + | Leu125His | + | Leu216Gly | |
| Asp59Glu | + | Val94Gly | + | Tyr205Gln | + | Tyr213Ile | |
| Ser155Glu | + | Met198Thr | + | Val202Met | + | Tyr205Thr | |
| Gly127Asn | + | Tyr166Pro | + | Phe188Leu | + | Thr214Glu | |
| Leu95Cys | + | Gly130Gln | + | Thr212Ser | + | Leu216Val | |
| Asp59Glu | + | Thr65Gly | + | Leu95Gly | + | Leu216Asn | |
| Ser131Glu | + | Gly201Ser | + | Val202Gln | + | Tyr205Gly | |
| Leu125Val | + | Tyr205Glu | + | Ser215Asp | + | Gly218Gln | |
| Val94Gly | + | Thr102Ser | + | Ser203Glu | + | Leu216Asn | |
| Asp59Glu | + | Gly60Gln | + | Thr212Gly | + | Leu216Cys | |
| Ala186Gln | + | Gly201Gln | + | Val202Pro | + | Ser203Glu | |
| Thr65Ser | + | Ser98Asp | + | Gln161Ser | + | Tyr205Cys | |
| Tyr166Ala | + | Ser187Glu | + | Tyr205Gly | + | Leu216Val | |
| Gly99Asp | + | Met198Cys | + | Pro209Gly | + | Thr212Asn | |
| Thr65Pro | + | Ile106Gly | + | Tyr205Gln | + | Leu216Glu | |
| Leu95Ser | + | Thr102Asn | + | Leu216Asp | + | Asn217Ser | |
| Thr58Gly | + | Gly127Ser | + | Tyr166Glu | + | Val202Asn | |
| Val94Pro | + | Tyr213Thr | + | Thr214Glu | + | Asn217Gln | |
| Ser97Glu | + | Gln161Asn | + | Tyr166Gly | + | Val202Ser | |
| Tyr103Met | + | Thr132Gly | + | Tyr166Met | + | Ser210Asn | |
| Leu95Met | + | Gly156Asn | + | Val202Glu | + | Leu216Gln | |
| Ser97Asp | + | Met198Ala | + | Val204Thr | + | Tyr205Thr | |
| Gly101Ser | + | Gly153Pro | + | Asn217Glu | + | Thr219Pro | |
| Ile106Met | + | Thr163Glu | + | Tyr166Ile | + | Thr212Ser | |
| Gly165Ser | + | Ser190Asp | + | Pro200Ser | + | Val202Met | |
| Gly62Ser | + | Gly153Asp | + | Thr163Ser | + | Gly201Gln | |
| Gly101Gln | + | Thr102Ser | + | Gly153Ser | + | Val202Asp | |
| Val94Ala | + | Leu95Gly | + | Leu125Thr | + | Gly130Asp | |
| Asn96Asp | + | Tyr205Ala | + | Thr212Pro | + | Thr219Gly | |
| Gly153Gln | + | Tyr205Ile | + | Thr212Gly | + | Ser215Glu | |
| Ile106Cys | + | Asn154Glu | + | Tyr205Ala | + | Leu216Ala | |
| Asn96Asp | + | Gly99Pro | + | Tyr205Val | + | Asn217Gln | |
| Ala105Thr | + | Leu125Thr | + | Val204Ala | + | Tyr205Met | |
| Thr102Pro | + | Gly156Pro | + | Tyr208Val | + | Thr212Asn | |
| Gly60Ser | + | Phe188Ile | + | Thr212Ser | + | Leu216Asp | |
| Ser100Asp | + | Tyr103Gln | + | Gly159Gln | + | Leu216Val | |
| Pro128Gly | + | Gly165Glu | + | Ser203Glu | + | Leu216Ser | |
| Ser129Glu | + | Thr132Gln | + | Met198Thr | + | Thr219Gln | |
| Val94Pro | + | Gly99Asn | + | Thr132Gly | + | Gly159Asp | |
| Ser155Asp | + | Gly165Ser | + | Tyr205His | + | Thr212Gly | |
| Gly99Asp | + | Phe188Val | + | Thr207Asn | + | Leu216Pro | |
| Thr102Gln | + | Gly126Asn | + | Gly159Asp | + | Leu216Asp | |
| Asp59Glu | + | Thr132Pro | + | Thr163Pro | + | Phe188Thr | |
| Gly101Ser | + | Ala105Glu | + | Ala186Pro | + | Thr212Gly | |
| Ser129Asp | + | Gly153Asn | + | Gly159Pro | + | Val202Met | |
| Gly60Pro | + | Asn96Asp | + | Gly126Gln | + | Tyr166Ala | |
| Thr65Gln | + | Gly99Pro | + | Tyr205Ala | + | Ser215Asp | |
| Val94Gln | + | Gln161Asp | + | Tyr205Pro | + | Leu216Met | |
| Asp59Glu | + | Gly60Glu | + | Ala186Gly | + | Gly218Asn | |
| Ser98Asp | + | Gly99Glu | + | Phe188Met | + | Tyr213Ala | |
| Ser160Asp | + | Gln161Asp | + | Tyr205Ser | + | Thr219Gln | |
| Ala105Gly | + | Ile106Cys | + | Tyr205Asp | + | Ser215Asp | |
| Pro200Asn | + | Tyr205Asp | + | Asn211Gln | + | Ser215Glu | |
| Tyr205Asp | + | Thr207Ser | + | Thr214Ser | + | Ser215Asp | |
| Asn61Asp | + | Thr65Gln | + | Ser97Asp | + | Tyr205Ala | |
| Leu125His | + | Ser203Glu | + | Ser215Glu | + | Leu216Asp | |
| Thr65Asn | + | Ser203Glu | + | Tyr205Cys | + | Ser215Asp | |
| Gly64Pro | + | Ala186Ser | + | Ser203Asp | + | Ser215Asp | |
| Pro128Ser | + | Ser203Asp | + | Tyr213Ala | + | Asn217Glu | |
| Val202His | + | Tyr205Val | + | Ser210Glu | + | Thr212Asp | |
| Gly99Asn | + | Gly130Ser | + | Ser210Glu | + | Thr212Asp | |
| Tyr205Ala | + | Ser210Glu | + | Thr212Asp | + | Gly218Gln | |
| Phe188Ala | + | Ser203Asp | + | Tyr205Asp | + | Thr212Ser | |
| Asn154Glu | + | Ser155Asp | + | Thr163Asn | + | Tyr213Thr | |
| Gly99Gln | + | Ser129Asp | + | Tyr166Glu | + | Leu216Thr | |
| Thr102Gly | + | Ala105Thr | + | Ser155Glu | + | Ser157Asp | |
| Gly127Pro | + | Ser157Glu | + | Gly159Asp | + | Gln161Asp | |
| Gly101Asn | + | Asn154Asp | + | Thr163Gly | + | Gly218Glu | |
| Pro128Ser | + | Ser158Asp | + | Thr163Asp | + | Asn217Ser | |
| Ile106Val | + | Thr214Asn | + | Ser215Asp | + | Asn217Asp | |
| Thr58Gly | + | Asn154Asp | + | Ser157Asp | + | Ser190Glu | |
| Leu125Asn | + | Gly153Glu | + | Thr163Asp | + | Thr214Pro | |
| Gly64Pro | + | Ser157Glu | + | Gln161Glu | + | Tyr205Cys | |
| Ser155Asp | + | Ser187Asp | + | Ser190Glu | + | Thr212Gln | |
| Val94Pro | + | Ser155Asp | + | Ser157Asp | + | Ser187Glu | |
| Gly126Gln | + | Ser203Asp | + | Ser215Glu | + | Gly218Asp | |
| Gly156Ser | + | Ser187Asp | + | Ser190Glu | + | Thr212Ser | |
| Asn154Asp | + | Ser187Asp | + | Val202Asn | + | Leu216Ser | |
| Asn162Asp | + | Gly165Asp | + | Thr212Gln | + | Leu216Cys | |
| Ser155Glu | + | Ser187Asp | + | Pro200Ser | + | Tyr213Val | |
| Asn96Glu | + | Thr102Asp | + | Ala105Pro | + | Tyr213Val | |
| Asn154Ser | + | Gly156Glu | + | Asn162Asp | + | Thr212Ser | |
| Asn61Glu | + | Ser100Asp | + | Tyr205Val | + | Leu216Gly | |
| Thr65Gly | + | Asn154Glu | + | Ser157Asp | + | Asn162Glu | |
| Tyr205Leu | + | Thr212Glu | + | Ser215Glu | + | Leu216Glu | |
| Asn61Gln | + | Gly62Glu | + | Ser98Asp | + | Thr214Gln | |
| Gly62Glu | + | Ser98Glu | + | Gly130Ser | + | Val202Pro | |
| Thr65Gln | + | Tyr205Met | + | Thr212Asp | + | Thr214Gly | |
| Ala105His | + | Phe188Asp | + | Val202Asp | + | Asn211Ser | |
| Asp59Glu | + | Pro209Ser | + | Asn211Asp | + | Thr212Glu | |
| Leu95Gln | + | Gly126Gln | + | Gly127Asp | + | Ser155Asp | |
| Gly60Asp | + | Val94His | + | Asn154Ser | + | Ser210Glu | |
| Thr58Gly | + | Gly126Glu | + | Ser155Asp | + | Gly201Pro | |
| Gly156Asn | + | Tyr166Pro | + | Thr212Glu | + | Ser215Glu | |
| Thr212Asp | + | Ser215Glu | + | Leu216Ala | + | Thr219Ser | |
| Thr58Asp | + | Gly101Ser | + | Ser210Asp | + | Thr212Glu | |
| Ile106Glu | + | Gly126Asp | + | Gly127Asn | + | Leu216Pro | |
| Asn61Ser | + | Gly99Asp | + | Thr102Asp | + | Ser104Asp | |
| Ser210Asp | + | Thr212Asp | + | Tyr213Pro | + | Ser215Glu | |
| Gly127Pro | + | Pro128Ser | + | Ala186Glu | + | Ser203Asp | |
| Gly101Glu | + | Thr102Asp | + | Ser129Asp | + | Leu216Asn | |
| Gly62Glu | + | Leu95Asp | + | Gly159Asn | + | Leu216Gly | |
| Asn61Asp | + | Ser97Asp | + | Ser210Glu | + | Thr212Gln | |
| Ser203Glu | + | Tyr205Pro | + | Thr212Ser | + | Thr219Glu | |
| Thr65Glu | + | Tyr103Pro | + | Ser215Asp | + | Asn217Asp | |
| Gln161Asp | + | Thr163Glu | + | Ser187Glu | + | Asn211Gln | |
| Gly153Glu | + | Tyr166Gly | + | Ser187Glu | + | Leu216Met | |
| Asp59Glu | + | Gly159Glu | + | Ser160Asp | + | Pro209Gln | |
| Gly60Asn | + | Ser129Glu | + | Ser158Asp | + | Gly159Asp | |
| Gly130Ser | + | Ser131Asp | + | Ser155Glu | + | Thr212Asn | |
| Gly130Asp | + | Asn154Glu | + | Ser155Asp | + | Gln161Asn | |
| Ser129Asp | + | Gly130Glu | + | Gly156Glu | + | Gln161Ser | |
| Gly99Glu | + | Ser100Asp | + | Ser203Glu | + | Leu216Ser | |
| Pro128Asp | + | Ser129Asp | + | Val202Asn | + | Ser215Glu | |
| Tyr103Asp | + | Ser104Glu | + | Thr212Pro | + | Ser215Glu | |
| Thr65Pro | + | Ser157Glu | + | Ser158Asp | + | Ser215Asp | |
| Thr58Asn | + | Asn96Asp | + | Ser97Asp | + | Ser187Asp | |
| Ser104Asp | + | Ile164Gly | + | Ser215Asp | + | Leu216Asp | |
| Ser157Asp | + | Ser215Asp | + | Leu216Glu | + | Gly218Gln | |
| Gln161Ser | + | Ser187Asp | + | Ser215Asp | + | Leu216Glu | |
| Thr58Pro | + | Ser104Asp | + | Thr212Glu | + | Tyr213Glu | |
| Thr102Glu | + | Ser160Glu | + | Gln161Asp | + | Leu216Val | |
| Asn61Glu | + | Gly62Glu | + | Ser203Asp | + | Thr212Gly | |
| Tyr205Val | + | Ser210Asp | + | Asn211Glu | + | Leu216Glu | |
| Asp59Glu | + | Gly126Ser | + | Tyr205Glu | + | Ser215Glu | |
| Pro128Asn | + | Ser129Asp | + | Tyr205Asp | + | Ser215Asp | |
| Gly101Glu | + | Tyr205Glu | + | Ser215Glu | + | Leu216His | |
| Ser155Glu | + | Ile164Ser | + | Tyr205Asp | + | Ser215Asp | |
| Tyr103Ala | + | Tyr166Glu | + | Tyr205Glu | + | Ser215Glu | |
| Gly60Glu | + | Ser97Glu | + | Gly99Asn | + | Asn162Glu | |
| Ser187Glu | + | Ser203Glu | + | Tyr205Asp | + | Tyr213Pro | |
| Ser157Glu | + | Ser203Glu | + | Tyr208Pro | + | Ser215Glu | |

TABLE 34-continued

Multi-loop Quadruple Mutation Variants

| | | | |
|---|---|---|---|
| Ser98Glu | + Ser203Glu | + Tyr205Val | + Ser215Glu |
| Gly127Gln | + Ser160Glu | + Ser203Asp | + Ser215Glu |
| Val94Glu | + Ser203Asp | + Ser215Asp | + Leu216Pro |
| Ser100Asp | + Ser203Glu | + Ser215Glu | + Leu216Thr |
| Ser157Asp | + Phe188Thr | + Ser203Asp | + Ser215Asp |
| Val94Gly | + Leu95Glu | + Ser203Glu | + Ser215Asp |
| Phe188Val | + Ser190Asp | + Ser203Asp | + Ser215Glu |
| Ser158Asp | + Ser203Asp | + Ser215Asp | + Asn217Ser |
| Ser157Asp | + Ser203Asp | + Ser215Asp | + Thr219Gln |
| Gly126Pro | + Gly153Glu | + Ser203Asp | + Ser215Glu |
| Ser131Glu | + Gly165Asn | + Ser203Asp | + Ser215Asp |
| Tyr103Glu | + Gly153Asp | + Ser190Glu | + Tyr205Val |
| Gly159Glu | + Ser203Glu | + Leu216Gln | + Asn217Glu |
| Ser100Asp | + Gly153Gln | + Thr163Asp | + Ser190Asp |
| Thr102Asp | + Gly127Glu | + Ser155Asp | + Tyr213Pro |
| Asn61Glu | + Asn154Glu | + Ser190Asp | + Val204Met |
| Asn154Asp | + Gln161Ser | + Ser190Asp | + Ser203Glu |
| Thr65Gly | + Gly127Asp | + Gly165Asp | + Ser203Asp |
| Asn96Asp | + Gly99Glu | + Gly101Asn | + Ser187Glu |
| Thr102Asp | + Ala105Glu | + Gln161Ser | + Pro209Asp |
| Gly127Glu | + Ser129Asp | + Gly130Ser | + Ser160Asp |
| Thr102Glu | + Ser104Glu | + Pro200Asn | + Thr212Glu |
| Ser98Asp | + Ser100Glu | + Pro128Gly | + Gly159Asp |
| Gly159Asp | + Gln161Asp | + Val204Gly | + Ser215Glu |
| Ser155Glu | + Phe188Glu | + Tyr205Asn | + Ser215Glu |
| Ser129Glu | + Thr132Asn | + Gly165Asp | + Gly218Asp |
| Ser100Glu | + Gly153Asp | + Gly165Gln | + Thr219Asp |
| Gly126Asp | + Ser131Glu | + Thr207Gly | + Gly218Gln |
| Asn61Asp | + Gly99Glu | + Tyr103Thr | + Ser131Asp |
| Gly99Asp | + Ser203Asp | + Tyr205Asp | + Thr212Asp |
| Ser190Glu | + Ser203Glu | + Tyr205Asp | + Leu216His |
| Gly60Pro | + Ser157Asp | + Ser203Glu | + Tyr205Asp |
| Ser157Glu | + Thr163Glu | + Pro209Ser | + Ser215Glu |
| Gly60Asn | + Ser157Asp | + Thr163Glu | + Asn211Asp |
| Thr102Glu | + Gly127Asn | + Gly130Glu | + Tyr205Gln |
| Asn61Glu | + Gly153Ser | + Pro209Asp | + Ser215Glu |
| Asp59Glu | + Asn61Gln | + Leu216Asp | + Gly218Asp |
| Leu125His | + Ser129Asp | + Ser131Asp | + Val202Glu |
| Ile106Cys | + Tyr205Asp | + Ser210Glu | + Leu216Asp |
| Ser97Glu | + Gly156Asp | + Thr163Asp | + Thr212Gln |
| Ser131Asp | + Asn154Gln | + Ser215Glu | + Asn217Asp |
| Ser104Glu | + Thr212Glu | + Ser215Asp | + Asn217Glu |
| Ser157Asp | + Ser187Asp | + Ser203Asp | + Thr212Gly |
| Asn61Asp | + Asn96Asp | + Ala105His | + Asn162Asp |
| Asn61Asp | + Asn96Glu | + Gly127Ser | + Gly130Asp |
| Thr58Gly | + Ser158Asp | + Asn211Asp | + Tyr213Asp |
| Ser158Asp | + Asn162Asp | + Thr212Asp | + Leu216Thr |
| Gly99Ser | + Ser157Asp | + Asn162Glu | + Leu216Asp |
| Gly159Gln | + Asn162Glu | + Ser190Asp | + Ser215Glu |
| Ser97Asp | + Ser100Asp | + Gly126Asn | + Ser160Asp |
| Gly60Glu | + Ser98Glu | + Gly153Gln | + Ala186Asp |
| Ser157Asp | + Ser160Asp | + Thr212Asp | + Ser215Glu |
| Gly62Pro | + Ser131Glu | + Gly165Glu | + Thr219Asp |
| Ser190Asp | + Val202Glu | + Ser215Glu | + Leu216Ala |
| Asn96Glu | + Gly153Asp | + Gly156Asp | + Gln161Asn |
| Tyr103Glu | + Ser131Asp | + Ser203Asp | + Leu216Cys |
| Gly130Glu | + Ser157Asp | + Ser187Asp | + Tyr208His |
| Asn61Asp | + Thr163Gln | + Ser203Asp | + Thr214Glu |
| Ser155Glu | + Ser158Asp | + Ser203Asp | + Tyr205Thr |
| Ser155Asp | + Gly156Ser | + Ser215Glu | + Thr219Asp |
| Gly60Gln | + Thr65Gln | + Asn96Asp | + Leu125Glu |
| Asp59Glu | + Asn96Glu | + Ser203Glu | + Thr214Asn |
| Asp59Glu | + Asn96Asp | + Ser215Asp | + Leu216Ile |
| Gly62Asp | + Ser97Glu | + Ala105His | + Ser131Glu |
| Leu125Asp | + Gly165Asp | + Ser203Asp | + Tyr213Gln |
| Leu95Glu | + Tyr166Asn | + Ser203Asp | + Thr214Glu |
| Gly101Asp | + Asn162Asp | + Gly165Glu | + Leu216Asn |
| Gly99Glu | + Tyr103Glu | + Ser129Glu | + Tyr205Asn |
| Asp59Glu | + Asn96Ser | + Thr212Glu | + Ser215Asp |
| Asn61Glu | + Ser100Asp | + Ala186Gly | + Thr212Glu |
| Thr65Gly | + Ser97Glu | + Gly101Glu | + Gly130Glu |
| Ala186Glu | + Phe188Tyr | + Thr212Asp | + Asn217Asp |
| Asn61Gln | + Gly156Glu | + Ser215Glu | + Thr219Glu |
| Gly99Gln | + Ser129Glu | + Ser155Glu | + Gly218Glu |
| Ser160Glu | + Thr163Asp | + Thr212Ser | + Ser215Asp |
| Asn96Asp | + Thr102Asp | + Ser157Asp | + Ala186His |
| Gly99Glu | + Ala105Asp | + Thr214Asn | + Leu216Val |
| Asn162Gln | + Ala186Asp | + Tyr205Ser | + Leu216Asp |
| Ser97Glu | + Gly156Glu | + Gly159Asp | + Val202Asn |
| Ile106Cys | + Ser129Glu | + Ser155Glu | + Ala186Glu |
| Ser100Glu | + Leu125Gly | + Gly127Glu | + Ser203Asp |
| Thr65Asp | + Ser131Asp | + Ile164Asn | + Thr212Asp |
| Ser97Glu | + Thr102Glu | + Gln161Ser | + Tyr205Leu |
| Asp59Glu | + Gly99Glu | + Ser203Asp | + Tyr205Asn |
| Asp59Glu | + Gly99Asp | + Gly126Ser | + Thr214Glu |
| Ser160Asp | + Pro209Asn | + Ser215Asp | + Gly218Glu |
| Ser155Glu | + Gly159Asn | + Pro209Glu | + Gly218Glu |
| Ser155Asp | + Asn211Asp | + Tyr213Met | + Gly218Asp |
| Ser129Asp | + Thr132Glu | + Ser160Glu | + Ala186Ser |
| Val94Glu | + Ser97Asp | + Gly101Pro | + Ser203Glu |
| Gly101Asp | + Gly126Asp | + Thr132Asp | + Thr212Asn |
| Ser98Glu | + Gly127Glu | + Thr163Asp | + Thr212Asn |
| Gly99Asp | + Gly101Pro | + Thr102Glu | + Ser203Glu |
| Gly159Asp | + Thr212Asp | + Ser215Asp | + Asn217Ser |
| Ser158Glu | + Asn162Gln | + Thr212Glu | + Ser215Asp |
| Val94Pro | + Ser155Asp | + Thr212Glu | + Ser215Glu |
| Gly99Gln | + Ile106Asp | + Thr212Glu | + Ser215Glu |
| Thr58Asp | + Tyr205Pro | + Thr212Glu | + Ser215Asp |
| Asp59Glu | + Ser98Glu | + Ser203Asp | + Tyr205Gly |
| Asp59Glu | + Ser100Asp | + Ser104Asp | + Ala105Pro |
| Asp59Glu | + Ser100Asp | + Ser104Asp | + Tyr205Ile |
| Pro128Glu | + Asn162Asp | + Thr212Glu | + Leu216Cys |
| Asn96Gln | + Thr102Asp | + Ser129Glu | + Asn162Glu |
| Ser97Glu | + Gly130Asn | + Ser155Glu | + Ala186Glu |
| Ala105Glu | + Ser155Glu | + Gln161Asp | + Tyr205Thr |
| Gly62Asp | + Ser158Asp | + Ser215Asp | + Leu216Asn |
| Thr102Asp | + Gly126Asp | + Ser158Asp | + Thr212Ser |
| Thr58Asn | + Gly64Pro | + Thr65Glu | + Val94Asp |
| Ser190Glu | + Ser203Glu | + Tyr213Glu | + Leu216His |
| Gly159Asp | + Ser203Asp | + Tyr205Cys | + Tyr213Asp |
| Ile106Asp | + Gly130Asp | + Ser215Asp | + Asn217Gln |
| Ser98Glu | + Thr102Asp | + Ser203Asp | + Thr214Gly |
| Gly99Gln | + Ser104Asp | + Gly130Asp | + Asn154Glu |
| Ser104Glu | + Gly126Ser | + Gly130Asp | + Asn217Glu |
| Asn96Glu | + Ser100Glu | + Ser104Glu | + Tyr205Asp |
| Asn61Gln | + Gly101Asp | + Ser157Asp | + Gly165Glu |
| Thr102Ser | + Val202Cys | + Thr214Glu | + Gly218Glu |
| Asn61Gln | + Ser104Glu | + Gly127Glu | + Gly165Pro |
| Thr65Gly | + Tyr205Glu | + Asn211Glu | + Leu216Cys |
| Gly99Gln | + Gly159Ser | + Pro209Asp | + Leu216Asp |
| Asp59Glu | + Ser158Asp | + Tyr205Pro | + Thr212Glu |
| Asp59Glu | + Ser131Glu | + Thr212Glu | + Leu216Ile |
| Ala105Asp | + Leu125Glu | + Asn211Glu | + Leu216Ile |
| Thr58Asp | + Gly156Ser | + Asn211Asp | + Ser215Glu |
| Ser157Glu | + Gly159Ser | + Gly165Pro | + Thr219Glu |
| Asn162Asp | + Tyr205Gln | + Thr212Glu | + Leu216Asp |
| Ser100Glu | + Met198Gln | + Thr212Asp | + Leu216Glu |
| Gly64Gln | + Pro128Glu | + Thr132Asp | + Thr163Gly |
| Gly62Gln | + Pro128Asp | + Thr132Asp | + Leu216Thr |
| Gly101Asp | + Ile106Met | + Leu125Gly | + Pro128Glu |
| Thr65Glu | + Asn96Glu | + Gly156Asp | + Leu216Cys |
| Ser104Asp | + Leu125Gln | + Ser129Asp | + Asn162Gln |
| Asp59Glu | + Gly130Glu | + Gly153Glu | + Tyr205Asn |
| Ser129Asp | + Ser155Asp | + Tyr205Val | + Leu216Asp |
| Ser129Glu | + Ser155Glu | + Gln161Asn | + Ser210Glu |
| Gly60Glu | + Gly127Asp | + Asn162Glu | + Phe188Asn |
| Gly62Gln | + Ser98Glu | + Ser187Asp | + Ser203Glu |
| Ser104Asp | + Gly130Gln | + Ser187Asp | + Ser203Glu |
| Asn61Asp | + Tyr103Ser | + Thr212Asp | + Thr219Asp |
| Asp59Glu | + Gly101Asp | + Gly159Pro | + Gln161Glu |
| Gly60Glu | + Leu125Ser | + Gly153Glu | + Val202Asp |
| Thr132Glu | + Ser157Glu | + Thr212Gly | + Thr219Asp |
| Gly101Glu | + Leu125Cys | + Gly130Glu | + Thr219Asp |
| Gly60Asp | + Pro128Glu | + Ser157Asp | + Tyr205Cys |
| Pro128Glu | + Asn154Gln | + Ser157Asp | + Ser203Asp |
| Ser97Asp | + Ala105Asp | + Ser203Asp | + Thr212Gln |
| Ser100Asp | + Ser158Glu | + Tyr166Asp | + Phe188Pro |
| Tyr205Thr | + Asn211Glu | + Ser215Glu | + Leu216Asn |

TABLE 35

Multi-loop Quintuple Mutation Variants

| | | | | | | | | |
|---|---|---|---|---|---|---|---|---|
| Tyr103Cys | + | Gly126Gln | + | Gly156Glu | + | Val202Gln | + | Thr212Gly |
| Val94Met | + | Gly101Asn | + | Thr102Asn | + | Tyr205Leu | + | Gly218Asp |
| Ser98Asp | + | Tyr103His | + | Leu125Cys | + | Gly159Asn | + | Met198Cys |
| Leu95Met | + | Gly101Pro | + | Tyr103Ala | + | Gly165Ser | + | Leu216Asp |
| Thr65Asp | + | Val94Thr | + | Thr132Gly | + | Asn154Ser | + | Thr219Gly |
| Val94Thr | + | Thr132Gly | + | Ala186Gln | + | Tyr205Cys | + | Thr214Gln |
| Thr163Gln | + | Tyr205Cys | + | Thr212Pro | + | Leu216Met | + | Gly218Gln |
| Leu95Asp | + | Gly101Gln | + | Ile106Gln | + | Gly126Asn | + | Val202Ala |
| Gly99Glu | + | Gly126Ser | + | Tyr166Ala | + | Asn211Gln | + | Leu216Asn |
| Gly60Asn | + | Gly159Glu | + | Gln161Ser | + | Asn162Gln | + | Leu216Ser |
| Ala186His | + | Val202His | + | Thr212Pro | + | Ser215Glu | + | Leu216Thr |
| Gly99Gln | + | Leu125Ile | + | Gly127Ser | + | Tyr205Val | + | Thr212Asp |
| Thr58Gly | + | Val94Gly | + | Tyr166Cys | + | Ser203Asp | + | Tyr205His |
| Val94Asp | + | Gly99Asn | + | Gln161Ser | + | Gly201Ser | + | Thr212Asn |
| Gly126Asn | + | Gly127Pro | + | Gly153Asp | + | Gly159Pro | + | Ile164Ala |
| Asn61Glu | + | Thr102Asn | + | Gly165Gln | + | Phe188Leu | + | Val202His |
| Val94Cys | + | Gly156Ser | + | Val202Thr | + | Tyr205Ala | + | Leu216Ala |
| Tyr103Gln | + | Gly126Gln | + | Gly156Pro | + | Tyr166Asn | + | Ser215Glu |
| Gly99Asn | + | Val202Pro | + | Thr212Asn | + | Tyr213Gly | + | Ser215Glu |
| Gly101Asp | + | Leu125Thr | + | Gln161Asn | + | Thr212Gly | + | Leu216Asn |
| Asn61Ser | + | Gly153Gln | + | Gly156Gln | + | Val202Gly | + | Asn211Gln |
| Asn61Gln | + | Ala105Thr | + | Tyr166Ile | + | Ala186Asn | + | Ser215Asp |
| Ala105Gln | + | Leu125Gly | + | Thr163Ser | + | Val202Gln | + | Asn217Asp |
| Pro200Ser | + | Val202Ser | + | Ser203Glu | + | Thr207Gly | + | Thr214Gly |
| Val94Asn | + | Gly130Pro | + | Tyr205Ser | + | Ser215Asp | + | Thr219Pro |
| Thr163Asn | + | Ala199Gln | + | Tyr205Asn | + | Thr212Ser | + | Ser215Glu |
| Leu95Met | + | Gly156Asn | + | Val202Cys | + | Leu216Gln | + | Gly218Glu |
| Val94His | + | Gly99Glu | + | Asn211Ser | + | Tyr213His | + | Leu216Met |
| Gly64Ser | + | Val94Gln | + | Ser157Asp | + | Tyr205Ser | + | Thr207Pro |
| Ile106Ala | + | Gly165Asn | + | Ser190Glu | + | Ala199Asn | + | Tyr205Asn |
| Asp59Glu | + | Gly159Ser | + | Gly165Asn | + | Phe188Thr | + | Asn217Gln |
| Gly130Pro | + | Ser155Glu | + | Gly159Asn | + | Tyr205Pro | + | Thr212Ser |
| Tyr103Gln | + | Ser155Glu | + | Val202Asn | + | Thr212Ser | + | Thr219Asn |
| Gly60Pro | + | Val94Ser | + | Ser100Glu | + | Tyr103Leu | + | Tyr205Ser |
| Gly60Gln | + | Leu95Val | + | Pro128Gly | + | Ser158Asp | + | Tyr205Thr |
| Thr132Gln | + | Asn162Ser | + | Gly165Asp | + | Tyr205Gly | + | Tyr208Cys |
| Gly62Asn | + | Val94Thr | + | Ala105His | + | Pro128Glu | + | Tyr205His |
| Thr58Pro | + | Gly156Pro | + | Val202Pro | + | Thr212Glu | + | Leu216Thr |
| Leu95Met | + | Gly99Gln | + | Tyr103Cys | + | Asn154Gln | + | Thr212Gln |
| Ser98Glu | + | Tyr205Asn | + | Pro209Gln | + | Tyr213His | + | Thr219Ser |
| Gly62Ser | + | Val94His | + | Tyr103Gln | + | Ser187Glu | + | Phe188Tyr |
| Gly62Gln | + | Asn96Ser | + | Gly165Glu | + | Val202Gly | + | Tyr205Thr |
| Gly60Pro | + | Ile106Thr | + | Ser160Glu | + | Thr214Gln | + | Leu216Ile |
| Ser100Asp | + | Ala105Thr | + | Tyr205Ile | + | Thr214Gly | + | Leu216Cys |
| Leu95Pro | + | Ala105Asn | + | Phe188Leu | + | Thr212Pro | + | Leu216Val |
| Asp59Glu | + | Gly60Ser | + | Gly127Pro | + | Tyr205Thr | + | Leu216Ala |
| Ala105Asn | + | Ser131Asp | + | Thr163Pro | + | Leu216His | + | Gly218Asn |
| Leu95Cys | + | Tyr103Met | + | Ile106Cys | + | Ala186Asp | + | Tyr205Met |
| Leu125Cys | + | Tyr205His | + | Leu216Asn | + | Asn217Ser | + | Thr219Asn |
| Asn96Ser | + | Gly153Glu | + | Asn154Gln | + | Ala186Gln | + | Thr212Asn |
| Gly101Gln | + | Ala105Pro | + | Gly130Asp | + | Asn154Gln | + | Gly156Asn |
| Thr58Gly | + | Gly159Pro | + | Thr163Ser | + | Tyr205Gln | + | Thr212Asn |
| Tyr205Pro | + | Thr212Asn | + | Tyr213Gln | + | Ser215Asp | + | Leu216Gln |
| Gly130Pro | + | Gly153Pro | + | Gln161Glu | + | Tyr205Met | + | Thr212Gln |
| Ala105Gly | + | Ser157Asp | + | Tyr166Asn | + | Val202Gly | + | Thr212Ser |
| Thr58Gln | + | Asn96Ser | + | Ser203Asp | + | Thr207Gly | + | Leu216Ser |
| Ser158Glu | + | Val202Ser | + | Thr212Asn | + | Thr214Gln | + | Thr219Asn |
| Asn61Ser | + | Ser100Glu | + | Tyr205Leu | + | Thr212Ser | + | Asn217Ser |
| Gly60Gln | + | Gly99Glu | + | Thr212Ser | + | Tyr213Gln | + | Leu216Thr |
| Leu125Asn | + | Ser129Asp | + | Asn162Ser | + | Ala186His | + | Tyr205Gln |
| Gly64Gln | + | Leu95Glu | + | Ala199Asn | + | Val204His | + | Leu216Met |
| Leu95His | + | Gly101Pro | + | Val204His | + | Tyr205Asn | + | Leu216Gln |
| Thr163Ser | + | Gly165Asn | + | Pro209Gly | + | Tyr213His | + | Leu216Asp |
| Gly127Gln | + | Ser131Asp | + | Thr132Pro | + | Tyr205Cys | + | Leu216Asn |
| Asn61Gln | + | Gly101Pro | + | Ser190Asp | + | Tyr205Pro | + | Thr214Gly |
| Gly126Asn | + | Pro200Gly | + | Val204Gly | + | Tyr205Asp | + | Thr212Asn |
| Asn61Gln | + | Val94Gln | + | Gly126Asp | + | Tyr205Val | + | Thr212Gln |
| Gly60Gln | + | Ile106Pro | + | Ser131Glu | + | Ile164Ala | + | Val202Pro |
| Gly101Ser | + | Tyr103Glu | + | Ser104Asp | + | Gly165Asn | + | Pro209Gln |
| Thr58Glu | + | Asp59Glu | + | Tyr166His | + | Val202Cys | + | Thr219Asn |
| Gly126Pro | + | Ala186His | + | Tyr205Asp | + | Tyr213Val | + | Ser215Asp |
| Gly60Asp | + | Ser97Glu | + | Ala105Pro | + | Leu125Cys | + | Gly153Pro |
| Asn154Ser | + | Pro209Ser | + | Thr214Glu | + | Ser215Asp | + | Leu216Glu |
| Thr163Pro | + | Ser203Glu | + | Val204Thr | + | Tyr205Cys | + | Ser215Asp |
| Gly62Ser | + | Met198Gln | + | Ser203Glu | + | Ser215Asp | + | Leu216His |
| Gly156Asn | + | Ser203Asp | + | Tyr205Met | + | Ser215Asp | + | Gly218Pro |
| Gly60Gln | + | Pro128Ser | + | Ser203Glu | + | Ser215Glu | + | Leu216Pro |

TABLE 35-continued

Multi-loop Quintuple Mutation Variants

| | | | | |
|---|---|---|---|---|
| Tyr166Cys | + Tyr205Glu | + Pro209Asn | + Ser215Glu | + Leu216Asp |
| Tyr103Leu | + Leu125Gly | + Gly153Glu | + Ser190Glu | + Leu216Ile |
| Gly99Pro | + Ile106Thr | + Gly153Asp | + Ser155Asp | + Ser190Asp |
| Thr65Pro | + Leu125His | + Ser210Glu | + Thr212Asp | + Tyr213Ala |
| Gly64Ser | + Thr65Ser | + Gly99Asn | + Pro209Glu | + Asn211Glu |
| Leu95Asn | + Gly101Asn | + Asn154Asp | + Gly156Glu | + Tyr166Gln |
| Ser155Glu | + Thr163Asp | + Tyr205Cys | + Thr212Pro | + Leu216Val |
| Gly159Pro | + Thr163Ser | + Ser203Asp | + Tyr205Asp | + Thr212Ser |
| Thr102Gln | + Gly126Asp | + Gly153Asp | + Phe188Thr | + Tyr205His |
| Asn61Ser | + Val202Glu | + Ser203Glu | + Tyr205Asp | + Thr212Pro |
| Thr58Gln | + Thr102Pro | + Tyr213Cys | + Ser215Glu | + Asn217Asp |
| Gly60Asp | + Gly62Glu | + Thr65Glu | + Gly126Asn | + Leu216Thr |
| Ala105Gly | + Gly126Pro | + Gly153Glu | + Leu216Thr | + Gly218Asp |
| Tyr103Gln | + Ala105Thr | + Val202Asp | + Tyr205His | + Ser215Glu |
| Val202Glu | + Tyr205Thr | + Pro209Asn | + Ser215Asp | + Leu216Met |
| Val94Asn | + Ala105Asn | + Ile106Val | + Ser203Glu | + Gly218Asp |
| Asn96Ser | + Ser203Asp | + Tyr205Ile | + Thr212Gln | + Gly218Asp |
| Asn61Asp | + Gly62Gln | + Thr65Asp | + Gly126Asn | + Gly159Pro |
| Gly153Gln | + Ala186Glu | + Tyr205Thr | + Leu216Thr | + Asn217Asp |
| Leu125Asp | + Gly126Asp | + Ala186Ser | + Gly218Glu | + Thr219Pro |
| Thr58Glu | + Thr65Glu | + Val94Gln | + Gly101Pro | + Gly165Gln |
| Gly153Glu | + Ser158Glu | + Thr163Glu | + Gly165Pro | + Leu216Met |
| Gly159Asp | + Thr163Glu | + Tyr166Thr | + Ala186His | + Pro200Ser |
| Leu125Thr | + Gly130Ser | + Asn154Asp | + Ser157Asp | + Ala186Glu |
| Asp59Glu | + Asn96Glu | + Gly101Glu | + Pro128Ser | + Thr212Asn |
| Asp59Glu | + Asn96Asp | + Gly101Asp | + Tyr166Asn | + Thr219Asn |
| Gly99Glu | + Gly101Glu | + Gly127Glu | + Tyr166Leu | + Asn217Gln |
| Ala186Gln | + Ser187Asp | + Leu216Pro | + Gly218Asp | + Thr219Gln |
| Thr58Pro | + Leu95Ile | + Gly126Glu | + Gly153Glu | + Phe188Asp |
| Thr58Glu | + Asn96Glu | + Gly99Asp | + Phe188Met | + Gly218Gln |
| Gly62Glu | + Asn162Ser | + Val202Met | + Thr212Asp | + Leu216Met |
| Gly62Pro | + Gly99Gln | + Ser104Glu | + Ser131Asp | + Tyr213Thr |
| Gly62Glu | + Gly130Ser | + Tyr205Glu | + Ser215Glu | + Leu216Asn |
| Gly126Gln | + Gly127Glu | + Asn154Glu | + Tyr213Pro | + Leu216His |
| Ser129Glu | + Asn154Glu | + Asn162Ser | + Gly165Asp | + Leu216Cys |
| Thr58Gly | + Leu125Asn | + Gly156Asp | + Gln161Glu | + Tyr205Gly |
| Gly126Ser | + Gly153Gln | + Gly156Glu | + Gln161Asp | + Tyr205Pro |
| Thr163Gln | + Val202His | + Tyr205Asp | + Pro209Gly | + Thr212Asp |
| Gly62Gln | + Val202Met | + Asn211Asp | + Thr212Asn | + Thr214Glu |
| Thr102Gln | + Gly126Pro | + Thr212Asp | + Ser215Glu | + Leu216Asn |
| Gly101Ser | + Gln161Asn | + Thr212Glu | + Ser215Asp | + Leu216Gln |
| Leu125Gln | + Ala186Glu | + Val202Cys | + Ser203Asp | + Ser215Aso |
| Ser129Glu | + Ser155Glu | + Thr163Asp | + Ala186Ser | + Tyr208Ser |
| Thr58Asn | + Leu125Glu | + Pro128Glu | + Thr163Ser | + Gly165Pro |
| Asn61Glu | + Gly62Asp | + Gly130Ser | + Asn211Asp | + Thr212Gly |
| Thr65Gln | + Asn154Asp | + Ser215Glu | + Leu216His | + Asn217Glu |
| Asp59Glu | + Ser97Glu | + Thr102Gln | + Ser210Asp | + Leu216Thr |
| Gly153Glu | + Ile164Thr | + Val202Gln | + Ser203Glu | + Asn217Glu |
| Val94His | + Leu125Cys | + Gly126Ser | + Ser155Glu | + Gln161Glu |
| Ser187Glu | + Tyr205Thr | + Thr212Asn | + Tyr213Gly | + Asn217Glu |
| Gly99Ser | + Gly130Glu | + Asn162Asp | + Thr163Glu | + Tyr205Asn |
| Pro128Gln | + Gly156Asp | + Ala186Glu | + Ser203Glu | + Tyr213Gln |
| Gly62Asp | + Gly156Asn | + Ala186Pro | + Thr212Glu | + Leu216Asp |
| Gly126Ser | + Tyr166Gly | + Ser203Asp | + Pro209Asp | + Ser215Asp |
| Tyr103Val | + Pro128Asp | + Gly153Asn | + Asn162Ser | + Ser190Asp |
| Gly130Pro | + Gly156Asn | + Gln161Asp | + Thr163Glu | + Ser187Glu |
| Leu125Pro | + Ser203Asp | + Pro209Gln | + Thr212Glu | + Leu216Asp |
| Leu95Asp | + Gly126Glu | + Pro128Gly | + Gly159Gln | + Ala186His |
| Gly62Ser | + Ser190Asp | + Thr214Gly | + Ser215Asp | + Gly218Asp |
| Gly64Asn | + Tyr103Ile | + Leu125Asp | + Ser203Asp | + Asn217Glu |
| Gly126Ser | + Gln161Asp | + Asn162Ser | + Thr214Glu | + Ser215Glu |
| Ile106Leu | + Gly126Asp | + Gly127Glu | + Gly130Gln | + Val202Glu |
| Asp59Glu | + Thr102Ser | + Ala105Gly | + Gly159Glu | + Ser160Glu |
| Leu95Asp | + Asn96Asp | + Tyr166Leu | + Val204Ala | + Gly218Glu |
| Gly130Glu | + Ser131Asp | + Gly153Gln | + Ser158Glu | + Ala199Pro |
| Gly60Glu | + Asn61Asp | + Gln161Asn | + Pro209Gln | + Ser215Glu |
| Thr65Asn | + Gly99Gln | + Asn154Asp | + Pro209Asp | + Ser210Glu |
| Asn154Glu | + Ser155Asp | + Tyr213Thr | + Ser215Glu | + Gly218Pro |
| Ser100Asp | + Asn154Glu | + Ser155Asp | + Pro209Ser | + Thr214Gly |
| Gly62Asn | + Gly153Asp | + Asn211Glu | + Thr212Asp | + Gly218Gln |
| Tyr103His | + Ser129Glu | + Tyr205Pro | + Asn211Asp | + Thr212Glu |
| Ser129Asp | + Asn162Gln | + Tyr205Leu | + Asn211Asp | + Thr212Asp |
| Ser100Glu | + Gly153Pro | + Thr163Pro | + Val202Glu | + Ser203Glu |
| Thr58Asp | + Thr65Pro | + Val202Glu | + Ser203Asp | + Leu216Asn |
| Thr65Pro | + Gly126Asn | + Ser157Glu | + Ser158Asp | + Ser215Asp |
| Gly101Asn | + Ser157Asp | + Ser158Glu | + Ser215Glu | + Leu216Ile |
| Asn96Glu | + Ser97Glu | + Gly159Asn | + Phe188His | + Ser210Glu |

TABLE 35-continued

Multi-loop Quintuple Mutation Variants

| | | | | | | | | | |
|---|---|---|---|---|---|---|---|---|---|
| Thr65Asn | + | Ser98Asp | + | Gly159Asn | + | Ser215Asp | + | Leu216Asp |
| Asn96Glu | + | Pro128Ser | + | Tyr205Cys | + | Ser215Glu | + | Leu216Glu |
| Ile106Gly | + | Ser155Glu | + | Thr212Asn | + | Ser215Glu | + | Leu216Asp |
| Leu125Glu | + | Thr163Asn | + | Val202Thr | + | Ser215Asp | + | Leu216Glu |
| Gly101Gln | + | Gly130Glu | + | Tyr205Ala | + | Ser215Glu | + | Leu216Glu |
| Pro128Gly | + | Ser210Asp | + | Thr212Ser | + | Ser215Glu | + | Leu216Glu |
| Ser104Asp | + | Ala105Glu | + | Met198Pro | + | Ser203Glu | + | Leu216Ser |
| Ser97Glu | + | Ser98Glu | + | Ala105Gly | + | Gly153Asp | + | Asn217Gln |
| Gly153Gln | + | Ser210Asp | + | Asn211Asp | + | Thr212Ser | + | Ser215Asp |
| Thr65Glu | + | Leu125Cys | + | Gly126Ser | + | Val202Glu | + | Ser215Asp |
| Thr102Gln | + | Gly165Asn | + | Ser203Glu | + | Tyr205Glu | + | Pro209Asp |
| Leu95Glu | + | Asn96Gln | + | Tyr205Glu | + | Pro209Ser | + | Ser215Glu |
| Gly126Asn | + | Tyr205Asp | + | Ser210Asp | + | Ser215Glu | + | Leu216Met |
| Gly62Gln | + | Leu95Pro | + | Ser158Asp | + | Tyr205Asp | + | Ser215Glu |
| Asn61Glu | + | Gly101Glu | + | Gly126Ser | + | Leu216Met | + | Thr219Ser |
| Gly156Asp | + | Ala186Gln | + | Ser190Glu | + | Ser203Glu | + | Thr212Pro |
| Gly60Glu | + | Ser97Glu | + | Gly99Asn | + | Asn162Glu | + | Asn217Ser |
| Thr58Pro | + | Ser160Asp | + | Ser190Asp | + | Val202Asn | + | Thr212Asn |
| Gln161Asn | + | Ser203Asp | + | Asn211Glu | + | Tyr213Cys | + | Ser215Glu |
| Pro128Glu | + | Gly165Gln | + | Ala186His | + | Ser203Glu | + | Ser215Glu |
| Gly101Pro | + | Thr132Ser | + | Ser158Glu | + | Ser203Glu | + | Ser215Glu |
| Pro128Ser | + | Ala186Gly | + | Ser203Glu | + | Ser210Glu | + | Ser215Asp |
| Asn61Gln | + | Ser158Asp | + | Ala186Ser | + | Ser203Asp | + | Ser215Glu |
| Leu95Val | + | Ser100Asp | + | Tyr166Met | + | Ser203Glu | + | Ser215Asp |
| Gly153Glu | + | Ala186Gln | + | Ser203Glu | + | Ser215Asp | + | Thr219Gly |
| Ser160Asp | + | Ser203Glu | + | Val204Gln | + | Thr212Pro | + | Ser215Glu |
| Thr58Pro | + | Leu95His | + | Ser155Asp | + | Ser203Asp | + | Ser215Asp |
| Asn154Gln | + | Ser157Asp | + | Ser203Glu | + | Thr212Ser | + | Ser215Glu |
| Leu95Gln | + | Ser100Asp | + | Ser203Glu | + | Tyr205His | + | Ser215Glu |
| Asn154Asp | + | Tyr166His | + | Ser203Asp | + | Tyr205Ala | + | Ser215Glu |
| Ser98Asp | + | Ser203Glu | + | Asn211Ser | + | Ser215Asp | + | Leu216Ser |
| Asn162Glu | + | Ser203Asp | + | Tyr208Asn | + | Thr212Ser | + | Ser215Asp |
| Gln161Asp | + | Thr163Gln | + | Ser203Glu | + | Ser215Glu | + | Leu216Thr |
| Leu95Cys | + | Ser129Glu | + | Ser203Asp | + | Asn211Gln | + | Ser215Asp |
| Thr132Asn | + | Asn154Glu | + | Ser203Asp | + | Thr212Asn | + | Ser215Asp |
| Pro128Gln | + | Ser131Asp | + | Gly156Asn | + | Ser203Glu | + | Ser215Asp |
| Thr58Glu | + | Asn61Ser | + | Gly99Pro | + | Ser203Glu | + | Ser215Asp |
| Ser100Asp | + | Gly153Ser | + | Ser203Asp | + | Tyr205Val | + | Ser215Glu |
| Ala105Glu | + | Ser203Asp | + | Thr212Asn | + | Ser215Glu | + | Gly218Asn |
| Thr102Asn | + | Ser104Asp | + | Gly127Asn | + | Ser203Asp | + | Ser215Asp |
| Gly62Asp | + | Leu125Thr | + | Gly153Glu | + | Gly165Ser | + | Ser190Glu |
| Gly153Glu | + | Phe188His | + | Ser190Glu | + | Ser203Glu | + | Leu216Gly |
| Thr58Asp | + | Phe188Asn | + | Ser203Glu | + | Tyr205Leu | + | Asn217Asp |
| Thr65Gly | + | Thr102Ser | + | Gly126Asp | + | Thr212Ser | + | Gly218Asp |
| Asp59Glu | + | Thr163Glu | + | Ser190Glu | + | Thr212Gln | + | Leu216Ser |
| Tyr166Val | + | Ser203Glu | + | Ser210Asp | + | Thr212Ser | + | Leu216Asp |
| Gly159Asp | + | Ser203Glu | + | Thr207Pro | + | Thr212Asn | + | Leu216Asp |
| Ser157Asp | + | Asn162Gln | + | Gly165Gln | + | Ser203Glu | + | Leu216Asp |
| Leu95Thr | + | Ser131Glu | + | Val202Ser | + | Ser203Asp | + | Leu216Glu |
| Ser100Asp | + | Gly127Asn | + | Ser203Asp | + | Tyr208Val | + | Leu216Asp |
| Thr102Gly | + | Ser129Glu | + | Ser203Ala | + | Tyr205Ala | + | Leu216Asp |
| Thr65Gln | + | Ser98Asp | + | Thr102Pro | + | Gly126Asp | + | Gly165Asp |
| Thr65Asn | + | Gly127Glu | + | Ser129Asp | + | Tyr205Ile | + | Ser215Glu |
| Gly60Asn | + | Ser203Glu | + | Tyr205Val | + | Ser210Asp | + | Thr212Glu |
| Val94Cys | + | Ser98Glu | + | Pro209Ser | + | Ser210Asp | + | Thr212Glu |
| Gly60Gln | + | Tyr103Asn | + | Pro128Glu | + | Ser157Asp | + | Gly159Asp |
| Ser98Glu | + | Ser100Asp | + | Ser203Glu | + | Thr212Gln | + | Leu216Thr |
| Gly60Glu | + | Thr65Asp | + | Thr132Gln | + | Asn154Ser | + | Leu216Asp |
| Asn96Asp | + | Ser100Asp | + | Thr102Pro | + | Tyr205Asp | + | Thr212Gln |
| Thr102Gly | + | Phe188His | + | Gly201Asn | + | Tyr205Glu | + | Gly218Asp |
| Asn154Gln | + | Ser155Asp | + | Tyr205Gln | + | Pro209Glu | + | Thr212Asp |
| Tyr103Val | + | Gly153Asn | + | Pro209Asp | + | Thr212Asp | + | Gly218Glu |
| Thr65Glu | + | Ile106Met | + | Leu125His | + | Tyr205Leu | + | Ser215Asp |
| Leu125Met | + | Gly156Asp | + | Tyr166Ser | + | Ser187Glu | + | Ser215Asp |
| Thr58Glu | + | Gly60Glu | + | Ser131Glu | + | Tyr205Val | + | Gly218Pro |
| Thr58Asp | + | Gly60Asp | + | Asn61Ser | + | Asn162Gln | + | Ser203Asp |
| Ser157Glu | + | Ser203Asp | + | Tyr205Asp | + | Thr212Ser | + | Leu216Cys |
| Thr58Asn | + | Thr102Gln | + | Ser155Glu | + | Ser157Asp | + | Thr212Glu |
| Ala105Gln | + | Ser155Asp | + | Ser157Asp | + | Ser203Asp | + | Thr212Gly |
| Thr163Glu | + | Val202Asp | + | Tyr205Cys | + | Leu216Pro | + | Gly218Glu |
| Thr58Gln | + | Asn61Glu | + | Ile106Thr | + | Pro209Asp | + | Ser215Asp |
| Gly62Asp | + | Ser97Glu | + | Asn154Ser | + | Tyr205Asp | + | Tyr213Val |
| Leu125Gln | + | Gly130Asp | + | Leu216Glu | + | Gly218Asp | + | Thr219Gly |
| Gly126Ser | + | Ser131Glu | + | Tyr205Ala | + | Leu216Asp | + | Gly218Glu |
| Ile106Ala | + | Ser160Glu | + | Asn162Glu | + | Ala186Gly | + | Ser203Asp |
| Asp59Glu | + | Thr65Asp | + | Asn162Asp | + | Leu216Ile | + | Asn217Ser |
| Asn96Gln | + | Thr102Pro | + | Gly127Glu | + | Ala186Pro | + | Ser190Asp |

TABLE 35-continued

Multi-loop Quintuple Mutation Variants

| | | | | |
|---|---|---|---|---|
| Gly99Asn + | Leu125Thr + | Ser157Glu + | Gly165Glu + | Thr212Gln |
| Val94His + | Gly126Asn + | Ser157Glu + | Gly165Glu + | Tyr205Val |
| Asp59Glu + | Asn61Ser + | Val202Asn + | Thr207Pro + | Asn211Asp |
| Asp59Glu + | Tyr103Ala + | Ser155Glu + | Pro209Glu + | Thr212Asn |
| Gly101Gln + | Gly127Glu + | Gly153Ser + | Asn154Glu + | Ser158Asp |
| Ser97Glu + | Thr212Ser + | Ser215Asp + | Leu216Cys + | Asn217Glu |
| Gly99Gln + | Ser157Glu + | Ser215Asp + | Leu216Ser + | Asn217Asp |
| Ser131Glu + | Gly159Asn + | Tyr205Met + | Ser215Glu + | Asn217Glu |
| Val94Ala + | Gly101Asp + | Gly156Gln + | Ser215Asp + | Asn217Asp |
| Asn61Asp + | Asn96Glu + | Pro209Ser + | Ser215Glu + | Leu216Ala |
| Asn61Glu + | Asn96Glu + | Gly127Ser + | Ser203Glu + | Thr214Ser |
| Gly99Pro + | Ser100Asp + | Thr102Glu + | Ala105Gly + | Asn211Glu |
| Ser155Glu + | Ala186Pro + | Tyr205Asp + | Leu216Cys + | Gly218Glu |
| Phe188Asp + | Ser203Asp + | Tyr213Ser + | Thr214Glu + | Gly218Asn |
| Ser129Asp + | Thr163Gly + | Gly165Glu + | Ser203Asp + | Tyr205Ile |
| Ser104Asp + | Ser158Glu + | Asn162Glu + | Val202Gln + | Leu216Val |
| Ser98Asp + | Ser158Asp + | Asn162Glu + | Leu216Ile + | Thr219Gly |
| Pro128Gly + | Ser158Asp + | Asn162Glu + | Val202Gln + | Asn217Glu |
| Thr102Glu + | Ala105Asn + | Ser129Asp + | Tyr208Thr + | Leu216Gln |
| Thr65Asn + | Ser157Asp + | Asn162Glu + | Ser203Asp + | Tyr205Gly |
| Ala105Gly + | Ser157Asp + | Ser160Glu + | Ala186His + | Ser210Asp |
| Ser98Glu + | Gly153Asp + | Val202Ser + | Tyr205Asn + | Gly218Asp |
| Gly62Asp + | Gly64Asn + | Gly99Pro + | Gly127Asp + | Gly153Glu |
| Thr58Ser + | Val94Met + | Ser104Glu + | Gly153Asp + | Tyr166Asp |
| Asn61Asp + | Thr65Gly + | Ala186Gln + | Ser210Asp + | Thr214Asp |
| Gly127Asn + | Val202Asp + | Ser210Glu + | Ser215Glu + | Asn217Ser |
| Gly62Asn + | Gly101Asp + | Tyr103Met + | Ser104Glu + | Ser203Glu |
| Gly159Asp + | Asn162Glu + | Ile164Ala + | Thr212Asn + | Ser215Asp |
| Ser98Asp + | Gly101Glu + | Asn154Gln + | Tyr205Gln + | Ser210Asp |
| Leu95Glu + | Tyr166Asn + | Phe188Met + | Ser203Asp + | Thr214Glu |
| Gly101Pro + | Ser129Glu + | Ser203Asp + | Thr214Glu + | Gly218Gln |
| Asn96Gln + | Asn162Glu + | Gly165Glu + | Val202Asp + | Tyr205Met |
| Thr65Gln + | Val94Asp + | Ser104Glu + | Leu125Asn + | Thr212Asp |
| Thr102Pro + | Ser155Asp + | Ser187Glu + | Tyr205Val + | Ser215Glu |
| Asn96Glu + | Thr102Gln + | Ala186Asp + | Phe188Gln + | Ser190Asp |
| Thr58Glu + | Asn61Glu + | Gly64Asn + | Ala105Pro + | Asn217Glu |
| Val94Ala + | Gly126Asp + | Asn154Glu + | Tyr166Pro + | Thr212Glu |
| Thr58Asn + | Asn61Ser + | Gly130Glu + | Phe188Glu + | Asn217Asp |
| Thr58Asp + | Ser97Asp + | Ile106Leu + | Gly153Gln + | Gly156Asp |
| Thr58Asp + | Ser97Glu + | Thr102Pro + | Ala105Ser + | Ser158Asp |
| Tyr103Glu + | Gly127Glu + | Asn154Gln + | Ser157Asp + | Thr163Ser |
| Asn96Gln + | Pro128Glu + | Gly130Gln + | Ser131Glu + | Ser157Asp |
| Gly127Glu + | Gly153Asn + | Pro209Asp + | Thr214Glu + | Thr219Ser |
| Ser100Asp + | Ile106Met + | Pro128Asn + | Ser190Asp + | Gly218Glu |
| Thr58Asp + | Asn96Asp + | Gly127Asp + | Tyr166Ala + | Ala186Ser |
| Asn96Glu + | Thr163Pro + | Phe188Asp + | Gly201Gln + | Val202Ala |
| Ser98Glu + | Gly127Asp + | Ser131Glu + | Val202Ala + | Thr214Ser |
| Gly99Asn + | Gly127Glu + | Ser131Glu + | Gly156Gln + | Asn211Glu |
| Val94Asp + | Pro128Asp + | Ser131Asp + | Tyr205Thr + | Leu216Ser |
| Gly101Glu + | Gly126Ser + | Gly127Asp + | Tyr205His + | Ser215Asp |
| Ser160Asp + | Tyr205Glu + | Asn211Gln + | Thr212Asp + | Thr219Gly |
| Gly62Asp + | Gly127Gln + | Gly153Pro + | Ser187Glu + | Leu216Glu |
| Gly60Asp + | Gly127Asp + | Gly159Pro + | Ser210Asp + | Gly218Asn |
| Asn61Ser + | Gly99Asp + | Thr102Asp + | Ser203Asp + | Thr212Gln |
| Gly126Pro + | Ser160Asp + | Tyr205Met + | Thr212Glu + | Ser215Asp |
| Thr65Ser + | Gly127Asp + | Thr132Ser + | Thr212Asp + | Ser215Asp |
| Asn154Ser + | Ser187Glu + | Thr212Glu + | Tyr213Gln + | Ser215Glu |
| Ser129Asp + | Gly153Glu + | Ser158Glu + | Gly165Asn + | Leu216Thr |
| Ile106His + | Leu125Pro + | Ser129Glu + | Ala186Glu + | Ser203Glu |
| Gly60Pro + | Gly62Gln + | Tyr205Thr + | Ser215Glu + | Thr219Glu |
| Asp59Glu + | Val94Pro + | Gly130Gln + | Ser187Asp + | Thr219Asp |
| Gly153Ser + | Ser155Glu + | Ser160Asp + | Asn162Ser + | Thr212Pro |
| Ser155Asp + | Gln161Glu + | Ala186Thr + | Thr214Gly + | Ser215Glu |
| Ser104Asp + | Gly130Asn + | Ser187Glu + | Thr212Gln + | Asn217Glu |
| Ala105Asn + | Ser203Glu + | Thr212Glu + | Asn217Ser + | Thr219Asp |
| Leu125His + | Gly165Gln + | Phe188Asp + | Ser203Glu + | Tyr205Leu |
| Asn96Asp + | Ser104Asp + | Gly201Pro + | Val202His + | Leu216Ser |
| Gly62Asp + | Tyr103Val + | Ser190Glu + | Asn211Glu + | Thr219Ser |
| Gly62Asp + | Ser190Glu + | Val202Ser + | Asn211Glu + | Thr214Gln |
| Ser100Asp + | Pro128Asp + | Tyr205Ile + | Thr212Gln + | Leu216His |
| Thr132Gly + | Gly156Asn + | Gly159Glu + | Ser190Asp + | Ser203Glu |
| Asn96Ser + | Ser98Asp + | Gly159Asp + | Ser190Asp + | Leu216Met |
| Val94Asp + | Ser98Glu + | Thr132Asn + | Phe188Cys + | Thr219Asp |
| Gly101Ser + | Tyr103Glu + | Gly153Glu + | Tyr166His + | Ser187Asp |
| Gly99Ser + | Ser160Asp + | Ser190Glu + | Val202Glu + | Tyr205Ser |
| Asn61Asp + | Gly99Gln + | Ala186Glu + | Thr212Gln + | Leu216Asp |
| Ala186His + | Phe188Gln + | Ser190Glu + | Pro200Ser + | Asn217Asp |

TABLE 35-continued

Multi-loop Quintuple Mutation Variants

| | | | | | | | | | |
|---|---|---|---|---|---|---|---|---|---|
| Asn61Ser | + | Thr65Asp | + | Ser129Glu | + | Tyr205Glu | + | Tyr213Gly | |
| Asn61Asp | + | Gly62Ser | + | Ser203Asp | + | Asn211Gln | + | Tyr213Glu | |
| Thr102Asn | + | Gly130Asp | + | Tyr166Ser | + | Tyr205Asp | + | Gly218Asp | |
| Asn61Glu | + | Asn154Gln | + | Gln161Asn | + | Tyr205Asp | + | Gly218Glu | |
| Gly99Glu | + | Gly127Asp | + | Thr163Pro | + | Tyr213Ile | + | Asn217Glu | |
| Gly101Gln | + | Gly126Asp | + | Ser131Asp | + | Gly156Asn | + | Ser203Glu | |
| Thr102Asp | + | Gly130Glu | + | Pro209Asn | + | Thr212Ser | + | Ser215Asp | |
| Thr58Ser | + | Ser100Glu | + | Ser104Glu | + | Ile164Leu | + | Ser215Glu | |
| Asp59Glu | + | Ile106Val | + | Gly127Glu | + | Tyr166Asn | + | Ser190Glu | |
| Gly99Ser | + | Pro128Asp | + | Gly156Asp | + | Tyr205Cys | + | Asn217Asp | |
| Thr65Asp | + | Leu95Glu | + | Gly99Pro | + | Ser158Asp | + | Tyr205Gln | |
| Ser97Asp | + | Ala105His | + | Ser155Glu | + | Tyr205Asn | + | Pro209Glu | |
| Gly62Asn | + | Thr65Asp | + | Ser97Glu | + | Ser131Glu | + | Leu216Gly | |
| Gly130Pro | + | Gly153Glu | + | Asn154Gln | + | Gln161Asp | + | Pro209Asn | |
| Gly159Ser | + | Tyr166Glu | + | Tyr205Asp | + | Thr212Pro | + | Thr219Glu | |
| Gly62Asp | + | Leu95Cys | + | Ser100Glu | + | Thr163Pro | + | Ser187Asp | |
| Thr58Gly | + | Gly159Glu | + | Ser187Asp | + | Ser203Glu | + | Thr219Asn | |
| Thr58Pro | + | Tyr166Asp | + | Val202Met | + | Pro209Asp | + | Ser215Asp | |
| Leu95Asp | + | Thr102Pro | + | Ala105Gly | + | Gly127Glu | + | Leu216Glu | |
| Pro128Glu | + | Gln161Asp | + | Phe188Gln | + | Ser203Glu | + | Asn217Gln | |
| Leu125Pro | + | Pro128Glu | + | Thr132Asn | + | Gln161Glu | + | Leu216Asp | |
| Ser97Glu | + | Thr102Asp | + | Val202Thr | + | Ser215Glu | + | Gly218Ser | |
| Asp59Glu | + | Ser100Asp | + | Phe188Gln | + | Thr212Ser | + | Ser215Glu | |
| Gly101Gln | + | Thr102Asn | + | Gly130Glu | + | Thr163Glu | + | Ser210Asp | |
| Asn61Glu | + | Gly101Asn | + | Ser129Glu | + | Tyr205Thr | + | Leu216Glu | |
| Leu95Glu | + | Ile164Val | + | Thr212Glu | + | Tyr213Gly | + | Leu216Asp | |
| Thr58Gln | + | Gly126Glu | + | Gly156Gln | + | Thr212Asp | + | Leu216Asp | |
| Leu125Met | + | Gly126Ser | + | Ser131Asp | + | Thr212Asp | + | Leu216Asp | |
| Gly60Asn | + | Asn96Gln | + | Ser104Glu | + | Thr212Asp | + | Leu216Glu | |
| Thr65Asp | + | Gly126Gln | + | Ser158Asp | + | Gly165Asp | + | Leu216Val | |
| Ser158Asp | + | Gly165Glu | + | Ser203Asp | + | Leu216Ser | + | Gly218Gln | |
| Gly101Asp | + | Leu125Gly | + | Pro128Ser | + | Ala186Gly | + | Thr219Gln | |
| Thr65Glu | + | Asn96Glu | + | Tyr103Val | + | Ser155Glu | + | Met198Ala | |
| Thr65Asp | + | Asn96Glu | + | Leu125His | + | Asn162Glu | + | Tyr166His | |
| Asn61Ser | + | Ser100Asp | + | Phe188Asp | + | Ser203Glu | + | Gly218Ser | |
| Ser104Glu | + | Gly156Gln | + | Phe188Asp | + | Ser203Glu | + | Thr212Gly | |
| Gly99Asp | + | Tyr205Asp | + | Pro209Asp | + | Thr212Pro | + | Tyr213Met | |
| Thr102Asp | + | Asn154Ser | + | Tyr166Glu | + | Ser203Asp | + | Gly218Ser | |
| Gly101Glu | + | Ser129Asp | + | Ser157Asp | + | Thr214Ser | + | Leu216Asn | |
| Asp59Glu | + | Gly101Asp | + | Gly127Ser | + | Gly159Pro | + | Gln161Glu | |
| Gly60Asn | + | Gly127Asp | + | Thr132Asp | + | Asn162Gln | + | Ser203Glu | |
| Thr58Asn | + | Gly60Asp | + | Gly130Glu | + | Val202Ser | + | Thr212Gly | |
| Ser100Asp | + | Tyr166Asp | + | Ala186His | + | Tyr205His | + | Leu216Thr | |
| Ser97Asp | + | Gly101Ser | + | Ala105Glu | + | Tyr205Met | + | Ser215Glu | |
| Ser97Glu | + | Ala105Glu | + | Leu125Ala | + | Ser158Asp | + | Tyr205Cys | |
| Ser100Glu | + | Ile106His | + | Gly127Ser | + | Ser158Glu | + | Tyr166Glu | |
| Thr102Asn | + | Gly130Ser | + | Ser131Asp | + | Asn211Asp | + | Ser215Glu | |
| Gly127Gln | + | Ser131Glu | + | Asn211Asp | + | Tyr213His | + | Ser215Glu | |
| Ser129Glu | + | Ser158Glu | + | Val202Gly | + | Ser215Asp | + | Leu216Gln | |
| Leu125Pro | + | Pro128Ser | + | Ser157Glu | + | Ser203Glu | + | Gly218Ser | |
| Thr65Gln | + | Gln161Glu | + | Ser210Glu | + | Thr212Gln | + | Ser215Glu | |
| Val94Met | + | Gly101Glu | + | Ala105Asn | + | Ala186His | + | Thr212Asp | |

TABLE 36

Multi-loop Sextuple Mutation Variants

| | | | | | | | | | | | |
|---|---|---|---|---|---|---|---|---|---|---|---|
| Asn 61Ser | + | Gly 64Gln | + | Gly101Asp | + | Thr132Gly | + | Gly165Gln | + | Tyr205Pro |
| Asn 96Ser | + | Gly101Ser | + | Ala105Gly | + | Asn154Glu | + | Tyr166Thr | + | Tyr205His |
| Val 94Ala | + | Leu 95Thr | + | Gly126Gln | + | Pro209Ser | + | Ser215Asp | + | Leu216Gly |
| Thr 65Gln | + | Leu125Asn | + | Asn162Asp | + | Tyr205Gln | + | Pro209Gly | + | Leu216Met |
| Thr163Gln | + | Tyr205Cys | + | Thr212Pro | + | Leu216Met | + | Asn217Gln | + | Gly218Gln |
| Gly 60Gln | + | Val 94Cys | + | Asn 96Ser | + | Gly127Pro | + | Gly159Asp | + | Asn162Ser |
| Gly 99Ser | + | Gly126Asn | + | Gly127Pro | + | Gly153Asp | + | Gly159Pro | + | Ile164Ala |
| Val 94Cys | + | Pro128Asp | + | Gly156Ser | + | Val202Thr | + | Tyr205Ala | + | Leu216Ala |
| Asn 61Gln | + | Ala105Thr | + | Gly153Gln | + | Gly156Gln | + | Tyr166Ile | + | Asn211Gln |
| Gly 60Asn | + | Ser104Asp | + | Ala105Asn | + | Gln161Ser | + | Thr163Ser | + | Tyr205Ala |
| Gly 64Ser | + | Val 94Asn | + | Gly101Asn | + | Leu125Asn | + | Gly130Asp | + | Leu216Cys |
| Gly159Pro | + | Gly165Pro | + | Ala186Thr | + | Gly201Pro | + | Thr212Pro | + | Leu216Ser |
| Gly 99Asn | + | Gly159Pro | + | Ser203Glu | + | Tyr205Leu | + | Asn211Gln | + | Thr212Ser |
| Thr 58Gln | + | Leu125Pro | + | Thr132Asp | + | Gly153Asn | + | Tyr213Ala | + | Leu216Gly |
| Ile106Ala | + | Asn154Glu | + | Asn162Gln | + | Met198Thr | + | Ala199Asn | + | Tyr205Asn |
| Asp 59Glu | + | Gly159Ser | + | Gly165Asn | + | Phe188Thr | + | Pro200Gln | + | Asn217Gln |
| Gly 99Ser | + | Gly126Asn | + | Thr132Gly | + | Ser187Asp | + | Val202Ser | + | Tyr205His |

TABLE 36-continued

Multi-loop Sextuple Mutation Variants

| | | | | | | | | | | |
|---|---|---|---|---|---|---|---|---|---|---|
| Tyr103Gln | + | Gly130Pro | + | Ser155Glu | + | Gly159Asn | + | Tyr205Pro | + | Thr212Ser |
| Gly 60Pro | + | Val 94Ser | + | Ser100Glu | + | Tyr103Leu | + | Tyr205Ser | + | Thr219Pro |
| Thr 58Gly | + | Leu125Ala | + | Val202Cys | + | Tyr205Asn | + | Ser215Asp | + | Leu216Ala |
| Val 94Thr | + | Ser104Glu | + | Gly130Pro | + | Thr212Pro | + | Leu216Asn | + | Gly218Ser |
| Ser 97Glu | + | Thr132Gly | + | Pro200Gly | + | Tyr205Ala | + | Asn211Ser | + | Tyr213Gln |
| Gly 62Asn | + | Leu 95Asp | + | Tyr166Val | + | Tyr205Cys | + | Asn211Ser | + | Leu216Val |
| Gly156Asn | + | Gly165Pro | + | Gly201Asn | + | Tyr213Ala | + | Thr214Gln | + | Asn217Glu |
| Gly 62Ser | + | Ser 98Asp | + | Gly126Ser | + | Tyr205Pro | + | Thr212Ser | + | Tyr213Thr |
| Ala105Gln | + | Gly127Ser | + | Gln161Asp | + | Thr163Gly | + | Tyr205Cys | + | Leu216Pro |
| Val 94Ala | + | Gly130Gln | + | Ala186His | + | Ser203Asp | + | Tyr205Cys | + | Thr214Gln |
| Thr 65Gln | + | Leu125Gly | + | Ser187Asp | + | Phe188Gln | + | Val202Asn | + | Thr212Asn |
| Thr 58Ser | + | Ile106Pro | + | Thr132Gly | + | Gln161Asn | + | Tyr205Asn | + | Thr212Asp |
| Ser100Asp | + | Ala105Thr | + | Leu125Pro | + | Tyr205Ile | + | Thr214Gly | + | Leu216Cys |
| Thr102Ser | + | Gly127Pro | + | Pro128Gly | + | Ser203Glu | + | Tyr208His | + | Tyr213Thr |
| Thr102Ser | + | Gln161Glu | + | Asn162Asp | + | Thr163Gln | + | Ala186His | + | Phe188Ile |
| Gly 62Pro | + | Pro128Asp | + | Ser129Asp | + | Gly156Asn | + | Tyr213Cys | + | Gly218Asn |
| Thr 58Gly | + | Gly127Pro | + | Ala186Gln | + | Val202Asp | + | Ser203Glu | + | Leu216Val |
| Gly156Ser | + | Phe188Gly | + | Ser203Glu | + | Tyr213Gln | + | Ser215Asp | + | Leu216Asp |
| Gly101Gln | + | Ala105His | + | Asn162Gln | + | Ala186Gly | + | Ser203Glu | + | Ser215Glu |
| Thr 58Pro | + | Thr163Asn | + | Ser203Glu | + | Tyr205Ile | + | Ser215Glu | + | Leu216Gln |
| Thr 65Asn | + | Gly127Glu | + | Gly156Asn | + | Tyr166Glu | + | Phe188Met | + | Thr212Pro |
| Leu 95Asp | + | Ser100Glu | + | Gly101Gln | + | Ile106Gln | + | Ile164Leu | + | Val202Ala |
| Tyr103Pro | + | Gly127Glu | + | Ser129Asp | + | Gly130Glu | + | Asn162Gln | + | Leu216His |
| Gly 60Gln | + | Gly165Ser | + | Ser203Glu | + | Tyr205Asp | + | Thr214Glu | + | Ser215Asp |
| Leu 95Asn | + | Leu125Pro | + | Ser203Asp | + | Tyr205Thr | + | Thr214Glu | + | Ser215Asp |
| Gly 62Asn | + | Tyr103Ile | + | Leu125Cys | + | Gly126Glu | + | Gly153Asp | + | Tyr166Cys |
| Gly 99Ser | + | Pro128Glu | + | Gly130Asp | + | Phe188Asn | + | Leu216Gly | + | Gly218Pro |
| Asp 59Glu | + | Gly 60Asp | + | Thr 65Asp | + | Asn162Ser | + | Thr163Gln | + | Tyr166Gln |
| Phe188Glu | + | Tyr205Thr | + | Thr212Asn | + | Tyr213Gly | + | Asn217Glu | + | Gly218Asp |
| Gly 62Gln | + | Ser203Glu | + | Tyr205Ser | + | Thr212Ser | + | Ser215Asp | + | Gly218Asp |
| Ser187Glu | + | Ser190Asp | + | Tyr205Val | + | Pro209Ser | + | Thr214Ser | + | Thr219Ser |
| Thr 58Ser | + | Asp 59Glu | + | Asn 96Asp | + | Asn154Ser | + | Ala186His | + | Leu216Ser |
| Thr 65Gly | + | Thr102Gly | + | Leu125Asp | + | Gly165Asp | + | Ala199Ser | + | Val202Thr |
| Leu125Asn | + | Ser158Glu | + | Gly159Asp | + | Ser190Glu | + | Thr212Gly | + | Leu216Val |
| Thr 58Pro | + | Asn 61Asp | + | Val 94Glu | + | Asn 96Asp | + | Gly126Ser | + | Gly165Pro |
| Ala186Glu | + | Val202Glu | + | Tyr205Ala | + | Tyr213Val | + | Ser215Asp | + | Asn217Glu |
| Tyr103Val | + | Ser203Glu | + | Tyr205Asp | + | Thr212Glu | + | Ser215Asp | + | Leu216Ile |
| Gly 62Ser | + | Ile106Leu | + | Pro128Ser | + | Asn1S4Asp | + | Ser157Glu | + | Thr214Ser |
| Val 94Asp | + | Gly 99Asp | + | Pro128Gln | + | Ala199Gln | + | Tyr205Gln | + | Leu216Ile |
| Asn 61Gln | + | Thr102Gln | + | Gly126Asp | + | Ser155Glu | + | Ser190Asp | + | Val202Ser |
| Leu125Asp | + | Gly126Asp | + | Ala186Ser | + | Tyr205Gln | + | Gly218Glu | + | Thr219Pro |
| Asn 61Glu | + | Ser100Asp | + | Thr102Asn | + | Gly165Pro | + | Phe188Leu | + | Val202His |
| Tyr103Gly | + | Tyr205Leu | + | Thr212Glu | + | Ser215Glu | + | Leu216Glu | + | Asn217Asp |
| Gly 99Pro | + | Ser104Glu | + | Ile106Thr | + | Ser131Asp | + | Gly201Gln | + | Thr214Ser |
| Leu 95Ile | + | Gly126Glu | + | Gly153Glu | + | Ser187Asp | + | Phe188Asp | + | Asn211Gln |
| Gly 62Asn | + | Leu 95Ser | + | Gly153Ser | + | Tyr205Asp | + | Thr212Glu | + | Leu216Asp |
| Ala105Gly | + | Ile106Cys | + | Ser155Asp | + | Tyr205Asp | + | Ser215Asp | + | Leu216Asp |
| Tyr103Ala | + | Ser155Glu | + | Tyr166Pro | + | Ser203Glu | + | Tyr205Glu | + | Ser215Glu |
| Pro128Gly | + | Asn162Glu | + | Gly165Asn | + | Ser203Glu | + | Tyr205Glu | + | Ser215Glu |
| Gly 99Pro | + | Leu125Gln | + | Gly130Asn | + | Ala186Asp | + | Phe188Ser | + | Ser203Glu |
| Ile106Asn | + | Gly156Glu | + | Gly159Asn | + | Phe188Asp | + | Ser215Glu | + | Gly218Asp |
| Gly156Pro | + | Asn162Asp | + | Ser203Glu | + | Tyr205Gln | + | Ser215Asp | + | Asn217Glu |
| Gly153Asn | + | Ser155Glu | + | Ser157Asp | + | Ser190Glu | + | Thr212Asp | + | Leu216Ile |
| Leu 95Glu | + | Gly 99Glu | + | Leu125Glu | + | Pro128Gly | + | Asn154Glu | + | Thr219Gly |
| Gly 60Asp | + | Ile106Met | + | Asn162Ser | + | Ser203Glu | + | Tyr205Asp | + | Leu216Asp |
| Ser 97Asp | + | Asn162Ser | + | Thr163Gln | + | Ser203Glu | + | Tyr205Asp | + | Leu216Asp |
| Leu125Ile | + | Gly159Glu | + | Ser203Glu | + | Thr214Glu | + | Ser215Glu | + | Leu216Gln |
| Gly156Ser | + | Ser158Glu | + | Tyr205Asp | + | Tyr213Glu | + | Ser215Asp | + | Leu216Cys |
| Gly 62Gln | + | Asn154Asp | + | Ser155Asp | + | Ser160Asp | + | Gly165Glu | + | Tyr205Met |
| Gly 64Pro | + | Ala186Glu | + | Ser187Asp | + | Ser203Glu | + | Tyr205His | + | Ser215Glu |
| Tyr103Asp | + | Tyr166Ser | + | Ala186Asn | + | Val202Glu | + | Ser203Asp | + | Tyr205Glu |
| Leu 95Gln | + | Gly126Gln | + | Gly127Asp | + | Pro128Ser | + | Ser155Asp | + | Ser158Glu |
| Asp 59Glu | + | Ile106His | + | Tyr205Ala | + | Tyr213Glu | + | Ser215Glu | + | Leu216Asp |
| Ser158Asp | + | Ser160Glu | + | Thr163Asp | + | Pro209Gln | + | Thr212Ser | + | Ser215Glu |
| Gly 62Asp | + | Tyr103Met | + | Val202Ser | + | Asn211Glu | + | Thr214Gln | + | Leu216Ala |
| Asp 59Glu | + | Ser 97Asp | + | Ser 98Asp | + | Gly153Ser | + | Gln161Asn | + | Ser203Glu |
| Leu125Asn | + | Gly153Glu | + | Ser157Asp | + | Thr163Glu | + | Val202Asp | + | Thr214Pro |
| Leu 95Glu | + | Ser100Asp | + | Leu125Asp | + | Pro128Asn | + | Ser131Asp | + | Tyr205Gly |
| Gly126Gln | + | Ser158Glu | + | Ser203Asp | + | Ser215Glu | + | Leu216Thr | + | Gly218Asp |
| Gly101Ser | + | Pro128Asp | + | Ser158Glu | + | Gly159Asp | + | Ala186Gly | + | Phe188Val |
| Ser187Glu | + | Ser203Asp | + | Tyr205Cys | + | Pro209Gln | + | Ser215Asp | + | Leu216Ser |
| Gly 62Ser | + | Ser187Glu | + | Met198Gln | + | Ser203Glu | + | Ser215Asp | + | Leu216His |
| Thr132Asn | + | Gly165Pro | + | Ser187Glu | + | Ser203Glu | + | Tyr205His | + | Leu216Asp |
| Asn 96Ser | + | Ser131Glu | + | Gly159Asp | + | Ser160Asp | + | Thr214Gln | + | Leu216Gly |
| Gly130Glu | + | Ser158Asp | + | Gly159Glu | + | Thr163Gln | + | Tyr205Thr | + | Thr207Asn |
| Gly130Asp | + | Ser131Glu | + | Gly165Pro | + | Ser190Glu | + | Val202Gly | + | Asn217Ser |
| Leu 95Thr | + | Gly130Glu | + | Ser131Glu | + | Tyr205Ala | + | Ser210Glu | + | Gly218Gln |

TABLE 36-continued

Multi-loop Sextuple Mutation Variants

| | | | | | | | | | | |
|---|---|---|---|---|---|---|---|---|---|---|
| Thr 58Gly | + | Ala105Glu | + | Ile106Gly | + | Tyr205Val | + | Ser215Glu | + | Leu216Asp |
| Thr 58Asp | + | Asp 59Glu | + | Leu125Asn | + | Ser203Glu | + | Tyr205Cys | + | Thr212Ser |
| Thr 58Glu | + | Asp 59Glu | + | Tyr103Asn | + | Pro209Gln | + | Thr212Asn | + | Ser215Glu |
| Thr 65Ser | + | Ser 97Asp | + | Ser 98Glu | + | Ser104Glu | + | Thr163Gln | + | Leu216Ser |
| Ser 97Glu | + | Ser 98Glu | + | Gly101Gln | + | Thr212Asn | + | Leu216His | + | Gly218Glu |
| Gly101Asp | + | Thr102Glu | + | Ile106Val | + | Thr163Pro | + | Tyr205Glu | + | Ser215Asp |
| Gly 60Pro | + | Ser129Glu | + | Val202Glu | + | Thr214Asp | + | Ser215Asp | + | Leu216Ile |
| Gly 62Asp | + | Gly 99Glu | + | Tyr205Asn | + | Asn211Asp | + | Tyr213Met | + | Thr214Asp |
| Thr 58Gly | + | Gly127Glu | + | Ser131Glu | + | Ser155Asp | + | Gly165Pro | + | Tyr205Cys |
| Gly159Asp | + | Tyr166Gly | + | Tyr205Asp | + | Tyr213Asn | + | Ser215Asp | + | Leu216Thr |
| Gly 62Glu | + | Gly101Ser | + | Thr132Gly | + | Ser203Glu | + | Asn211Asp | + | Tyr213Glu |
| Asn 96Asp | + | Ser 97Asp | + | Leu125Pro | + | Gly127Gln | + | Ser203Asp | + | Ser215Asp |
| Asp 59Glu | + | Val 94Glu | + | Ser 98Asp | + | Ser104Glu | + | Leu125Asn | + | Tyr213Gly |
| Ser155Asp | + | Gly156Gln | + | Ser190Asp | + | Tyr205Glu | + | Thr212Ser | + | Leu216Ala |
| Val 94Met | + | Gly 99Pro | + | Ile106Thr | + | Ser155Asp | + | Ser190Asp | + | Thr212Glu |
| Gln161Ser | + | Thr163Glu | + | Val202Ala | + | Ser203Glu | + | Asn211Ser | + | Ser215Asp |
| Gly156Glu | + | Ala186Asn | + | Ser203Asp | + | Thr212Glu | + | Ser215Glu | + | Leu216Gln |
| Ser 98Glu | + | Ser203Asp | + | Val204Cys | + | Ser215Asp | + | Asn217Ser | + | Thr219Gln |
| Asn 61Gln | + | Thr165Ser | + | Ser131Asp | + | Ser203Glu | + | Ser215Glu | + | Leu216Cys |
| Ile106Val | + | Thr132Ser | + | Ser158Glu | + | Ser203Glu | + | Thr214Ser | + | Ser215Glu |
| Val 94Thr | + | Gly153Glu | + | Ala186Gln | + | Ser203Glu | + | Ser215Glu | + | Thr219Gly |
| Val 91Met | + | Thr102Asp | + | Pro128Glu | + | Ser131Asp | + | Gly165Asn | + | Thr219Ser |
| Ser155Asp | + | Gln161Asp | + | Ser190Glu | + | Ser203Glu | + | Thr212Ser | + | Leu216Cys |
| Asn 61Glu | + | Ser100Asp | + | Thr132Pro | + | Ala186Gly | + | Ser210Glu | + | Thr212Glu |
| Ala105Glu | + | Thr132Ser | + | Gly201Ser | + | Ser203Glu | + | Thr212Pro | + | Asn217Asp |
| Thr 58Gly | + | Gly 62Pro | + | Ala105Asp | + | Ser203Asp | + | Tyr208Ile | + | Leu216Glu |
| Asn 96Asp | + | Gly 99Asp | + | Ile106Gly | + | Asn154Gln | + | Gln161Asn | + | Thr214Glu |
| Asn 96Glu | + | Gly 99Glu | + | Thr102Asn | + | Gly127Ser | + | Ser203Glu | + | Asn217Gln |
| Asp 59Glu | + | Gly127Asp | + | Ser129Asp | + | Tyr213His | + | Leu216Val | + | Thr219Gly |
| Thr 65Glu | + | Tyr205Ser | + | Pro209Gln | + | Ser210Glu | + | Thr212Glu | + | Thr219Asp |
| Thr 58Asp | + | Asn 96Ser | + | Ser158Glu | + | Gln161Asp | + | Gly201Gln | + | Tyr205Val |
| Asp 59Glu | + | Asn 61Glu | + | Tyr166His | + | Phe188Val | + | Thr212Gly | + | Ser215Asp |
| Thr102Glu | + | Gly126Pr6 | + | Gly127Asn | + | Val202Asn | + | Pro209Asp | + | Asn211Glu |
| Asn 61Glu | + | Gly159Gln | + | Ser187Asp | + | Pro209Asp | + | Asn211Asp | + | Gly218Ser |
| Ser 97Asp | + | Ser 98Glu | + | Gly156Asp | + | Ser158Glu | + | Thr163Gln | + | Pro209Gln |
| Gly 60Gln | + | Gly130Asn | + | Ser155Glu | + | Phe188Glu | + | Tyr205Asn | + | Ser215Glu |
| Val 94Asp | + | Ile106Glu | + | Pro128Asp | + | Ser131Asp | + | Tyr205Thr | + | Leu216Ser |
| Gly 60Pro | + | Ser 98Asp | + | Ser100Glu | + | Pro128Gly | + | Ser157Asp | + | Gly159Asp |
| Thr 58Asn | + | Gly 99Asp | + | Thr102Gln | + | Pro209Asp | + | Thr212Glu | + | Tyr213Met |
| Thr 65Glu | + | Tyr103Gln | + | Gly156Pr6 | + | Tyr166Asn | + | Phe188Tyr | + | Ser215Glu |
| Val 94Asp | + | Gly101Glu | + | Ile164Gly | + | Ala186Pro | + | Ser203Asp | + | Leu216Pro |
| Gly 60Asn | + | Asn 61Glu | + | Gly153Ser | + | Pro209Asp | + | Asn211Asp | + | Ser215Glu |
| Thr132Gly | + | Ser157Glu | + | Ser187Asp | + | Ser203Asp | + | Tyr205Met | + | Ser215Asp |
| Asn 61Asp | + | Asn 96Glu | + | Gly156Asn | + | Ser203Glu | + | Thr212Gln | + | Ser215Glu |
| Gly 99Pro | + | Ser158Glu | + | Ser160Glu | + | Tyr205His | + | Thr212Ser | + | Ser215Glu |
| Gly101Pro | + | Ser157Glu | + | Ser203Asp | + | Tyr205Asp | + | Thr212Ser | + | Leu216Cys |
| Val 94Ala | + | Pro128Ser | + | Gly156Gln | + | Ser190Asp | + | Ser203Asp | + | Tyr205Glu |
| Ile106Met | + | Leu125Ile | + | Ser160Asp | + | Ser203Asp | + | Tyr205Glu | + | Leu216Ser |
| Leu 95Glu | + | Ser 97Glu | + | Thr102Glu | + | Gly159Asp | + | Tyr205Leu | + | Leu216Ala |
| Leu125Cys | + | Gly126Ser | + | Gly159Asp | + | Gln161Glu | + | Ser215Glu | + | Asn217Glu |
| Ser100Glu | + | Thr102Gly | + | Ala105Thr | + | Ser155Glu | + | Ser157Asp | + | Asn162Ser |
| Ser 98Glu | + | Gly127Asn | + | Ser157Asp | + | Gln161Asn | + | Asn162Asp | + | Gly165Glu |
| Asn 61Gln | + | Ser100Asp | + | Ser104Glu | + | Ile106Asp | + | Ser215Asp | + | Leu216Ala |
| Ser131Glu | + | Gly159Asn | + | Val202Cys | + | Ser215Asp | + | Leu216Asp | + | Thr219Glu |
| Leu125Cys | + | Gln161Asp | + | Asn162Glu | + | Ser203Asp | + | Leu216Thr | + | Gly218Glu |
| Gly101Asp | + | Ala105Asp | + | Gly126Asn | + | Gln161Ser | + | Ala186Pro | + | Thr214Glu |
| Ser100Glu | + | Thr102Glu | + | Tyr103Thr | + | Gly126Asp | + | Ser160Glu | + | Leu216Met |
| Gly127Gln | + | Asn154Ser | + | Ser157Glu | + | Thr163Glu | + | Ser215Glu | + | Asn217Glu |
| Leu 95Ile | + | Asn 96Glu | + | Thr102Gly | + | Tyr103Glu | + | Gly126Glu | + | Gly165Glu |
| Ser129Asp | + | Ser131Asp | + | Thr132Asn | + | Gly159Ser | + | Tyr213Gln | + | Thr214Glu |
| Gly101Pro | + | Gly126Glu | + | Ser129Asp | + | Tyr205Glu | + | Ser215Glu | + | Leu216Gly |
| Leu 95Met | + | Pro128Gly | + | Ser129Glu | + | Gly153Glu | + | Thr163Gly | + | Leu216Ser |
| Gly 60Glu | + | Val202Met | + | Tyr205Ile | + | Thr212Glu | + | Ser215Glu | + | Leu216Asp |
| Thr 58Ser | + | Ser158Asp | + | Gln161Asn | + | Thr163Asp | + | Leu216Asp | + | Gly218Asp |
| Ile106Ser | + | Ser158Asp | + | Ser187Asp | + | Ser190Asp | + | Tyr205Met | + | Ser215Asp |
| Ser187Glu | + | Val202Gln | + | Tyr205Asn | + | Thr214Glu | + | Leu216Glu | + | Gly218Ser |
| Asp 59Glu | + | Ser100Asp | + | Gly126Pro | + | Gly127Asp | + | Tyr166Glu | + | Thr212Asn |
| Asp 59Glu | + | Gly 62Pro | + | Gly127Asn | + | Ala186Pro | + | Val202Glu | + | Pro209Asp |
| Asp 59Glu | + | Asn 96Glu | + | Gly101Glu | + | Thr102Gln | + | Pro128Ser | + | Leu216Glu |
| Gly159Asp | + | Asn162Asp | + | Ala186Gln | + | Val202Gln | + | Ser203Glu | + | Ser215Asp |
| Gly159Ser | + | Ala186Asn | + | Ser210Asp | + | Tyr213Pro | + | Ser215Asp | + | Asn217Asp |
| Ser104Asp | + | Ser131Asp | + | Thr132Gln | + | Asn162Ser | + | Gly165Asp | + | Tyr208Cys |
| Gly156Glu | + | Ser158Asp | + | Thr163Gly | + | Ser203Asp | + | Thr212Asn | + | Leu216Ser |
| Gly 64Pro | + | Thr 65Glu | + | Ala105Asp | + | Val202Thr | + | Ser215Asp | + | Leu216Glu |
| Thr 58Pro | + | Gly 99Ser | + | Ser100Asp | + | Gly101Ser | + | Thr102Asp | + | Asn211Glu |
| Gly 62Glu | + | Asn 96Ser | + | Ser100Asp | + | Gly101Ser | + | Ser210Asp | + | Tyr213Ala |
| Gly 60Pro | + | Gln161Asp | + | Gly165Asp | + | Phe188Val | + | Ser190Glu | + | Ser210Glu |

TABLE 36-continued

Multi-loop Sextuple Mutation Variants

| | | | | | | | | | | |
|---|---|---|---|---|---|---|---|---|---|---|
| Gly153Gln | + | Ser155Asp | + | Gly159Asn | + | Pro209Glu | + | Thr212Asp | + | Ser215Asp |
| Thr 58Gln | + | Thr102Glu | + | Ser129Glu | + | Gly130Asp | + | Tyr205Ala | + | Ser215Asp |
| Tyr103Ser | + | Asn154Asp | + | Ser187Glu | + | Val202Asn | + | Ser203Glu | + | Leu216Ser |
| Leu125Pro | + | Pro128Ser | + | Ser157Glu | + | Gln161Glu | + | Ser203Glu | + | Gly218Ser |
| Ser 97Glu | + | Gly 99Asp | + | Ala105Ser | + | Leu125Asp | + | Gly165Asp | + | Tyr205Asp |
| Thr 65Asp | + | Leu 95Cys | + | Ser 97Asp | + | Asn162Ser | + | Thr212Glu | + | Ser215Asp |
| Ser 97Glu | + | Ser100Glu | + | Gly156Asn | + | Ser157Glu | + | Ser160Glu | + | Tyr205Pro |
| Leu 95Asp | + | Ala105Asp | + | Ser157Glu | + | Val202His | + | Tyr205Ile | + | Leu216Met |
| Leu 95His | + | Gly156Pro | + | Ser157Asp | + | Asn162Glu | + | Ser187Glu | + | Leu216Asp |
| Ser100Glu | + | Leu125Gly | + | Gly127Glu | + | Ser203Asp | + | Tyr208Val | + | Leu216Asp |
| Asn154Ser | + | Gly165Asp | + | Ser190Glu | + | Thr212Gly | + | Ser215Asp | + | Gly218Pro |
| Thr 58Gln | + | Ser 98Glu | + | Gly153Asp | + | Val202Ser | + | Tyr205Asn | + | Gly218Asp |
| Asn 61Gln | + | Thr132Gly | + | Gly156Glu | + | Ser158Glu | + | Ser215Asp | + | Thr219Glu |
| Val 94Glu | + | Ser 97Glu | + | Ala105Asp | + | Gly165Pro | + | Leu216Met | + | Thr219Asp |
| Val 94Glu | + | Ser 97Glu | + | Ala105Asp | + | Asn154Gln | + | Gln161Asp | + | Ala186Asn |
| Gly130Gln | + | Ser155Glu | + | Ser158Glu | + | Ala186Gln | + | Ser203Asp | + | Leu216cys |
| Asn 61Gln | + | Ser160Asp | + | Ser203Glu | + | Val204Asn | + | Thr212Glu | + | Ser215Glu |
| Thr102Glu | + | Ala105Asp | + | Ser131Glu | + | Ser203Glu | + | Tyr205Ala | + | Thr214Asn |
| Thr 58Pro | + | Ser155Glu | + | Gly159Asn | + | Pro209Glu | + | Thr212Glu | + | Gly218Glu |
| Asp 59Glu | + | Gly 99Asp | + | Gly126Ser | + | Met198Thr | + | Thr212Asp | + | Gly218Pro |
| Thr132Ser | + | Asn154Ser | + | Ser157Asp | + | Val202Glu | + | Ser215Asp | + | Leu216Gly |
| Val 94Asp | + | Gly 99Asn | + | Ser100Asp | + | Gly139Ser | + | Asn154Gln | + | Ser215Asp |
| Pro128Glu | + | Gly156Ser | + | Ser160Glu | + | Ser187Asp | + | Ser190Glu | + | Thr212Ser |
| Asn 61Gln | + | Ser 98Glu | + | Ile106cys | + | Ser203Asp | + | Tyr205Gly | + | Gly218Asp |
| Ala105His | + | Ser158Glu | + | Ser187Glu | + | Ser203Glu | + | Tyr205Leu | + | Ser215Glu |
| Asn 96Ser | + | Gly 99Gln | + | Gly153Glu | + | Ala186Glu | + | Tyr205Glu | + | Ser215Glu |
| Asp 59Glu | + | Ser 98Glu | + | Gly153Glu | + | Ser155Glu | + | Phe188Pro | + | Leu216His |
| Asn162Asp | + | Gly165Asp | + | Val204Gln | + | Tyr205Thr | + | Ser210Asp | + | Thr212Pro |
| Gly101Pro | + | Gly156Asp | + | Tyr166Asp | + | Ser190Glu | + | Tyr205Asp | + | Thr212Asn |
| Gly126Asp | + | Thr132Asp | + | Ser155Asp | + | Ser157Asp | + | Val202Gly | + | Tyr213Ser |
| Gly 60Asp | + | Asn 61Asp | + | Asn154Glu | + | Ser158Glu | + | Gly165Gln | + | Tyr213Gln |
| Gly 62Glu | + | Leu125His | + | Ser131Asp | + | Ser215Asp | + | Tyr166Leu | + | Ser203Glu |
| Asp 59Glu | + | Val 94Asp | + | Thr102Gly | + | Ser203Glu | + | Tyr205Asp | + | Thr219Gly |
| Ser104Glu | + | Tyr166Cys | + | Val202Thr | + | Thr212Asp | + | Ser215Asp | + | Asn217Glu |
| Ser100Asp | + | Gly126Pro | + | Asn154Asp | + | Gly201Ser | + | Ser203Glu | + | Thr219Asp |
| Gly101Asp | + | Pro128Asp | + | Ser155Asp | + | Ser187Asp | + | Thr207Gly | + | Thr212Gln |
| Ile106Ser | + | Ser160Glu | + | Ser190Asp | + | Ser203Asp | + | Ser215Glu | + | Leu216Val |
| Gly 99Asp | + | Gly153Asp | + | Ser160Asp | + | Phe188Leu | + | Ser190Asp | + | Ser210Asp |
| Ser158Asp | + | Gly165Asn | + | Ser190Glu | + | Val202His | + | Tyr205Asp | + | Tyr213Leu |
| Thr 65Asp | + | Leu 95Thr | + | Ser131Glu | + | Val202Ser | + | Ser203Asp | + | Leu216Glu |
| Asn 61Glu | + | Gly165Ser | + | Met198Gln | + | Val202Glu | + | Tyr205Glu | + | Leu216Asn |
| Val 94A1a | + | Gly126Asp | + | Asn154Glu | + | Tyr166Pro | + | Val202Glu | + | Thr212Glu |
| Ser 97Glu | + | Leu125Glu | + | Ser155Glu | + | Gly159Asn | + | Tyr166Asp | + | Leu216Val |
| Asn 96Glu | + | Ser 97Asp | + | Thr102Gln | + | Leu125Asp | + | Leu216Glu | + | Thr219Gln |
| Tyr103Cys | + | Ser160Glu | + | Thr163Asp | + | Tyr208Ser | + | Leu216Met | + | Gly218Glu |
| Val 94Cys | + | Leu125Glu | + | Ser155Asp | + | Gly156Asp | + | Gly201Gln | + | Ser215Glu |
| Asn 61Ser | + | Thr 65Glu | + | Val 94Asp | + | Tyr103Pro | + | Ser215Asp | + | Asn217Asp |
| Gly 99Gln | + | Gly127Asp | + | Thr132Pro | + | Ser155Glu | + | Ser187Glu | + | Ser203Asp |
| Ser 98Glu | + | Ser129Glu | + | Gly153Glu | + | Ser190Asp | + | Tyr213Val | + | Thr214Pro |
| Asn 61Ser | + | Gly130Glu | + | Phe188Glu | + | Tyr205Asp | + | Thr212Pro | + | Asn217Asp |
| Ser158Asp | + | Gly159Glu | + | Val202Ser | + | Tyr205Met | + | Pro209Glu | + | Ser215Glu |
| Asn 61Asp | + | Gly 99Asn | + | Gly101Asp | + | Ser203Asp | + | Tyr205Asp | + | Thr212Pro |
| Ser 98Asp | + | Ser100Asp | + | Ser104Glu | + | Gly153Glu | + | Phe188Gly | + | Gly218Asn |
| Leu 95Val | + | Gly 99Asp | + | Tyr103Val | + | Ala105Asp | + | Tyr205Asp | + | Ser215Asp |
| Asp 59Glu | + | Asn 61Asp | + | Ser160Glu | + | Pro200Asn | + | Asn211Ser | + | Thr212Asp |
| Gly 62Glu | + | Thr 65Gly | + | Ser 97Asp | + | Thr102Pro | + | Ser131Glu | + | Leu216Asp |
| Gly126Pro | + | Pro128Glu | + | Gly156Asp | + | Ser158Asp | + | Tyr205Asn | + | Asn217Asp |
| Asp 59Glu | + | Gly130Asn | + | Ser155Asp | + | Ser210Asp | + | Tyr213Gly | + | Gly218Asn |
| Asn 96Gln | + | Gly 99Glu | + | Ser100Asp | + | Pro128Asp | + | Tyr205Cys | + | Asn217Glu |
| Pro128Gly | + | Ser129Asp | + | Asn162Glu | + | Gly165Asn | + | Ser203Asp | + | Ser215Asp |
| Asn 96Ser | + | Ser100Glu | + | Tyr103Glu | + | Tyr205His | + | Ser215Glu | + | Leu216Pro |
| Asn 96Glu | + | Ser 98Glu | + | Ala186Asp | + | Val202Asn | + | Tyr213Met | + | Leu216Glu |
| Gly 99Asp | + | Ser158Asp | + | Asn162Asp | + | Thr163Asp | + | Ser187Glu | + | Ala199Gly |
| Leu 95Ser | + | Ser 97Asp | + | Ser 98Glu | + | Gly165Glu | + | Leu216Ile | + | Gly218Glu |
| Gly101Asp | + | Leu125Asp | + | Gln161Asn | + | Tyr205Asp | + | Thr212Gly | + | Leu216Asn |
| Ser160Asp | + | Val202His | + | Ser203Asp | + | Thr212Asp | + | Tyr213Val | + | Leu216Asp |
| Leu 95Val | + | Tyr103Glu | + | Ala105Glu | + | Thr163Ser | + | Thr212Asp | + | Leu216Glu |
| Ser129Asp | + | Gly130Ser | + | Ser157Asp | + | Gly165Asp | + | Tyr205Asp | + | Leu216Gln |
| Thr132Asn | + | Gly156Glu | + | Tyr166Thr | + | Ser203Glu | + | Thr212Glu | + | Asn217Glu |
| Asn 61Gln | + | Ser 97Glu | + | Ser187Glu | + | Ser203Glu | + | Pro209Gln | + | Ser215Glu |
| Gly101Gln | + | Ala105Asp | + | Ser187Glu | + | Ser203Asp | + | Ser215Glu | + | Leu216His |
| Gly 99Asn | + | Ser104Asp | + | Thr132Gly | + | Ser187Asp | + | Ser203Glu | + | Ser215Asp |
| Gly 62Asp | + | Asn 96Gln | + | Ser104Glu | + | Tyr205Gln | + | Thr212Asp | + | Tyr213Val |
| Val 94Gly | + | Asn 96Asp | + | Ala105Glu | + | Asn162Asp | + | Asn211Gln | + | Thr212Gln |
| Ser 97Glu | + | Ser187Asp | + | Ser203Glu | + | Tyr213Gln | + | Leu216Glu | + | Asn217Gln |
| Gly 64Pro | + | Ser104Glu | + | Gly126Glu | + | Tyr166Ser | + | Tyr205Glu | + | Ser215Glu |
| Gly130Asn | + | Thr132Asp | + | Ser187Glu | + | Pro209Gln | + | Thr214Glu | + | Ser215Glu |

TABLE 36-continued

Multi-loop Sextuple Mutation Variants

| | | | | | | | | | | |
|---|---|---|---|---|---|---|---|---|---|---|
| Gly126Glu | + | Ser160Asp | + | Tyr166Met | + | Val202Thr | + | Thr214Asp | + | Ser215Glu |
| Ser 98Asp | + | Gly101Ser | + | Gly130Asp | + | Ser158Glu | + | Gly159Asp | + | Leu216Ala |
| Thr 58Glu | + | Tyr103Pro | + | Gly130Glu | + | Ser131Asp | + | Ser158Glu | + | Ala199Pro |
| Gly 60Asp | + | Asn 61Asp | + | Ser131Asp | + | Gly153Ser | + | Thr163Glu | + | Val202Cys |
| Gly 99Asp | + | Pro128Asn | + | Asn162Glu | + | Thr212Ser | + | Leu216Glu | + | Asn215Glu |
| Gly 60Ser | + | Ser 98Asp | + | Asn154Asp | + | Ser155Glu | + | Gly159Pro | + | Asn211Glu |
| Tyr103Pro | + | Ser104Glu | + | Leu125Cys | + | Val202Glu | + | Ser203Glu | + | Pro209Glu |
| Gly101Gln | + | Ser104Asp | + | Leu125Val | + | Val202Asp | + | Ser203Asp | + | Thr212Asp |
| Thr 65Asn | + | Ser 98Asp | + | Gly159Asn | + | Gly165Asp | + | Ser215Asp | + | Leu216Asp |
| Gly127Glu | + | Gly165Pro | + | Tyr205Cys | + | Ser210Asp | + | Ser215Glu | + | Leu216Glu |
| Val 94Ser | + | Ser 98Glu | + | Gly 99Asp | + | Gly156Asp | + | Phe188Leu | + | Ser203Glu |
| Gly 62Asp | + | Gly101Glu | + | Ser160Glu | + | Gln161Asp | + | Tyr205Met | + | Thr212Pro |
| Ser 97Asp | + | Ser 98Glu | + | Ala105His | + | Ser157Glu | + | Thr212Ser | + | Ser215Asp |
| Gly 62Gln | + | Ser 97Glu | + | Ser 98Asp | + | Gly126Glu | + | Gly130Pro | + | Thr212Glu |
| Val 94Glu | + | Ser 97Asp | + | Leu125Asn | + | Thr163Ser | + | Ser210Asp | + | Leu216Ile |
| Leu 95Glu | + | Asn 96Gln | + | Gly159Glu | + | Tyr205Glu | + | Pro209Ser | + | Ser215Glu |
| Ser129Glu | + | Asn154Ser | + | Thr212Glu | + | Ser215Asp | + | Gly218Asp | + | Thr219Ser |
| Asp 59Glu | + | Gly127Gln | + | Val202Glu | + | Asn211Glu | + | Thr212Ser | + | Ser215Asp |
| Ser104Asp | + | Ala105Pro | + | Ser187Glu | + | Ser203Glu | + | Tyr205Asp | + | Tyr213Pro |
| Thr 58Pro | + | Asn 96Asp | + | Gly127Glu | + | Ser155Glu | + | Asn162Ser | + | Thr212Ser |
| Thr 58Gly | + | Leu125Asn | + | Gly156Asp | + | Gln161Glu | + | Tyr205Gly | + | Ser215Asp |
| Gly 60Ser | + | Gly156Asp | + | Pro209Ser | + | Thr214Asp | + | Leu216Thr | + | Thr219Asp |
| Leu125His | + | Gly127Gln | + | Ser131Glu | + | Ser203Asp | + | Asn211Asp | + | Ser215Glu |
| Thr 58Glu | + | Pro128Glu | + | Gly165Gln | + | Ala186His | + | Ser203Glu | + | Ser215Glu |
| Ser131Asp | + | Ser158Glu | + | Ser203Asp | + | Tyr205His | + | Ser215Asp | + | Leu216Gln |
| Thr 65Asn | + | Gly130Asp | + | Ser158Asp | + | Ser203Asp | + | Pro209Ser | + | Ser215Glu |
| Gly 60Gln | + | Thr102Glu | + | Ser157Asp | + | Ser203Asp | + | Ser215Asp | + | Thr219Gln |
| Gly 64Gln | + | Gly127Asp | + | Ser160Glu | + | Ser203Asp | + | Ser215Glu | + | Gly218Gln |
| Ile106Leu | + | Thr132Asp | + | Thr163Asp | + | Ser203Glu | + | Ser215Asp | + | Leu216Ile |
| Gly126Ser | + | Ser160Asp | + | Thr212Glu | + | Ser215Glu | + | Leu216Val | + | Thr219Ser |
| Gly 60Pro | + | Gly101Asn | + | Ser158Glu | + | Tyr205Ile | + | Thr212Asp | + | Ser215Glu |
| Gly 62Glu | + | Gly 99Ser | + | Val202Ser | + | Tyr205Asp | + | Thr212Asn | + | Thr214Ser |
| Val 94His | + | Thr132Glu | + | Gly165Asp | + | Tyr166cys | + | Ser203Asp | + | Leu216Glu |
| Gly 62Asn | + | Ser131Asp | + | Ser157Glu | + | Gln161Asn | + | Ser203Glu | + | Leu216Glu |
| Gly 60Pro | + | Val 94Asp | + | Ala105Glu | + | Gly127Pro | + | Gln161Asp | + | Ser210Asp |
| Gly 62Gln | + | Ser 97Asp | + | Asn154Asp | + | Ser190Asp | + | Ser203Glu | + | Thr212Ser |
| Ser 97Glu | + | Asn154Glu | + | Gly159Asn | + | Ser190Asp | + | Tyr205Thr | + | Asn211Glu |
| Thr 65Glu | + | Ser 98Asp | + | Thr102Pro | + | Gly126Asp | + | Gly165Asp | + | Gly218Gln |
| Asn 96Glu | + | Tyr103Asp | + | Gly159Asp | + | Asn162Asp | + | Tyr208Leu | + | Thr212Pro |
| Gly 62Asp | + | Ser104Glu | + | Ile106Asp | + | Ser157Asp | + | Gly218Ser | + | Thr219Pro |
| Asn 96Glu | + | Gly 99Asp | + | Ser160Asp | + | Gly201Ser | + | Asn211Gln | + | Ser215Glu |
| Ile106Pro | + | Gly153Asp | + | Gly165Glu | + | Tyr166Ser | + | Ser203Asp | + | Thr212Asp |
| Ser 97Asp | + | Gly 99Asn | + | Ser158Asp | + | Ser210Glu | + | Thr212Glu | + | Leu216Thr |
| Asp 59Glu | + | Ser 98Asp | + | Ser160Asp | + | Gly201Ser | + | Thr212Gly | + | Tyr213Asn |
| Val 94Ser | + | Ser 97Asp | + | Ser187Glu | + | Ser190Asp | + | Pro209Asp | + | Leu216Asn |
| Gly101Asp | + | Gly126Asp | + | Ser131Asp | + | Asn154Glu | + | Gly156Asn | + | Ser203Asp |
| Gly 64Ser | + | Ser 98Glu | + | Ser100Glu | + | Ala186Glu | + | Thr212Glu | + | Leu216Pro |
| Ser 97Asp | + | Gly 99Asp | + | Val202Asp | + | Thr207Asn | + | Asn211Glu | + | Leu216Met |
| Thr 65Pro | + | Thr132Gly | + | Ala186Asp | + | Val202Ala | + | Ser203Glu | + | Thr212Asp |
| Ile106Asp | + | Gly127Ser | + | Asn154Glu | + | Gly156Glu | + | Thr214Pro | + | Ser215Glu |
| Thr 58Asp | + | Ser129Glu | + | Thr132Asn | + | Gly165Val | + | Leu216Val | + | Gly218Asp |
| Thr 58Pro | + | Gly 60Glu | + | Gly 62Glu | + | Thr102Asp/ | + | Ser158Glu | + | Leu216Ala |
| Pro128Asp | + | Asn154Glu | + | Phe188Val | + | Val202Cys | + | Ser203Asp | + | Tyr205Asn |
| Gly101Gln | + | Ala105His | + | Ser155Asp | + | Tyr166Val | + | Ala186Asp | + | Pro209Glu |
| Leu 95Val | + | Ser155Glu | + | Tyr166Ala | + | Ala186Glu | + | Ser210Asp | + | Leu216Met |
| Asn 96Asp | + | Gly101Glu | + | Asn162Glu | + | Val202Thr | + | Ser210Asp | + | Leu216Asn |
| Ser129Glu | + | Ser157Asp | + | Phe188Ala | + | Ser190Glu | + | Val202Ser | + | Tyr205Glu |
| Ser131Asp | + | Ser158Asp | + | Ser160Asp | + | Tyr205Ile | + | Ser215Asp | + | Leu216Met |
| Gly 62Glu | + | Leu 95Glu | + | Tyr103Pro | + | Ala186His | + | Ser203Glu | + | Thr207Gly |
| Ser100Glu | + | Leu125Ala | + | Ser157Glu | + | Ser203Asp | + | Tyr205Asp | + | Leu216Cys |
| Thr102Gln | + | Ser104Asp | + | Gly153Pro | + | Ser158Glu | + | 'Ser203Glu | + | Tyr205Asp |
| Asn 61Glu | + | Asn 96Gln | + | Ser 98Asp | + | Ser158Asp | + | Thr212Asn | + | Thr219Asp |
| Val 94Thr | + | Thr132Asp | + | Ser155Asp | + | Ser157Glu | + | Thr207Gly | + | Ser215Asp |
| Pro128Gly | + | Gly130Pro | + | Ser158Glu | + | Ser187Glu | + | Phe188Cys | + | Ser203Asp |
| Thr 65Glu | + | Gly130Pro | + | Gly159Glu | + | Gly165Asp | + | Phe188Met | + | Pro209Asp |
| Thr163Glu | + | Val202Asp | + | Tyr205Cys | + | Thr212Asp | + | Leu216Pro | + | Gly218Glu |
| Ser 97Asp | + | Gly101Asn | + | Gly130Asp | + | Asn154Asp | + | Thr163Gly | + | Gly218Glu |
| Thr 65Gly | + | Ala105Glu | + | Ser155Asp | + | Gln161Glu | + | Phe188Val | + | Asn217Gln |
| Thr 65Gln | + | Tyr103Asp | + | Pro128Glu | + | Ser155Asp | + | Ser215Asp | + | Leu216Ser |
| Thr132Glu | + | Ala186Gln | + | Ser167Glu | + | Val202Pro | + | Thr207Gly | + | Asn217Asp |
| Gly 60Glu | + | Ser129Glu | + | Ser131Glu | + | Gly165Asn | + | Ser203Glu | + | Pro209Gln |
| Gly101Pro | + | Pro128Asp | + | Gly130Asp | + | Ser203Glu | + | Tyr205Ile | + | Thr212Asp |
| Val 94Glu | + | Asn 96Glu | + | Asn154Asp | + | Tyr205Ala | + | Thr212Glu | + | Leu216Cys |
| Ser 97Glu | + | Thr102Ser | + | Ser157Asp | + | Ser215Asp | + | Leu216Ser | + | Asn217Glu |
| Ser 98Asp | + | Gly156Glu | + | Ser158Glu | + | Gln161Ser | + | Ser203Asp | + | Gly218Asn |
| Gly130Ser | + | Gly156Asp | + | Ser158Glu | + | Ser210Asp | + | Thr212Gln | + | Ser215Asp |
| Ser100Glu | + | Thr102Asp | + | Gly126Pro | + | Gly127Ser | + | Ser187Glu | + | Ser215Glu |

TABLE 36-continued

Multi-loop Sextuple Mutation Variants

| | | | | | | | | | | |
|---|---|---|---|---|---|---|---|---|---|---|
| Asn 96Glu | + | Gly127Ser | + | Pro128Gln | + | Ser190Asp | + | Tyr213Asp | + | Ser215Glu |
| Pro128Glu | + | Gly153Ser | + | Ser158Glu | + | Gly165Ser | + | Ala186Gly | + | Ser187Glu |
| Thr 65Glu | + | Gly153Asp | + | Thr163Asp | + | Gly165Asn | + | Met198His | + | Ser203Glu |
| Leu125Gly | + | Ser129Glu | + | Thr163Glu | + | Ala186His | + | Ser203Glu | + | Tyr205Leu |
| Thr 58Glu | + | Asn 61Ser | + | Thr 65Gly | + | Ser158Asp | + | Asn162Asp | + | Ser203Glu |
| Thr 65Asn | + | Val 94Thr | + | Gly126Glu | + | Ser157Asp | + | Asn162Glu | + | Leu216Asp |
| Asp 59Glu | + | Ser 97Glu | + | Pro128Asn | + | Thr132Glu | + | Ser157Asp | + | Tyr205Gly |
| Thr 58Glu | + | Gly 60Gln | + | Leu 95Glu | + | Val202Gln | + | Tyr205Gln | + | Ser215Asp |
| Asp 59Glu | + | Ser157Asp | + | Asn162Asp | + | Tyr166Asn | + | Leu216Ile | + | Asn217Glu |
| Ser157Glu | + | Asn162Glu | + | Phe188Gly | + | Ser203Asp | + | Asn211Asp | + | Thr212Ser |
| Ser157Glu | + | Asn162Asp | + | Ser210Asp | + | Thr212Ser | + | Tyr213Leu | + | Leu216Asp |
| Gly 60Pro | + | Ser 97Glu | + | Ser100Asp | + | Ala105His | + | Ser203Glu | + | Asn211Asp |
| Asn 61Asp | + | Leu125His | + | Gly156Asn | + | Pro200Gln | + | Thr212Glu | + | Leu216Asp |
| Thr 65Asp | + | Ser 97Asp | + | Leu125Asn | + | Ser157Glu | + | Thr163Gly | + | Thr212Asp |
| Gly 62Glu | + | Thr 65Asn | + | Asn162Glu | + | Thr163Ser | + | Asn211Asp | + | Ser215Glu |
| Val 94Glu | + | Asn 96Ser | + | Gly101Pro | + | Thr102Asp | + | Ser155Glu | + | Thr212Asp |
| Gly 60Glu | + | Ser 98Glu | + | Gly 99Gln | + | Ser104Glu | + | Ala105Thr | + | Thr214Asp |
| Ser155Asp | + | Ser187Asp | + | Ala199Gln | + | Ser203Asp | + | Tyr205Val | + | Thr212Glu |
| Ser104Glu | + | Ile106Cys | + | Thr163Ser | + | Gly165Glu | + | Ser190Glu | + | Thr212Asp |
| Val 94Thr | + | Ile106Asp | + | Gly130Asn | + | Ser131Asp | + | Ser203Glu | + | Tyr205Pro |
| Ser 98Glu | + | Pro128Glu | + | Ser155Asp | + | Ser160Glu | + | Ala186Ser | + | Pro209Asn |
| Thr 58Glu | + | Gly159Ser | + | Tyr186Glu | + | Ser190Glu | + | Thr212Pro | + | Leu216Ser |
| Leu 95Glu | + | Leu125His | + | Gly126Asp | + | Tyr205Gln | + | Ser215Asp | + | Thr219Asn |
| Asp 59Glu | + | Gly 99Asp | + | Ala105Glu | + | Ala186Pro | + | Ser187Asp | + | Thr212Pro |
| Asn 96Gln | + | Ser 98Glu | + | Gly104Pro | + | Thr132Glu | + | Val202Asp | + | Ser215Asp |
| Gly 99Asp | + | Pro128Asp | + | Thr132Asn | + | Val202Asp | + | Ser215Asp | + | Leu216His |
| Val 94Gln | + | Gly101Asp | + | Ser104Asp | + | Thr163Pro | + | Ser187Asp | + | Ser215Asp |
| Leu 95Met | + | Gly101Asp | + | Ser104Glu | + | Gly153Glu | + | Tyr205Ala | + | Ser215Glu |
| Gly101Glu | + | Ser104Glu | + | Ser203Asp | + | Tyr205Ile | + | Ser210Glu | + | Thr212Pro |
| Val 94Glu | + | Ser100Glu | + | Ile100Met | + | Gly130Glu | + | Val202Glu | + | Thr214Asn |
| Ser 98Asp | + | Ile106Asp | + | Asn154Asp | + | Gly165Asp | + | Val202Met | + | Leu216Gln |
| Leu 95Met | + | Thr102Ser | + | Gly127Asn | + | Ser190Glu | + | Val202Gly | + | Asn217Asp |
| Gly 62Pro | + | Ile106Gln | + | Gly126Asp | + | Ser129Glu | + | Ser160Asp | + | Ser215Asp |
| Gly 62Asp | + | Asn154Glu | + | Ser160Glu | + | Ala186Thr | + | Ser187Asp | + | Leu216Thr |
| Gly 62Ser | + | Thr 65Ser | + | Ser155Asp | + | Gly159Glu | + | Ser203Glu | + | Thr219Gln |

II. Cleaning Compositions

In another embodiment of the present invention, an effective amount of one or more of the enzyme variants are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet).

The cleaning compositions also comprise, in addition to the Subtilisin DY variants described hereinbefore, one or more cleaning composition materials compatible with the protease enzyme. the term "cleaning composition material", as used herein, means any liquid, solid or gaseous material selected for the particular type of cleaning composition desired and the form of the product (e.g., liquid, granule, bar, spray, stick, paste, gel), which materials are also compatible with the Subtilisin DY variant used in the composition. The specific selection of cleaning composition materials are readily made by considering the surface material to be cleaned, the desired form of the composition for the cleaning condition during use (e.g., through the wash detergent use). The term "compatible", as used herein, means the cleaning composition materials do not reduce the proteolytic activity of the Subtilisin DY variant to such an extent that the protease is not effective as desired during normal use situations. Specific cleaning composition materials are exemplified in detail hereinafter.

As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like. Preferably the cleaning compositions comprise from about 0.0001% to about 10% of one or more enzyme variants of the present invention, more preferably from about 0.001% to about 1%, more preferably still from about 0.01% to about 0.1%. Several examples of various cleaning compositions wherein the enzyme variants may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics.

The enzyme variants of the present invention can be used in a variety of detergent compositions where high sudsing and good insoluble substrate removal are desired. Thus the enzyme variants can be used with various conventional ingredients to provide fully-formulated hard-surface cleaners, dishwashing compositions, fabric laundering compositions and the like. Such compositions can be in the form of liquids, granules, bars and the like. Such compositions can be formulated as modem "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3^-M^+)CH_3$ and $CH_3(CH_2)y(CHOSO_3^-M^+)CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide andlor betaine or sultaine surfactants is also preferred, depending on the desires of the formulator.) Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

1. Hard Surface Cleaning Compositions

As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more of the enzyme variants, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

EXAMPLES 7–12

Liquid Hard Surface Cleaning Compositions

| Component | Example No. | | | | | |
|---|---|---|---|---|---|---|
| | 7 | 8 | 9 | 10 | 11 | 12 |
| Phe188Asp | 0.05 | 0.50 | 0.02 | 0.03 | 0.10 | 0.03 |
| Val202Ala | — | — | — | — | 0.20 | 0.02 |
| $Na_2$DIDA* | | | | | | |
| EDTA** | — | — | 2.90 | 2.90 | — | — |
| Na Citrate | — | — | — | — | 2.90 | 2.90 |
| $NaC_{12}$ Alkyl-benzene sulfonate | 1.95 | — | 1.95 | — | 1.95 | — |
| $NaC_{12}$ Alkylsulfate | — | 2.20 | — | 2.20 | — | 2.20 |
| $NaC_{12}$(ethoxy)*** sulfate | — | 2.20 | — | 2.20 | — | 2.20 |
| $C_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**$Na_4$ ethylenediamine diacetic acid
***Diethyleneglycol monohexyl ether
****All formulas adjusted to pH 7

In Examples 7–10, the Subtilisin DY variants recited in Tables 2–36, among others, are substituted for Phe188Asp, with substantially similar results.

In Examples 11–12, any combination of the Subtilisin DY variants recited in Tables 2–36, among others, are substituted for Phe188Asp and Val202Ala, with substantially similar results.

EXAMPLES 13–18

Spray Compositions for Cleaning Hard Surfaces and Removing Household Mildew

| Component | Example No. | | | | | |
|---|---|---|---|---|---|---|
| | 13 | 14 | 15 | 16 | 17 | 18 |
| Asn96Asp + Tyr103His | 0.50 | 0.05 | 0.60 | 0.30 | 0.20 | 0.30 |
| Pro200Gly + Gly201Ser + Ser210Asp | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is about 7.

In Examples 13–16, the Subtilisin DY variants recited in Tables 2–36, among others, are substituted for Asn 96Asp+Tyr103His, with substantially similar results.

In Examples 17–18, any combination of the Subtilisin DY variants recited in Tables 2–36, among others, are substituted for Asn 96Asp+Tyr103His and Pro200Gly+Gly201Ser+Ser210Asp, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

EXAMPLES 19–24

Dishwashing Composition

| Component | Example No. | | | | | |
|---|---|---|---|---|---|---|
| | 19 | 20 | 21 | 22 | 23 | 24 |
| Gly127Asn | 0.05 | 0.50 | 0.02 | 0.40 | 0.10 | 0.03 |
| Gly201Asn + Tyr205Gly + Thr207Gln + Tyr213Ile | — | — | — | — | 0.40 | 0.02 |
| $C_{12}$—$C_{14}$ N-methyl-glucamide | 0.90 | 0.90 | 0.90 | 0.90 | 0.90 | 0.90 |
| $C_{12}$ ethoxy (1) sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy (2) carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $CaCl_2$) | 0.40 | 0.40 | 0.40 | 0.40 | 0.40 | 0.40 |
| Water | balance to 100% | | | | | |

Product pH is adjusted to 7.

In Examples 19–22, the Subtilisin DY variants recited in Tables 2–36, among others, are substituted for Gly127Asn, with substantially similar results.

In Examples 23–24, any combination of the Subtilisin DY variants recited in Tables 2–36, among others, are substituted for Gly127Asn and Gly201Asn+Tyr205Gly+Thr207Gln+Tyr213Ile, with substantially similar results.

3. Fabric Cleaning Compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular Fabric Cleaning Compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

| Granular Fabric Cleaning Composition | | | | |
|---|---|---|---|---|
| | Example No. | | | |
| Component | 25 | 26 | 27 | 28 |
| Gly156Glu + Asn162Gln | 0.10 | 0.20 | 0.03 | 0.05 |
| Leu95Glu | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the Subtilisin DY variants recited in Tables 2–36, among others, are substituted for Gly156Glu+Asn162Gln, with substantially similar results.

In Examples 27–28, any combination of the Subtilisin DY variants recited in Tables 2–36, among others, are substituted for Gly156Glu+Asn162Gln and Leu 95Glu, with substantially similar results.

EXAMPLES 29–32

| Granular Fabric Cleaning Composition | | | | |
|---|---|---|---|---|
| | Example No. | | | |
| Component | 29 | 30 | 31 | 32 |
| Gln161Glu | 0.10 | 0.20 | 0.03 | 0.05 |
| Ala186Ser + Phe188Ala + Ser190Glu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$—$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the Subtilisin DY variants recited in Tables 2–36, among others, are substituted for Gln161Glu, with substantially similar results.

In Examples 31–32, any combination of the Subtilisin DY variants recited in Tables 2–36, among others, are substituted for Gln161Glu and Ala186Ser+Phe188Ala+Ser190Glu, with substantially similar results.

EXAMPLES 33–36

| Granular Fabric Cleaning Composition | | | | |
|---|---|---|---|---|
| | Example No. | | | |
| Component | 33 | 34 | 35 | 36 |
| Asn96Gln + Ile106Ala | 0.10 | 0.20 | 0.03 | 0.05 |
| Gly60Asn + Asn61Glu + Gly153Ser + Pro209Asp + Asn211Asp + Ser215Glu | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 33–34, the Subtilisin DY variants recited in Tables 2–36, among others, are substituted for Asn 96Gln+Ile106Ala, with substantially similar results.

In Examples 35–36, any combination of the Subtilisin DY variants recited in Tables 2–36, among others, are substituted for Asn 96Gln+Ile106Ala and Gly, 60Asn+Asn 61Glu+Gly153Ser+Pro209Asp+Asn211Asp+Ser215Glu, with substantially similar results.

EXAMPLES 37–40

| Granular Fabric Cleaning Composition | | | | |
|---|---|---|---|---|
| | Example No. | | | |
| Component | 37 | 38 | 39 | 40 |
| Gly60Asn | 0.10 | 0.20 | 0.03 | 0.05 |
| Ala186Asn + Ser187Asp + Phe188Gln + Ser190Glu | — | — | 0.02 | 0.05 |
| $C_{12}$ alkyl benzene sulfonate | 12.00 | 12.00 | 12.00 | 12.00 |
| Zeolite A (1–10 micrometer) | 26.00 | 26.00 | 26.00 | 26.00 |
| 2-butyl octanoic acid | 4.00 | 4.00 | 4.00 | 4.00 |
| $C_{12}$—$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 37–38, the Subtilisin DY variants recited in Tables 2–36, among others, are substituted for Gly60Asn, with substantially similar results.

In Examples 39–40, any combination of the Subtilisin DY variants recited in Tables 2–36, among others, are substituted for Gly60Asn and Ala186Asn+Ser187Asp+Phe188Gln+Ser190Glu, with substantially similar results.

EXAMPLES 41–42

Granular Fabric Cleaning Composition

| Component | Example No. 41 | Example No. 42 |
|---|---|---|
| Linear alkyl benzene sulphonate | 11.4 | 10.70 |
| Tallow alkyl sulphate | 1.80 | 2.40 |
| $C_{14–15}$ alkyl sulphate | 3.00 | 3.10 |
| $C_{14–15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Ser215Asp | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 43–44

Granular Fabric Cleaning Composition

| Component | Example No. 43 | Example No. 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Val202Met + Thr212Pro | 0.4 | 0.4 |
| Fillers (e.g., silicates; carbonates; perfumes; water) | Up to 100 | Up to 100 |

EXAMPLE 45

Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly (4-vinylpyridine)-N-oxide | 0.1 |
| Copolymer of vinylimidazole and vinylpyrrolidone | 0.1 |
| PEG2000 | 0.2 |
| Thr65Glu + Ile106Met + Leu125His + Tyr205Leu + Ser215Asp | 0.5 |
| Lipase | 0.2 |
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis (2-morpholino-4-anilino-s-triazin-6-ylamino) stilbene-2,2'-disulphonate | 0.25 |
| Disodium-4,4'-bis (2-sulfostyril) biphenyl | 0.05 |
| Water, Perfume and Minors | Up to 100 |

EXAMPLE 46

Granular Fabric Cleaning Composition

| Component | Weight % |
|---|---|
| Linear alkyl benzene sulphonate | 7.6 |
| $C_{16}$—$C_{18}$ alkyl sulfate | 1.3 |
| $C_{14–15}$ alcohol 7 times ethoxylated | 4.0 |
| Coco-alkyl-dimethyl hydroxyethyl ammonium chloride | 1.4 |
| Dispersant | 0.07 |
| Silicone fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Thr207Asn + Tyr208Gln + Thr212Ser + Tyr213Glu + Ser215Glu | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 47

Granular Fabric Cleaning Composition

| Component | Weight % |
|---|---|
| Linear alkyl benzene sulfonate | 6.92 |
| Tallow alkyl sulfate | 2.05 |
| $C_{14–15}$ alcohol 7 times ethoxylated | 4.4 |
| $C_{12–15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Gly 60Asp + Asn 61Asp + Gly 62Asp + Thr 65Gln | 0.2 |
| Lipase | 0.36 |

-continued

Granular Fabric Cleaning Composition

| Component | Weight % |
|---|---|
| Cellulase | 0.13 |
| Perborate tetrahydrate | 11.64 |
| Perborate monohydrate | 8.7 |
| Tetraacetylethylene diamine | 5.0 |
| Diethylene tramine penta methyl phosphonic acid | 0.38 |
| Magnesium sulfate | 0.40 |
| Brightener | 0.19 |
| Perfume, silicone, suds suppressors | 0.85 |
| Minors | Up to 100 | b. Liquid Fabric Cleaning Compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 48–52

Liquid Fabric Cleaning Compositions

| | Example No. | | | | |
|---|---|---|---|---|---|
| Component | 48 | 49 | 50 | 51 | 52 |
| Val94Gly + Gly99Pro + Ile106Val | 0.05 | 0.03 | 0.30 | 0.03 | 0.10 |
| Gly218Pro | — | — | — | 0.01 | 0.20 |
| $C_{12}$—$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the Subtilisin DY variants recited in Tables 2–36, among others, are substituted for Val94Gly+Gly99Pro+Ile106Val, with substantially similar results.

In Examples 51–52, any combination of the Subtilisin DY variants recited in Tables 2–36, among others, are substituted for Val94Gly+Gly99Pro+Ile106Val and Gly218Pro, with substantially similar results.

EXAMPLES 53–57

Liquid Fabric Cleaning Compositions

| | Example No. | | | | |
|---|---|---|---|---|---|
| Component | 53 | 54 | 55 | 56 | 57 |
| Gly156Ser | 0.05 | 0.03 | 0.30 | 0.03 | 0.10 |
| Ser187Glu | — | — | — | 0.01 | 0.20 |
| $C_{12}$—$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |

-continued

Liquid Fabric Cleaning Compositions

| | Example No. | | | | |
|---|---|---|---|---|---|
| Component | 53 | 54 | 55 | 56 | 57 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 53–55 the Subtilisin DY variants recited in Tables 2–36, among others, are substituted for Gly156Ser, with substantially similar results.

In Examples 56–57, any combination of the Subtilisin DY variants recited in Tables 2–36, among others, are substituted for Gly156Ser and Ser187Glu, with substantially similar results.

EXAMPLES 58–59

Liquid Fabric Cleaning Composition

| | Example No. | |
|---|---|---|
| Component | 58 | 59 |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Gly101Glu + Ser104Glu + Ser203Asp + Tyr205Ile + Ser210Glu + Thr212Pro | 0.2 | 0.2 |
| Polyvinyl pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Waters and minors | up to 100 parts | |

In each of Examples 58 and 59 herein, the Subtilisin DY variants recited in Tables 2–36, among others, are substituted for Gly101Glu+Ser104Glu+Ser203Asp+Tyr205Ile+Ser210Glu+Thr212Pro, with substantially similar results.

EXAMPLES 60–62

Liquid Fabric Cleaning Composition

| | Example No. | | |
|---|---|---|---|
| Component | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |
| NaCumene Sulfonate | 1.80 | 3.00 | 3.00 |

-continued

Liquid Fabric Cleaning Composition

| Component | Example No. 60 | 61 | 62 |
|---|---|---|---|
| NaFormate | 0.08 | 0.08 | 0.08 |
| NaOH | 6.70 | 3.80 | 3.80 |
| Silicon anti-foam agent | 1.16 | 1.18 | 1.18 |
| Asn61Glu + Gly64Ser + Thr65Gly | 0.0145 | — | — |
| Ser129Asp + Gly130Asn | — | 0.0145 | — |
| Leu216Asn | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | balance to 100% | | | c. Bar Fabric Cleaning Compositions

Bar fabric cleaning compositions of the present invention suitable for hand-washing soiled fabrics contain an effective amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

EXAMPLES 63–66

Bar Fabric Cleaning Compositions

| Component | Example No. 63 | 64 | 65 | 66 |
|---|---|---|---|---|
| Val202Ser + Asn211Asp | 0.3 | — | 0.1 | 0.02 |
| Gly156Gln + Ile164Thr | — | — | 0.4 | 0.03 |
| $C_{12}$—$C_{16}$ alkyl sulfate, Na | 20.0 | 20.0 | 20.0 | 20.00 |
| $C_{12}$—$C_{14}$ N-methyl glucamide | 5.0 | 5.0 | 5.0 | 5.00 |
| $C_{11}$—$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10μ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Examples 63–64 the Subtilisin DY variants recited in Tables 2–36, among others, are substituted for Val202Ser+Asn211Asp, with substantially similar results.

In Examples 65–46, any combination of the Subtilisin DY variants recited in Tables 2–36, among others, are substituted for Val202Ser+Asn211Asp and Gly156Gln+Ile164Thr, with substantially similar results.

EXAMPLES 67–70

Bar Fabric Cleaning Compositions

| Component | Example No. 67 | 68 | 69 | 70 |
|---|---|---|---|---|
| Val204Thr + Pro209Asp + Tyr213Cys | 0.3 | — | 0.1 | 0.02 |
| Gly126Gln + Thr214Gly + Ser215Glu | — | 0.3 | 0.4 | 0.03 |
| $C_{12}$—$C_{16}$ alkyl sulfate, Na | 20.0 | 20.0 | 20.0 | 20.00 |
| $C_{12}$—$C_{14}$ N-methyl glucamide | 5.0 | 5.0 | 5.0 | 5.00 |
| $C_{11}$—$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10μ) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates, and the like.

In Example 67, the Subtilisin DY variants recited in Tables 2–36, among others, are substituted for Val204Thr+Pro209Asp+Tyr213Cys, with substantially similar results.

In Example 68, the Subtilisin DY variants recited in Tables 2–36, among others, are substituted for Gly126Gln+Thr214Gly+Ser215Glu, with substantially similar results.

In Examples 69–70, any combination of the Subtilisin DY variants recited in Tables 2–36, among others, are substituted for Val204Thr+Pro209Asp+Tyr213Cys and Gly126Gln+Thr214Gly+Ser215Glu, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral Cleaning Compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more enzyme variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 71–74

Dentifrice Composition

| Component | Example No. | | | |
|---|---|---|---|---|
| | 71 | 72 | 73 | 74 |
| Thr214Asp | 2.000 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 71–74 the Subtilisin DY variants recited in Tables 2–36, among others, are substituted for Thr214Asp, with substantially similar results.

EXAMPLES 75–78

Mouthwash Composition

| Component | Example No. | | | |
|---|---|---|---|---|
| | 75 | 76 | 77 | 78 |
| Thr132Glu | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 75–78, the Subtilisin DY variants recited in Tables 2–36, among others, are substituted for Thr132Glu, with substantially similar results.

EXAMPLES 79–82

Lozenge Composition

| Component | Example No. | | | |
|---|---|---|---|---|
| | 79 | 80 | 81 | 82 |
| Ser97Glu + Ile106Leu | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the Subtilisin DY variants recited in Tables 2–36, among others, are substituted for Ser 97Glu+ Ile106Leu, with substantially similar results.

EXAMPLES 83–86

Chewing Gum Composition

| Component | Example No. | | | |
|---|---|---|---|---|
| | 83 | 84 | 85 | 86 |
| Leu125Ala + Ser129Glu + Gly130Pro + Ser131Asp | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L. A. Dreyfus Company.

In Examples 83–86, the Subtilisin DY variants recited in Tables 2–36, among others, are substituted for Leu125Ala+ Ser129Glu+Gly130Pro+Ser131Asp, with substantially similar results.

2. Denture Cleaning Compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

EXAMPLES 87–90

Two-layer Effervescent Denture Cleansing Tablet

| Component | Example No. | | | |
|---|---|---|---|---|
|  | 87 | 88 | 89 | 90 |
| Acidic Layer | | | | |
| Thr212Pro + Thr219Pro | 1.0 | 1.5 | 0.01 | 0.05 |
| Tartaric acid | 24.0 | 24.0 | 24.00 | 24.00 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In Examples 87–90, the Subtilisin DY variants recited in Tables 2–36, among others, are substituted for Thr212Pro+Thr219Pro, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Meaken and Rees, issued Sep. 5, 1989; U.S. Pat. No. Re. 32,672, Huth, Lam and Kirai, reissued May 24, 1988; U.S. Pat. No. 4,609,493, Schäfer, issued Sep. 2, 1986; U.S. Pat. No. 4,690,793, Ogunbiyi and Smith, issued Sep. 1, 1987; U.S. Pat. No. 4,614,549, Ogunbiyi, Riedhammer and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present invention is illustrated by the following examples.

EXAMPLES 91–94

Enzymatic Contact Lens Cleaning Solution

| Component | Example No. | | | |
|---|---|---|---|---|
|  | 91 | 92 | 93 | 94 |
| Gly156Glu + Thr163Ser + Asn211Ser + Thr212Asn | 0.01 | 0.5 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethylene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the Subtilisin DY variants recited in Tables 2–36, among others, are substituted for Gly156Glu+Thr163Ser+Asn211Ser+Thr212Asn, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A Subtilisin DY variant having a modified amino acid sequence of the Subtilisin DY wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at one or more positions in one of the loop regions; wherein A. when the substitution occurs in the first loop region, the substitution occurs at one of positions 60, 64 or 65; wherein
  a. when a substitution occurs at position 60, the substituting amino acid is Asn, Gln, Pro or Ser;
  b. when a substitution occurs at position 64, the substituting amino acid is Asn, Asp, Gln, Glu, Pro or Ser; and
  c. when a substitution occurs at position 65, the substituting amino acid is Asn, Asp, Gln, Glu, Gly, Pro or Ser;
B. when the substitution occurs in the second loop region, the substitution occurs at one of positions 94, 95, 96, 99 or 105; wherein
  a. when a substitution occurs at position 94, the substituting amino acid is Ala, Gln, Gly, His, Met, Pro or Ser;
  b. when a substitution occurs at position 95, the substituting amino acid is Ala, Asn, Asp, Cys, Gln, Glu, Gly, His, Ile, Met, Pro, Ser, Thr or Val;
  c. when a substitution occurs at position 96, the substituting amino acid is Gln or Ser;
  d. when a substitution occurs at position 99, the substituting amino acid is Asn, Gln, Pro or Ser; and
  e. when a substitution occurs at position 105, the substituting amino acid is Asn, Gln, Gly, His, Pro, Ser or Thr;

C. when the substitution occurs in the third loop region, the substitution occurs at one of positions 128, 131 or 132; wherein
  a. when a substitution occurs at position 128, the substituting amino acid is Asn, Gln or Ser;
  b. when a substitution occurs at position 131, the substituting amino acid is Asp or Glu; and
  c. when a substitution occurs at position 132, the substituting amino acid is Asn, Gln, Gly, Pro or Ser;
D. when the substitution occurs in the fourth loop region, the substitution occurs at position 154 wherein the substituting amino acid is Ser;
E. when a substitution occurs in the fifth loop region, the substitution occurs at position 188; wherein the substituting amino acid is Ala, Asn, Cys, Gln, Gly, His, Ile, Leu, Met, Pro, Ser, Thr, Tyr or Val; and
F. when the substitution occurs in the sixth loop region, the substitution occurs at one of positions 199, 200, 201, 202, 204, 205, 206, 207, 208, 209, 211, 212, 213, or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly, or Ser;
  c. when a substitution occurs at position 201, the substituting amino acid is Asn, Asp, Gln, Glu, Pro or Ser;
  d. when a substitution occurs at position 202, the substituting amino acid is Ala, Cys, Gln, Gly, His, Met, Pro or Ser;
  e. when a substitution occurs at position 204, the substituting amino acid is Ala, Cys, Gln, Gly, His, Met, Pro or Ser;
  f. when a substitution occurs at position 205, the substituting amino acid is Ala, Asn, Gln, Gly, His, Ile, Leu, Met, Pro or Ser;
  g. when a substitution occurs at position 206, the substituting amino acid is Asp or Glu;
  h. when a substitution occurs at position 207, the substituting amino acid is Asn, Gln, Gly, Pro or Ser;
  i. when a substitution occurs at position 208, the substituting amino acid is Ala, Asn, Cys, Gln, Gly, His, Ile, Met, Pro or Ser;
  j. when a substitution occurs at position 209, the substituting amino acid is Asn, Gln, Gly, or Ser;
  k. when a substitution occurs at position 211, the substituting amino acid is Gln or Ser;
  l. when a substitution occurs at position 212, the substituting amino acid is Asn, Gln, Gly, Pro or Ser;
  m. when a substitution occurs at position 213, the substituting amino acid is Ala, Asn, Cys, Gln, Gly, His, Ile, Leu, Met or Pro; and
  n. when a substitution occurs at position 219, the substituting amino acid is Asn, Asp, Gln, Glu, Gly, Pro or Ser;
whereby the Subtilisin DY variant has decreased adsorption to, and increased hydrolysis of, an insoluble substrate as compared to wild-type Subtilisin DY and wherein an amino acid substitution at the subtilisin DY positions 94 to 103, 106, 125 to 128, 153 to 166, 188, 203, 212 to 214 and 216 is combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

2. The Subtilisin DY variant of claim 1, wherein the substitution occurs in the first loop region.
3. The Subtilisin DY variant of claim 1, wherein the substitution occurs in the second loop region.
4. The Subtilisin DY variant of claim 1, wherein the substitution occurs in the third loop region.
5. The Subtilisin DY variant of claim 1, wherein the substitution occurs in the fourth loop region.
6. The Subtilisin DY variant of claim 1, wherein the substitution occurs in the fifth loop region.
7. The Subtilisin DY variant of claim 1, wherein one or more substitutions occur in the sixth loop region.
8. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
  A. when a substitution occurs in the first loop region, the substitution occurs at one or more of positions 58, 59, 60, 61, 62, 64 or 65; wherein
    a. when a substitution occurs at position 58, the substituting amino acid is Asn, Asp, Gln, Glu, Gly, Pro or Ser;
    b. when a substitution occurs at position 59, the substituting amino acid is Glu;
    c. when a substitution occurs at position 60, the substituting amino acid is Asn, Asp, Gln, Glu, Pro or Ser;
    d. when a substitution occurs at position 61, the substituting amino acid is Asp, Gln, Glu or Ser;
    e. when a substitution occurs at position 62, the substituting amino acid is Asn, Asp, Gln, Glu, Pro or Ser;
    f. when a substitution occurs at position 64, the substituting amino acid is Asn, Asp, Gln, Glu, Pro or Ser; and
    g. when a substitution occurs at position 65, the substituting amino acid is Asn, Asp, Gln, Glu, Gly, Pro or Ser;
  B. when a substitution occurs in the second loop region, the substitution occurs at one or more of positions 94, 95, 96, 97, 98, 99, 100, 101, 102, 103, 104, 105 or 106; wherein
    a. when a substitution occurs at position 94, the substituting amino acid is Ala, Asn, Asp, Cys, Gln, Glu, Gly, His, Met, Pro, Ser or Thr;
    b. when a substitution occurs at position 95, the substituting amino acid is Ala, Asn, Asp, Cys, Gln, Glu, Gly, His, Ile, Met, Pro, Ser, Thr or Val;
    c. when a substitution occurs at position 96, the substituting amino acid is Asp, Gln, Glu or Ser; but when position 96 is substituted the variant is not a double, triple, quadruple, quintuple, sextuple, or septuple mutation variant having substitutions at positions selected from the group consisting of 103, 154, 155, 165, 188, and 216;
    d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 155, 165, 188, and 216;
    e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 155, 165, 188, and 216;
- f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 155, 165, 188, and 216;
- g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 155, 165, 188, and 216;
- h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;
- i. when a substitution occurs at position 102, the substituting amino acid is Asn, Asp, Gln, Glu, Gly, Pro or Ser; but when position 102 is substituted the variant is not a double, triple, quadruple, quintuple, or sextuple mutation variant having substitutions at positions selected from the group consisting of 103, 155, 165, 188, and 216;
- j. when a substitution occurs at position 103, the substituting amino acid is Ala, Asn, Asp, Cys, Gln, Glu, Gly, His, Ile, Leu, Met, Pro, Ser, Thr or Val;
- k. when a substitution occurs at position 104, the substituting amino acid is Asp or Glu;
- l. when a substitution occurs at position 105, the substituting amino acid is Asn, Asp, Gln, Glu, Gly, His, Pro, Ser or Thr; and
- m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein
- a. when a substitution occurs at position 125, the substituting amino acid is Ala, Asn, Asp, Cys, Gln, Glu, Gly, His, Ile, Met, Pro, Ser, Thr or Val;

but when position 125 is substituted the variant is not a double, triple, quadruple, quintuple, sextuple, or septuple mutation variant having substitutions at positions selected from the group consisting of 103, 154, 155, 165, 188, and 216;
- b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;
- c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;
- d. when a substitution occurs at position 128, the substituting amino acid is Asn, Asp, Gln, Glu, Gly, or Ser; but when position 128 is substituted the variant is not a double, triple, quadruple, quintuple, sextuple, or septuple mutation variant having substitutions at positions selected from the group consisting of 103, 154, 155, 165, 188, and 216;
- e. when a substitution occurs at position 129, the substituting amino acid is Asp or Glu;
- f. when a substitution occurs at position 130, the substituting amino acid is Asn, Asp, Gln, Glu, Pro or Ser;
- g. when a substitution occurs at position 131, the substituting amino acid is Asp or Glu; and
- h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein
- a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;
- b. when a substitution occurs at position 154, the substituting amino acid is Asp, Gln, Glu or Ser;
- c. when a substitution occurs at position 155, the substituting amino acid is Asp or Glu;
- d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;
- e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;
- f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;
- g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;
- h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;
  i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;
  j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;
  k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;
  l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;
  m. when a substitution occurs at position 165, the substituting amino acid is Asn, Asp, Gln, Glu, Pro or Ser; and
  n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;
E. when a substitution occurs in the fifth loop region, the substitution occurs at one or more of positions 186, 187, 188, 189 or 190; wherein
  a. when a substitution occurs at position 186, the substituting amino acid is Asn, Asp, Gln, Glu, Gly, His, Pro, Ser or Thr;
  b. when a substitution occurs at position 187, the substituting amino acid is Asp or Glu;
  c. when a substitution occurs at position 188, the substituting amino acid is Ala, Asn, Asp, Cys, Gln, Glu, Gly, His, Ile, Leu, Met, Pro, Ser, Thr, Tyr or Val;
  d. when a substitution occurs at position 189, the substituting amino acid is Asp or Glu; and
  e. when a substitution occurs at position 190, the substituting amino acid is Asp or Glu; and
F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly, or Ser;
  c. when a substitution occurs at position 201, the substituting amino acid is Asn, Asp, Gln, Glu, Pro or Ser;
  d. when a substitution occurs at position 202, the substituting amino acid is Ala, Asn, Asp, Cys, Gln, Glu, Gly, His, Met, Pro, Ser or Thr;
  e. when a substitution occurs at position 203, the substituting amino acid is Asp or Glu;
  f. when a substitution occurs at position 204, the substituting amino acid is Ala, Asn, Asp, Cys, Gln, Glu, Gly, His, Met, Pro, Ser, or Thr;
  g. when a substitution occurs at position 205, the substituting amino acid is Ala, Asn, Asp, Cys, Gln, Glu, Gly, His, Ile, Leu, Met, Pro, Ser, Thr or Val;
  h. when a substitution occurs at position 206, the substituting amino acid is Asp or Glu;
  i. when a substitution occurs at position 207, the substituting amino acid is Asn, Asp, Gln, Glu, Gly, Pro or Ser;
  j. when a substitution occurs at position 208, the substituting amino acid is Ala, Asn, Asp, Cys, Gln, Glu, Gly, His, Ile, Leu, Met, Phe, Pro, Ser, Thr or Val;
  k. when a substitution occurs at position 209, the substituting amino acid is Asn, Asp, Gln, Glu, Gly, or Ser;
  l. when a substitution occurs at position 210, the substituting amino acid is Asp or Glu;
  m. when a substitution occurs at position 211, the substituting amino acid is Asp, Gln, Glu or Ser;
  n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
  o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
  p. when a substitution occurs at position 214, the substituting amino acid is Asn, Asp, Gln, Glu, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;
  q. when a substitution occurs at position 215, the substituting amino acid is Asp or Glu;
  r. when a substitution occurs at position 216, the substituting amino acid is Ala, Asn, Asp, Cys, Gln, Glu, Gly, His, Ile, Met, Pro, Ser, Thr or Val;
  s. when a substitution occurs at position 217, the substituting amino acid is Asp, Gln, Glu or Ser; but wherein when the substituting amino acid at position 217 is Ser, the variant is not a double mutation variant having a substitution of Ser at a position selected from the group consisting of 130 and 165;
  t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

9. The Subtilisin DY variant of claim 8, wherein two or more substitutions occur in the first loop region.

10. The Subtilisin DY variant of claim 8, wherein two or more substitutions occur in the second loop region.

11. The Subtilisin DY variant of claim 8, wherein two or more substitutions occur in the third loop region.

12. The Subtilisin DY variant of claim 8, wherein two or more substitutions occur in the fourth loop region.

13. The Subtilisin DY variant of claim 8, wherein two or more substitutions occur in the fifth loop region.

14. The Subtilisin DY variant of claim 8, wherein two or more substitutions occur in the sixth loop region.

15. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one of positions 60, 64 or 65; wherein
  a. when a substitution occurs at position 60, the substituting amino acid is Asn, Gln, Pro or Ser;
  b. when a substitution occurs at position 64, the substituting amino acid is Asn, Asp, Gln, Glu, Pro or Ser; and
  c. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
  a. when a substitution occurs at position 94, the substituting amino acid is Ala, Asn, Asp, Cys, Gln, Glu, Gly, His, Met, Pro, Ser or Thr;
  b. when a substitution occurs at position 95, the substituting amino acid is Ala, Asn, Asp, Cys, Gln, Glu, Gly, His, Ile, Met, Pro, Ser, Thr or Val;
  c. when a substitution occurs at position 96, the substituting amino acid is Asp, Gln, Glu or Ser; but when position 96 is substituted the variant is not a double, triple, quadruple, quintuple, sextuple, or septuple mutation variant having substitutions at positions selected from the group consisting of 103, 154, 155, 165, 188, and 216;
  d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 155, 165, 188, and 216;
  e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 155, 165, 188, and 216;
  f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 155, 165, 188, and 216;
  g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 155, 165, 188, and 216;
  h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;
  i. when a substitution occurs at position 102, the substituting amino acid is Asn, Asp, Gln, Glu, Gly, Pro or Ser; but when position 102 is substituted the variant is not a double, triple, quadruple, quintuple, or sextuple mutation variant having substitutions at positions selected from the group consisting of 103, 155, 165, 188, and 216;
  j. when a substitution occurs at position 103, the substituting amino acid is Ala, Asn, Asp, Cys, Gln, Glu, Gly, His, Ile, Leu, Met, Pro, Ser, Thr or Val;
  k. when a substitution occurs at position 104, the substituting amino acid is Asp or Glu;
  l. when a substitution occurs at position 105, the substituting amino acid is Asn, Asp, Gln, Glu, Gly, His, Pro, Ser or Thr; and
  m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein
  a. when a substitution occurs at position 125, the substituting amino acid is Ala, Asn, Asp, Cys, Gln, Glu, Gly, His, Ile, Met, Pro, Ser, Thr or Val;
  but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 128, the substituting amino acid is Asn, Asp, Gln, Glu, Gly, or Ser; but when position 128 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;

b. when a substitution occurs at position 154, the substituting amino acid is Asp, Gln, Glu or Ser;

c. when a substitution occurs at position 155, the substituting amino acid is Asp or Glu;

d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;

e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;

f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;

h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;

i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;

j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;

l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu; and

113 e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly, or Ser;
  c. when a substitution occurs at position 201, the substituting amino acid is Asn, Asp, Gln, Glu, Pro or Ser;
  d. when a substitution occurs at position 202, the substituting amino acid is Ala, Asn, Asp, Cys, Gln, Glu, Gly, His, Met, Pro, Ser or Thr;
  e. when a substitution occurs at position 203, the substituting amino acid is Asp or Glu;
  f. when a substitution occurs at position 204, the substituting amino acid is Ala, Asn, Asp, Cys, Gln, Glu, Gly, His, Met, Pro, Ser, or Thr;
  g. when a substitution occurs at position 205, the substituting amino acid is Ala, Asn, Asp, Cys, Gln, Glu, Gly, His, Ile, Leu, Met, Pro, Ser, Thr or Val;
  h. when a substitution occurs at position 206, the substituting amino acid is Asp or Glu;
  i. when a substitution occurs at position 207, the substituting amino acid is Asn, Asp, Gln, Glu, Gly, Pro or Ser;
  j. when a substitution occurs at position 208, the substituting amino acid is Ala, Asn, Asp, Cys, Gln, Glu, Gly, His, Ile, Leu, Met, Phe, Pro, Ser, Thr or Val;
  k. when a substitution occurs at position 209, the substituting amino acid is Asn, Asp, Gln, Glu, Gly, or Ser;
  l. when a substitution occurs at position 210, the substituting amino acid is Asp or Glu;
  m. when a substitution occurs at position 211, the substituting amino acid is Asp, Gln, Glu or Ser;
  n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
  o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
  p. when a substitution occurs at position 214, the substituting amino acid is Asn, Asp, Gln, Glu, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;
  q. when a substitution occurs at position 215, the substituting amino acid is Asp or Glu;
  r. when a substitution occurs at position 216, the substituting amino acid is Ala, Asn, Asp, Cys, Gln, Glu, Gly, His, Ile, Met, Pro, Ser, Thr or Val;
  s. when a substitution occurs at position 217, the substituting amino acid is Asp, Gln, Glu or Ser;
  t. when a substitution occurs at position 218, the substituting amino acid is Asn, Asp, Gln, Glu, Pro or Ser; and
  u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

16. The Subtilisin DY variant of claim 15, wherein two or more substitutions occur in the first loop region.

17. The Subtilisin DY variant of claim 15, wherein two or more substitutions occur in the second loop region.

18. The Subtilisin DY variant of claim 15, wherein two or more substitutions occur in the third loop region.

19. The Subtilisin DY variant of claim 15, wherein two or more substitutions occur in the fourth loop region.

20. The Subtilisin DY variant of claim 15, wherein two or more substitutions occur in the fifth loop region.

21. The Subtilisin DY variant of claim 15, wherein two or more substitutions occur in the sixth loop region.

22. A Subtilisin DY variant having a modified amino acid sequence of the Subtilisin DY wild-type amino acid sequence set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
  A. when a substitution occurs in the first loop region, the substitution occurs at one or more of positions 58, 59, 60, 61, 62, 64 or 65; wherein
    a. when a substitution occurs at position 58, the substituting amino acid is Asn, Asp, Gln, Glu, Gly, Pro or Ser;
    b. when a substitution occurs at position 59, the substituting amino acid is Glu;
    c. when a substitution occurs at position 60, the substituting amino acid is Asn, Asp, Gln, Glu, Pro or Ser;
    d. when a substitution occurs at position 61, the substituting amino acid is Asp, Gln, Glu or Ser;
    e. when a substitution occurs at position 62, the substituting amino acid is Asn, Asp, Gln, Glu, Pro or Ser;
    f. when a substitution occurs at position 64, the substituting amino acid is Asn, Asp, Gln, Glu, Pro or Ser; and
    g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 99, 101, 102, 103, 105 or 106; wherein
   a. when a substitution occurs at position 94, the substituting amino acid is Ala, Cys, Gln, Gly, His, Met, Pro or Ser;
   b. when a substitution occurs at position 95, the substituting amino acid is Ala, Asn, Asp, Cys, Gln, Glu, Gly, His, Ile, Met, Pro, Ser, Thr or Val;
   c. when a substitution occurs at position 96, the substituting amino acid is Gln or Ser; but when position 96 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 99, the substituting amino acid is Asn, Gln, Pro or Ser; but when position 99 is substituted the variant is not a double, triple, quadruple, quintuple, or sextuple mutation variant having substitutions at positions selected from the group consisting of 103, 155, 165, 188, and 216;
   e. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;
   f. when a substitution occurs at position 102, the substituting amino acid is Asn, Gln, Gly, Pro or Ser; but when position 102 is substituted the variant is not a double, triple, quadruple, quintuple, or sextuple mutation variant having substitutions at positions selected from the group consisting of 103, 155, 165, 188, and 216;
   g. when a substitution occurs at position 103, the substituting amino acid is Ala, Asn, Cys, Gln, Gly, His, Ile, Leu, Met, Pro or Ser;
   h. when a substitution occurs at position 105, the substituting amino acid is Asn, Gln, Gly, His, Pro, Ser or Thr; and
   i. when a substitution occurs at position 106, the substituting amino acid is Ala, Cys, Gln, Gly, His, Met, Pro, Ser or Val; but when position 106 is substituted the variant is not a double, triple, quadruple, quintuple, sextuple, or septuple mutation variant having substitutions at positions selected from the group consisting of 103, 154, 155, 165, 188, and 216;
C. when a substitution occurs in the third loop region, the substitution occurs at one or more of positions 125, 126, 127, 128, 129, 130, 131 or 132; wherein
   a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;
   b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;
   c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 128, the substituting amino acid is Asn, Asp, Gln, Glu, Gly, or Ser; but when position 128 is substituted the variant is not a double, triple, quadruple, quintuple, sextuple, or septuple mutation variant having substitutions at positions selected from the group consisting of 103, 154, 155, 165, 188, and 216;
   e. when a substitution occurs at position 129, the substituting amino acid is Asp or Glu;
   f. when a substitution occurs at position 130, the substituting amino acid is Asn, Asp, Gln, Glu, Pro or Ser;
   g. when a substitution occurs at position 131, the substituting amino acid is Asp or Glu; and
   h. when a substitution occurs at position 132, the substituting amino acid is Asn, Asp, Gln, Glu, Gly, Pro or Ser;
D. when a substitution occurs in the fourth loop region, the substitution occurs at one or more of positions 153, 154, 155, 156, 157, 158, 159, 160, 161, 162, 163, 164, 165 or 166; wherein
   a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;
   b. when a substitution occurs at position 154, the substituting amino acid is Asp, Gln, Glu or Ser;
   c. when a substitution occurs at position 155, the substituting amino acid is Asp or Glu;
   d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;
   e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;
   f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;
   g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;

h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;

i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;

j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;

l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu; and e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly, or Ser;

c. when a substitution occurs at position 201, the substituting amino acid is Asn, Asp, Gln, Glu, Pro or Ser;

d. when a substitution occurs at position 202, the substituting amino acid is Ala, Asn, Asp, Cys, Gln, Glu, Gly, His, Met, Pro, Ser or Thr;

e. when a substitution occurs at position 203, the substituting amino acid is Asp or Glu;

f. when a substitution occurs at position 204, the substituting amino acid is Ala, Asn, Asp, Cys, Gln, Glu, Gly, His, Met, Pro, Ser, or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Phe, Pro, Ser, Thr or Val;

k. when a substitution occurs at position 209, the substituting amino acid is Asn, Asp, Gln, Glu, Gly, or Ser;

l. when a substitution occurs at position 210, the substituting amino acid is Asp or Glu;

m. when a substitution occurs at position 211, the substituting amino acid is Asp, Gln, Glu or Ser;

n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;

o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;

p. when a substitution occurs at position 214, the substituting amino acid is Asn, Asp, Gln, Glu, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;

q. when a substitution occurs at position 215, the substituting amino acid is Asp or Glu;

r. when a substitution occurs at position 216, the substituting amino acid is Ala, Asn, Asp, Cys, Gln, Glu, Gly, His, Ile, Met, Pro, Ser, Thr or Val;

s. when a substitution occurs at position 217, the substituting amino acid is Asp, Gln, Glu or Ser;

t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

23. The Subtilisin DY variant of claim 22, wherein two or more substitutions occur in the first loop region.

24. The Subtilisin DY variant of claim 22, wherein two or more substitutions occur in the second loop region.

25. The Subtilisin DY variant of claim 22, wherein two or more substitutions occur in the third loop region.

26. The Subtilisin DY variant of claim 22, wherein two or more substitutions occur in the fourth loop region.

27. The Subtilisin DY variant of claim 22, wherein two or more substitutions occur in the fifth loop region.

28. The Subtilisin DY variant of claim 12, wherein two or more substitutions occur in the sixth loop region.

29. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 59, 60, 61, 62, 64 or 65; wherein
   a. when a substitution occurs at position 58, the substituting amino acid is Asn, Asp, Gln, Glu, Gly, Pro or Ser;
   b. when a substitution occurs at position 59, the substituting amino acid is Glu;
   c. when a substitution occurs at position 60, the substituting amino acid is Asn, Asp, Gln, Glu, Pro or Ser;
   d. when a substitution occurs at position 61, the substituting amino acid is Asp, Gln, Glu or Ser;
   e. when a substitution occurs at position 62, the substituting amino acid is Asn, Asp, Gln, Glu, Pro or Ser;
   f. when a substitution occurs at position 64, the substituting amino acid is Asn, Asp, Gln, Glu, Pro or Ser; and
   g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
   a. when a substitution occurs at position 94, the substituting amino acid is Ala, Asn, Asp, Cys, Gln, Glu, Gly, His, Met, Pro, Ser or Thr;
   b. when a substitution occurs at position 95, the substituting amino acid is Ala, Asn, Asp, Cys, Gln, Glu, Gly, His, Ile, Met, Pro, Ser, Thr or Val;
   c. when a substitution occurs at position 96, the substituting amino acid is Asp, Gln, Glu or Ser; but when position 96 is substituted the variant is not a double, triple, quadruple, quintuple, sextuple, or septuple mutation variant having substitutions at positions selected from the group consisting of 103, 154, 155, 165, 188, and 216;
   d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 155, 165, 188, and 216;
   e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 155, 165, 188, and 216;
   f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 155, 165, 188, and 216;
   g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 155, 165, 188, and 216;
   h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;
   i. when a substitution occurs at position 102, the substituting amino acid is Asn, Asp, Gln, Glu, Gly, Pro or Ser; but when position 102 is substituted the variant is not a double, triple, quadruple, quintuple, or sextuple mutation variant having substitutions at positions selected from the group consisting of 103, 155, 165, 188, and 216;
   j. when a substitution occurs at position 103, the substituting amino acid is Ala, Asn, Asp, Cys, Gln, Glu, Gly, His, Ile, Leu, Met, Pro, Ser, Thr or Val;
   k. when a substitution occurs at position 104, the substituting amino acid is Asp or Glu;
   l. when a substitution occurs at position 105, the substituting amino acid is Asn, Asp, Gln, Glu, Gly, His, Pro, Ser or Thr; and
   m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 128, 131 or 132; wherein a. when a substitution occurs at position 125, the substituting amino acid is Ala, Asn, Cys, Gln, Gly, His, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 128, the substituting amino acid is Asn, Gln or Ser; but when position 128 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 131, the substituting amino acid is Asp or Glu; and e. when a substitution occurs at position 132, the substituting amino acid is Asn, Gln, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;

b. when a substitution occurs at position 154, the substituting amino acid is Asp, Gln, Glu or Ser;

c. when a substitution occurs at position 155, the substituting amino acid is Asp or Glu;

d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;

e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;

f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;

h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;

i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;

j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;

l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu; and e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;
b. when a substitution occurs at position 200, the substituting amino acid is Asn, Asp, Gln, Glu, Gly, or Ser;
c. when a substitution occurs at position 201, the substituting amino acid is Asn, Asp, Gln, Glu, Pro or Ser;
d. when a substitution occurs at position 202, the substituting amino acid is Ala, Asn, Asp, Cys, Gln, Glu, Gly, His, Met, Pro, Ser or Thr;
e. when a substitution occurs at position 203, the substituting amino acid is Asp or Glu;
f. when a substitution occurs at position 204, the substituting amino acid is Ala, Asn, Asp, Cys, Gln, Glu, Gly, His, Met, Pro, Ser, or Thr;
g. when a substitution occurs at position 205, the substituting amino acid is Ala, Asn, Asp, Cys, Gln, Glu, Gly, His, Ile, Leu, Met, Pro, Ser, Thr or Val;
h. when a substitution occurs at position 206, the substituting amino acid is Asp or Glu;
i. when a substitution occurs at position 207, the substituting amino acid is Asn, Asp, Gln, Glu, Gly, Pro or Ser;
j. when a substitution occurs at position 208, the substituting amino acid is Ala, Asn, Asp, Cys, Gln, Glu, Gly, His, Ile, Leu, Met, Phe, Pro, Ser, Thr or Val;
k. when a substitution occurs at position 209, the substituting amino acid is Asn, Asp, Gln, Glu, Gly, or Ser;
l. when a substitution occurs at position 210, the substituting amino acid is Asp or Glu;
m. when a substitution occurs at position 211, the substituting amino acid is Asp, Gln, Glu or Ser;
n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;
p. when a substitution occurs at position 214, the substituting amino acid is Asn, Asp, Gln, Glu, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;
q. when a substitution occurs at position 215, the substituting amino acid is Asp or Glu;
r. when a substitution occurs at position 216, the substituting amino acid is Ala, Asn, Asp, Cys, Gln, Glu, Gly, His, Ile, Met, Pro, Ser, Thr or Val;
s. when a substitution occurs at position 217, the substituting amino acid is Asp, Gln, Glu or Ser;
t. when a substitution occurs at position 218, the substituting amino acid is Asn, Asp, Gln, Glu, Pro or Ser; and
u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

30. The Subtilisin DY variant of claim 29, wherein two or more substitutions occur in the first loop region.

31. The Subtilisin DY variant of claim 29, wherein two or more substitutions occur in the second loop region.

32. The Subtilisin DY variant of claim 29, wherein two or more substitutions occur in the third loop region.

33. The Subtilisin DY variant of claim 29, wherein two or more substitutions occur in the fourth loop region.

34. The Subtilisin DY variant of claim 29, wherein two or more substitutions occur in the fifth loop region.

35. The Subtilisin DY variant of claim 29, wherein two or more substitutions occur in the sixth loop region.

36. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 59, 60, 61, 62, 64 or 65; wherein
  a. when a substitution occurs at position 58, the substituting amino acid is Asn, Asp, Gln, Glu, Gly, Pro or Ser;
  b. when a substitution occurs at position 59, the substituting amino acid is Glu;
  c. when a substitution occurs at position 60, the substituting amino acid is Asn, Asp, Gln, Glu, Pro or Ser;
  d. when a substitution occurs at position 61, the substituting amino acid is Asp, Gln, Glu or Ser;
  e. when a substitution occurs at position 62, the substituting amino acid is Asn, Asp, Gln, Glu, Pro or Ser;
  f. when a substitution occurs at position 64, the substituting amino acid is Asn, Asp, Gln, Glu, Pro or Ser; and
  g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
  a. when a substitution occurs at position 94, the substituting amino acid is Ala, Asn, Asp, Cys, Gln, Glu, Gly, His, Met, Pro, Ser or Thr;

b. when a substitution occurs at position 95, the substituting amino acid is Ala, Asn, Asp, Cys, Gln, Glu, Gly, His, Ile, Met, Pro, Ser, Thr or Val;

c. when a substitution occurs at position 96, the substituting amino acid is Asp, Gln, Glu or Ser; but when position 96 is substituted the variant is not a double, triple, or quadruple mutation variant having substitutions at positions selected from the group consisting of 103, 188, and 216;

d. when a substitution occurs at position 97, the substituting amino acid is Asp or Glu; but when position 97 is substituted the variant is not a double, triple, or quadruple mutation variant having substitutions at positions selected from the group consisting of 103, 188, and 216;

e. when a substitution occurs at position 98, the substituting amino acid is Asp or Glu; but when position 98 is substituted the variant is not a double, triple, or quadruple mutation variant having substitutions at positions selected from the group consisting of 103, 188, and 216;

f. when a substitution occurs at position 99, the substituting amino acid is Asn, Asp, Gln, Glu, Pro or Ser; but when position 99 is substituted the variant is not a double, triple, or quadruple mutation variant having substitutions at positions selected from the group consisting of 103, 188, and 216;

g. when a substitution occurs at position 100, the substituting amino acid is Asp or Glu; but when position 100 is substituted the variant is not a double, triple, or quadruple mutation variant having substitutions at positions selected from the group consisting of 103, 188, and 216;

h. when a substitution occurs at position 101, the substituting amino acid is Asn, Asp, Gln, Glu, Pro or Ser; but when position 101 is substituted the variant is not a double, triple, or quadruple mutation variant having substitutions at positions selected from the group consisting of 103, 188, and 216;

i. when a substitution occurs at position 102, the substituting amino acid is Asn, Asp, Gln, Glu, Gly, Pro or Ser; but when position 102 is substituted the variant is not a double, triple, or quadruple mutation variant having substitutions at positions selected from the group consisting of 103, 188, and 216;

j. when a substitution occurs at position 103, the substituting amino acid is Ala, Asn, Asp, Cys, Gln, Glu, Gly, His, Ile, Leu, Met, Pro, Ser, Thr or Val;

k. when a substitution occurs at position 104, the substituting amino acid is Asp or Glu;

l. when a substitution occurs at position 105, the substituting amino acid is Asn, Asp, Gln, Glu, Gly, His, Pro, Ser or Thr; and m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, or quadruple mutation variant having substitutions at positions selected from the group consisting of 103, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, or quadruple mutation variant having substitutions at positions selected from the group consisting of 103, 188, and 216;

b. when a substitution occurs at position 126, the substituting amino acid is Asn, Asp, Gln, Glu, Pro or Ser; but when position 126 is substituted the variant is not a double, triple, or quadruple mutation variant having substitutions at positions selected from the group consisting of 103, 188, and 216;

c. when a substitution occurs at position 127, the substituting amino acid is Asn, Asp, Gln, Glu, Pro or Ser; but when position 127 is substituted the variant is not a double, triple, or quadruple mutation variant having substitutions at positions selected from the group consisting of 103, 188, and 216;

d. when a substitution occurs at position 128, the substituting amino acid is Asn, Asp, Gln, Glu, Gly, or Ser; but when position 128 is substituted the variant is not a double, triple, or quadruple mutation variant having substitutions at positions selected from the group consisting of 103, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 154, 156 or 166; wherein a. when a substitution occurs at position 154, the substituting amino acid is Gln or Ser;

b. when a substitution occurs at position 156, the substituting amino acid is Asn, Asp, Gln, Glu, Pro or Ser; but when position 156 is substituted the variant is not a double, triple, or quadruple mutation variant having substitutions at positions selected from the group consisting of 103, 188, and 216; and c. when a substitution occurs at position 166, the substituting amino acid is Ala, Gly, His, Ile, Leu, Met or Pro; but when position 166 is substituted the variant is not a double, triple, or quadruple mutation variant having substitutions at positions selected from the group consisting of 103, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;

c. when a substitution occurs at position 188, the substituting amino acid is Ala, Asn, Asp, Cys, Gln, Glu, Gly, His, Ile, Leu, Met, Pro, Ser, Thr, Tyr or Val;

d. when a substitution occurs at position 189, the substituting amino acid is Asp or Glu; and e. when a substitution occurs at position 190, the substituting amino acid is Asp or Glu; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;
b. when a substitution occurs at position 200, the substituting amino acid is Asn, Asp, Gln, Glu, Gly, or Ser;
c. when a substitution occurs at position 201, the substituting amino acid is Asn, Asp, Gln, Glu, Pro or Ser;
d. when a substitution occurs at position 202, the substituting amino acid is Ala, Asn, Asp, Cys, Gln, Glu, Gly, His, Met, Pro, Ser or Thr;
e. when a substitution occurs at position 203, the substituting amino acid is Asp or Glu;
f. when a substitution occurs at position 204, the substituting amino acid is Ala, Asn, Asp, Cys, Gln, Glu, Gly, His, Met, Pro, Ser, or Thr;
g. when a substitution occurs at position 205, the substituting amino acid is Ala, Asn, Asp, Cys, Gln, Glu, Gly, His, Ile, Leu, Met, Pro, Ser, Thr or Val;
h. when a substitution occurs at position 206, the substituting amino acid is Asp or Glu;
i. when a substitution occurs at position 207, the substituting amino acid is Asn, Asp, Gln, Glu, Gly, Pro or Ser;
j. when a substitution occurs at position 208, the substituting amino acid is Ala, Asn, Asp, Cys, Gln, Glu, Gly, His, Ile, Leu, Met, Phe, Pro, Ser, Thr or Val;
k. when a substitution occurs at position 209, the substituting amino acid is Asn, Asp, Gln, Glu, Gly, or Ser;
l. when a substitution occurs at position 210, the substituting amino acid is Asp or Glu;
m. when a substitution occurs at position 21 1, the substituting amino acid is Asp, Gln, Glu or Ser;
n. when a substitution occurs at position 212, the substituting amino acid is Asn, Asp, Gln, Glu, Gly, Pro or Ser; but when position 212 is substituted the variant is not a double, triple, or quadruple mutation variant having substitutions at positions selected from the group consisting of 103, 188, and 216;
o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, or quadruple mutation variant having substitutions at positions selected from the group consisting of 103, 188, and 216;
p. when a substitution occurs at position 214, the substituting amino acid is Asn, Asp, Gln, Glu, Gly, Pro or Ser; but when position 214 is substituted the variant is not a double, triple, or quadruple mutation variant having substitutions at positions selected from the group consisting of 103, 188, and 216;
q. when a substitution occurs at position 215, the substituting amino acid is Asp or Glu;
r. when a substitution occurs at position 216, the substituting amino acid is Ala, Asn, Asp, Cys, Gln, Glu, Gly, His, Ile, Met, Pro, Ser, Thr or Val;
s. when a substitution occurs at position 217, the substituting amino acid is Asp, Gln, Glu or Ser;
t. when a substitution occurs at position 218, the substituting amino acid is Asn, Asp, Gln, Glu, Pro or Ser; and
u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

37. The Subtilisin DY variant of claim 36, wherein two or more substitutions occur in the first loop region.
38. The Subtilisin DY variant of claim 36, wherein two or more substitutions occur in the second loop region.
39. The Subtilisin DY variant of claim 36, wherein two or more substitutions occur in the third loop region.
40. The Subtilisin DY variant of claim 36, wherein two or more substitutions occur in the fourth loop region.
41. The Subtilisin DY variant of claim 36, wherein two or more substitutions occur in the fifth loop region.
42. The Subtilisin DY variant of claim 36, wherein two or more substitutions occur in the sixth loop region.
43. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein
A. when a substitution occurs in the first loop region, the substitution occurs at one or more of positions 58, 59, 60, 61, 62, 64 or 65; wherein
  a. when a substitution occurs at position 58, the substituting amino acid is Asn, Asp, Gln, Glu, Gly, Pro or Ser;
  b. when a substitution occurs at position 59, the substituting amino acid is Glu;
  c. when a substitution occurs at position 60, the substituting amino acid is Asn, Asp, Gln, Glu, Pro or Ser;
  d. when a substitution occurs at position 61, the substituting amino acid is Asp, Gln, Glu or Ser;
  e. when a substitution occurs at position 62, the substituting amino acid is Asn, Asp, Gln, Glu, Pro or Ser;
  f. when a substitution occurs at position 64, the substituting amino acid is Asn, Asp, Gln, Glu, Pro or Ser; and
  g. when a substitution occurs at position 65, the substituting amino acid is Asn, Asp, Gln, Glu, Gly, Pro or Ser;
B. when a substitution occurs in the second loop region, the substitution occurs at one or more of positions 94, 95, 96, 97, 98, 99, 100, 101, 102, 103, 104, 105 or 106; wherein
  a. when a substitution occurs at position 94, the substituting amino acid is Ala, Asn, Asp, Cys, Gln, Glu, Gly, His, Met, Pro, Ser or Thr;
  b. when a substitution occurs at position 95, the substituting amino acid is Ala, Asn, Asp, Cys, Gln, Glu, Gly, His, Ile, Met, Pro, Ser, Thr or Val;

c. when a substitution occurs at position 96, the substituting amino acid is Asp, Gln, Glu or Ser; but when position 96 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 155, 165, 188, and 216;

e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 155, 165, 188, and 216;

f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 155, 165, 188, and 216;

g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 155, 165, 188, and 216;

h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;

i. when a substitution occurs at position 102, the substituting amino acid is Asn, Asp, Gln, Glu, Gly, Pro or Ser; but when position 102 is substituted the variant is not a double, triple, quadruple, quintuple, or sextuple mutation variant having substitutions at positions selected from the group consisting of 103, 155, 165, 188, and 216;

j. when a substitution occurs at position 103, the substituting amino acid is Ala, Asn, Asp, Cys, Gln, Glu, Gly, His, Ile, Leu, Met, Pro, Ser, Thr or Val;

k. when a substitution occurs at position 104, the substituting amino acid is Asp or Glu;

l. when a substitution occurs at position 105, the substituting amino acid is Asn, Asp, Gln, Glu, Gly, His, Pro, Ser or Thr; and m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 128, the substituting amino acid is Asn, Asp, Gln, Glu, Gly, or Ser; but when position 128 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;

b. when a substitution occurs at position 154, the substituting amino acid is Asp, Gln, Glu or Ser;

c. when a substitution occurs at position 155, the substituting amino acid is Asp or Glu;

d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;

e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;

f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;

h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;

i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;

j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;

l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;

E. when a substitution occurs in the fifth loop region, the substitution occurs at position 188; wherein the substituting amino acid is Ala, Asn, Cys, Gln, Gly, His, Ile, Leu, Met, Pro, Ser, Thr, Tyr or Val; and F. when a substitution occurs in the sixth loop region, the substitution occurs at one or more of positions 199, 200, 201, 202, 203, 204, 205, 206, 207, 208, 209, 210, 211, 212, 213, 214, 215, 216, 217, 218 or 219; wherein a. when a substitution occurs at position 199, the substituting amino acid is Asn, Asp, Gln, Glu, Gly, His, Pro, Ser or Thr;

b. when a substitution occurs at position 200, the substituting amino acid is Asn, Asp, Gln, Glu, Gly, or Ser;

c. when a substitution occurs at position 201, the substituting amino acid is Asn, Asp, Gln, Glu, Pro or Ser;

d. when a substitution occurs at position 202, the substituting amino acid is Ala, Asn, Asp, Cys, Gln, Glu, Gly, His, Met, Pro, Ser or Thr;

e. when a substitution occurs at position 203, the substituting amino acid is Asp or Glu;

f. when a substitution occurs at position 204, the substituting amino acid is Ala, Asn, Asp, Cys, Gln, Glu, Gly, His, Met, Pro, Ser, or Thr;

g. when a substitution occurs at position 205, the substituting amino acid is Ala, Asn, Asp, Cys, Gln, Glu, Gly, His, Ile, Leu, Met, Pro, Ser, Thr or Val;

h. when a substitution occurs at position 206, the substituting amino acid is Asp or Glu;

i. when a substitution occurs at position 207, the substituting amino acid is Asn, Asp, Gln, Glu, Gly, Pro or Ser;

j. when a substitution occurs at position 208, the substituting amino acid is Ala, Asn, Asp, Cys, Gln, Glu, Gly, His, Ile, Leu, Met, Phe, Pro, Ser, Thr or Val;

k. when a substitution occurs at position 209, the substituting amino acid is Asn, Asp, Gln, Glu, Gly, or Ser;

l. when a substitution occurs at position 210, the substituting amino acid is Asp or Glu;

m. when a substitution occurs at position 211, the substituting amino acid is Asp, Gln, Glu or Ser;

n. when a substitution occurs at position 212, the substituting amino acid is Asn, Asp, Gln, Glu, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;

o. when a substitution occurs at position 213, the substituting amino acid is Ala, Asn, Asp, Cys, Gln, Glu, Gly, His, Ile, Leu, Met, Pro, Ser, Thr or Val; but when position 213 is substituted the variant is not a double, triple, quadruple, quintuple, sextuple, or septuple mutation variant having substitutions at positions selected from the group consisting of 103, 154, 155, 165, 188, and 216;

p. when a substitution occurs at position 214, the substituting amino acid is Asn, Asp, Gln, Glu, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;

q. when a substitution occurs at position 215, the substituting amino acid is Asp or Glu;

r. when a substitution occurs at position 216, the substituting amino acid is Ala, Asn, Asp, Cys, Gln, Glu, Gly, His, Ile, Met, Pro, Ser, Thr or Val;

s. when a substitution occurs at position 217, the substituting amino acid is Asp, Gln, Glu or Ser;

t. when a substitution occurs at position 218, the substituting amino acid is Asn, Asp, Gln, Glu, Pro or Ser; and u. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY and wherein glutamate and aspartate substitutions at both subtilisin DY positions 207 and 213, or substitutions at either of 207 and 213 combined with a serine substitution at position 217, are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219 and wherein glutamate and aspartate substitutions at both subtilisin DY positions 61 and 165 are combined with at least one further substitution at a corresponding position selected from subtilisin DY positions 59, 60, 64, 65, 104, 105, 129, 131, 132, 187, 189, 190, 199 to 202, 204, 206, 209 to 211, 215 and 219.

44. The Subtilisin DY variant of claim 43, wherein two or more substitutions occur in the first loop region.

45. The Subtilisin DY variant of claim 43, wherein two or more substitutions occur in the second loop region.

46. The Subtilisin DY variant of claim 43, wherein two or more substitutions occur in the third loop region.

47. The Subtilisin DY variant of claim 43, wherein two or more substitutions occur in the fourth loop region.

48. The Subtilisin DY variant of claim 43, wherein one substitution occurs in the fifth loop region.

49. The Subtilisin DY variant of claim 43, wherein two or more substitutions occur in the sixth loop region.

50. A Subtilisin DY variant having a modified amino acid sequence of the Subtilisin DY wild-type amino acid sequence as set forth in SEQ ID NO:1, the wild-type amino acid sequence comprising a first loop region, a second loop region, a third loop region, a fourth loop region, a fifth loop region and a sixth loop region; wherein the modified amino acid sequence comprises a substitution at two or more positions in one or more of the loop regions; wherein A. when a substitution occurs in the first loop region, the substitution occurs at one or more of positions 58, 59, 60, 61, 62, 64 or 65; wherein
  a. when a substitution occurs at position 58, the substituting amino acid is Asn, Asp, Gln, Glu, Gly, Pro or Ser;
  b. when a substitution occurs at position 59, the substituting amino acid is Glu;
  c. when a substitution occurs at position 60, the substituting amino acid is Asn, Asp, Gln, Glu, Pro or Ser;
  d. when a substitution occurs at position 61, the substituting amino acid is Asp, Gln, Glu or Ser;
  e. when a substitution occurs at position 62, the substituting amino acid is Asn, Asp, Gln, Glu, Pro or Ser;
  f. when a substitution occurs at position 64, the substituting amino acid is Asn, Asp, Gln, Glu, Pro or Ser; and
  g. when a substitution occurs at position 65, the substituting amino acid is Asn, Asp, Gln, Glu, Gly, Pro or Ser;

B. when a substitution occurs in the second loop region, the substitution occurs at one or more of positions 94, 95, 96, 97, 98, 99, 100, 101, 102, 103, 104, 105 or 106; wherein
  a. when a substitution occurs at position 94, the substituting amino acid is Ala, Asn, Asp, Cys, Gln, Glu, Gly, His, Met, Pro, Ser or Thr;
  b. when a substitution occurs at position 95, the substituting amino acid is Ala, Asn, Asp, Cys, Gln, Glu, Gly, His, Ile, Met, Pro, Ser, Thr or Val;
  c. when a substitution occurs at position 96, the substituting amino acid is Asp, Gln, Glu or Ser; but when position 96 is substituted the variant is not a double, triple, quadruple, quintuple, sextuple, or septuple mutation variant having substitutions at positions selected from the group consisting of 103, 154, 155, 165, 188, and 216;
  d. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 103, 155, 165, 188, and 216;
  e. when a substitution occurs at position 98, the substituting amino acid is Asp or Glu; but when position 98 is substituted the variant is not a double, triple, quadruple, quintuple, or sextuple mutation variant having substitutions at positions selected from the group consisting of 103, 155, 165, 188, and 216;
  f. when a substitution occurs at position 99, the substituting amino acid is Asn, Asp, Gln, Glu, Pro or Ser; but when position 99 is substituted the variant is not a double, triple, quadruple, quintuple, or sextuple mutation variant having substitutions at positions selected from the group consisting of 103, 155, 165, 188, and 216;
  g. when a substitution occurs at position 100, the substituting amino acid is Asp or Glu; but when position 100 is substituted the variant is not a double, triple, quadruple, quintuple, or sextuple mutation variant having substitutions at positions selected from the group consisting of 103, 155, 165, 188, and 216;
  h. when a substitution occurs at position 101, the substituting amino acid is Asn, Asp, Gln, Glu, Pro or Ser; but when position 101 is substituted the variant is not a double, triple, quadruple, quintuple, or sextuple mutation variant having substitutions at positions selected from the group consisting of 103, 155, 165, 188, and 216;
  i. when a substitution occurs at position 102, the substituting amino acid is Asn, Asp, Gln, Glu, Gly, Pro or Ser; but when position 102 is substituted the variant is not a double, triple, quadruple, quintuple, or sextuple mutation variant having substitutions at positions selected from the group consisting of 103, 155, 165, 188, and 216;
  j. when a substitution occurs at position 103, the substituting amino acid is Ala, Asn, Asp, Cys, Gln, Glu, Gly, His, Ile, Leu, Met, Pro, Ser, Thr or Val;
  k. when a substitution occurs at position 104, the substituting amino acid is Asp or Glu;
  l. when a substitution occurs at position 105, the substituting amino acid is Asn, Asp, Gln, Glu, Gly, His, Pro, Ser or Thr; and
  m. when a substitution occurs at position 106, the substituting amino acid is Ala, Asn, Asp, Cys, Gln, Glu, Gly, His, Leu, Met, Pro, Ser, Thr or Val; but when position 106 is substituted the variant is not a double, triple, quadruple, quintuple, sextuple, or septuple mutation variant having substitutions at positions selected from the group consisting of 103, 154, 155, 165, 188, and 216;

C. when a substitution occurs in the third loop region, the substitution occurs at one or more of positions 125, 126, 127, 128, 129, 130, 131 or 132; wherein a. when a substitution occurs at position 125, the substituting amino acid is Ala, Asn, Asp, Cys, Gln, Glu, Gly, His, Ile, Met, Pro, Ser, Thr or Val; but when position 125 is substituted the variant is not a double, triple, quadruple, quintuple, sextuple, or septuple mutation variant having substitutions at positions selected from the group consisting of 103, 154, 155, 165, 188, and 216;

b. when a substitution occurs at position 126, the substituting amino acid is Asn, Asp, Gln, Glu, Pro or Ser; but when position 126 is substituted the variant is not a double, triple, quadruple, quintuple, sextuple, or septuple mutation variant having substitutions at positions selected from the group consisting of 103, 154, 155, 165, 188, and 216;

c. when a substitution occurs at position 127, the substituting amino acid is Asn, Asp, Gln, Glu, Pro or Ser; but when position 127 is substituted the variant is not a double, triple, quadruple, quintuple, sextuple, or septuple mutation variant having substitutions at positions selected from the group consisting of 103, 154, 155, 165, 188, and 216;

d. when a substitution occurs at position 128, the substituting amino acid is Asn, Asp, Gln, Glu, Gly, or Ser; but when position 128 is substituted the variant is not a double, triple, quadruple, quintuple, sextuple, or septuple mutation variant having substitutions at positions selected from the group consisting of 103, 154, 155, 165, 188, and 216;

e. when a substitution occurs at position 129, the substituting amino acid is Asp or Glu;

f. when a substitution occurs at position 130, the substituting amino acid is Asn, Asp, Gln, Glu, Pro or Ser;

g. when a substitution occurs at position 131, the substituting amino acid is Asp or Glu; and h. when a substitution occurs at position 132, the substituting amino acid is Asn, Asp, Gln, Glu, Gly, Pro or Ser;

D. when a substitution occurs in the fourth loop region, the substitution occurs at one or more of positions 153, 154, 155, 156, 157, 158, 159, 160, 161, 162, 163, 164, 165 or 166; wherein a. when a substitution occurs at position 153, the substituting amino acid is Asn, Asp, Gln, Glu, Pro or Ser; but when position 153 is substituted the variant is not a double, triple, quadruple, quintuple, or sextuple mutation variant having substitutions at positions selected from the group consisting of 103, 155, 165, 188, and 216;

b. when a substitution occurs at position 154, the substituting amino acid is Asp, Gln, Glu or Ser;

c. when a substitution occurs at position 155, the substituting amino acid is Asp or Glu;

d. when a substitution occurs at position 156, the substituting amino acid is Asn, Asp, Gln, Glu, Pro or Ser; but when position 156 is substituted the variant is not a double, triple, quadruple, quintuple, or sextuple mutation variant having substitutions at positions selected from the group consisting of 103, 155, 165, 188, and 216;

e. when a substitution occurs at position 157, the substituting amino acid is Asp or Glu; but when position 157 is substituted the variant is not a double, triple, quadruple, quintuple, or sextuple mutation variant having substitutions at positions selected from the group consisting of 103, 155, 165, 188, and 216;

f. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 103, 155, 165, 188, and 216;

g. when a substitution occurs at position 159, the substituting amino acid is Asn, Asp, Gln, Glu, Pro or Ser; but when position 159 is substituted the variant is not a double, triple, quadruple, quintuple, or sextuple mutation variant having substitutions at positions selected from the group consisting of 103, 155, 165, 188, and 216;

h. when a substitution occurs at position 160, the substituting amino acid is Asp or Glu; but when position 160 is substituted the variant is not a double, triple, quadruple, quintuple, or sextuple mutation variant having substitutions at positions selected from the group consisting of 103, 155, 165, 188, and 216;

i. when a substitution occurs at position 161, the substituting amino acid is Asn, Asp, Glu or Ser; but when position 161 is substituted the variant is not a double, triple, quadruple, quintuple, or sextuple mutation variant having substitutions at positions selected from the group consisting of 103, 155, 165, 188, and 216;

j. when a substitution occurs at position 162, the substituting amino acid is Asp, Gln, Glu or Ser; but when position 162 is substituted the variant is not a double, triple, quadruple, quintuple, or sextuple mutation variant having substitutions at positions selected from the group consisting of 103, 155, 165, 188, and 216;

k. when a substitution occurs at position 163, the substituting amino acid is Asn, Asp, Gln, Glu, Gly, Pro or Ser; but when position 163 is substituted the variant is not a double, triple, quadruple, quintuple, or sextuple mutation variant having substitutions at positions selected from the group consisting of 103, 155, 165, 188, and 216;

l. when a substitution occurs at position 164, the substituting amino acid is Ala, Asn, Asp, Cys, Gln, Glu, Gly, His, Leu, Met, Pro, Ser, Thr or Val; but when position 164 is substituted the variant is not a double, triple, quadruple, quintuple, or sextuple mutation variant having substitutions at positions selected from the group consisting of 103, 155, 165, 188, and 216;

m. when a substitution occurs at position 165, the substituting amino acid is Asn, Asp, Gln, Glu, Pro or Ser; and n. when a substitution occurs at position 166, the substituting amino acid is Ala, Asn, Asp, Cys, Gln, Glu, Gly, His, Ile, Leu, Met, Pro, Ser, Thr or Val; but when position 166 is substituted the variant is not a double, triple, quadruple, quintuple, or sextuple mutation variant having substitutions at positions selected from the group consisting of 103, 155, 165, 188, and 216;

E. when a substitution occurs in the fifth loop region, the substitution occurs at one or more of positions 186, 187, 188, 189 or 190; wherein a. when a substitution occurs at position 186, the substituting amino acid is Asn, Asp, Gln, Glu, Gly, His, Pro, Ser or Thr;

b. when a substitution occurs at position 187, the substituting amino acid is Asp or Glu;
c. when a substitution occurs at position 188, the substituting amino acid is Ala, Asn, Asp, Cys, Gln, Glu, Gly, His, Ile, Leu, Met, Pro, Ser, Thr, Tyr or Val;
d. when a substitution occurs at position 189, the substituting amino acid is Asp or Glu; and
e. when a substitution occurs at position 190, the substituting amino acid is Asp or Glu; and F. when a substitution occurs in the sixth loop region, the substitution occurs at one or more of positions 199, 200, 201, 202, 204, 205, 206, 207, 208, 209, 211, 212, 213, 214, 216, or 219; wherein
  a. when a substitution occurs at position 199, the substituting amino acid is Asn, Asp, Gln, Glu, Gly, His, Pro, Ser or Thr;
  b. when a substitution occurs at position 200, the substituting amino acid is Asn, Asp, Gln, Glu, Gly, or Ser;
  c. when a substitution occurs at position 201, the substituting amino acid is Asn, Asp, Gln, Glu, Pro or Ser;
  d. when a substitution occurs at position 202, the substituting amino acid is Ala, Cys, Gln, Gly, His, Met, Pro or Ser;
  e. when a substitution occurs at position 204, the substituting amino acid is Ala, Cys, Gln, Gly, His, Met, Pro or Ser;
  f. when a substitution occurs at position 205, the substituting amino acid is Ala, Asn, Gln, Gly, His, Ile, Leu, Met, Pro or Ser;
  g. when a substitution occurs at position 206, the substituting amino acid is Asp or Glu;
  h. when a substitution occurs at position 207, the substituting amino acid is Asn, Gln, Gly, Pro or Ser;
  i. when a substitution occurs at position 208, the substituting amino acid is Ala, Asn, Cys, Gln, Gly, His, Ile, Met, Pro or Ser;
  j. when a substitution occurs at position 209, the substituting amino acid is Asn, Gln, Gly, or Ser;
  k. when a substitution occurs at position 211, the substituting amino acid is Gln or Ser;
  l. when a substitution occurs at position 212, the substituting amino acid is Asn, Gln, Gly, Pro or Ser; but when position 212 is substituted the variant is not a double, triple, quadruple, quintuple, sextuple, or septuple mutation variant having substitutions at positions selected from the group consisting of 103, 154, 155, 165, 188, and 216;
  m. when a substitution occurs at position 213, the substituting amino acid is Ala, Asn, Cys, Gln, Gly, His, Ile, Leu, Met or Pro; but when position 213 is substituted the variant is not a double, triple, quadruple, quintuple, sextuple, or septuple mutation variant having substitutions at positions selected from the group consisting of 103, 154, 155, 165, 188, and 216;
  n. when a substitution occurs at position 214, the substituting amino acid is Asn, Gln, Gly, Pro or Ser; but when position 214 is substituted the variant is not a double, triple, quadruple, quintuple, sextuple, or septuple mutation variant having substitutions at positions selected from the group consisting of 103, 154, 155, 165, 188, and 216;
  o. when a substitution occurs at position 216, the substituting amino acid is Ala, Asn, Cys, Gln, Gly, His, Ile, Met, Pro, Ser, Thr or Val; and
  p. when a substitution occurs at position 219, the substituting amino acid is Asn, Asp, Gln, Glu, Gly, Pro or Ser;

whereby the Subtilisin DY variant has decreased adsorption to, and increased hydrolysis of, an insoluble substrate as compared to wild-type Subtilisin DY.

51. The Subtilisin DY variant of claim 50, wherein two or more substitutions occur in the first loop region.

52. The Subtilisin DY variant of claim 50, wherein two or more substitutions occur in the second loop region.

53. The Subtilisin DY variant of claim 50, wherein two or more substitutions occur in the third loop region.

54. The Subtilisin DY variant of claim 50, wherein two or more substitutions occur in the fourth loop region.

55. The Subtilisin DY variant of claim 50, wherein two or more substitutions occur in the fifth loop region.

56. The Subtilisin DY variant of claim 50, wherein two or more substitutions occur in the sixth loop region.

57. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the Subtilisin DY variant of claim 8 and a cleaning composition carrier.

58. The cleaning composition of claim 57, wherein the cleaning composition is a hard surface cleaning composition.

59. The cleaning composition of claim 57, wherein the cleaning composition is a fabric cleaning composition.

60. The fabric cleaning composition of claim 57, wherein the composition is in the form of a liquid.

61. The fabric cleaning composition of claim 60, wherein the composition further comprises at least about 5% surfactant and at least about 5% builder, by weight of the composition.

62. The fabric cleaning composition of claim 61 further comprising cleaning composition materials selected from the group consisting of solvents, buffers, enzymes, soil release agents, clay soil removal agents, dispersing agents, brighteners, suds supressors, fabric softeners, suds boosters, enzyme stabilizers, bleaching agents, dyes, perfumes, and mixtures thereof.

63. The fabric cleaning composition of claim 61 further comprising at least one bleaching agent.

64. A cleaning composition selected from the group consisting of a hard surface cleaning composition, a dishwashing composition, an oral cleaning composition, a denture cleansing composition, a contact lens cleaning composition and a fabric cleaning composition, wherein the, cleaning composition comprises the Subtilisin DY variant of claim 14 and a cleaning composition carrier.

65. A DNA sequence encoding the Subtilisin DY variant of claim 8.

* * * * *